US010538571B2

(12) United States Patent
Greenberg et al.

(10) Patent No.: US 10,538,571 B2
(45) Date of Patent: Jan. 21, 2020

(54) COMPOSITIONS AND METHODS FOR NEUROLOGICAL DISEASES

(71) Applicant: Coda Biotherapeutics, Inc., South San Francisco, CA (US)

(72) Inventors: Kenneth P. Greenberg, South San Francisco, CA (US); Orion Keifer, Jr., South San Francisco, CA (US); Stefanie Makinson, South San Francisco, CA (US); Anthony Lau, South San Francisco, CA (US)

(73) Assignee: Coda Biotherapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/201,142

(22) Filed: Nov. 27, 2018

(65) Prior Publication Data

US 2019/0161529 A1     May 30, 2019

Related U.S. Application Data

(60) Provisional application No. 62/590,911, filed on Nov. 27, 2017, provisional application No. 62/659,911, filed on Apr. 19, 2018.

(51) Int. Cl.
| | | |
|---|---|---|
| *C07K 14/705* | (2006.01) | |
| *A61P 25/00* | (2006.01) | |
| *C12N 7/00* | (2006.01) | |
| *A61K 38/00* | (2006.01) | |

(52) U.S. Cl.
CPC ............ *C07K 14/705* (2013.01); *A61P 25/00* (2018.01); *C12N 7/00* (2013.01); *A61K 38/00* (2013.01); *C12N 2710/10043* (2013.01)

(58) Field of Classification Search
CPC .................................................. C07K 14/705
See application file for complete search history.

(56) References Cited

U.S. PATENT DOCUMENTS

| | | | |
|---|---|---|---|
| 5,658,776 | A | 8/1997 | Flotte et al. |
| 6,518,480 | B1 | 2/2003 | Conklin |
| 6,566,118 | B1 | 5/2003 | Atkinson et al. |
| 6,989,264 | B2 | 1/2006 | Atkinson et al. |
| 6,995,006 | B2 | 2/2006 | Atkinson et al. |
| 7,883,846 | B2 | 2/2011 | Miesenbock et al. |
| 8,435,762 | B2 | 5/2013 | Sternson et al. |
| 8,957,036 | B2 | 2/2015 | Cascio et al. |
| 2006/0188484 | A1 | 8/2006 | Rabinowitz et al. |
| 2010/0130420 | A1 | 5/2010 | Sternson et al. |
| 2016/0375097 | A1 | 12/2016 | Kaetzel et al. |
| 2017/0081384 | A1 | 3/2017 | Cascio et al. |
| 2017/0190758 | A1 | 7/2017 | Xu et al. |
| 2018/0009862 | A1* | 1/2018 | Sternson ............. A61K 38/012 |
| 2018/0078658 | A1 | 3/2018 | Fishell et al. |
| 2018/0193414 | A1 | 7/2018 | Greenberg et al. |

FOREIGN PATENT DOCUMENTS

| | | | |
|---|---|---|---|
| WO | WO 98/22607 A1 | 5/1998 | |
| WO | WO 99/06562 A1 | 2/1999 | |
| WO | WO 99/11764 A1 | 3/1999 | |
| WO | WO 00/28004 A1 | 5/2000 | |
| WO | WO 00/73316 A2 | 12/2000 | |
| WO | WO 00/73431 A2 | 12/2000 | |
| WO | WO 01/23001 A2 | 4/2001 | |
| WO | WO 01/83752 A2 | 11/2001 | |
| WO | WO 2004/112727 A2 | 12/2004 | |
| WO | WO 2005/072364 A2 | 8/2005 | |
| WO | WO 2005/005610 A2 | 11/2005 | |
| WO | WO 2010/042799 A2 | 4/2010 | |
| WO | WO2014/093251 * | 6/2014 | ........... C07K 14/705 |
| WO | WO 2015/136247 A1 | 9/2015 | |
| WO | WO 2016/161124 A8 | 10/2016 | |
| WO | WO 2017/049252 A1 | 3/2017 | |
| WO | WO 2018/009832 A1 | 1/2018 | |
| WO | WO 2018/175443 A1 | 9/2018 | |

OTHER PUBLICATIONS

Bouzat et al (Nature. Aug. 19, 2004; 430: 896-900). (Year: 2004).*
Bitner et al. (Preclinical characterization of a selective alpha-7 neuronal nicotinic acetylcholine receptor agonist ABT-126. Alzheimer's & Dementia. Poster P4-310; Jul. 2013; 9(4): 817-818) (Year: 2013).*
Grutter et al., "Molecular tuning of fast gating in pentameric ligand-gated ion channels," PNAS, Dec. 13, 2005, vol. 102, No. 50, pp. 18207-18212.
Sine et al., "Naturally Occurring Mutations at the Acetylcholine Receptor Binding Site Independently Alter ACh Binding and Channel Gating," J Gen Physiol., 2002; 120(4): 483-496.
Ambuel et al., "Assessing distress in pediatric intensive care environments: the COMFORT scale," J Pediatr Psychol. Feb. 1992;17(1):95-109.
Bennett, "The LANSS Pain Scale: the Leeds assessment of neuropathic symptoms and signs," Pain. May 2001; 92(1-2):147-157.
Bishop et al., "Unnatural Ligands for Engineered Proteins: New Tools for Chemical Genetics," Annu. Rev. Biophys. Biomol. Struct., 2000, vol. 29, pp. 577-606.
Bodnar et al., "Discovery and Structure-Activity Relationship of Quinuclidine Benzamides as Agonists of α7 Nicotinic Acetylcholine Receptors," J. Med. Chem., 2005, 48(4):905-908.
Brake et al., "New structural motif for ligand-gated ion channels defined by an ionotropic ATP receptor," Nature, 1994, vol. 371, pp. 519-523.
Cleeland and Ryan, "Pain assessment: global use of the Brief Pain Inventory," Ann Acad Med Singapore. Mar. 1994; 23(2):129-138.
Craig et al., "Stable expression and characterisation of a human α7 nicotinic subunit chimera: a tool for functional high-throughput screening," European Journal of Pharmacology, Oct. 2004, vol. 502, pp. 31-40.

(Continued)

*Primary Examiner* — Scott Long
(74) *Attorney, Agent, or Firm* — Cooley LLP

(57) ABSTRACT

Compositions and methods are provided for modulating the activity of cells using engineered receptors, polynucleotide encoded engineered receptors, and gene therapy vectors comprising polynucleotides encoding engineered receptors. These compositions and methods find particular use in modulating the activity of neurons, for example in the treatment of disease or in the study of neuronal circuits.

28 Claims, 30 Drawing Sheets
(10 of 30 Drawing Sheet(s) Filed in Color)
Specification includes a Sequence Listing.

(56) References Cited

OTHER PUBLICATIONS

Duan et al., "Expanding AAV Packaging Capacity with Trans-splicing or Overlapping Vectors: A Quantitative Comparison," Molecular Therapy, vol. 4, No. 4, Oct. 2001, pp. 383-391.
Eiselé et al., "Chimaeric nicotinic-serotonergic receptor combines distinct ligand binding and channel specificities," Nature (1993), 366, pp. 479-483.
Feldt, "The checklist of nonverbal pain indicators (CNPI)," Pain Manag Nurs., Mar. 2000; 1(1):13-21.
Finnerup et al., "Algorithm for neuropathic pain treatment: An evidence based proposal," Pain, 2005, 118(3): 289-305.
Finnerup et al., "The evidence for pharmacological treatment of neuropathic pain," Pain, 2010;150(3):573-581.
Fleming et al., "Adeno-Associated Virus and Lentivirus Vectors Mediate Efficient and Sustained Transduction of Cultured Mouse and Human Dorsal Root Ganglia Sensory Neurons," Human Gene Therapy, 2001, vol. 12, No. 1, pp. 77-86.
Galietta et al., "Green fluorescent protein-based halide indicators with improved chloride and iodide affinities," FEBS Letters 2001, 499: 220-224.
Gelinas et al., "Validation of the Critical-Care Pain Observation Tool in Adult Patients," (2006) Am. J. Crit. Care 15:420.
Geurts et al., "Radiofrequency lesioning of dorsal root ganglia for chronic lumbosacral radicular pain: a randomised, double-blind, controlled trial," Lancet, 2003; 361: 21-26.
Ghosh et al., "Viral serotype and the transgene sequence influence overlapping adeno-associated viral (AAV) vector-mediated gene transfer in skeletal muscle," J Gene Med. Mar. 2006; 8(3): 298-305. doi:10.1002/jgm.835.
Ghosh et al., "A Hybrid Vector System Expands Adeno-associated Viral Vector Packaging Capacity in a Transgene-independent Manner," Molecular Therapy, vol. 16, No. 1, Jan. 2008, 124-130.
Ghosh et al., "Efficient Transgene Reconstitution with Hybrid Dual AAV Vectors Carrying the Minimized Bridging Sequences," Human Gene Therapy 22:77-83 (Jan. 2011).
Gracely and Kwilosz, "The Descriptor Differential Scale: applying psychophysical principles to clinical pain assessment," Pain, 1988;35(3):279-288.
Hardy et al., Pain Sensations and Reactions, 1952, Baltimore, The Williams & Wilkins Co, pp. 67-85.
Hartrick et al., "The numeric rating scale for clinical pain measurement: a ratio measure?" Pain Pract, Dec. 2003;3(4):310-316.
Hicks et al., "The Faces Pain Scale—Revised: toward a common metric in pediatric pain measurement," Pain, 93 (2001) 173-183.
Huskisson, "Measurement of Pain," The Journal of Rheumatology, 1982, 9:5, 768-769.
Inoue et al., "Packaging Cells Based on Inducible Gene Amplification for the Production of Adeno-Associated Virus Vectors," J Virol., Sep. 1998;72(9):7024-7031.
Jensen et al., "Pharmacological characterisation of strychnine and brucine analogues at glycine and $\alpha 7$ nicotinic acetylcholine receptors," European Journal of Pharmacology, 2006, vol. 539, pp. 27-33.
Jensen et al., "The subjective experience of acute pain. An assessment of the utility of 10 indices," Clin J Pain., 1989;5(2):153-159.
Katz and Melzack, "Measurement of pain," Surg Clin North Am. Apr. 1999; 79(2):231-252.
Kawashima et al., "A novel and efficient method for the stable expression of heteromeric ion channels in mammalian cells," Receptors and Channels, 1998, vol. 5, No. 2, pp. 53-60.
Kruger et al., "A yellow fluorescent protein-based assay for high-throughput screening of glycine and GABAA receptor chloride channels," Neuroscience Letters, (2005) 380: 340-345.
Kügler et al., "Neuron-Specific Expression of Therapeutic Proteins: Evaluation of Different Cellular Promoters in Recombinant Adenoviral Vectors," Molecular and Cellular Neuroscience, vol. 17, Issue 1, Jan. 2001, pp. 78-96.
Machida, "Viral Vectors for Gene Therapy: Methods and Protocols," Humana Press, 2003, 606 pages.
Magnus et al., "Chemical and genetic engineering of selective ion-ligand channel interactions," Science, Sep. 2, 2011; 333(6047): 1292-1296.
Magnus et al., "Supporting Online Material for Chemical and genetic engineering of selective ion-ligand channel interactions," Science, Sep. 2, 2011; 333(6047): 1292-1296.
Mailis and Taenzer, "Evidence-based guideline for neuropathic pain interventional treatments: Spinal cord stimulation, intravenous infusions, epidural injections and nerve blocks," Pain Res Manag., May/Jun. 2012;17(3):150-158.
Melzack, "The McGill Pain Questionnaire: major properties and scoring methods," Pain, 1975;1(3):277-299.
Ozguler et al., "Using the Dallas Pain Questionnaire to Classify Individuals With Low Back Pain in a Working Population," Spine, 2002, 27(16):1783-1789.
Payen et al., "Assessing pain in critically ill sedated patients by using a behavioral pain scale," Crit Care Med., Dec. 2001; 29(12):2258-2263.
Quiram et al., "Identification of Residues in the Neuronal $\alpha 7$ Acetylcholine Receptor That Confer Selectivity for Conotoxin Iml," The Journal of Biological Chemistry, 1998, 273(18):11001-11006.
Samulski et al., "Helper-Free Stocks of Recombinant Adeno-Associated Viruses: Normal Integration Does Not Require Viral Gene Expression," J Virol, Sep. 1989;63(9):3822-3828.
Schmader, "Epidemiology and impact on quality of life of postherpetic neuralgia and painful diabetic neuropathy," Clin J Pain. Nov.-Dec. 2002; 18(6):350-354.
Shields et al., "Spared nerve injury model of neuropathic pain in the mouse: a behavioral and anatomic analysis," The Journal of Pain, 2003, 4(8), 465-470.
Snowball et al., "Changing channels in pain and epilepsy: Exploiting ion channel gene therapy for disorders of neuronal hyperexcitability," FEBS Letters (2015) 589:1620-1634.
Sternson et al., "Chemogenetic Tools to Interrogate Brain Functions," Annual Review of Neuroscience, 2014, 37:387-407.
Stewart et al., "Validation of the Alder Hey Triage Pain Score," Arch Dis Child 2004;89:625-630.
Thompson et al., "The structural basis of function in Cys-loop receptors," Quarterly Reviews of Biophysics, vol. 43, Issue 4, Nov. 2010, pp. 449-499.
Walker et al., "Photolabile protecting groups for an acetylcholine receptor ligand. Synthesis and photochemistry of a new class of o-nitrobenzyl derivatives and their effects on receptor function," Biochemistry, 1986, vol. 25, No. 7, pp. 1799-1805.
Wolter, "Spinal cord stimulation for neuropathic pain: current perspectives," Journal of Pain Research, 2014:7 651-663.
Xiao et al., "Production of High-Titer Recombinant Adeno-Associated Virus Vectors in the Absence of Helper Adenovirus," J Virol., Mar. 1998;72(3):2224-2232.
Zemelman et al., "Photochemical gating of heterologous ion channels: Remote control over genetically designated populations of neurons," PNAS, Feb. 4, 2003, vol. 100, No. 3, pp. 1352-1357.

* cited by examiner

Fig. 2

Generate ~12 "parental" receptors (LBD/iPD fusions)

Generate mutant library (mutate LBDs via error prone PCR)

1° screen (HT yeast screen for functional mutants against ligands)

2° screen (LT in vitro functional screen using mammalian cells with ligands)

In vitro validation & characterization (electrophysiology on neurons)

In vivo validation (in appropriate animal model)

Fig. 8A

| | Acetylcholine | | | | | | | AZD-0328 | | | | | | Amino acid | Mutation |
|---|---|---|---|---|---|---|---|---|---|---|---|---|---|---|
| | 10uM | 10uM | 100uM | 100uM | 3mM | 3mM | | 100nM | 100nM | 300nM | 300nM | 30uM | 30uM | | |
| SEQ ID 33 | 20.867 | 27.799 | ░ | ░ | ░ | ░ | | ░ | ░ | ░ | ░ | ░ | ░ | | |
| SEQ ID 29 | ░ | ░ | ░ | ░ | ░ | ░ | | ░ | ░ | ░ | ░ | ░ | ░ | | |
| SEQ ID 33 variants | 10.109 | ░ | 9.316 | ░ | 7.934 | 11.636 | | 7.435 | 9.033 | 3.826 | 6.302 | 42.118 | 63.956 | W77 | H |
| | | ░ | 64.362 | 56.647 | ░ | ░ | | 16.825 | 2.633 | 18.687 | 0.958 | 22.650 | ░ | W77 | I |
| | 2.552 | 0.529 | 69.309 | 78.773 | ░ | ░ | | 28.245 | 20.458 | 47.912 | 82.32 | ░ | ░ | W77 | V |
| | 8.214 | 4.948 | 72.421 | 79.864 | ░ | ░ | | 2.212 | 5.871 | 12.053 | 12.586 | ░ | ░ | W77 | F |
| | 0.477 | 2.371 | ░ | 47.813 | 14.377 | ░ | | 0.919 | 0.803 | 44.279 | 22.473 | ░ | 9.448 | W77 | Y |
| | | 11.835 | 30.054 | 48.527 | ░ | ░ | | 8.074 | 3.076 | 1.03 | 6.925 | ░ | ░ | W77 | D |
| | | 9.639 | 26.175 | 4.322 | ░ | ░ | | 3.239 | 0.189 | -7.522 | 6.608 | ░ | ░ | W77 | A |
| | -0.796 | | 2.038 | 10.853 | ░ | ░ | | 5.727 | 4.173 | 2.366 | 0.071 | ░ | ░ | W77 | G |
| | | 1.391 | 12.452 | 10.615 | 51.113 | 19.256 | | 10.729 | -10.127 | 2.829 | 0.407 | 25.02 | 26.124 | W77 | Q |
| | -6.137 | -14.278 | 29.004 | 2.411 | ░ | 25.798 | | ░ | -18.441 | ░ | 19.35 | 31.034 | 33.787 | W77 | C |
| | 13.347 | 9.602 | 4.544 | 17.964 | ░ | ░ | | 6.954 | 17.865 | 9.139 | 20.444 | ░ | ░ | W77 | N |
| | 14.725 | 6.996 | 2.708 | ░ | 17.137 | 12.045 | | 10.583 | 13.223 | 12.003 | 9.973 | ░ | ░ | W77 | E |
| | -0.595 | 3.821 | ░ | 17.316 | 15.578 | 5.158 | | 6.645 | 9.599 | 18.539 | 12.747 | ░ | ░ | I | I |
| | 4.809 | 11.127 | ░ | ░ | ░ | 17.305 | | 19.29 | -8.503 | ░ | -10.022 | ░ | ░ | S | S |
| | -16.873 | 12.38 | -10.484 | ░ | ░ | ░ | | 9.582 | 14.113 | 12.33 | 11.37 | ░ | ░ | D | D |
| | -5.956 | 11.403 | ░ | ░ | ░ | ░ | | 17.545 | -3.663 | 59.47 | 50.59 | ░ | ░ | F | F |
| | 14.570 | 16.834 | 60.291 | 45.127 | ░ | ░ | | | 6.512 | ░ | 72.339 | ░ | ░ | C | C |
| | -6.873 | -10.037 | 43.913 | 56.949 | ░ | ░ | | 15.458 | 11.252 | ░ | 69.734 | ░ | ░ | Y | Y |
| | 7.953 | 16.623 | 57.777 | 58.617 | ░ | ░ | | 3.301 | -10.064 | ░ | 66.357 | ░ | ░ | H | H |
| | 4.503 | -14.088 | 32.316 | 27.316 | ░ | ░ | | 5.485 | 12.215 | 70.4 | 68.878 | 79.477 | ░ | K | K |
| | 13.733 | 19.477 | 9.821 | 19.361 | ░ | ░ | | 13.839 | -6.514 | 70.556 | 45.632 | ░ | ░ | P | P |
| | 11.826 | 12.408 | 1.234 | 0.729 | ░ | 76.807 | | 14.126 | -12.672 | 45.632 | 36.809 | ░ | ░ | Q | Q |
| | 13.857 | 15.236 | 10.796 | ░ | ░ | 78.3 | | 8.611 | 1.412 | 41.962 | 52.515 | ░ | ░ | G | G |
| | 9.111 | ░ | ░ | ░ | ░ | 73.825 | | 14.33 | 14.13 | -2.182 | 9.674 | ░ | ░ | A | A |
| | ░ | ░ | ░ | ░ | ░ | ░ | | 3.058 | 6.218 | 2.197 | 3.376 | ░ | ░ | | |
| | 10.284 | 10.555 | 4.98 | 10.608 | 45.528 | 31.836 | | ░ | ░ | 2.661 | ░ | ░ | ░ | R101 | L |

| | Acetylcholine | | | | | | AZD-0328 | | | | | | | |
|---|---|---|---|---|---|---|---|---|---|---|---|---|---|---|
| | 10uM | 10uM | 100uM | 100uM | 3mM | 3mM | 100nM | 100nM | 300nM | 300nM | 30uM | 30uM | Amino acid | Mutation |
| | 7,376 | 6.7 | 7,445 | 6,998 | | | 8.67 | 10,111 | | | | | T128 | Q |
| | 6,905 | 11,493 | 4,531 | 20,583 | | | | | 19,428 | | | | T128 | C |
| | 5,893 | 2,954 | 12,299 | 5,003 | 29,544 | | | | 6,133 | | | | T128 | N |
| | 6,889 | 5,165 | 10,937 | 6,517 | 34,776 | | 10,404 | 12,506 | 7,953 | | | | T128 | Y |
| | 4,317 | 1,755 | 3,098 | 5,03 | 33,439 | 33.24 | | | -4.73 | -0.302 | | | T128 | D |
| | 10,201 | 8,367 | -4.8 | 6,515 | 52.63 | 42,062 | 11,444 | 11,611 | 9,991 | 7,084 | | | T128 | K |
| | 12,555 | 12,382 | 9,386 | 14,272 | 71,344 | 61,115 | 16,164 | 14,653 | 8,821 | 11,147 | | | T128 | H |
| | 6,826 | 14,226 | 27,188 | 28,546 | 50,674 | 73,435 | 10,036 | 18,114 | 51,294 | 48.49 | | | T128 | V |
| | 4,937 | 3,387 | 7,55 | 2,078 | 6,747 | -5,618 | 11,76 | 7,977 | 9,242 | 7,453 | | | N129 | I |
| | 6,173 | 6,145 | 16,274 | 11,145 | 19,342 | 32,583 | 10,957 | 13,638 | 15,999 | 2,11 | | | N129 | V |
| | 6,738 | 3,799 | 3,78 | 5,285 | 4,198 | 5,142 | 6,813 | 1,319 | 7,813 | -10,302 | | | N129 | P |
| | 13,438 | 8,73 | 8,538 | 12,849 | 3,451 | 7,8 | 15,746 | 15,574 | 13,372 | 5,593 | | | N129 | W |
| | 1,747 | 8,211 | 7,577 | 15,355 | 9,501 | 7,284 | 6,972 | 18,941 | 5,45 | 1,349 | | | N129 | T |
| | 5,417 | 0,622 | 8,831 | 7,759 | 4,92 | 4,898 | 1,691 | 0,912 | 9,548 | 5,056 | | | N129 | D |
| | 7,959 | 7,555 | 11,107 | 12,437 | 6,829 | 8,041 | 7,124 | 4,035 | 2,576 | 8,006 | | | N129 | E |
| | 9,186 | 2,456 | 14,23 | 10,833 | 8,041 | 8,363 | 11,445 | 14,098 | 8,709 | 9,97 | | | N129 | G |
| | 6,222 | 8,236 | 11,441 | 8,99 | 44,486 | 18,493 | 14,33 | 10,3 | 3,165 | 2,176 | | | N129 | A |
| | 8,186 | 9,57 | 10,033 | 14,954 | | | 11,093 | 8,799 | 11,3 | 10,486 | | | N129 | S |
| | 6,738 | 9,01 | 11,891 | 13,826 | | | 9,223 | 11,496 | 3,724 | 10,407 | | | N129 | Q |
| | 13,063 | 7,593 | 5,851 | 13,406 | 38,623 | 44,524 | 17,409 | 12,355 | 14,04 | 30,104 | | | N129 | C |
| | 7,657 | 3,695 | 4,666 | 9,004 | | | 6,028 | 7,443 | 18,455 | 46,328 | | | N129 | Y |
| | 11,215 | 7,153 | 7,615 | 11,326 | | | 12,409 | 12,355 | 35,455 | 52,417 | | | N129 | F |
| | 14,433 | 5,825 | 8,234 | 8,016 | | | 11,837 | 9,709 | 31,806 | 37,231 | | | N129 | M |
| | 9,048 | 7,079 | 2,95 | 2,833 | | | 6,654 | 6,457 | 32,769 | 64,428 | | | N129 | R |
| | 5,828 | 5,825 | 7,615 | 7,323 | | | 0,789 | 4,373 | 60,298 | 57,395 | | | N129 | H |
| | 11,839 | 10,772 | 12,365 | 31,95 | | | 16,442 | 3,361 | 56,873 | | | | N129 | L |
| | 4,408 | 5,704 | 0,795 | 4,774 | 25,856 | 27,313 | 1,506 | 4,046 | 10,218 | 10,069 | 30,433 | 33,789 | L131 | P |
| | 9,893 | 0,435 | 7,963 | 3,572 | 45,363 | 51,036 | 17,766 | 13,983 | 52,577 | 44,526 | | | L131 | T |

{ SEQ ID 33 variants }

Fig. 8D

| | Acetylcholine | | | | | | AZD-0328 | | | | | | Amino acid | Mutation |
|---|---|---|---|---|---|---|---|---|---|---|---|---|---|---|
| 10uM | 10uM | 100uM | 100uM | 3mM | 3mM | 100nM | 100nM | 300nM | 300nM | 30uM | 30uM | | | |
| 3.932 | -10.344 | -5.595 | 7.042 | 80.939 | 80.979 | 1.688 | 8.127 | 32.709 | 26.851 | 81.679 | 81.182 | L131 | K |
| 2.379 | 1.696 | 2.398 | -1.491 | 80.595 | 80.119 | 5.254 | 7.158 | 89.907 | 70.106 | 81.521 | 80.923 | L131 | R |
| 12.472 | -10.451 | 71.302 | 73.095 | 82.278 | 81.279 | 0.309 | 9.028 | 3.135 | 2.663 | 83.236 | 82.479 | L141 | G |
| 10.377 | -0.575 | 52.167 | 49.36 | 80.091 | 83.102 | 2.911 | 7.115 | 3.583 | 3.353 | 82.222 | 82.56 | L141 | A |
| 7.328 | 5.513 | 28.656 | 27.204 | 79.05 | 79.436 | 1.251 | -0.232 | 0.45 | 2.832 | 80.864 | 79.849 | L141 | V |
| 5.194 | 6.614 | 41.961 | 4.146 | 80.111 | 80.156 | 0.399 | 4.193 | 1.456 | 4.205 | 81.905 | 81.091 | L141 | D |
| 20.499 | 13.707 | 78.495 | 13.979 | 84.278 | 80.94 | 10.498 | 9.299 | 16.452 | 21.59 | 82.165 | 82.798 | L141 | H |
| 28.116 | 18.795 | 71.594 | 72.846 | 81.521 | 78.111 | 4.174 | 19.335 | 32.257 | 15.705 | 84.343 | 83.413 | L141 | C |
| 5.304 | 5.719 | 78.086 | 80.376 | 80.599 | 80.089 | 27.504 | 15.49 | 77.318 | 23.334 | 81.567 | 81.341 | L141 | Y |
| 0.374 | 1.72 | 6.884 | 8.38 | 60.74 | 63.195 | -10.065 | -5.633 | 9.605 | 6.573 | 16.151 | 18.192 | L141 | P |
| 11.923 | -11.588 | 6.411 | -0.211 | 77.93 | 76.118 | 8.358 | -8.358 | 10.469 | 2.466 | 81.402 | 81.592 | L141 | W |
| 11.208 | 12.992 | 13.604 | 18.338 | 46.621 | 39.269 | 16.483 | 16.774 | 13.413 | -9.801 | 45.375 | 47.641 | L141 | S |
| 2.017 | 12.679 | 17.358 | 0.65 | 81.34 | 81.601 | 3.991 | 1.374 | -0.73 | 2.371 | 82.611 | 82.961 | L141 | Q |
| 6.581 | 6.482 | 10.205 | 3.21 | 79.136 | 80.679 | 2.068 | 8.839 | 3.963 | 2.199 | 81.653 | 83.493 | L141 | T |
| 12.471 | 13.496 | 21.159 | 28.979 | 82.869 | 82.338 | 4.904 | 3.578 | 3.975 | 8.153 | 81.998 | 83.128 | L141 | N |
| 13.864 | -9.402 | 2.934 | 3.539 | 50.15 | 55.996 | 14.257 | 5.757 | 11.061 | 1.696 | 59.531 | 73.137 | L141 | R |
| 5.771 | -5.291 | 12.381 | 33.648 | 70.73 | 78.194 | 0.726 | 5.077 | 8.476 | 0.473 | 72.949 | 70.036 | L141 | E |
| 11.192 | 3.201 | 81.767 | 82.165 | 84.172 | 84.336 | 38.957 | 25.629 | 82.831 | 81.322 | 84.237 | 80.897 | L141 | H |
| 22.808 | 15.989 | 16.534 | 81.685 | 84.306 | 81.614 | 14.93 | 13.683 | 14.833 | 10.4 | 64.258 | 63.786 | S170 | W |
| 3.275 | -10.445 | -8.667 | 1.713 | 81.168 | 82.484 | -1.587 | -2.608 | 7.34 | 40.447 | 85.373 | 85.875 | S170 | Q |
| 5.373 | 11.313 | 5.334 | 13.053 | 84.869 | 82.64 | 7.494 | 7.053 | 46.106 | 17.696 | 83.197 | 85.086 | S170 | E |
| 5.221 | -4.603 | 16.953 | 28.141 | 82.573 | 55.996 | 4.698 | 1.749 | 11.789 | 11.933 | 84.127 | 83.869 | S170 | Y |
| 11.383 | 14.111 | 10.647 | 7.801 | 7.501 | 4.948 | 8.016 | 3.181 | 12.816 | 11.122 | 51.421 | 39.587 | W171 | Y |
| 12.276 | 7.063 | 10.489 | 33.593 | 85.599 | 86.189 | -4.409 | 2.36 | -3.487 | 1.758 | 84.883 | 85.233 | W171 | G |
| 16.827 | 9.137 | 19.264 | 10.903 | 82.811 | 82.267 | 6.179 | -3.142 | -8.095 | 2.587 | 85.237 | 85.224 | W171 | A |
| 3.108 | 4.167 | 6.539 | 16.722 | 84.156 | 82.155 | 1.134 | 7.727 | 4.21 | 4.561 | 81.279 | 62.961 | W171 | P |
| -0.578 | 7.464 | 13.86 | 10.027 | 51.003 | 45.709 | -0.52 | -0.832 | 0.806 | 2.59 | 85.092 | 85.078 | W171 | F |
| 20.122 | 36.614 | 21.619 | 17.435 | 80.053 | 80.053 | 8.675 | 3.674 | 15.95 | 10.911 | 42.831 | 47.109 | W171 | S |

SEQ ID 33 variants

*Fig. 8E*

| | | Acetylcholine | | | | | | AZD-0328 | | | | | | | |
|---|---|---|---|---|---|---|---|---|---|---|---|---|---|---|---|
| Mutation | Amino acid | 10uM | 10uM | 100uM | 100uM | 3mM | 3mM | 100nM | 100nM | 300nM | 300nM | 30uM | 30uM | | |
| C | W171 | 10.333 | | | | | | | | | | | | | |
| H | W171 | 13.758 | 15.721 | 14.94 | 15.098 | 34.261 | 44.392 | 10.403 | | 9.993 | | 59.182 | 63.133 | | |
| F | S172 | -1.307 | -6.802 | -11.454 | -11.715 | 6.212 | 6.254 | 14.425 | 12.176 | 11.326 | 10.537 | 72.943 | 73.637 | | |
| Y | S172 | 5.548 | 6.225 | 0.929 | 3.712 | 4.57 | 7.005 | 3.699 | 3.559 | 7.051 | 1.367 | | | | |
| R | S172 | 9.919 | -0.322 | -6.855 | -4.777 | 3.286 | 10.219 | 1.693 | -3.194 | -4.127 | -6.311 | | | | |
| C | S172 | 12.807 | 36.799 | 50.377 | 59.762 | | | | | 17.526 | 23.618 | | | | |
| I | S172 | | 5.089 | 67.116 | | | | | | | 9.554 | | | | |
| M | S172 | | 25.749 | 43.459 | 47.542 | | | | 5.689 | 5.745 | 9.246 | | | | |
| L | S172 | 2.225 | 10.264 | 0.529 | 10.642 | 65.421 | 48.811 | 10.982 | 1.287 | 74.331 | 6.12 | | | | |
| Q | S172 | | 2.372 | 7.45 | 8.386 | | 34.956 | 5.859 | 7.39 | 11.204 | 2.616 | | | | |
| N | S172 | 4.31 | 7.129 | 7.136 | 11.096 | 28.796 | | 7.972 | -8.587 | 4.425 | 7.564 | | | | |
| H | S172 | 5.542 | -4.849 | 14.167 | 23.677 | | | 6.669 | -11.829 | 7.332 | 5.875 | | | | |
| G | S172 | 8.684 | 3.137 | 1.897 | 6.645 | | | 9.804 | 0.184 | 23.113 | 32.617 | | | | |
| K | S172 | 5.789 | 0.559 | 4.65 | -1.753 | | | 3.573 | 6.452 | 45.957 | | | | | |
| A | S172 | 3.389 | 1.338 | 10.076 | 17.442 | 39.576 | 51.528 | 9.206 | 5.27 | 13.825 | 23.388 | | | | |
| F | Y210 | -2.266 | 1.69 | 0.979 | 3.626 | | | 1.958 | 3.222 | 3.042 | 8.19 | | | | |
| W | Y210 | 10.515 | 0.333 | 21.567 | 13.032 | | | 6.027 | 5.949 | 2.575 | 0.553 | | | | |
| A | Y210 | 11.383 | 18.064 | -13.846 | 2.495 | 6.126 | 2.213 | 0.902 | 2.181 | 3.915 | 0.221 | 52.008 | 6.229 | | |
| L | C212 | 7.332 | 10.325 | 12.168 | 3.379 | 17.006 | 18.174 | -4.723 | -1.565 | 5.734 | 6.012 | 31.38 | 57.485 | | |
| F | C212 | 6.585 | 5.589 | 0.008 | 3.116 | 47.29 | 43.523 | 7.04 | -0.722 | 3.167 | 1.544 | 7.169 | 15.025 | | |
| Y | C212 | 12.279 | 1.411 | 9.231 | 2.788 | 74.215 | 51.215 | 1.325 | -0.048 | 3.801 | 1.553 | 15.61 | 18.506 | | |
| K | C212 | 12.564 | 3.313 | 4.314 | 0.473 | | 64.092 | 6.167 | 2.674 | 4.147 | 5.181 | 14.065 | 18.231 | | |
| H | C212 | 8.903 | 7.462 | 9.323 | 8.482 | 49.054 | 33.678 | 0.76 | 6.543 | 8.051 | 5.228 | 10.621 | 6.259 | | |
| I | C212 | 4.621 | 5.49 | 0.583 | 3.482 | | | 4.729 | 2.69 | 1.302 | -0.457 | | | | |
| V | C212 | 10.329 | 10.394 | 8.619 | 12.291 | | | 3.563 | 9.847 | 10.472 | 3.556 | | | | |
| P | C212 | 1.807 | 8.11 | 2.19 | 5.386 | 55.673 | 57.819 | 4.763 | 4.375 | 3.642 | 3.551 | 29.117 | 40.462 | | |
| M | C212 | 5.72 | 7.741 | 4.457 | 0.297 | 49.271 | | 2.532 | 4.165 | 2.686 | 0.534 | 56.807 | 57.796 | | |
| W | C212 | 0.117 | 0.65 | 0.512 | 1.504 | | | 1.09 | 0.908 | 0.793 | 4.377 | 28.376 | 28.168 | | |

SEQ ID 33 variants

Fig. 8F

| | Acetylcholine | | | | | AZD-0328 | | | | | Amino acid | Mutation |
|---|---|---|---|---|---|---|---|---|---|---|---|---|
| 10uM | 10uM | 100uM | 100uM | 3mM | 3mM | 100nM | 100nM | 300nM | 300nM | 30uM | 30uM | | |
| 5.409 | 2.45 | 1.03 | 2.647 | 82.116 | 80.923 | 3.801 | 2.106 | 0.829 | 1.665 | 81.552 | 80.126 | C212 | R |
| 4.368 | 3.2 | 0.572 | 2.178 | 58.541 | 47.818 | -5.333 | -4.771 | 3.892 | 2.109 | 9.586 | 10.13 | C213 | M |
| 3.416 | -3.111 | 4.998 | -5.53 | 34.524 | 32.807 | 6.778 | 3.841 | 7.064 | 4.753 | 37.308 | 35.2 | C213 | A |
| 1.892 | -4.111 | 3.881 | 1.069 | 38.943 | 79 | 2.647 | 1.928 | 2.169 | 3.843 | 29.477 | 31.802 | C213 | L |
| 16.662 | -3.923 | 0.819 | 2.555 | 67.12 | 40.203 | 6.345 | 1.448 | 4.541 | 4.95 | 50.598 | 45.819 | C213 | I |
| 2.662 | 4.034 | 2.682 | 3.012 | 70.628 | 65.41 | 5.35 | 9.696 | 3.692 | 0.129 | 50.654 | 54.23 | C213 | V |
| 1.127 | -2.39 | 3.781 | -4.103 | 31.507 | 21.781 | 0.213 | 3.285 | 4.52 | 1.009 | 40.828 | 48.876 | C213 | P |
| 11.643 | 11.455 | 7.928 | 4.849 | 76.426 | 74.619 | 1.938 | 3.638 | 7.285 | 5.183 | 78.094 | 77.871 | C213 | F |
| 7.54 | -1.394 | 0.407 | 0.747 | 70.865 | 48.747 | -6.15 | -3.88 | 4 | 3.449 | 59.292 | 65.984 | C213 | W |
| 7.671 | 10.741 | 8.275 | 5.87 | 81.904 | 82.605 | 0.83 | 2.036 | 28.977 | 31.636 | 80.335 | 82.86 | C213 | F |
| 12.817 | 7.866 | 9.12 | 3.641 | 37.682 | 41.026 | -1.003 | 4.238 | 5.748 | 0.567 | 5.531 | 12.718 | Y217 | T |
| 8.228 | 7.413 | 1.205 | 5.032 | 72.373 | 70.104 | 3.415 | 3.103 | 2.895 | 2.679 | 51.291 | 43.961 | Y217 | A |
| 6.088 | 4.604 | 6.807 | 3.753 | 76.884 | 78.604 | 4.414 | 5.839 | 0.973 | 1.777 | 61.923 | 57.385 | Y217 | I |
| 8.495 | 14.772 | 8.037 | 3.462 | 88.344 | 80.133 | 2.083 | 1.164 | 3.446 | 3.511 | 43.399 | 38.8 | Y217 | V |
| 8.238 | 9.36 | 8.675 | 28.62 | 27.066 | 33.39 | 1.891 | 6.5 | 2.421 | 6.416 | 24.222 | 15.967 | Y217 | M |
| 5.859 | 8.696 | 10.467 | 11.496 | 80.235 | 80.853 | -0.294 | -2.986 | 12.479 | 12.674 | 80.032 | 81.06 | Y217 | W |
| 11.601 | 7.001 | 7.242 | 6.051 | 79.492 | 77.41 | 2.128 | 5.395 | 4.137 | 3.289 | 78.633 | 78.003 | Y217 | S |
| 7.612 | 6.716 | 4.732 | 1.185 | 28.765 | 29.987 | 9.808 | 1.758 | 7.648 | 3.035 | 22.721 | 23.829 | Y217 | Q |
| 10.391 | 7.529 | 4.732 | 1.185 | 51.361 | 49.396 | 5.654 | 4.841 | 5.358 | 1.753 | 41.694 | 28.869 | Y217 | C |
| 15.492 | 1.445 | 1.407 | 0.818 | 20.874 | 18.309 | 5.052 | 3.559 | 4.285 | 7.826 | 31.33 | 30.912 | Y217 | H |

SEQ ID 33 variants

Fig. 8G

| | 10uM | 10uM | 100uM | 100uM | 3mM | 3mM | | 100nM | 100nM | 300nM | 300nM | 30uM | 30uM | Amino acid | Mutation |
|---|---|---|---|---|---|---|---|---|---|---|---|---|---|---|---|
| SEQ ID 33 | 18.703 | 18.97 | | | | | | | | | | | | | |
| SEQ ID 29 | 1.96 | 4.029 | 5.452 | 5.99 | 3.158 | 6.095 | | 8.336 | 5.325 | 8.052 | 8.239 | 7.297 | 1.287 | | |
| SEQ ID 33 variants | 19.297 | 31.263 | 80.444 | 78.98 | 81.413 | 80.485 | | 11.631 | 8.336 | 33.988 | 7.231 | 78.052 | 78.053 | W77 | M |
| | 12.311 | 9.132 | 58.305 | 54.251 | 80.485 | 73.498 | | 3.792 | 5.85 | 9.389 | 10.658 | 5.074 | 10.509 | Y115 | W |
| | | | | 16.578 | | | | 18.698 | 41.68 | | | | | S172 | T |
| | 12.907 | 36.799 | 50.37 | 59.762 | 68.277 | 72.358 | | 14.242 | 15.601 | 17.526 | 23.618 | 74.852 | 78.018 | S172 | C |

Fig. 8H

| | 10uM | 10uM | 100uM | 100uM | 3mM | 3mM | | 100nM | 100nM | 300nM | 300nM | 30uM | 30uM | Amino acid | Mutation |
|---|---|---|---|---|---|---|---|---|---|---|---|---|---|---|---|
| SEQ ID 33 | 13.204 | 23.203 | | | | | | | | | | | | | |
| SEQ ID 29 | 8.106 | 4.64 | 5.99 | | 6.095 | 8.164 | | 7.931 | | 9.05 | | 8.169 | | | |
| SEQ ID 33 variants | 7.135 | 5.087 | 7.860 | | 63.506 | 88.692 | | 44.726 | 42.897 | 33.073 | | | | L131 | S |
| | 9.893 | 0.435 | 22.528 | 3.972 | 45.363 | 51.016 | | 13.983 | 17.766 | 44.576 | 69.607 | | | L131 | T |
| | 6.046 | 7.12 | 16.578 | | 80.094 | 79.579 | | 64.243 | 57.154 | 6.479 | 52.577 | 80.1 | | L131 | D |
| | 1.864 | 0.236 | 4.693 | 3.597 | 80.257 | 80.672 | | 68.726 | 66.241 | | | | | S172 | D |

Fig. 8I

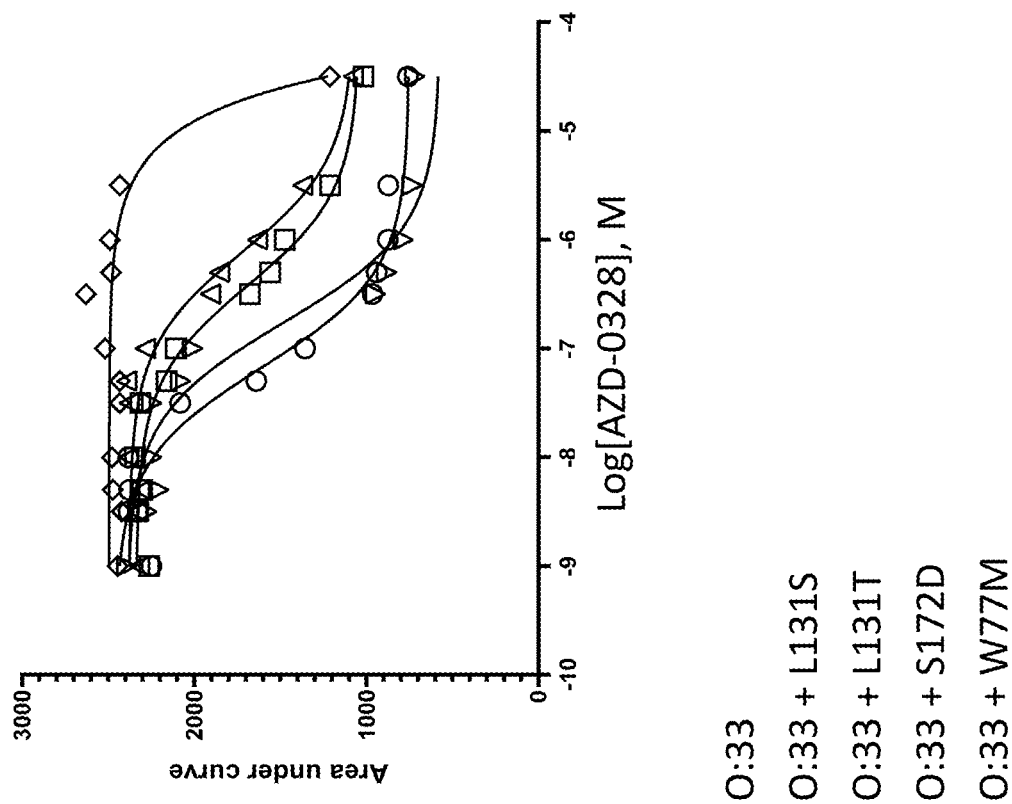
*Fig. 9A*
*Fig. 9B*
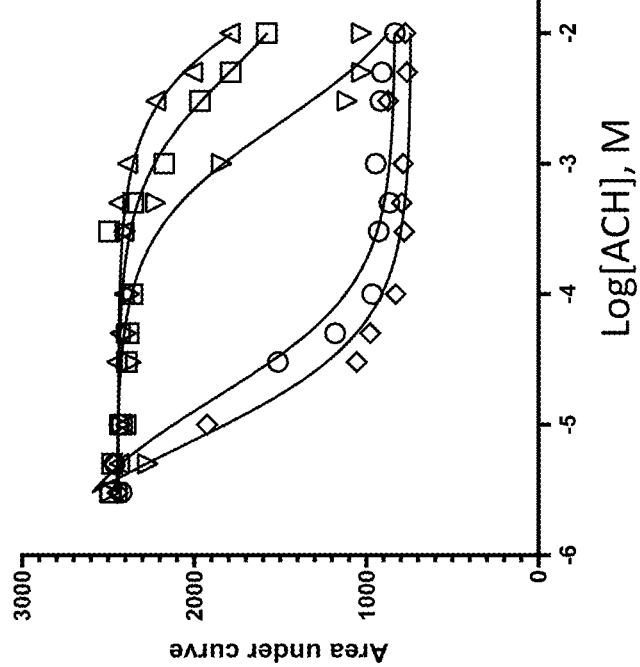

COMPOSITIONS AND METHODS FOR NEUROLOGICAL DISEASES

CROSS REFERENCE TO RELATED APPLICATIONS

Pursuant to 35 U.S.C. § 119 (e), this application claims priority to the filing date of the U.S. Provisional Patent Application Ser. No. 62/590,911 filed Nov. 27, 2017 and of the U.S. Provisional Patent Application Ser. No. 62/659,911, filed Apr. 19, 2018; the full disclosures of which are herein incorporated by reference.

DESCRIPTION OF THE TEXT FILE SUBMITTED ELECTRONICALLY

The sequence listing associated with this application is provided in text format in lieu of a paper copy, and is hereby incorporated by reference into the specification. The name of the text file containing the sequence listing is SWCH-012_04US_ST25.txt. The text file is 178 kb, was created on Nov. 27, 2018, and is being submitted electronically via EFS-Web.

FIELD

This disclosure pertains to engineered receptors and the use of engineered receptors and small molecule ligands to modulate the activity of cells and treat disease.

BACKGROUND

Intractable neurological disease is often associated with aberrantly acting neurons. Attempts to develop therapies to treat these conditions have been hampered by a lack of tractable target proteins associated with the disease. For example, unrelieved chronic pain is a critical health problem in the US and worldwide. A report by the Institute of Medicine estimated that 116 million Americans suffer from pain that persists for weeks to years, with resulting annual costs exceeding $560 million. There are no adequate long-term therapies for chronic pain sufferers, leading to significant cost for both society and the individual. Pain often results in disability and, even when not disabling, it has a profound effect on the quality of life. Pain treatment frequently fails even when the circumstances of care delivery are optimal, such as attentive, well-trained physicians; ready access to opioids; use of adjuvant analgesics; availability of patient-controlled analgesia; and evidence-based use of procedures like nerve blocks and IT pumps.

The most commonly used therapy for chronic pain is the application of opioid analgesics and nonsteroidal anti-inflammatory drugs, but these drugs can lead to addiction and may cause side effects, such as drug dependence, tolerance, respiratory depression, sedation, cognitive failure, hallucinations, and other systemic side effects. Despite the wide usage of pharmaceuticals, there is a strikingly low success rate for its effectiveness in pain relief. A large randomized study with various medications found only one out of every two or three patients achieving at least 50% pain relief (Finnerup et al., 2005). A follow-up study using the most developed pharmacological treatments found the same results, indicating that there was no improvement in the efficacy of medications for pain (Finnerup et al., Pain, 150(3):573-81, 2010).

More invasive options for the treatment of pain include nerve blocks and electrical stimulation. A nerve block is a local anesthetic injection usually in the spinal cord to interrupt pain signals to the brain, the effect of which only lasts from weeks to months. Nerve blocks are not the recommended treatment option in most cases (Mailis and Taenzer, Pain Res Manag. 17(3):150-158, 2012). Electrical stimulation involves providing electric currents to block pain signals. Although the effect may last longer than a nerve block, complications arise with the electrical leads itself: dislocation, infection, breakage, or the battery dying. One review found that 40% of patients treated with electrical stimulation for neuropathy experienced one or more of these issues with the device (Wolter, 2014).

The most invasive, and least preferred, method for managing pain is complete surgical removal of the nerve or section thereof that is causing the pain. This option is only recommended when the patient has exhausted the former and other less invasive, treatments and found them ineffective. Radiofrequency nerve ablation uses heat to destroy problematic nerves and provides a longer pain relief than a nerve block. However, one study found no difference between the control and treatment groups in partial radiofrequency lesioning of the DRG for chronic lumbosacral radicular pain (Geurts et al., 2003). Other surgical methods for surgically removing the pain nerves suffer from similar shortcomings and have serious side effects long-term, including sensory or motor deficits, or cause pain elsewhere.

Methods for treating neurological disorders should be safe, efficient and cost-effective. Gene therapy could provide non-invasive treatment options for a variety of neurological diseases, including managing pain. However, to date, gene therapy methods have not found widespread use in the treatment of neurological diseases. The present disclosure addresses these needs.

BRIEF DESCRIPTION OF THE DRAWINGS

The disclosure is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures:

FIG. 2 shows a schematic of a protocol for development and characterization of engineered LGIC receptors and mutants thereof of the present disclosure.

FIG. 4A shows results with wild type alpha-7 nAChR. FIG. 4B shows results with SEQ ID NO:16. FIG. 4C shows results with SEQ ID NO:35. FIG. 4D shows results with SEQ ID NO:33. FIG. 4E shows results with SEQ ID NO:41. FIG. 4F shows results with SEQ ID NO:37. Solid boxes: protein sequence from the human wild type α7-nAChR. Striped boxes: protein sequence from the human alpha1 glycine receptor. Doses are shown above each recording, scale bars=1 s. Currents in FIG. 4A were measured in single cell mode, where traces represent conductance from 1 cell per recording. Currents in FIG. 4B-FIG. 4F were measured in ensemble mode, where traces represent summation of conductances from up to 20 cells sampled per recording, with recordings that passed QC in grey and the composite median trace shown in black.

FIG. 5A-FIG. 5B shows the response profile of wild type α7-nAChR to acetylcholine, nicotine, and ABT-126 (FIG. 5A) and TC-6987, AZD-0328, and Facinicline/RG3487 (FIG. 5B). FIG. 5C-FIG. 5D shows the response profile of SEQ ID NO:33 to acetylcholine, nicotine, and ABT-126 (FIG. 5C) and TC-6987, AZD-0328, and Facinicline/RG3487 (FIG. 5D). FIG. 5E-FIG. 5F shows the response profile of SEQ ID NO:41 to acetylcholine, nicotine, and ABT-126 (FIG. 5E) and TC-6987, AZD-0328, and Facinicline/RG3487 (FIG. 5F). Currents were measured on a manual patch clamp system following 5-10 s applications of increasing doses of compound as listed across the top of each panel. Left panels, Exemplary currents in an oocyte expressing the designated receptor. $EC_{50}$s for each ligand as estimated from concentration-response curves shown on the right are marked with an asterisk, while shifts in $EC_{50}$ relative to wild type α7-nAChR are marked by black arrows. Right panels, Concentration-response curves from the data shown on the left. Currents were normalized to unity for the maximal response. The continuous line through the data points is the best fit obtained with the Hill equation.

FIG. 8A-FIG. 8I provides heat maps of the percent quench of YFP fluorescence in mutants of engineered chimera SEQ ID NO:33 that comprise single amino acid substitutions following stimulation by various doses of either acetylcholine or AZD-0328. FIG. 8A-FIG. 8F show mutants that exhibit a rightward shift in responses (decreased sensitivity) to both acetylcholine and AZD-0328, demonstrating an overlap in the amino acids critical for binding and activation by both compounds. FIG. 8G shows mutants that exhibit a leftward shift in response to acetylcholine but a rightward shift in response to AZD-0328, demonstrating the ability of a single mutation to decouple responses to ligand. FIG. 8H shows mutants that exhibit a far rightward shift to acetylcholine as compared to the parental chimera but no significant change in response to AZD-0328, demonstrating the ability of a single mutation to significantly reduce activation by acetylcholine without affecting activation by other ligands. FIG. 8I shows mutants that exhibit a strong leftward shift of response (increased sensitivity) to both acetylcholine and AZD-0328. Ligand doses are written across the top of each chart (n=2 for each dose). Numbers in the boxes indicate the absolute amount of quench observed. Dark blue=80% maximal quench of YFP reporter. Light blue=quench of 30-80%. White=10-30%. Orange=0-10% quench. Negative values represent non-responders that have a negative quench due to a stimulation artifact. SEQ ID NO:29 is a non-responding chimera used as a negative control.

FIG. 9A-FIG. 9B provide dose response curves of select mutants of engineered chimera SEQ ID NO:33 to acetylcholine and AZD-0328. FIG. 9A show responses of mutants comprising substitutions L131S (open square), L131T (open up triangle), and S172D (open down triangle) and demonstrate a far rightward shift (i.e., 2 log (100 fold) increase in $EC_{50}$) in the dose response curve for acetylcholine compared to that of unmutated SEQ ID NO:33 (open circles). In contrast, a W77M substitution (open diamond) exhibits no shift in the dose response to acetylcholine. FIG. 9B show responses of mutants comprising substitutions at L131S (open square), L131T (open up triangle), and S172D (open down triangle), and result in a slight rightward shift (i.e., 1 log increase in $EC_{50}$) in dose response to AZD-0328 as compared to the unmutated SEQ ID NO:33 chimera, while a W77M substitution produces a dramatic rightward shift (>2 log increase in $EC_{50}$) in the dose response.

FIG. 10A shows substitution of L131S causes a significant right-ward shift (80-fold) in the $EC_{50}$ of acetylcholine relative to parental chimera SEQ ID NO:33 (see FIG. 4E), while the $EC_{50}$ for AZD-0328 is only (2-fold) right-ward shifted. FIG. 10B shows substitution of S172D causes a significant rightward shift (58-fold) in the $EC_{50}$ of acetylcholine relative to the parental chimera, while the $EC_{50}$ for AZD-0328 on S172D is only (2-fold) right-ward shifted. FIG. 10C shows substitution of W77M causes a moderate leftward shift (2-fold) in the $EC_{50}$ of acetylcholine relative to the parental chimera, while the $EC_{50}$ for AZD-0328 on W77M is significantly rightward shifted (>2.5 log). FIG. 10D shows substitution of L131T causes a significant rightward shift (~2.5 log) in the $EC_{50}$ of acetylcholine relative to the parental chimera, while the $EC_{50}$ for AZD-0328 on this mutant shows a moderate rightward shift (~1 log). Asterisks mark estimated $EC_{50}$ for each ligand on L131S. Arrow shows degree of shift in $EC_{50}$ relative to SEQ ID NO:33. Triangles mark estimated $EC_{50}$ for each ligand on the wild type α7-nAChR.

BRIEF SUMMARY

Figure 1:
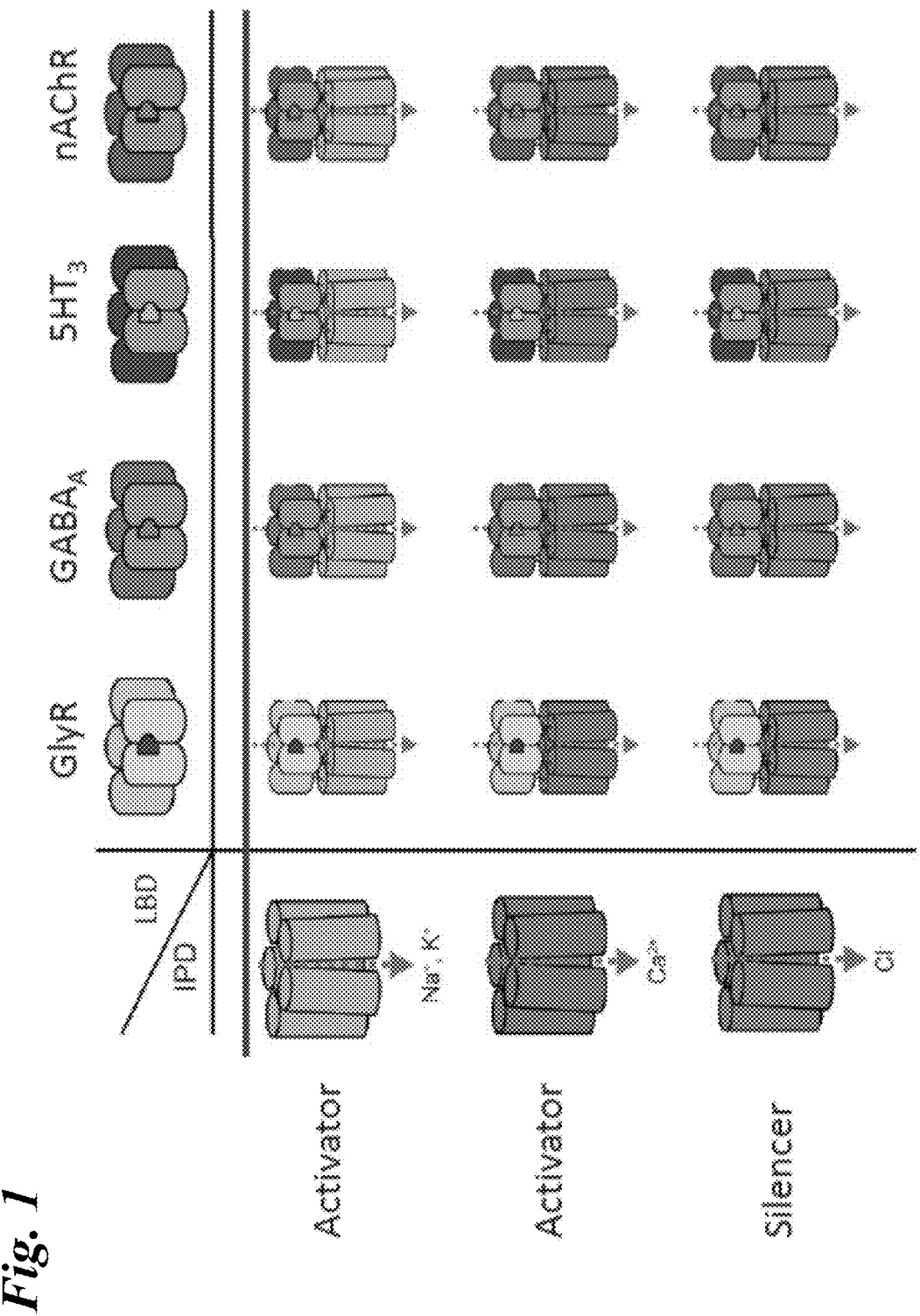
FIG. 1 shows schematics of exemplary engineered chimeric LGIC receptors.

Compositions and methods are provided for modulating the activity of cells using engineered receptors, polynucleotide encoded engineered receptors, and gene therapy vectors comprising polynucleotides encoding engineered receptors. These compositions and methods find particular use in modulating the activity of neurons, for example in the treatment of disease or in the study of neuronal circuits.

In some aspects of the present disclosure, the disclosure is directed to an engineered receptor, wherein the engineered receptor is a chimeric ligand gated ion channel (LGIC) receptor and comprises a ligand binding domain derived from a first wild type Cys-loop LGIC receptor, a Cys-loop domain from a second wild-type Cys-loop LGIC receptor; and an ion pore domain derived from the second wild type Cys-loop LGIC receptor. In some embodiments, the first and the second wild type Cys-loop LGIC receptor are the same. In other embodiments, the first and the second wild type Cys-loop LGIC receptor are different. In some embodiments, the first wild type Cys-loop LGIC receptor is selected from an acetylcholine receptor (AchR), e.g. α7-nAChR; a Glycine receptor, (GlyR), e.g. GlyRα1; a λ-aminobutyric acid (GABA) receptor; and a serotonin receptor, e.g. 5HT3. In some embodiments, the second wild type Cys-loop LGIC receptor is selected from an acetylcholine receptor (AchR), e.g. α7-nAChR; a Glycine receptor, (GlyR), e.g. GlyRα1; a λ-aminobutyric acid (GABA) receptor; and a serotonin receptor, e.g. 5HT3. In certain embodiments, the first wild type Cys-loop LGIC receptor is α7-nAChR. In certain embodiments, the second wild type Cys-loop LGIC receptor is GlyRα1. In some such embodiments, the Cys-loop domain comprises amino acids 166-180 of GlyRα1. In other such embodiments, the Cys-loop domain comprises amino acids 166-172 of GlyRα1. In some such embodiments, the engineered receptor has a sequence identity of 85% or more to SEQ ID NO:33. In some embodiments, the receptor further comprises a β1-2 loop domain from the second wild type Cys-loop LGIC receptor. In some such embodiments, the β1-2 loop domain comprises amino acids 81-84 of GlyRα1. In some such embodiments, the engineered receptor has a sequence identity of 85% or more to SEQ ID NO:41.

In some embodiments, the ligand binding domain comprises one or more amino acid substitutions at a residue corresponding to a residue of α7-nAChR selected from the group consisting of W77, Y94, R101, W108, Y115, T128, N129, V130, L131, Q139, L141, Y151, S170, W171, S172, S188, Y190, Y210, C212, C213 and Y217. In some embodiments, the one or more amino acid substitutions is a loss of function mutation that decreases the potency of acetylcholine on the receptor while substantially maintaining the potency of a non-native ligand on the receptor. In certain such embodiments, the substitution is selected from a substitution corresponding to L131S, L131T, L131D, or S172D of α7-nAChR. In certain such embodiments, the non-native ligand is selected from AZD-0328, TC6987, ABT-126 and Facinicline/RG3487. In other embodiments, the one or more amino acid substitutions is a gain of function mutation that increases the potency of acetylcholine on the receptor. In certain such embodiments, the substitution is selected from a substitution corresponding to L131N, L141W, S170G, S170A, S170L, S170I, S170V, S170P, S170F, S170M, S170T, S170C, S172T, S172C, S188I, S188V, S188F, S188M, S188Q, S188T, S188P, or S188W of α7-nAChR.

In some aspects of the present disclosure, the disclosure is directed to a polynucleotide encoding an engineered receptor as described herein. In some aspects of the disclosure, the present disclosure is directed to a vector comprising a polynucleotide encoding an engineered receptor as described herein. In some aspects of the disclosure, the present disclosure is directed to a pharmaceutical composition comprising a polynucleotide encoding an engineered receptor as described herein or a vector comprising the polynucleotide encoding an engineered receptor as described herein and a pharmaceutically acceptable vehicle.

In some aspects of the present disclosure, the disclosure is directed to an engineered receptor, wherein the engineered receptor is a ligand gated ion channel (LGIC) receptor and comprises (a) a ligand binding domain derived from a first wild type LGIC receptor, wherein the ligand binding domain comprises at least one amino acid mutation that changes the function of the ligand binding domain relative to the wild type receptor; and (b) an ion pore domain derived from a second wild type LGIC receptor. In some embodiments, at least one amino acid mutation is a loss of function mutation. In some embodiments, the at least one amino acid mutation is a gain of function mutation. In some embodiments, the at least one amino acid mutation is both a loss of function and a gain of function mutation, i.e. the mutation that provides for the loss of function and gain of function are the same mutation. In other embodiments, the at least one loss-of-function amino acid mutation and the at least one gain-of-function amino acid mutation are mutations at different amino acid residues of the ligand binding domain. In some embodiments, the first and the second wild type LGIC receptor are the same. In some embodiments, the first and the second wild type LGIC receptor are different. In some embodiments, the first and/or second LGIC receptor is a Cys-loop receptor LGIC. In some such embodiments, the first and/or second wild type LGIC receptor is selected from the group consisting of a glycine receptor (GlyR), a λ-aminobutyric acid (GABA) receptor, a serotonin receptor, and an acetylcholine receptor (AchR). In some embodiments, the first and/or second LGIC receptor is selected from an ATP-gated cation channel receptor, an inwardly rectifying potassium channel receptor (Kir), a potassium voltage-gated channel receptor, and an ATP-binding cassette transporter receptor.

In some embodiments, the first and/or second LGIC receptor is a $GABA_A$ receptor. In some embodiments, the first and/or second LGIC receptor is a 5 hydroxytryptamine (5-$HT_3$) receptor. In some embodiments, the first and/or second LGIC receptor is a nicotinic AchR (nAchR). In some embodiments, the first and/or second LGIC receptor is a P2X receptor. In some embodiments, the first and/or second LGIC receptor is a KCNQ or $K_v7$ receptor. In some embodiments, the first and/or second LGIC receptor is a cystic fibrosis transmembrane conductance regulator (CFTR) receptor.

In some embodiments, the engineered receptors of the present disclosure are homomeric receptors. In some embodiments, the engineered receptors are heteromeric receptors.

In some embodiments, the engineered receptors of the present disclosure comprise a ligand binding domain that is less than 99%, 98%, 97%, 95%, or less than 90% homologous to a native, or wild type, ligand binding domain. In some embodiments, the engineered receptors of the present disclosure comprise a ligand binding domain sharing a sequence identity of 85% or more to a wild type ligand binding domain. In some embodiments, the engineered receptors of the present disclosure comprise a ligand binding domain sharing a sequence identity of 90% or more to a wild type, ligand binding domain. In some embodiments, the engineered receptors of the present disclosure comprise a ligand binding domain sharing a sequence identity of 95% or more to a wild type, ligand binding domain. In some embodiments, the engineered receptors of the present disclosure comprise one or more amino acid mutations introduced into the ligand binding domain. In some embodiments, the one or more amino acid mutations are introduced into the ligand binding domain by an error prone polymerase chain reaction (PCR). In some embodiments, the one or more amino acid mutations are introduced into the ligand binding domain by site directed mutagenesis. In some embodiments, the one or more amino acid mutations are introduced into the ligand binding domain by de novo gene synthesis.

In some embodiments, the engineered receptors of the present disclosure comprise at least one loss-of-function amino acid mutation that inhibits the binding of an endogenous ligand to the engineered receptor or decreases the binding affinity of the endogenous ligand for the engineered receptor. In some embodiments, the engineered receptors of the present disclosure comprise at least one gain-of-function amino acid mutation that increases the binding affinity of a binding agent for the engineered receptor or modulates an effect of the binding agent on the engineered receptor.

In some embodiments, the at least one gain-of function amino acid mutations increases the affinity of the engineered receptor for an agonist ligand compared to the affinity of the wild type receptor for the agonist ligand. In some embodiments, the agonist ligand is selected from the group consisting of ABT-089, ABT-126, ABT-418, ABT-894, Alfadolone, AQW-051, AZD0328, AZD7325, Basmisanil, Bilobalide, Cannabidiol, Cilansetron, CP-409092, DDP733, EVP-6124, GTS-21, Iptakalim, MK-0777/L83098, MDL-27531, MEM-3454/RG3487, MEM-63908, Moxidectin, NRX-1050, NRX-1060, P-9939, PH-399733, QH-ii-066, Rapastinel, Renzapride, Retigabine, S-18841, SL-75102, SL-651498, SR-57227, SSR-180711, and TC-5619/AT-101. In certain embodiments, the ligand is selected from the group consisting of AZD0328, ABT-126, AQW-051, Cannabidiol, Cilansetron, PH-399733, FACINICLINE/RG3487/MEM-3454, and TC-5619/AT-101.

In some embodiments, the at least one gain-of-function mutations results in an antagonist ligand functioning as an agonist ligand. In some embodiments, the antagonist ligand is selected from the group consisting of 468816, ACEA-2085, DA-9701, Eslicarbazepine acetate, Gavestinel, GV-196771, GW-468816, HMR-2371, L-695902, L-701324, MDL-100748, MDL-102288, MDL-105519, PD-165650, Tedatioxetine, UK-315716, and ZD-9379.

In some embodiments, the at least one gain of function amino acid mutations results in a modulator ligand functioning as an agonist ligand. In some embodiments, the modulator ligand is selected from the group consisting of AQW-051, AZD7325, CTP-656, Gavestinel, and Ivermectin.

In some embodiments, the engineered receptors of the present disclosure comprise a ligand binding domain derived from a GlyR. In some embodiments, the engineered receptors of the present disclosure comprise a ligand binding domain derived from a GABA receptor. In some embodiments, the engineered receptors of the present disclosure comprise a ligand binding domain is derived from an nAChR. In some embodiments, the engineered receptors of the present disclosure comprise a ligand binding domain that is derived from a 5HT$_3$. In some embodiments, the engineered receptors of the present disclosure comprise a ligand binding domain that is derived from a P2X receptor. In some embodiments, the engineered receptors of the present disclosure comprise a ligand binding domain that is derived from a Kir receptor. In some embodiments, the engineered receptors of the present disclosure comprise a ligand binding domain that is derived from a KCNQ receptor. In some embodiments, the engineered receptors of the present disclosure comprise a ligand binding domain that is derived from a CFTR receptor.

In some embodiments, the engineered receptors of the present disclosure comprise an ion pore domain derived from a GlyR. In some embodiments, the engineered receptors of the present disclosure comprise an ion pore domain derived from a GABA receptor. In some embodiments, the engineered receptors of the present disclosure comprise an ion pore domain derived from a nAChR. In some embodiments, the engineered receptors of the present disclosure comprise an ion pore domain derived from a 5HT$_3$ receptor. In some embodiments, the engineered receptors of the present disclosure comprise an ion pore domain derived from a P2X receptor. In some embodiments, the engineered receptors of the present disclosure comprise an ion pore domain derived from a Kir receptor. In some embodiments, the engineered receptors of the present disclosure comprise an ion pore domain derived from a KCNQ receptor. In some embodiments, the engineered receptors of the present disclosure comprise an ion pore domain derived from a CFTR receptor. In some embodiments, the ion pore domain comprises a non-desensitizing mutation.

In some embodiments, the present disclosure comprises a polynucleotide encoding an engineered receptor described herein. In some embodiments, the present disclosure comprises a viral vector comprising a polynucleotide encoding an engineered receptor described herein. In some embodiments, the viral vector is an adenoviral vector, a retroviral vector, an adeno-associated viral (AAV) vector, or a herpes simplex-1 viral vector (HSV-1). In some embodiments, the AAV vectors is selected from the group consisting of AAV1, AAV2, AAV3b, AAV4, AAV5, AAV6, AAV7, AAV8, AAV9, and AAVrh10. In some embodiments, the AAV vector is selected from AAV5, AAV6, and AAV9. In some embodiments, the vector is derived from a vector selected from the group consisting of AAV1, AAV2, AAV3b, AAV4, AAV5, AAV6, AAV7, AAV8, AAV9, and AAVrh10. In some embodiments, the AAV vector is derived from AAV-5, AAV-6 or AAV-9.

In some aspects of the present disclosure, a method is provided of treating a neurological disorder in a subject in need thereof comprising administering to said subject a polynucleotide encoding an engineered ligand-gated ion channel (LGIC) receptor, and administering to said subject a binding agent, wherein said binding agent acts as an agonist of the engineered LGIC receptor. In some embodiments, the polynucleotide delivered to the subject by a non-viral method. In some embodiments, the non-viral method is lipofection, nanoparticle delivery, particle bombardment, electroporation, sonication, or microinjection. In some embodiments, the polynucleotide is delivered to the subject in a viral vector. In some embodiments, the viral vector is an adenoviral vector, a retroviral vector, an adeno-associated viral (AAV) vector, or a herpes simplex-1 viral vector (HSV-1). In some embodiments, the AAV vectors is selected from the group consisting of AAV1, AAV2, AAV3b, AAV4, AAV5, AAV6, AAV7, AAV8, AAV9, AAVrh10. In some embodiments, the AAV vector is selected from AAV5, AAV6, and AAV9. In some embodiments, the vector is derived from a vector selected from the group consisting of AAV1, AAV2, AAV3b, AAV4, AAV5, AAV6, AAV7, AAV8, AAV9, and AAVrh10. In some embodiments, the AAV vector is derived from AAV-5, AAV-6 or AAV-9.

In some embodiments, the method comprises expressing the engineered receptor in an excitable cell. In some embodiments, the excitable cell is a neuron or a myocyte. In some embodiments, the neuron is a dorsal root ganglion, a motor neuron, an excitatory neuron, an inhibitory neuron, or a sensory neuron.

In some embodiments, the subject suffers from pain. In some embodiments, the subject suffers from a seizure disorder. In some embodiments, the subject suffers from a movement disorder. In some embodiments, the subject suffers from an eating disorder. In some embodiments, the subject suffers from a spinal cord injury. In some embodiments, the subject suffers from neurogenic bladder. In some embodiments, the subject suffers from a spasticity disorder. In some embodiments, the subject suffers from pruritus. In some embodiments, the subject suffers from Alzheimer's disease, Parkinson's disease, post-traumatic stress disorder (PTSD), gastroesophageal reflux disease (GERD), addiction, anxiety, depression, memory loss, dementia, sleep apnea, stroke, narcolepsy, urinary incontinence, essential tremor, movement disorder, or atrial fibrillation. In some embodiments, the method further comprises measuring the symptoms of the diseases after administration of the binding agent, wherein the symptoms of the diseases are reduced. In some embodiments the subject is a human.

In some embodiments, the binding agent is selected from the group consisting of 468816, ABT-089, ABT-126, ABT-418, ABT-894, ACEA-2085, Alfadolone, AQW-051, AZD0328, AZD7325, Basmisanil, Bilobalide, Cannabidiol, Cilansetron, CP-409092, CTP-656, DA-9701, DDP733, Eslicarbazepine Acetate, EVP-6124, Gavestinel, Gavestinel, GTS-21, GV-196771, GW-468816, HMR-2371, Iptakalim, L-695902, L-701324, MK-0777/L83098, MDL-100748, MDL-102288, MDL-105519, MDL-27531, MEM-3454/RG3487, MEM-63908, Moxidectin, NRX-1050, NRX-1060, P-9939, PD-165650, PH-399733, QH-ii-066, Rapastinel, Retigabine, S-18841, SL-75102, SL-651,498, SR-57227, SSR-180,711, TC-5619/AT-101, Tedatioxetine, UK-315716, and ZD-9379. In certain embodiments, the ligand is selected from the group consisting of AZD0328, ABT-126, AQW-051, Cannabidiol, Cilansetron, PH-399733, FACINICLINE/RG3487/MEM-3454, and TC-5619/AT-101. In some embodiments, the polynucleotide and/or the binding agent are administered subcutaneously, orally, intrathecally, topically, intravenously, intraganglionically, intracranially, intraspinally, cisterna magna, or intraneurally. In some embodiments of this method, the binding agent is administered at least one week after the polynucleotide.

In some embodiments, the present disclosure comprises a composition comprising an engineered receptor described herein, a polynucleotide described herein, or a viral vector described herein.

DETAILED DESCRIPTION

A. Overview

Compositions and methods are provided for modulating the activity of cells using engineered ligand gated ion channel (LGIC) receptors, polynucleotide encoded engineered LGIC receptors, and gene therapy vectors comprising polynucleotides encoding engineered LGIC receptors. These compositions and methods find particular use in modulating the activity of neurons, for example in the treatment of disease or in the study of neuronal circuits. In addition, reagents, devices and kits thereof that find use in practicing the subject methods are provided.

In particular, the present disclosure provides engineered receptors that bind to and signal in response to known drugs, ligands, and/or binding agents. In some embodiments, the engineered receptors described herein demonstrate increased affinity for a known agonist binding agent. In some embodiments, the engineered receptors described herein demonstrate an affinity for an antagonist or modulator binding agent and respond to the antagonist and/or modulator agents as if they were agonist agents. The present disclosure further provides for methods of treating neurological diseases in subjects in need thereof. The present disclosure increases the number of clinical indications that a known drug may be used for by utilizing engineered receptors that respond to a known drug in a manner that is distinct from the wild-type endogenous receptor.

Before the present methods and compositions are described, it is to be understood that this disclosure is not limited to particular method or composition described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

B. Definitions

As used in this specification and the appended claims, the singular forms "a," "an" and "the" include plural references unless the content clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

As used in this specification, the term "and/or" is used in this disclosure to either "and" or "or" unless indicated otherwise.

Throughout this specification, unless the context requires otherwise, the word "comprise", or variations such as "comprises" or "comprising" refers to the inclusion of a stated element or integer or group of elements or integers but not the exclusion of any other element or integer or group of elements or integers. Further, the statement of numerical ranges throughout this specification specifically includes all integers and decimal points in between.

Throughout this specification, unless the context requires otherwise, the phrase "consisting essentially of" refers to a limitation of the scope of composition, method, or kit described to the specified materials or steps that do not materially affect the basic and novel characteristic(s) of the subject disclosure. For example, a ligand binding domain "consisting essentially of" a disclosed sequence has the amino acid sequence of the disclosed sequence plus or minus about 5 amino acid residues at the boundaries of the sequence, e.g. about 5 residues, 4 residues, 3 residues, 2 residues or about 1 residue less than the recited bounding amino acid residue, or about 1 residue, 2 residues, 3 residues, 4 residues, or 5 residues more than the recited bounding amino acid residue.

Throughout this specification, unless the context requires otherwise, the phrase "consisting of" refers to the exclusion from the composition, method, or kit of any element, step, or ingredient not specified in the claim. For example, a ligand binding domain "consisting of" a disclosed sequence consists only of the disclosed amino acid sequence.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "isolated" means material that is substantially or essentially free from components that normally accompany is as found in its native state. In some embodiments, the terms "obtained" or "derived" are used synonymously with isolated.

The terms "subject," "patient," and "individual" are used interchangeably herein to refer to any animal that exhibits pain that can be treated with the vectors, compositions, and methods contemplated herein. In some embodiments, a subject may refer to a vertebrate, preferably a mammal. Mammals include, but are not limited to, murines, simians, humans, farm animals, sport animals, and pets. Suitable subjects (e.g., patients) include laboratory animals (such as mouse, rat, rabbit, or guinea pig), farm animals, and domestic animals or pets (such as a cat or dog). Non-human primates and, preferably, human patients, are included. In some embodiments, a "sample" may be taken from a subject.

The term "sample" refers to a volume and/or mass of biological material that is subjected to analysis. In some embodiments, a sample comprises a tissue sample, cell sample, a fluid sample, and the like. In some embodiments, a sample is taken from or provided by a subject (e.g., a human subject). In some embodiments, a sample comprises a portion of tissue taken from any internal organ, a cancerous, pre-cancerous, or non-cancerous tumor, brain, skin, hair (including roots), eye, muscle, bone marrow, cartilage, white adipose tissue, and/or brown adipose tissue. In some embodiments, a fluid sample comprises buccal swabs, blood, cord blood, saliva, semen, urine, ascites fluid, pleural fluid, spinal fluid, pulmonary lavage, tears, sweat, and the like. Those of ordinary skill in the art will appreciate that, in some embodiments, a "sample" is a "primary sample" in that it is obtained directly from a source (e.g., a subject). In some embodiments, a "sample" is the result of processing of a primary sample, for example to remove certain potentially contaminating components, to isolate certain components, and/or to purify certain components of interest. In some embodiments, a sample is a cell or population of cells (e.g., a neuronal cell). A cell sample may be derived directly from a subject (e.g., a primary sample) or may be a cell line. Cell lines may include non-mammalian cells (e.g., insect cells, yeast cells, and/or bacterial cells) or mammalian cells (e.g., immortalized cell lines).

"Treating" or "treatment" as used herein refers to delivering a composition (e.g., an engineered receptor and/or a binding agent) to a subject and/or population of cells to affect a physiologic outcome. In particular embodiments, treatment results in an improvement (e.g., reduction, amelioration, or remediation) of one or more disease symptoms. The improvement may be an observable or measurable improvement, or may be an improvement in the general feeling of well-being of the subject. Treatment of a disease can refer to a reduction in the severity of disease symptoms. In some embodiments, treatment can refer to a reduction in the severity of disease symptoms to levels comparable to those prior to disease onset. In some embodiments, treatment may refer to a short-term (e.g., temporary or acute) and/or a long-term (e.g., sustained or chronic) reduction in disease symptoms. In some embodiments, treatment may refer to a remission of disease symptoms. In some embodiments, treatment may refer to the prophylactic treatment of a subject at risk of developing a particular disease in order to prevent disease development. Prevention of disease development can refer to complete prevention of the disease symptoms, a delay in disease onset, a lessening of the severity of the symptoms in a subsequently developed disease, or reducing the likelihood of disease development.

As used herein, "management" or "controlling" refers to the use of the compositions or methods contemplated herein, to improve the quality of life for an individual suffering from a particular disease. In certain embodiments, the compositions and methods described herein provide analgesia to a subject suffering from pain.

A "therapeutically effective amount" is an amount of a composition required to achieve a desired therapeutic outcome. The therapeutically effective amount may vary according to factors such as, but not limited to, disease state and age, sex, and weight of the subject. Generally, a therapeutically effective amount is also one in which any toxic or detrimental effects of a composition are outweighed by the therapeutically beneficial effects. A "therapeutically effective amount" includes an amount of a composition that is effective to treat a subject. A "prophylactically effective amount" refers to an amount of a composition required to achieve a desired prophylactic result. In some embodiments, the prophylactically effective amount may be less than the therapeutically effective amount, as a prophylactic dose is used in subjects prior to or at an earlier stage of disease.

An "increase" refers to an increase in a value (e.g., increased binding affinity, increased physiologic response, increased therapeutic effect, etc.) of at least 5% as compared to a reference or control level. For example, an increase may include a 5, 6, 7, 8, 9, 10, 15, 20, 25, 30, 35, 40, 45, 50, 60, 70, 80, 90, 100, 150, 200, 250, 500, 1000% or more increase. Increase also means an increase that is 1.1, 1.2, 1.5, 2, 3, 4, 5, 6, 7, 8, 9, 10, 15, 20, 30 or more times (e.g., 500, 1000 times) higher than a reference or control level.

A "decrease" refers to a decrease in a value (e.g., decreased binding affinity, decreased physiologic response, decreased therapeutic effect, etc.) of at least 5% as compared to a reference or control level. For example, a decrease may include a 5, 6, 7, 8, 9, 10, 15, 20, 25, 30, 35, 40, 45, 50, 60, 70, 80, 90, 100, 150, 200, 250, 500, 1000% or more decrease. Decrease also means a decrease that is 1.1, 1.2, 1.5, 2, 3, 4, 5, 6, 7, 8, 9, 10, 15, 20, 30 or more times (e.g., 500, 1000 times) lower than a reference or control level.

By "maintain," or "preserve," or "maintenance," or "no change," or "no substantial change," or "no substantial decrease" refers generally to a physiologic and/or therapeutic effect that is comparable to an effect caused by either vehicle, or a control molecule/composition. A comparable response is one that is not significantly different or measurable different from the reference response The terms "reference" or "control" level are used interchangeably herein and refer the value of a particular physiologic and/or therapeutic effect in a subject or sample that has not been treated with a composition described herein, or a subject or sample that has been treated with a vehicle control. In some embodiments, a reference level refers to a value of a particular physiologic and/or therapeutic effect that is measure in a subject or sample prior to the administration of a composition described herein (e.g., a baseline level).

"Receptor-ligand binding" and "ligand binding" are used interchangeably herein and refer to the physical interaction between a receptor (e.g., a LGIC) and a ligand. The term "ligand" as used herein may refer to an endogenous or naturally occurring ligand. For example, in some embodiments, a ligand refers to a neurotransmitter (e.g., λ-aminobutyric acid (GABA), acetylcholine, serotonin, and others) and signaling intermediate (e.g., phosphatidylinositol 4,5-bisphosphate ($PIP_2$)), amino acids (e.g., glycine), or nucleotides (e.g., ATP). In some embodiments, a ligand may refer to a non-native, i.e. synthetic or non-naturally occurring, ligand (e.g., a binding agent). For example, in some embodiments, a ligand refers to a small molecule. Ligand binding can be measured by a variety of methods known in the art (e.g., detection of association with a radioactively labeled ligand).

"Binding affinity" generally refers to the strength of the sum total of noncovalent interactions between a single binding site of a receptor and a ligand. Unless indicated otherwise, as used herein, "binding affinity" refers to intrinsic binding affinity which reflects a 1:1 interaction between members of a binding pair (e.g., receptor and ligand). The affinity of a molecule X for its partner Y can generally be represented by the dissociation constant ($K_d$). Affinity can be measured by common methods known in the art, including those described herein.

The terms "specific binding affinity" or "specific binding" are used interchangeably throughout the specification and claims and refer to binding which occurs between a paired species of molecules, e.g., receptor and ligand. When the interaction of the two species produces a non-covalently bound complex, the binding which occurs is typically electrostatic, hydrogen-bonding, or the result of lipophilic interactions. In various embodiments, the specific binding between one or more species is direct. In one embodiment, the affinity of specific binding is about 2 times greater than background binding (non-specific binding), about 5 times greater than background binding, about 10 times greater than background binding, about 20 times greater than background binding, about 50 times greater than background binding, about 100 times greater than background binding, or about 1000 times greater than background binding or more.

"Signaling" refers to the generation of a biochemical or physiological response as a result of ligand binding to a receptor (e.g., as a result of a binding agent binding to an engineered receptor described herein).

The terms "native" and "wildtype" are used interchangeably throughout the specification and claims to refer a composition found in nature.

The terms "non-native", "variant", and "mutant" are used interchangeably throughout the specification and the claims to refer to a mutant of a native, or wild type, composition, for example a variant polypeptide having less than 100% sequence identity with the native, or wild type, sequence.

The term "parental" or "starter" are used interchangeably throughout the specification and claims to refer to an initial composition that is modified, or derivatized, to create an engineered composition having novel properties.

The term "engineered" is used throughout the specification and claims to refer to a non-naturally occurring composition having properties that are distinct from the parental composition from which it was derivatized.

In general, "sequence identity" or "sequence homology" refers to the nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and intervening integer values. Typically, the percent identities between a disclosed sequence and a claimed sequence are at least 80%, at least 85%, at least 90%, at least 95%, or at least 98%.

As used herein, "substantially identical" refers to having a sequence identity that is 85% or more, for example 90% or more, e.g. 95%, 96%, 97%, 98%, 99%, 99.5%, 99.9%, or 100%, wherein the activity of the composition is unaltered by the modifications in the sequence that result in the difference in sequence identity.

C. Engineered Receptors

The present disclosure is directed to engineered receptors, engineered receptor mutants, and methods for their use. The term "receptor" as used herein refers to any protein that is situated on the surface of a cell and that can mediate signaling to and/or from the cell. The term "engineered receptor" is used herein to refer to a receptor that has been experimentally altered such that it is physically and/or functionally distinct from a corresponding parental receptor. In some embodiments, the parental receptor is a wild-type receptor. The term "wild-type receptor" is used herein to refer to a receptor having a polypeptide sequence that is identical to the polypeptide sequence of a protein found in nature. Wild-type receptors include receptors that naturally occur in humans as well as orthologs that naturally occur in other eukaryotes, e.g. protist, fungi, plants or animals, for example yeast, insects, nematodes, sponge, mammals, non-mammalian vertebrates. In other embodiments, the parental receptor is a non-native receptor; that is, it is a receptor that does not occur in nature, for example, a receptor that is engineered from a wild type receptor. For example, a parental receptor may be an engineered receptor comprising one or more subunits from one wild-type receptor with one or more subunits from a second wild-type receptor. The resulting proteins are therefore comprised of subunits from two or more wild-type receptors. Engineered receptors of the present disclosure include, for example, parental receptors, parental receptor mutants, and switch receptors.

In some aspects, an engineered receptor of the present disclosure comprises at least one amino acid mutation relative to the corresponding parental receptor, e.g. one or more mutations in one or more domains of a wild-type receptor. By an "amino acid mutation" it is meant any difference in an amino acid sequence relative to a corresponding parental sequence, e.g. an amino acid substitution, deletion, and/or insertion. In some embodiments, the engineered receptor shares a sequence identity of 99%, 98%, 95%, 90%, 85%, 80%, 70%, 60%, 50%, or less with the corresponding parental receptor. In some embodiments, the parental receptor mutant has a sequence identity of 85% or more with the corresponding parental receptor, e.g. 90% or more or 95% or more, for example, 96%, 97%, 98% or 99% identity with the corresponding parental receptor. In some embodiments, an engineered receptor (e.g., a parental receptor mutant) is generated by error prone PCR.

In some embodiments, the amino acid mutation is a loss-of-function amino acid mutation relative to a corresponding parental receptor. "Loss-of-function" amino acid mutations refer to one or more mutations that reduce, substantially decrease, or abolish the function of the engineered receptor relative to the parental receptor, for example by reducing the binding of an endogenous ligand to an engineered receptor relative to the binding of endogenous ligand to the parental receptor, or by reducing the activity of signaling pathway(s) downstream of the engineered receptor that are typically activated in response to the binding of a binding agent to the corresponding parental receptor.

In some embodiments, the amino acid mutation is a gain-of-function amino acid mutation relative to a corresponding parental receptor. "Gain-of-function" amino acid mutations refer to one or more mutations that modify the function of the engineered receptor relative to the parental receptor, for example by altering or enhancing the affinity of an engineered receptor for a binding agent relative to the binding of endogenous ligand to the parental receptor, or by altering or enhancing the activity of the signaling pathways that are activated in response to the binding of a binding agent to an engineered receptor relative to the binding of the endogenous ligand to the corresponding parental receptor. In some embodiments, a gain-of-function mutation results in an increased affinity of the engineered receptor for a binding agent. In particular embodiments, a gain-of-function mutation results in an increased affinity of the engineered receptor for an agonist binding agent. In some embodiments, a gain-of-function mutation results in an antagonist binding agent acting as an agonist binding agent upon binding to the engineered receptor (e.g., results in the activation of agonist signaling pathways instead of antagonist signaling pathways). In some embodiments, a gain-of-function mutation results in a modulator binding agent acting as an agonist binding agent upon binding to the engineered receptor. In some embodiments, the subject engineered receptor of the present disclosure comprises one or more loss-of-function amino acid mutations and one or more gain-of-function amino acid mutations relative to a corresponding parental receptor.

In some embodiments, the loss of function mutation and the gain of function mutation are at the same residue, i.e. they are the same mutation. In other embodiments, the loss of function mutation and the gain of function mutation are mutations at different amino acid residues. In some embodiments, the subject engineered receptor comprising the loss of function mutation and/or gain of function mutation shares a sequence identity of 99%, 98%, 95%, 90%, 85%, 80%, 70%, 60%, 50%, or less with the corresponding parental receptor, e.g. wild type receptor or non-native receptor. In some embodiments, the subject engineered receptor shares a sequence identity of 85% or more with the corresponding parental receptor, for example 85%, 90%, or 95% or more sequence identity, in some instances 96%, 97%, 98% or more sequence identity, e.g. 99% or 99.5% sequence identity.

In some aspects, engineered receptors of the present disclosure include receptors produced by the combination of one or more amino acid sequences, e.g. subunits, from one wild-type receptor with one or more amino acid sequences, e.g. subunits, from a second wild-type receptor. In other words, the engineered receptor comprises amino acid sequences that are heterologous to one another, where by "heterologous", it is meant not occurring together in nature. Such receptors are referred to herein as "chimeric receptors". In some embodiments, chimeric receptors serve as parental receptors from which an engineered receptor of the present disclosure is generated.

In some embodiments, a parental receptor mutant demonstrates increased affinity for an agonist binding agent. In some embodiments, a ligand or a binding agent that functions as an antagonist or modulator when binding to a wild type receptor functions as an agonist when binding to a parental receptor mutant.

In some embodiments, the engineered receptor is a "ligand-gated ion channel" or LGIC. An LGIC refers to a large group of transmembrane proteins that allow passage of ions upon activation by a specific ligand (e.g., chemical or binding agent). LGIC are composed of at least two domains: a ligand binding domain and a transmembrane ion pore domain. Ligand binding to an LGIC results in activation of the LGIC and opening of the ion pore. Ligand binding causes a drastic change in the permeability of the channel to a specific ion or ions; effectively no ions can pass through the channel when it is inactive or closed but up to $10^7$ ions/second can pass through upon ligand binding. In some embodiments, LGICs respond to extracellular ligands (e.g., neurotransmitters) and facilitate an influx of ions into the cytosol. In some embodiments, LGICs respond to intracellular ligands (e.g., nucleotides such at ATP and signaling intermediates such as $PIP_2$) and facilitate an efflux of ions from the cytosol into the extracellular environment. Importantly, activation of LGIC results in the transport of ions across the cellular membrane (e.g., $Ca^{2+}$, $Na^+$, $K^+$, $Cl^-$, etc.) and does not result in the transport of the ligand itself.

LGIC receptors are comprised of multiple subunits and can be either homomeric receptors or heteromeric receptors. A homomeric receptor is comprised of subunits that are all the same type. A heteromeric receptor is comprised of subunits wherein at least one subunit is different from at least one other subunit comprised within the receptor. For example, the glycine receptor is comprised of 5 subunits of which there are two types: α-subunits, of which there are four isoforms ($\alpha_1$-$\alpha_4$) and β-subunits, of which there is a single known isoform. An exemplary homomeric GlyR is a GlyR comprised of 5 $\alpha_1$-GlyR subunits. Similarly, a homomeric $GABA_A$ receptor may be comprised of $\beta_3$-$GABA_A$ subunits, and an nAchR receptor may be comprised of $\alpha_7$-nAchR subunits. An exemplary heteromeric GlyR may be comprised of one or more α-subunits and one or more of β-subunits (e.g., an $\alpha_1\beta$-GlyR). Subunits of example LGIC receptors are shown in Table 1.

TABLE 1

LGIC Receptors and Subunits

| Receptor | Subunits | Subunit Isoforms |
|---|---|---|
| GlyR | GLRA1 | |
| | GLRA2 | |
| | GLRB | |
| $5HT_3$ | 5-HT3A | |
| | 5-HT3B | |
| | 5-HT3C | |
| | 5-HT3D | |
| | 5-HT3E | |
| nAChR | α | α1 |
| | | α2 |
| | | α3 |
| | | α4 |
| | | α5 |
| | | α6 |
| | | α7 |
| | | α8 |
| | | α9 |
| | | α10 |

TABLE 1-continued

LGIC Receptors and Subunits

| Receptor | Subunits | Subunit Isoforms |
|---|---|---|
| | β | β1 |
| | | β2 |
| | | β3 |
| | | β4 |
| | γ | γ |
| | δ | δ |
| | ε | ε |
| $GABA_A$ | α | α1 |
| | | α2 |
| | | α3 |
| | | α4 |
| | | α5 |
| $GABA_A$ | α | α6 |
| | β | β1 |
| | | β2 |
| | | β3 |
| | γ | γ1 |
| | | γ2 |
| | | γ3 |
| | δ | δ |
| | ε | ε |
| | π | π |
| | ρ | ρ1 |
| | | ρ2 |
| | | ρ3 |
| P2X | P2X1 | |
| | P2X2 | |
| | P2X3 | |
| | P2X4 | |
| | P2X5 | |
| | P2X6 | |
| | P2X7 | |
| KCNQ | α | $K_v\alpha1$ |
| | | $K_v\alpha2$ |
| | | $K_v\alpha3$ |
| | | $K_v\alpha4$ |
| | | $K_v\alpha5$ |
| | | $K_v\alpha6$ |
| | | $K_v\alpha7$ |
| | | $K_v\alpha8$ |
| | | $K_v\alpha9$ |
| | | $K_v\alpha10$ |
| | | $K_v\alpha11$ |
| | | $K_v\alpha12$ |
| | β | $K_v\beta1$ |
| | | $K_v\beta2$ |
| | | $K_v\beta3$ |
| | | minK |
| | | MiRP1 |
| | | MiRP2 |
| | | MiRP3 |
| | | KCNE1-like |
| | | KCNIP1 |
| | | KCNIP2 |
| | | KCNIP3 |
| | | KCNIP4 |

Illustrative examples of families of LGICs suitable for use in particular embodiments include, but are not limited to Cys-loop receptors such as Glycine receptors (GlyR), serotonin receptors (e.g., 5-HT3 receptors), λ-Aminobutyric Acid A (GABA-A) receptors, and Nicotinic acetylcholine receptors (nAchR); as well as Acid-sensing (proton-gated) ion channels (ASICs), Epithelial sodium channels (ENaC), Ionotropic glutamate receptors, IP3 receptor, P2X receptors, the Ryanodine receptor, and Zinc activated channels (ZAC).

Specific non-limiting examples of LGICs that are suitable for use with the methods described herein include: HTR3A; HTR3B; HTR3C; HTR3D; HTR3E; ASIC1; ASIC2; ASIC3; SCNN1A; SCNN1B; SCNN1D; SCNN1G; GABRA1; GABRA2; GABRA3; GABRA4; GABRA5; GABRA6; GABRB1; GABRB2; GABRB3; GABRG1; GABRG2; GABRG3; GABRD; GABRE; GABRQ; GABRP;

GABRR1; GABRR2; GABRR3; GLRA1; GLRA2; GLRA3; GLRA4; GLRB; GRIA1; GRIA2; GRIA3; GRIA4; GRID1; GRID2; GRIK1; GRIK2; GRIK3; GRIK4; GRIK5; GRIN1; GRIN2A; GRIN2B; GRIN2C; GRIN2D; GRIN3A; GRIN3B; ITPR1; ITPR2; ITPR3; CHRNA1; CHRNA2; CHRNA3; CHRNA4; CHRNA5; CHRNA6; CHRNA7; CHRNA9; CHRNA10; CHRNB1; CHRNB2; CHRNB3; CHRNB4; CHRNG; CHRND; CHRNE; P2RX1; P2RX2; P2RX3; P2RX4; P2RX5; P2RX6; P2RX7; RYR1; RYR2; RYR3; and ZACN.

TRPV1, TRPM8 and P2X$_2$ are members of large LGIC families that share structural features as well as gating principles. For example TRPV4, similar to TRPV1, is also triggered by heat, but not by capsaicin; and P2X$_3$, is triggered by ATP, but desensitizes more rapidly than P2X$_2$. TRPV1, TRPM8 and P2X$_2$ are, therefore, non-limiting examples of LGIC suitable for use in particular embodiments.

In one embodiment, the engineered receptor is a TRPV1 or TRPM8 receptor or a mutein thereof. TRPV1 and TRPM8, are vanilloid and menthol receptors expressed by nociceptive neurons of the peripheral nervous system. Both channels are thought to function as non-selective, sodium- and calcium-permeable homotetramers. In addition, both channels and their principal agonists—capsaicin and cooling compounds, such as menthol, respectively—are virtually absent from the central nervous system. Capsaicin and some cooling compounds, including menthol and icilin, contain potential acceptor sites for photolabile blocking groups. Association of a photolabile blocking group with such an acceptor would result in a ligand-gated ion channel in which light acts as an indirect trigger by releasing the active ligand.

In one embodiment, the engineered receptor is a P2X$_2$ receptor or a mutein thereof. P2X$_2$ is an ATP-gated non-selective cation channel distinguished by its slow rate of desensitization. P2X$_2$ may be used as a selectively addressable source of depolarizing current and present a platform for the generation of engineered channel-ligand combinations that lack natural agonists altogether.

Non-limiting examples of sequences of wild-type LGIC receptor that find use in the generation of engineered receptors of the present disclosure include the following. In the sequences, the signal peptide is italicized, the ligand binding domain is bolded, and the ion pore domain is underlined:

In some embodiments, the wild-type LGIC receptor is a human alpha 1 glycine receptor (GlyRα1) (GenBank Accession No. NP_001139512.1, SEQ ID NO:2), encoded by the GLRA1 gene (GenBank Accession No. NM_001146040.1 (SEQ ID NO:1):

(a)

(SEQ ID NO: 2)
*MYSFNTLRLYLWETIVFFSLAASKEAEA*ARSAPKPMSPSDFLDKLMGRTS

GYDARIRPNFKGPPVNVSCNIFINSFGSIAETTMDYRVNIFLRQQWNDPR

LAYNEYPDDSLDLDPSMLDSIWKPDLFFANEKGAHFHEITTDNKLLRISR

NGNVLYSIRITLTLACPMDLKNFPMDVQTCIMQLESFGYTMNDLIFEWQE

QGAVQVADGLTLPQFILKEEKDLRYCTKHYNTGKFTCIEARFHLERQMGY

YLIQMYIPSLLIVILSWISFWINMDAAPARVGLGITTVLTMTTQSSGSRA

SLPKVSYVKAIDIWMAVCLLFVFSALLEYAAVNFVSRQHKELLRFRRKRR

HHKSPMLNLFQEDEAGEGRFNFSAYGMGPACLQAKDGISVKGANNSNTTN

PPPAPSKSPEEMRKLFIQRAKKIDKISRIGFPMAFLIFNMFYWIIYKIVR

REDVHNQ.

In some embodiments, the wild-type LGIC receptor is a human nicotinic cholinergic receptor alpha 7 subunit (α7-nAchR) (GenBank Accession No. NP_000737.1, SEQ ID NO:4), encoded by the CHRNA7 gene (GenBank Accession No. NM_000746.5 (SEQ ID NO:3):

(a)

(SEQ ID NO: 4)
*MRCSPGGVWLALAASLLHVSLQ*GEFQRKLYKELVKNYNPLERPVAN

DSQPLTVYFSLSLLQIMDVDEKNQVLTTNIWLQMSWTDHYLQWNVSEYPG

VKTVRFPDGQIWKPDILLYNSADERFDATFHTNVLVNSSGHCQYLPPGIF

KSSCYIDVRWFPFDVQHCKLKFGSWSYGGWSLDLQMQEADISGYIPNGEW

DLVGIPGKRSERFYECCKEPYPDVTFTVTMRRRTLYYGLNLLIPCVLISA

LALLVFLLPADSGEKISLGITVLLSLTVFMLLVAEIMPATSDSVPLIAQY

FASTMIIVGLSVVVTVIVLQYHHHDPDGGKMPKWTRVILLNWCAWFLRMK

RPGEDKVRPACQHKQRRCSLASVEMSAVAPPPASNGNLLYIGFRGLDGVH

CVPTPDSGVVCGRMACSPTHDEHLLHGGQPPEGDPDLAKILEEVRYIANR

FRCQDESEAVCSEWKFAACVVDRLCLMAFSVFTIICTIGILMSAPNFVEA

VSKDFA.

In some embodiments, the wild-type LGIC receptor is a human 5-hydroxytryptamine receptor 3A (5HT3A, GenBank Accession No. NP_998786.2, SEQ ID NO:6), encoded by the HTR3A gene (GenBank Accession No. NM_213621.3, SEQ ID NO:5):

(a)

(SEQ ID NO: 6)
*MLGKLAMLLWVQQALLALLLPTL*LAQGEARRSRNTTRPALLRLSDY

LLTNYRKGVRPVRDWRKPTTVSIDVIVYAILNVDEKNQVLTTYIWYRQYW

TDEFLQWNPEDFDNITKLSIPTDSIWVPDILINEFVDVGKSPNIPYVYIR

HQGEVQNYKPLQVVTACSLDIYNFPFDVQNCSLTFTSWLHTIQDINISLW

RLPEKVKSDRSVFMNQGEWELLGVLPYFREFSMESSNYYAEMKFYVVIRR

RPLFYVVSLLLPSIFLMVMDIVGFYLPPNSGERVSFKITLLLGYSVFLII

VSDTLPATAIGTPLIGKAPPGSRAQSGEKPAPSHLLHVSLASALGCTGVY

FVVCMALLVISLAETIFIVRLVHKQDLQQPVPAWLRHLVLERIAWLLCLR

EQSTSQRPPATSQATKTDDCSAMGNHCSHMGGPQDFEKSPRDRCSPPPPP

REASLAVCGLLQELSSIRQFLEKRDEIREVARDWLRVGSVLDKLLFHIYL

LAVLAYSITLVMLWSIWQYA.

In some embodiments, the wild-type LGIC receptor is a human 5-hydroxytryptamine receptor 3B (5HT3B GenBank Accession No. NP_006019.1, SEQ ID NO:57), encoded by the HTR3B gene (GenBank Accession No. NM_006028.4, SEQ ID NO:56):

(a)

(SEQ ID NO: 57)
*MLSSVMAPLWACILVAAGILA*TDTHHPQDSALYHLSKQLLQKYHKE

VRPVYNWTKATTVYLDLFVHAILDVDAENQILKTSVWYQEVWNDEFLSWN

SSMFDEIREISLPLSAIWAPDIIINEFVDIERYPDLPYVYVNSSGTIENY

-continued
KPIQVVSACSLETYAFPFDVQNCSLTFKSILHTVEDVDLAFLRSPEDIQH

DKKAFLNDSEWELLSVSSTYSILQSSAGGFAQIQFNVVMRRHP<u>LVYVVSL</u>

<u>LIPSIFLMLVDLGSFYLPPNCRARIVFKTSVLVGYTVFRVNMSNQVPRSV</u>

<u>GSTPLIGHFFTICMAFLVLSLAKSIVLVKFLHDEQRGGQEQPFLCLRGDT</u>

<u>DADRPRVEPRAQRAVVTESSLYGEHLAQPGTLKEVWSQLQSISNYLQTQD</u>

<u>QTDQQEAEWLVLLSRFDRLLFQSYLFMLGIYTITLCSLWALWGGV</u>.

In some embodiments, the wild-type LGIC receptor is a human Gamma-aminobutyric acid receptor A (GABA-A), subunit beta-3 (GABA-A β3) (GenBank Accession No. NP_000805.1, SEQ ID NO:8), encoded by the GABRB3 gene (GenBank Accession No. NM_000814.5, SEQ ID NO:7):

(a)
(SEQ ID NO: 8)
*MWGLAGGRLFGIFSAPVLVAVVCCA*QSVNDPGNMSFVKETVDKLLK

GYDIRLRPDFGGPPVCVGMNIDIASIDMVSEVNMDYTLTMYFQQYWRDKR

LAYSGIPLNLTLDNRVADQLWVPDTYFLNDKKSFVHGVTVKNRMIRLHPD

GTVLYGLRITTTAACMMDLRRYPLDEQNCTLEIESYGYTTDDIEFYWRGG

DKAVTGVERIELPQFSIVEHRLVSRNVVFATGAYPRLSLSFRLKRNIGY

<u>FILQTYMPSILITILSWVSFWINVDASAARVALGITTVLTMTTINTHLRE</u>

<u>TLPKIPYVKAIDMYLMGCFVFVFLALLEYAFVNYIFFGRGPQRQKKLAEK</u>

<u>TAKAKNDRSKSESNRVDAHGNILLTSLEVHNEMNEVSGGIGDTRNSAISF</u>

<u>DNSGIQYRKQSMPREGHGRFLGDRSLPHKKTHLRRRSSQLKIKIPDLTDV</u>

<u>NAIDRWSRIVFPFTFSLFNLVYWLYYVN</u>.

In some embodiments, the wild-type LGIC receptor is a human GABA-A, subunit rho1 (ρ1) (GABA-A ρ1) (GenBank Accession No. NP_002033.2, SEQ ID NO:10), encoded by the GABRR1 gene (GenBank Accession No. NM_002042.4, SEQ ID NO:9):

(a)
(SEQ ID NO: 10)
*MLAVPNMRFGIFLLWWGWVLA*TESRMHWPGREVHEMSKKGRPQRQR

REVHEDAHKQVSPILRRSPDITKSPLTKSEQLLRIDDHDFSMRPGFGGPA

IPVGVDVQVESLDSISEVDMDFTMTLYLRHYWKDERLSFPSTNNLSMTFD

GRLVKKIWVPDMFFVHSKRSFIHDTTTDNVMLRVQPDGKVLYSLRVTVTA

MCNMDFSRFPLDTQTCSLEIESYAYTEDDLMLYWKKGNDSLKTDERISLS

QFLIQEFHTTTKLAFYSSTGWYNRLYINFTLRRHIFF<u>FLLQTYFPATLMV</u>

<u>MLSWVSFWIDRRAVPARVPLGITTVLTMSTIITGVNASMPRVSYIKAVDI</u>

<u>YLWVSFVFVFLSVLEYAAVNYLTTVQERKEQKLREKLPCTSGLPPPRTAM</u>

<u>LDGNYSDGEVNDLDNYMPENGEKPDRMMVQLTLASERSSPQRKSQRSSYV</u>

<u>SMRIDTHAIDKYSRIIFPAAYILFNLIYWSIFS</u>.

In some embodiments, the wild-type LGIC receptor is a human GABA-A, subunit rho2 (ρ2) (GABA-A ρ2) (GenBank Accession No. NP_002034.3, SEQ ID NO:12), encoded by the GABRR2 gene (GenBank Accession No. NM_002043.4, SEQ ID NO:11):

(a)
(SEQ ID NO: 12)
*MPYFTRLILFLFCLMVLVES*RKPKRKRWTGQVEMPKPSHLYKKNLDVTKI

RKGKPQQLLRVDEHDFSMRPAFGGPAIPVGVDVQVESLDSISEVDMDFTM

TLYLRHYWKDERLAFSSASNKSMTFDGRLVKKIWVPDVFFVHSKRSFTHD

TTTDNIMLRVFPDGHVLYSMRITVTAMCNMDFSHFPLDSQTCSLELESYA

YTDEDLMLYWKNGDESLKTDEKISLSQFLIQKFHTTSRLAFYSSTGWYNR

LYINFTLRRHIFF<u>FLLQTYFPATLMVMLSWVSFWIDRRAVPARVSLGITT</u>

<u>VLTMTTIITGVNASMPRVSYVKAVDIYLWVSFVFVFLSVLEYAAVNYLTT</u>

<u>VQERKERKLREKFPCMCGMLHSKTMMLDGSYSESEANSLAGYPRSHILTE</u>

<u>EERQDKIVVHLGLSGEANAARKKGLLKGQTGFRIFQNTHAIDKYSRLIFP</u>

<u>ASYIFFNLIYWSVFS</u>.

In some embodiments, the wild-type LGIC receptor is a human GABA-A, subunit rho3 (ρ3) (GABA-A ρ3) (GenBank Accession No. NP_001099050.1, SEQ ID NO:14), encoded by the GABRR3 gene (GenBank Accession No. NM_001105580.2, SEQ ID NO:13):

(a)
(SEQ ID NO: 14)
*MVLAFQLVSFTYIWIILKPNVCA*ASNIKMTHQRCSSSMKQTCKQETRMKK

DDSTKARPQKYEQLLHIEDNDFAMRPGFGGSPVPVGIDVHVESIDSISET

NMDFTMTFYLRHYWKDERLSFPSTANKSMTFDHRLTRKIWVPDIFFVHSK

RSFIHDTTMENIMLRVHPDGNVLLSLRITVSAMCFMDFSRFPLDTQNCSL

ELESYAYNEDDLMLYWKHGNKSLNTEEHMSLSQFFIEDFSASSGLAFYSS

TGWYNRLFINFVLRRHVFF<u>FVLQTYFPAILMVMLSWVSFWIDRRAVPARV</u>

<u>SLGITTVLTMSTIITAVSASMPQVSYLKAVDVYLWVSSLFVFLSVIEYAA</u>

<u>VNYLTTVEERKQFKKTGKISRMYNIDAVQAMAFDGCYHDSEIDMDQTSLS</u>

<u>LNSEDFMRRKSICSPSTDSSRIKRRKSLGGHVGRIILENNHVIDTYSRIL</u>

<u>FPIVYILFNLFYWGVYV</u>.

In some aspects, the subject engineered receptor is a chimeric receptor. In some embodiments, the chimeric receptor comprises a ligand binding domain sequence from at least at first LGIC and an ion pore conduction domain sequence, or more simply, "ion pore domain sequence" from a least a second LGIC. In some embodiments, the first and second LGIC are Cys-loop receptors. Ligand binding domain sequences and ion pore domain sequences of the Cys-loop receptors are well known in the art and can be readily identified from the literature by use of publicly available software, e.g. PubMed, Genbank, Uniprot, and the like. In the sequences described above, the ligand binding domain is bolded, and the ion pore domain is underlined.

In some embodiments, the ligand binding domain of the chimeric receptor comprises the ligand binding domain sequence of a human glycine receptor. In some embodiments, the human glycine receptor is human GlyRα1 (SEQ ID NO:2). In some such embodiments, the ligand binding domain comprises about amino acids 29-235 of GlyRα1, e.g. amino acids 29-235, amino acids 29-240, amino acids 29-246, amino acids 29-248, amino acids 29-250, or amino acids 29-252 of SEQ ID NO:2. In certain such embodiments, the ligand binding domain consists essentially of amino acids 29-235 of SEQ ID NO:2, consists essentially of amino acids 29-240 of SEQ ID NO:2, consists essentially of amino acids 29-246 of SEQ ID NO:2, consists essentially of amino acids 29-248 of SEQ ID NO:2, consists essentially of amino acids 29-250 of SEQ ID NO:2, consists essentially of amino acids 29-252 of SEQ ID NO:2. In some embodiments, the ion pore domain sequence is from a Cys-loop receptor other than the human GlyRα1.

In some embodiments, the ligand binding domain of the chimeric receptor comprises the ligand binding domain sequence of a human nicotinic cholinergic receptor. In some embodiments, the human nicotinic cholinergic receptor is human α7-nAChR. In some such embodiments, the ligand binding domain comprises about amino acids 23-220 of α7-nAChR (SEQ ID NO:4), e.g. amino acids 23-220, amino acids 23-226, amino acids 23-229, amino acids 23-230, in some instances amino acids 23-231 of SEQ ID NO:4. In certain such embodiments, the ligand binding domain consists essentially of amino acids 23-220 of SEQ ID NO:4, consists essentially of amino acids 23-226 of SEQ ID NO:4, consists essentially of amino acids 23-229 of SEQ ID NO:4, consists essentially of amino acids 23-230 of SEQ ID NO:4, or consists essentially of amino acids 23-231 of SEQ ID NO:4. In some embodiments, the ion pore domain sequence is from a Cys-loop receptor other than the human α7-nAChR.

In some embodiments, the ligand binding domain of the chimeric receptor comprises the ligand binding domain sequence of a human serotonin receptor. In some embodiments, the human serotonin receptor is human 5HT3A or 5HT3B. In some such embodiments, the ligand binding domain comprises about amino acids 23-247 of 5HT3A (SEQ ID NO:6), e.g. amino acids 23-240, amino acids 30-245, amino acids 23-247, amino acids 23-250, in some instances amino acids 30-255 of SEQ ID NO:6. In certain embodiments, the ligand binding domain consists essentially of amino acids 23-240 of SEQ ID NO:6, consists essentially of amino acids 23-245 of SEQ ID NO:6, consists essentially of amino acids 30-247 of SEQ ID NO:6, consists essentially of amino acids 23-250 of SEQ ID NO:6, consists essentially of amino acids 23-255 of SEQ ID NO:6. In some such embodiments, the ligand binding domain comprises about amino acids 21-239 of 5HT3B (SEQ ID NO:57), e.g. amino acids 21-232, amino acids 21-235, amino acids 21-240, amino acids 21-245, in some instances amino acids 21-247 of SEQ ID NO:57. In certain embodiments, the ligand binding domain consists essentially of amino acids 21-239 of SEQ ID NO:57, consists essentially of amino acids 21-232 of SEQ ID NO:57, consists essentially of amino acids 21-235 of SEQ ID NO:57, consists essentially of amino acids 21-240 of SEQ ID NO:57, consists essentially of amino acids 21-245 of SEQ ID NO:57. In some embodiments, the ion pore domain sequence is from a Cys-loop receptor other than the human 5-hydroxytryptamine receptor 3.

In some embodiments, the ligand binding domain of the chimeric receptor comprises the ligand binding domain sequence of a human GABA receptor. In some embodiments, the human GABA receptor is human GABA-A β3. In some such embodiments, the ligand binding domain comprises about amino acids 26-245 of GABA-A β3 (SEQ ID NO:8), e.g. amino acids 26-240, amino acids 26-245, amino acids 26-248, amino acids 26-250, in some instances amino acids 26-255 of SEQ ID NO:8. In certain such embodiments, the ligand binding domain consists essentially of amino acids 26-240 of SEQ ID NO:8, consists essentially of amino acids 26-245 of SEQ ID NO:8, consists essentially of amino acids 26-248 of SEQ ID NO:8, consists essentially of amino acids 26-250 of SEQ ID NO:8, or consists essentially of amino acids 26-255 of SEQ ID NO:8. In some embodiments, the ion pore domain sequence is from a Cys-loop receptor other than the human GABA-A receptor.

In some embodiments, the ion pore domain to which the ligand binding domain is fused conducts anions, e.g. it comprises an ion pore domain sequence of a human glycine receptor or a human serotonin receptor. In other embodiments, the ion conduction pore domain to which the ligand binding domain is fused conducts cations, e.g. it comprises an ion pore domain sequence of a human acetylcholine receptor or a human gamma-aminobutyric acid receptor A.

In some embodiments, the ion pore domain comprises the ion pore domain sequence of a human glycine receptor. In some embodiments, the human glycine receptor is human GlyRα1. In some such embodiments, the ion pore domain comprises about amino acids 245-457 of GlyRα1 (SEQ ID NO:2), e.g. amino acids 240-457, amino acids 245-457, amino acids 248-457, amino acids 249-457, amino acids 250-457, amino acids 255-457, or amino acids 260-457 of SEQ ID NO:2. In certain such embodiments, the ion pore domain consists essentially of amino acids 245-457 of SEQ ID NO:2, consists essentially of amino acids 248-457 of SEQ ID NO:2, consists essentially of amino acids 249-457 of SEQ ID NO:2, or consists essentially of amino acids 250-457 of SEQ ID NO:2.

In some embodiments, the ion pore domain comprises the ion pore domain sequence of a human nicotinic cholinergic receptor. In some embodiments, the human nicotinic cholinergic receptor is human α7-nAChR. In some such embodiments, the ion pore domain comprises about amino acids 230-502 of α7-nAChR (SEQ ID NO:4), e.g. amino acids 227-502, amino acids 230-502, amino acids 231-502, amino acids 232-502, or amino acids 235-502. In certain such embodiments, the ion pore domain consists essentially of amino acids 227-502 of SEQ ID NO:4, consists essentially of amino acids 230-502 of SEQ ID NO:4, consists essentially of amino acids 231-502 of SEQ ID NO:4, consists essentially of amino acids 232-502 of SEQ ID NO:4, or consists essentially of amino acids 235-502 of SEQ ID NO:4.

In some embodiments, the ion pore domain comprises the ion pore domain sequence of a human serotonin receptor. In some embodiments, the human serotonin receptor is human 5HT3A or 5HT3B. In some such embodiments, the ion pore domain comprises about amino acids 248-516 of 5HT3A (SEQ ID NO:6), e.g. amino acids 240-516, amino acids 245-516, amino acids 248-516, amino acids 250-516, or amino acids 255-516 of SEQ ID NO:6. In certain such embodiments, the ion pore domain consists essentially of amino acids 240-516 of SEQ ID NO:6, consists essentially of amino acids 245-516 of SEQ ID NO:6, consists essentially of amino acids 248-516 of SEQ ID NO:6, consists essentially of amino acids 250-516 of SEQ ID NO:6, or consists essentially of amino acids 253-516. In some such embodiments, the ion pore domain comprises about amino acids 240-441 of 5HT3B (SEQ ID NO:57), e.g. amino acids 230-441, amino acids 235-441, amino acids 240-441, amino acids 245-441, or amino acids 250-441 of SEQ ID NO:57. In certain such embodiments, the ion pore domain consists essentially of amino acids 230-441 of SEQ ID NO:57, consists essentially of amino acids 235-441 of SEQ ID NO:57, consists essentially of amino acids 240-441 of SEQ ID NO:57, consists essentially of amino acids 245-441 of SEQ ID NO:57, or consists essentially of amino acids 250-441.

In some embodiments, the ion pore domain comprises the ion pore domain sequence of a human GABA receptor. In some embodiments, the human GABA receptor is human GABA-A β3. In some such embodiments, the ion pore domain comprises about amino acids 246-473 of GABA-A β3 (SEQ ID NO:8), e.g. amino acids 240-473, amino acids 245-473, amino acids 247-473, amino acids 250-473, or amino acids 253-473 of SEQ ID NO:8. In certain such embodiments, the ion pore domain consists essentially of amino acids 240-473 of SEQ ID NO:8, amino acids 245-473 of SEQ ID NO:8, amino acids 247-473 of SEQ ID NO:8, amino acids 250-473 of SEQ ID NO:8, or amino acids 253-473 of SEQ ID NO:8.

In some embodiments, the ion pore domain of the subject chimeric ligand-gated ion channel comprises an M2-M3 linker domain that is heterologous to the M2-M3 linker domain of the ion pore domain. By an "M2-M3 linker domain", or "M2-M3 linker", it is meant the sequence within an ion pore domain of a LGIC that is flanked at its amino (N) terminus by the C-terminal end of transmembrane domain 2 (M2) of the receptor and at its carboxy (C) terminus by the N-terminal end of transmembrane domain 3 (M3) of the receptor. The M2-M3 linker of a LGIC may be readily determined from the art and/or by using any publicly available protein analysis tool, e.g. Expasy, uniProt, etc. Typically, when the ion pore domain of a chimeric receptor comprises a heterologous M2-M3 linker, the M2-M3 linker is derived from the same receptor as the ligand binding domain of the chimeric receptor. For example, when the subject ligand-gated ion channel comprises a ligand binding domain from an AChR and an ion pore domain from a GlyR, the subject ligand-gated ion channel may comprise an ion pore domain sequence from a GlyR except for the M2-M3 linker, which would instead be derived from a AChR. In some embodiments, the ion pore domain is from GlyRα1 and the M2-M3 linker is from α7-nAChR. In some such embodiments, the M2-M3 linker sequence that is removed from the GlyRα1 is about amino acids 293-311 of GlyRα1 (SEQ ID NO:2), e.g. amino acids 304-310, 293-306, 298-310, 305-311, etc. In some such embodiments, the M2-M3 linker that is inserted is about amino acids 281-295 of α7-nAChR (SEQ ID NO:4), e.g. amino acids 290-295, 281-290, 281-295, 287-292, etc. or a sequence having about 95% identity or more to amino acids 281-295 of α7-nAChR.

In some embodiments, the ligand binding domain of the subject chimeric ligand-gated ion channel comprises a Cys-loop domain sequence that is heterologous to the Cys-loop sequence of the ligand binding domain. By a "Cys-loop domain sequence", or "Cys-loop sequence", it is meant the domain within a ligand binding domain of a Cys-loop LGIC that forms a loop structure flanked by a cysteine at the N-terminus and the C-terminus. Without wishing to be bound by theory, it is believed that upon binding of the ligand to the ligand binding domain, the Cys-loop structurally moves to be in close proximity to the M2-M3 loop, this movement mediating the biophysical translation of ligand binding in the extracellular domain to signal transduction in the ion pore domain (as reviewed in Miller and Smart, Trends in Pharmacological Sci 2009: 31(4)). The substitution of an endogenous Cys-loop sequence with a heterologous Cys-loop sequence may increase the conductivity of the LGIC by 1.5-fold or more, e.g. at least 2-fold, 3-fold or 4-fold, in some instances at least 5-fold or 6-fold, and at certain doses, at least 7-fold, 8-fold, 9-fold or 10-fold. The Cys-loop domain of a Cys-loop receptor may be readily determined from the art and/or by using any publicly available protein analysis tool, e.g. Expasy, uniProt, etc. Typically, when the ligand binding domain of a chimeric receptor comprises a heterologous Cys-loop sequence, the Cys-loop sequence is derived from the same receptor as the ion pore domain of the chimeric receptor. For example, when the subject chimeric ligand-gated ion channel comprises a ligand binding domain from an AChR and an ion pore domain from a GlyR, the subject ligand-gated ion channel may comprise ligand binding domain sequence from an AChR except for the sequence of the Cys-loop domain, which is instead derived from a GlyR. In some embodiments, the ligand binding domain is from α7-nAChR and the Cys-loop sequence is from GlyRα1. In some such embodiments, the Cys-loop sequence that is removed from the α7-nAChR is about amino acids 150-164 of α7-nAChR (SEQ ID NO:4), e.g. amino acids 150-157 of α7-nAChR. In some such embodiments, the Cys loop sequence that is inserted is about amino acids 166-180 of GlyRα1 (SEQ ID NO:2), e.g. amino acids 166-172 of GlyRα1, or a sequence having about 95% identity or more to amino acids 166-180 of GlyRα1.

In some embodiments, the ligand binding domain of the subject chimeric ligand-gated ion channel comprises a β1-2 loop domain sequence that is heterologous to the β1-2 loop domain sequence of the ligand binding domain. By a "β1-2 loop domain sequence", or "β1-2 loop, or β1-β2 loop", it is meant the domain within a ligand binding domain of a Cys-loop LGIC that is flanked at its N-terminus by the C-terminus of the β1 sheet and, at its C-terminus, by the N-terminus of the β2 sheet. Without wishing to be bound by theory, it is believed that the β1-2 loop helps to mediate biophysical translation of ligand binding in the extracellular domain to the ion pore domain and subsequent signal transduction (i.e. chloride influx in case of GlyR). It is believed that upon binding of ligand, the β1-2 loop, together with the Cys-loop, come in close proximity to the M2-M3 loop to mediate the biophysical translation of ligand binding in the extracellular domain to signal transduction in the ion pore domain where the M2-M3 loop resides (as reviewed in Miller and Smart, supra). The substitution of an endogenous β1-2 loop sequence with a heterologous β1-2 loop sequence may increase the conductivity of the LGIC by 1.5-fold or more, e.g. at least 2-fold, 3-fold or 4-fold, in some instances at least 5-fold or 6-fold, and at certain doses, at least 7-fold, 8-fold, 9-fold or 10-fold. The β1-2 loop of a Cys-loop receptor may be readily determined from the art and/or by using any publicly available protein analysis tool, e.g. Expasy, uniProt, etc. Typically, when the ligand binding domain of a chimeric receptor comprises a heterologous β1-2 loop sequence, the β1-2 loop sequence is derived from the same receptor as the ion pore domain of the chimeric receptor. For example, when the subject chimeric ligand-gated ion channel comprises a ligand binding domain from an AChR and an ion pore domain from a GlyR, the subject ligand-gated ion channel may comprise ligand binding domain sequence from an AChR except for the sequence of the β1-2 loop domain, which is instead derived from a GlyR. In some embodiments, the ligand binding domain is from α7-nAChR and the β1-2 loop sequence is from GlyRα1. In some embodiments, the β1-2 loop sequence that is removed from the α7-nAChR is about amino acids 67-70 of α7-nAChR (SEQ ID NO:4), e.g. amino acids 67-70, 66-71 or 64-72 of α7-nAChR. In some embodiments, the β1-2 loop sequence that is inserted is about amino acids 79-85 of GlyRα1 (SEQ ID NO:2), e.g. amino acids 81-84, 79-85, or 81-84 of GlyRα1, or a sequence having about 95% identity or more to amino acids 79-85 of GlyRα1.

Non-limiting examples of sequences of chimeric LGIC receptors of the present disclosure include the sequences disclosed herein as SEQ ID NO:15-SEQ ID NO:52. In some embodiments, the chimeric LGIC receptor or the polynucleotide that encodes it has a sequence identity of 85% or more to a sequence provided in SEQ ID NO:15-SEQ ID NO:52 herein, e.g. a sequence identity of 90% or more, 93% or more, or 95% or more, i.e. 96%, 97%, 98%, 99% or 100% to a sequence provided in SEQ ID NO:15-SEQ ID NO:52. In the sequences, the signal peptide is italicized, the ligand binding domain is bolded, and the ion pore domain is underlined.

Figure 3:
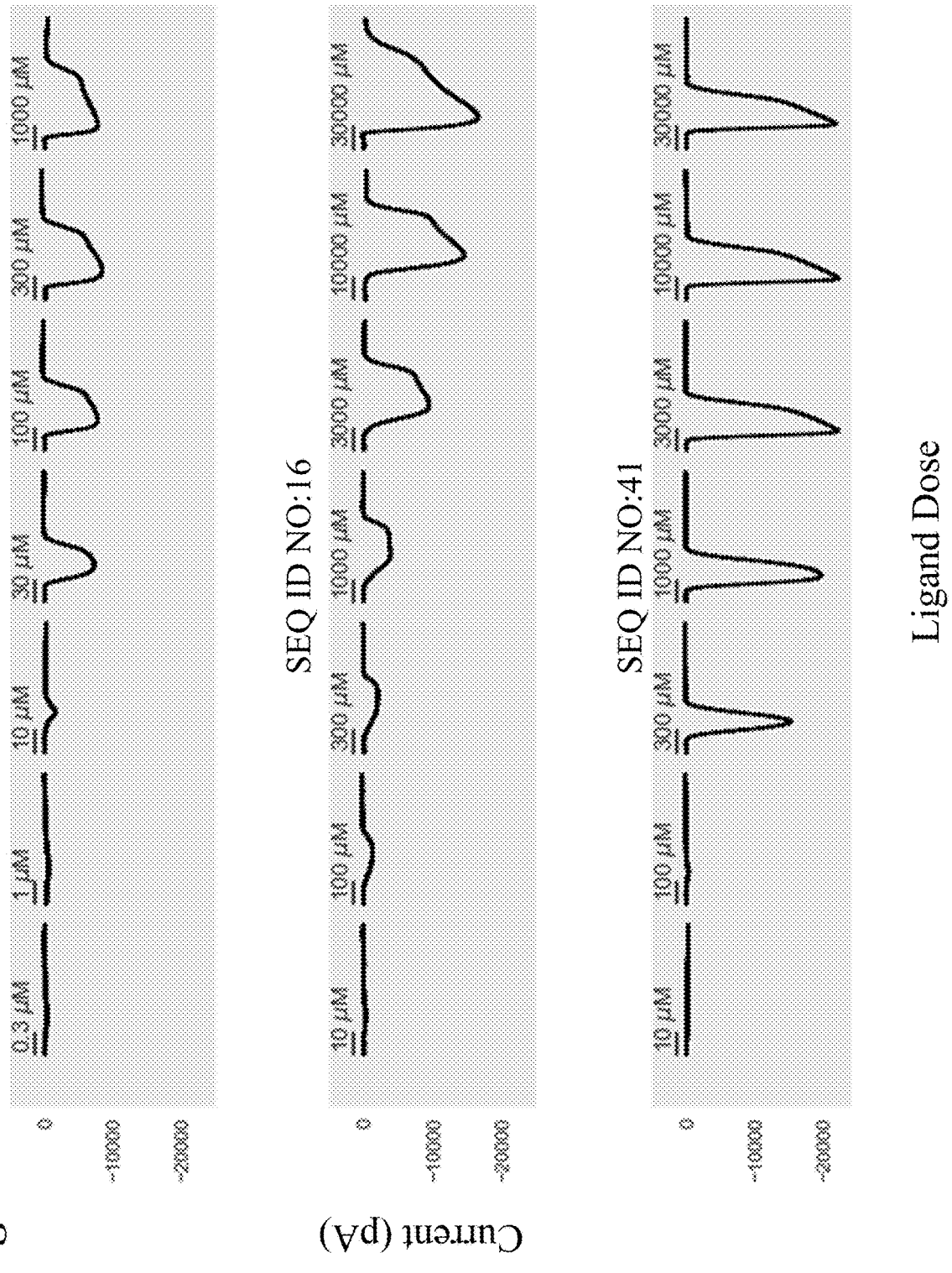
FIG. 3 shows examples of the dose-response curves of several functional CHRNA7/GLRA1 chimeric receptors to their native ligand, acetylcholine. These receptors show an inward current in response to varying doses of the ligand acetylcholine when applied for 1 second. Voltage clamp recordings were performed in HEK293T cells transiently expressing the channel and correspond to conductance currents summed from up to 20 cells patched simultaneously using the automated patch clamp system IonFlux (Fluxion Biosciences) in Ensemble mode.
Figure 4A:
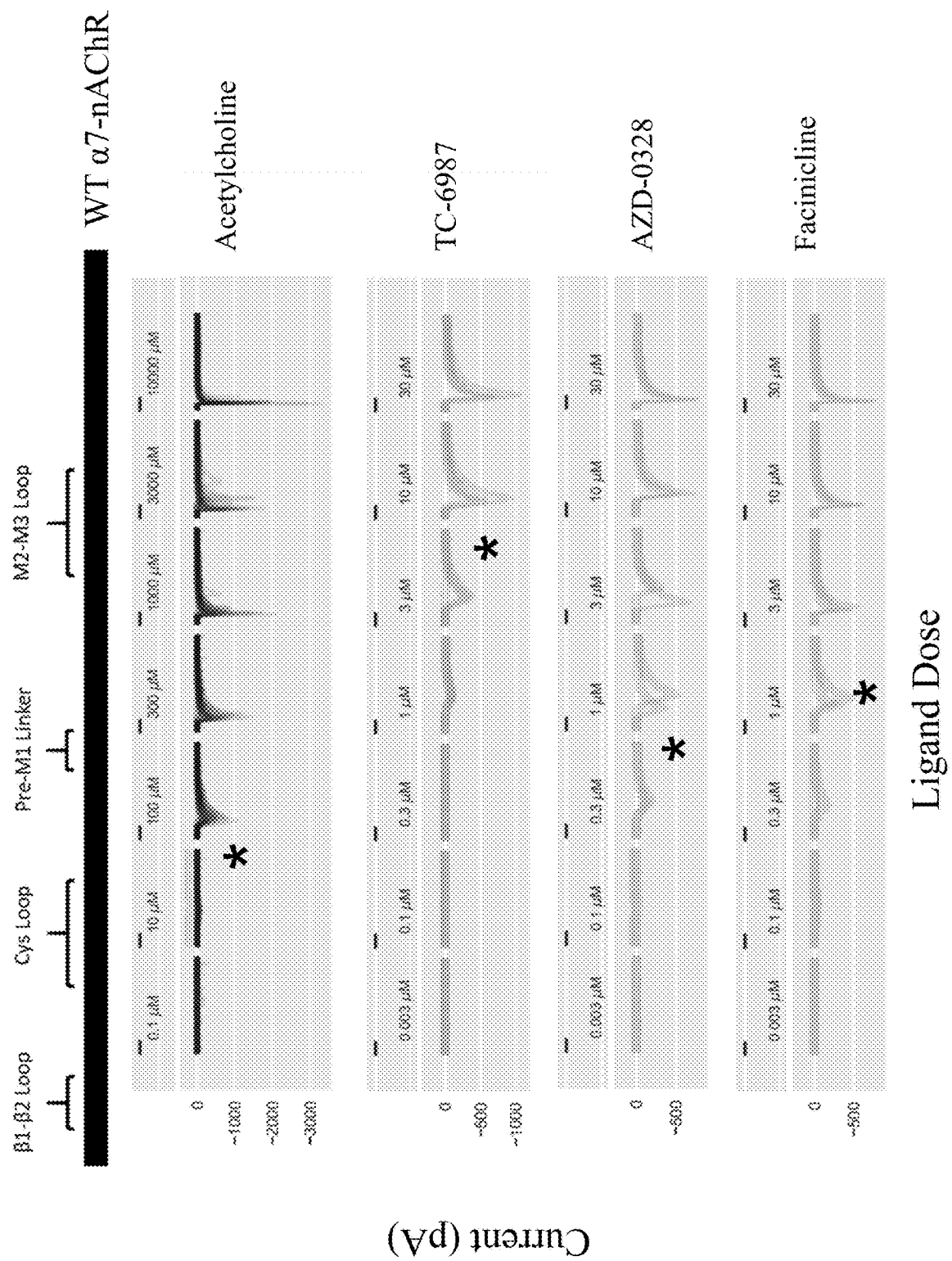
FIG. 4A-FIG. 4F show the ligand-dependent response profiles of wild type alpha-7 nAChR and various engineered chimeric LGIC receptors to acetylcholine as well as to non-native ligands TC-6987, AZD-0328, and Facinicline/RG3487. Receptors were transiently expressed in HEK293T cells and currents were measured on an automated patch clamp system (Fluxion Biosciences) following 1 second addition of drug.
Figure 4B:
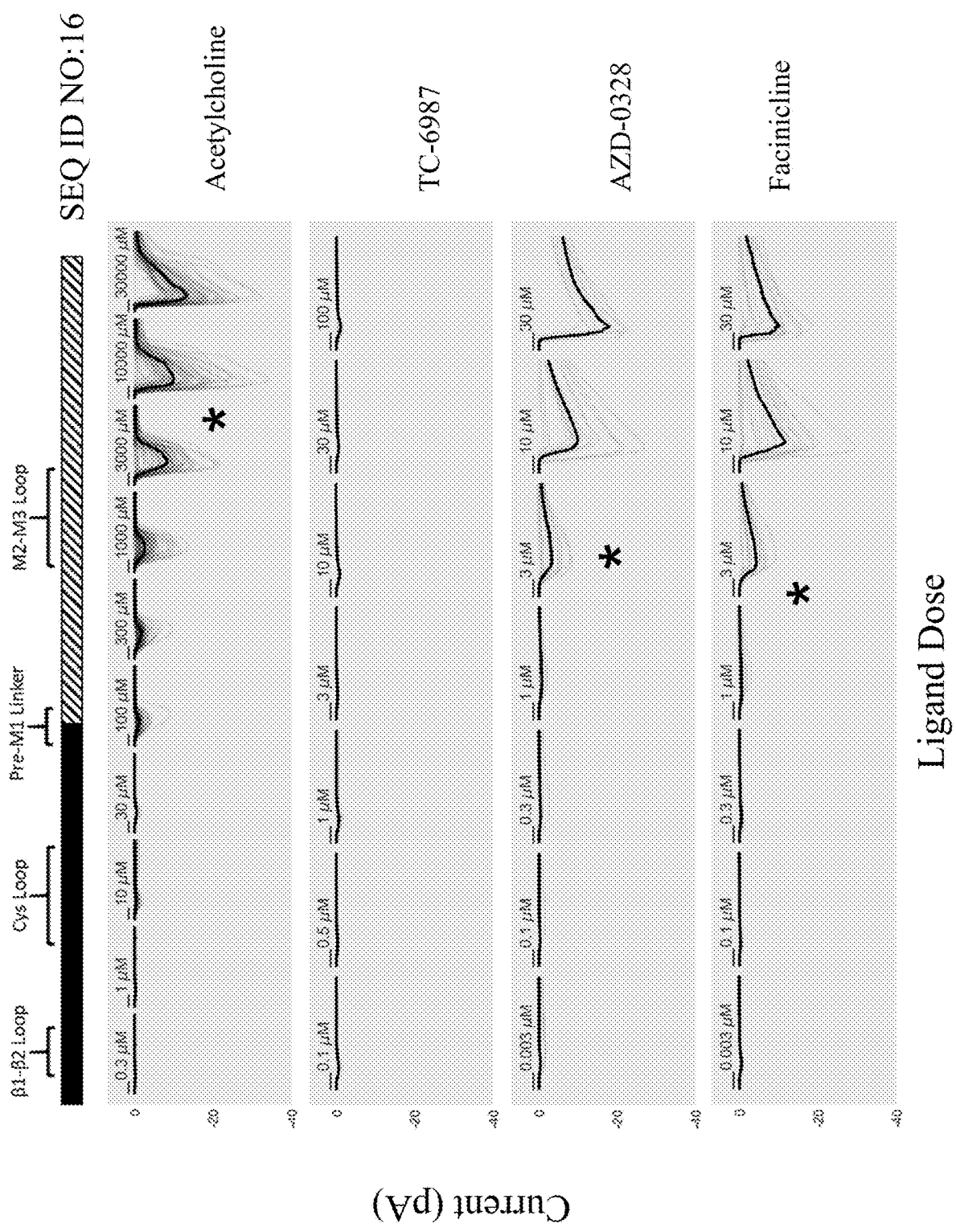
Figure 4C:
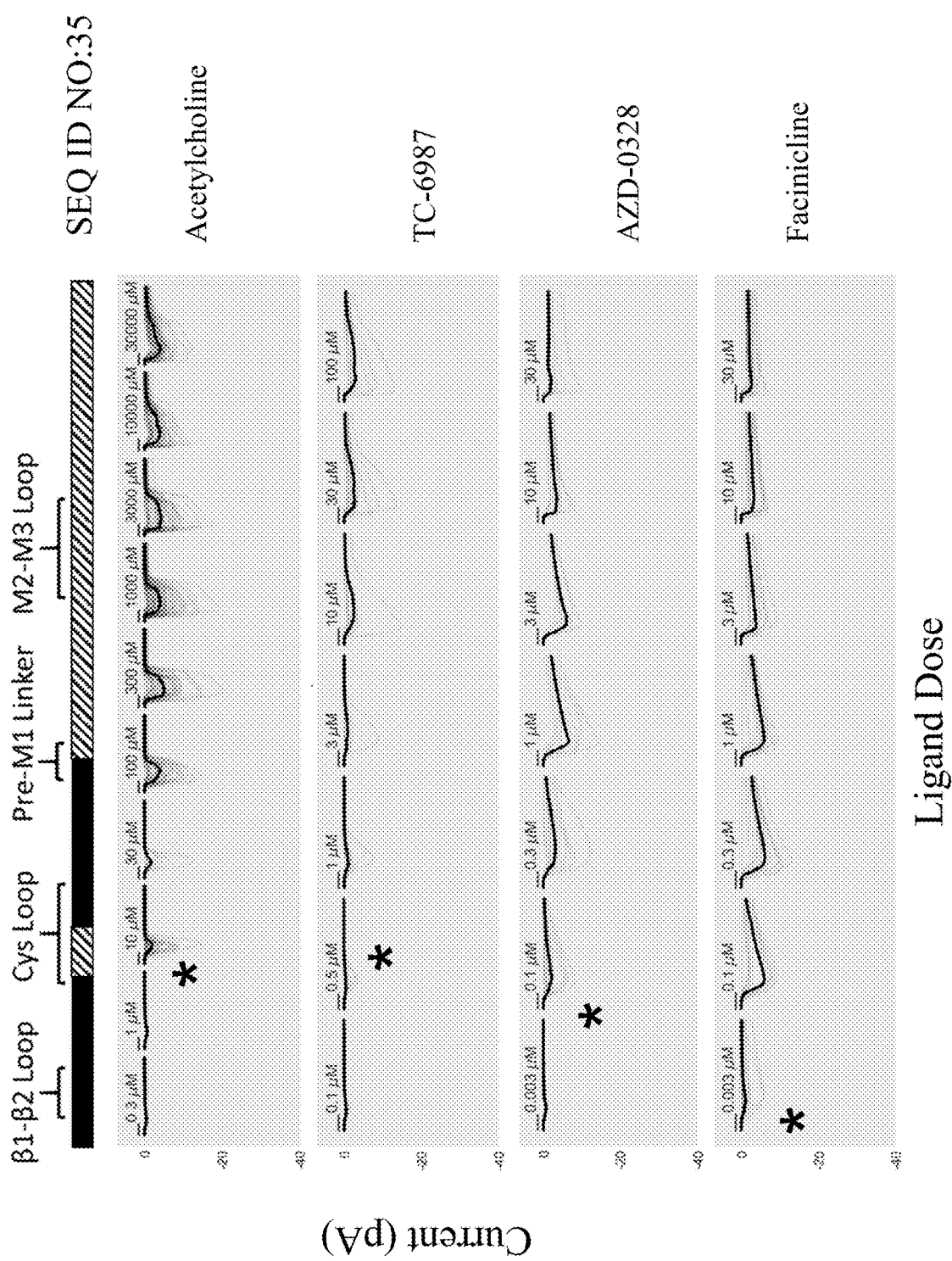
Figure 4D:
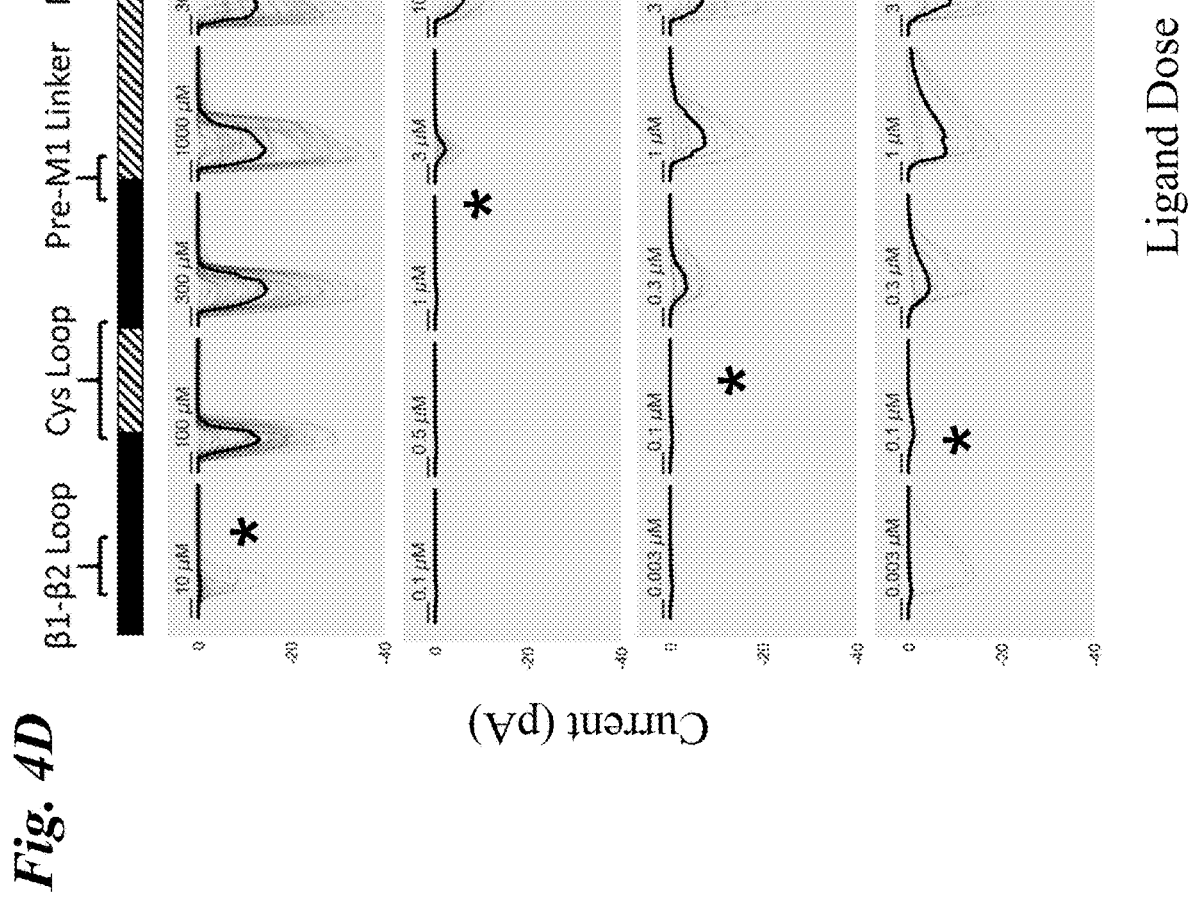
Figure 4E:
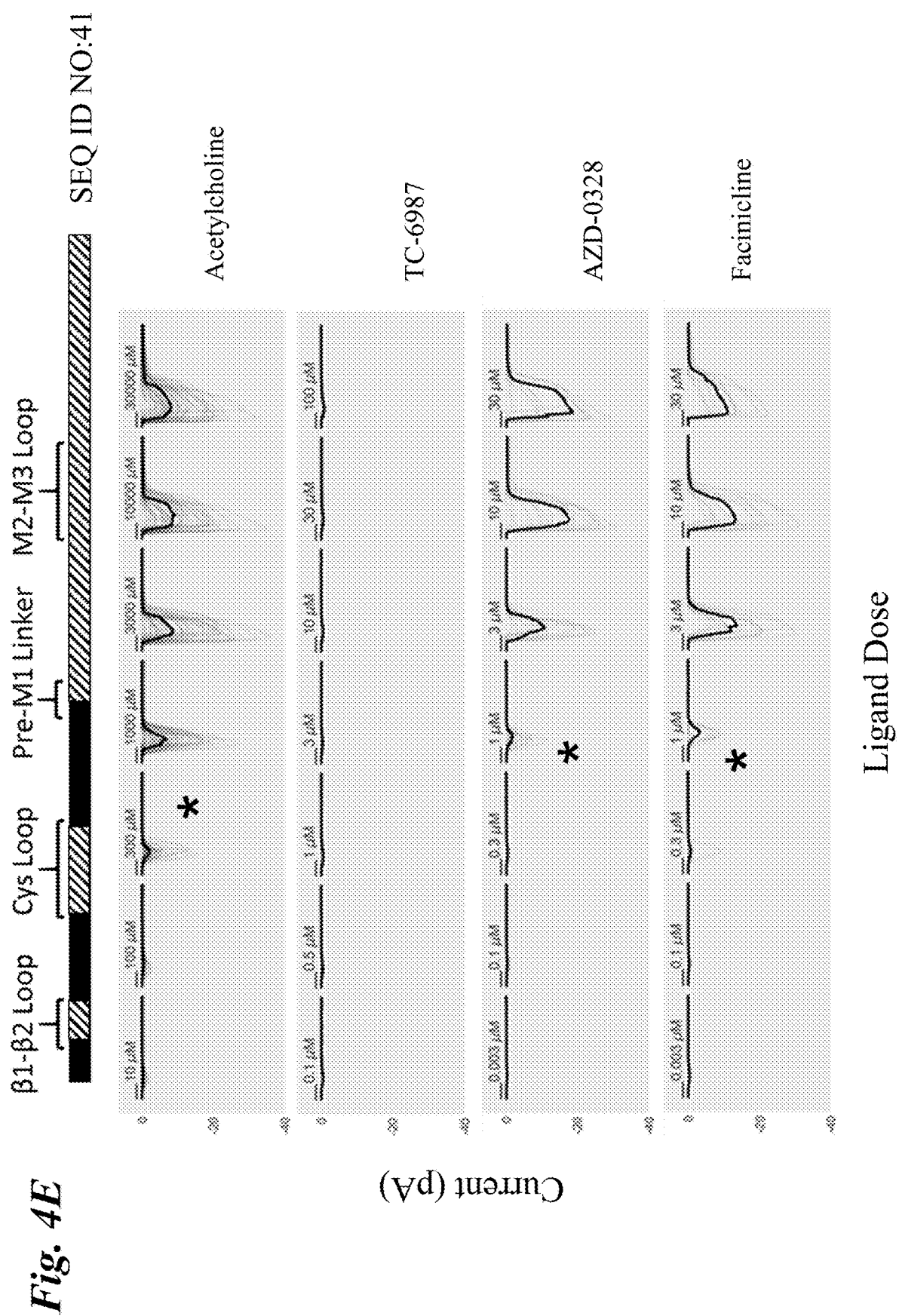
Figure 4F:
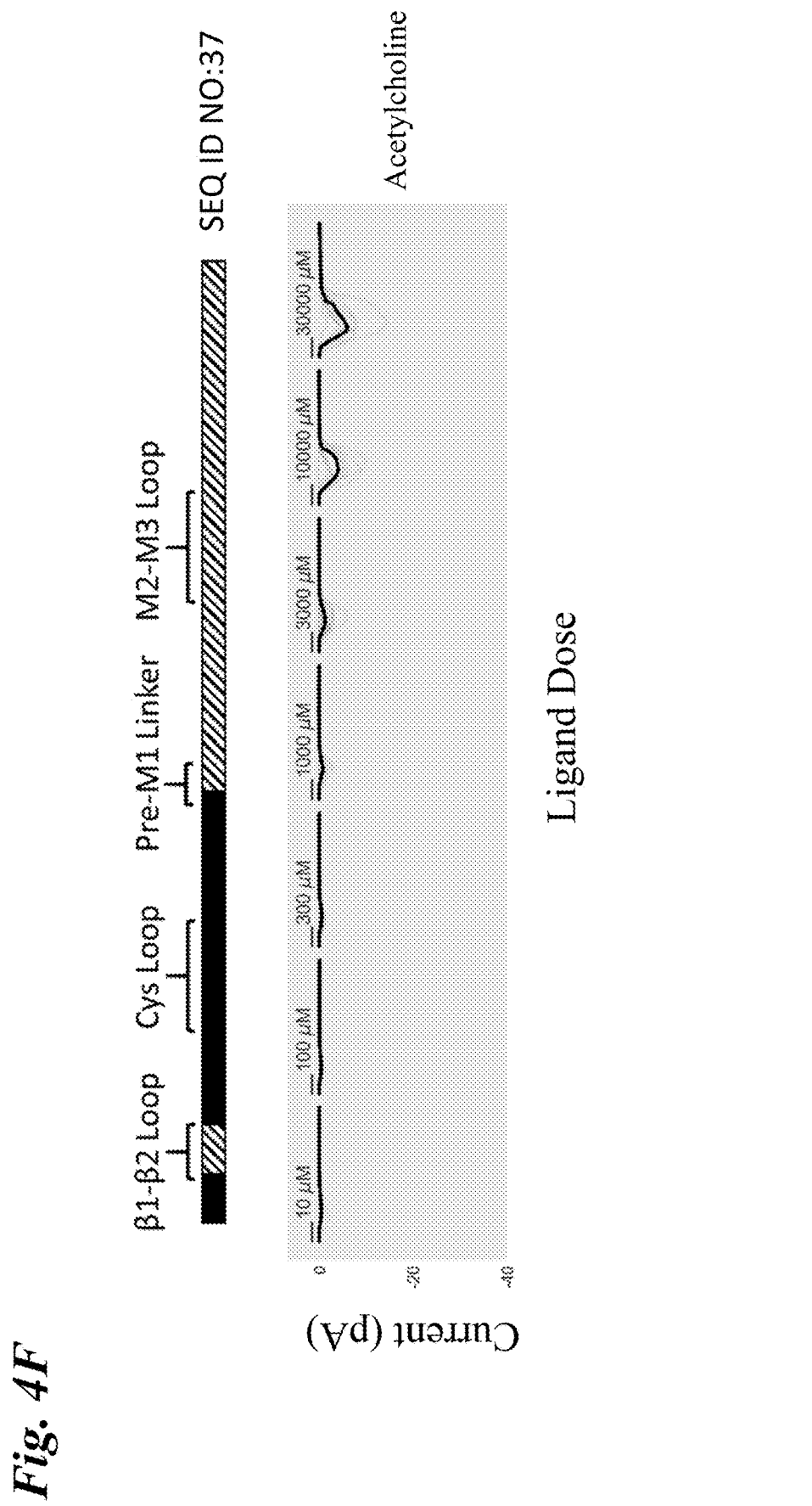
Figure 5A:
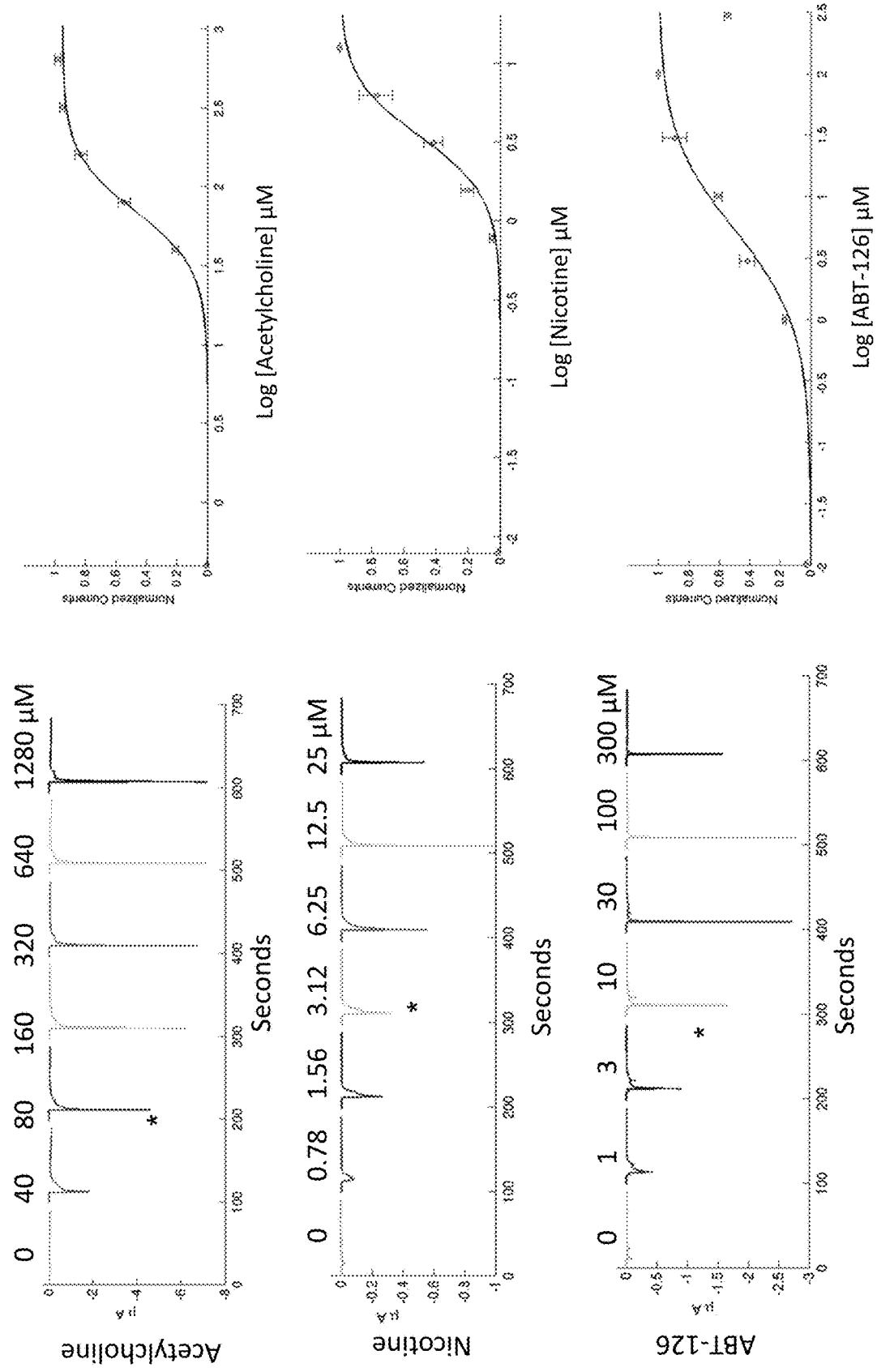
FIG. 5A-FIG. 5F show the ligand-dependent response profiles of wild type alpha-7 nAChR and various engineered chimeric LGIC receptors expressed in *Xenopus* oocytes to acetylcholine as well as to non-native ligands ABT-126, TC-6987, AZD-0328, and Facinicline/RG3487.
Figure 5B:
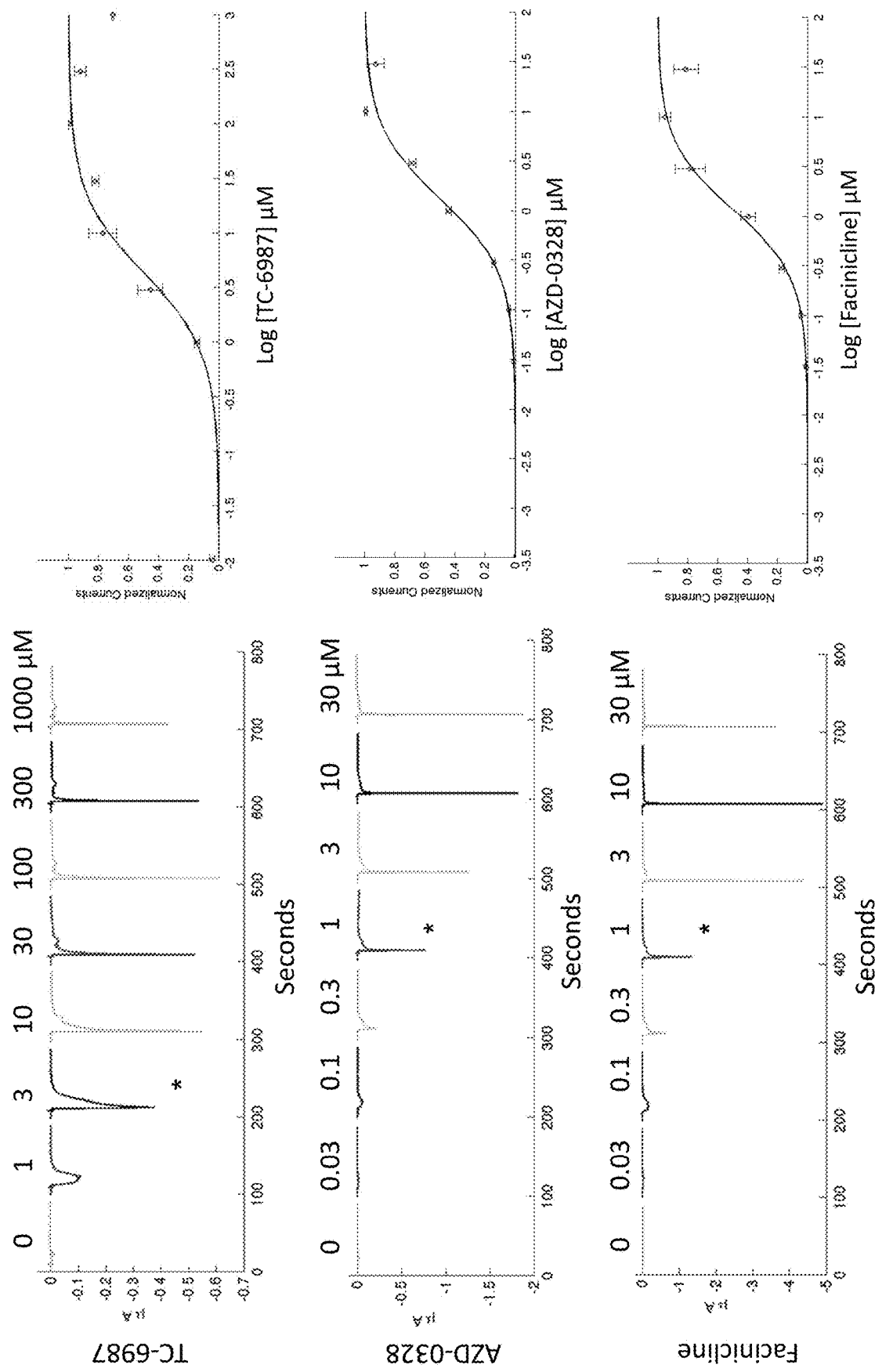
Figure 5C:
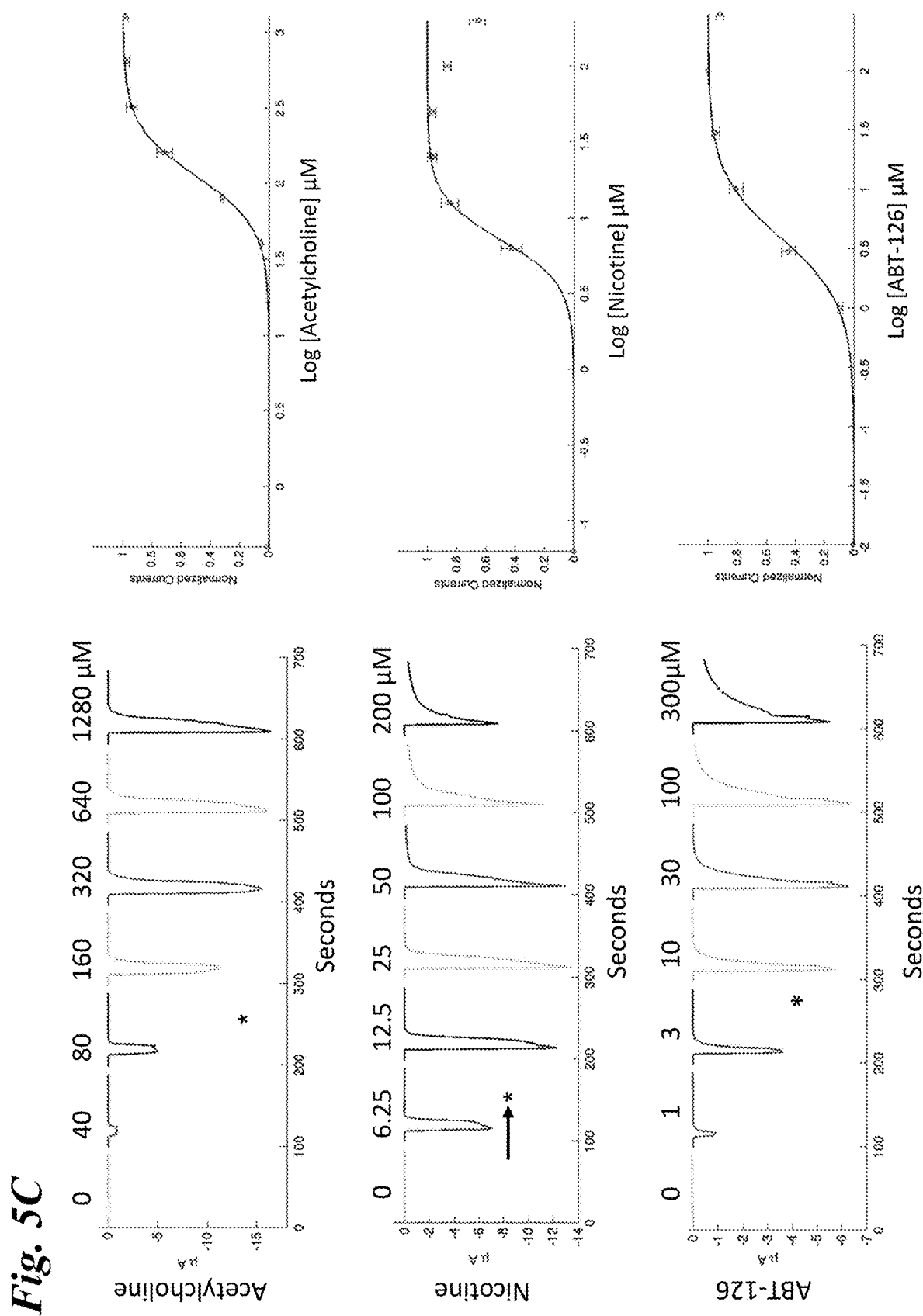
Figure 5D:
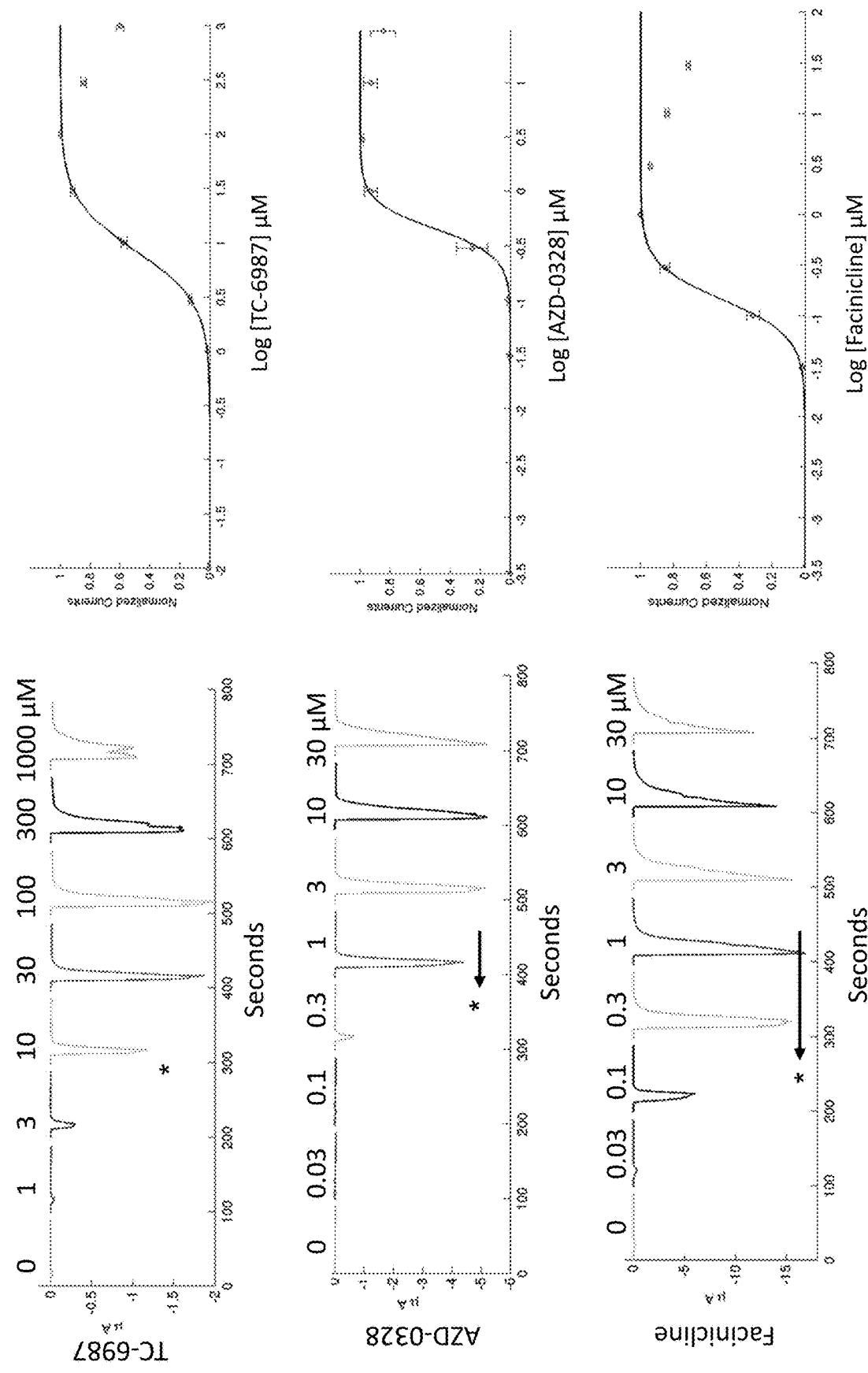
Figure 5E:
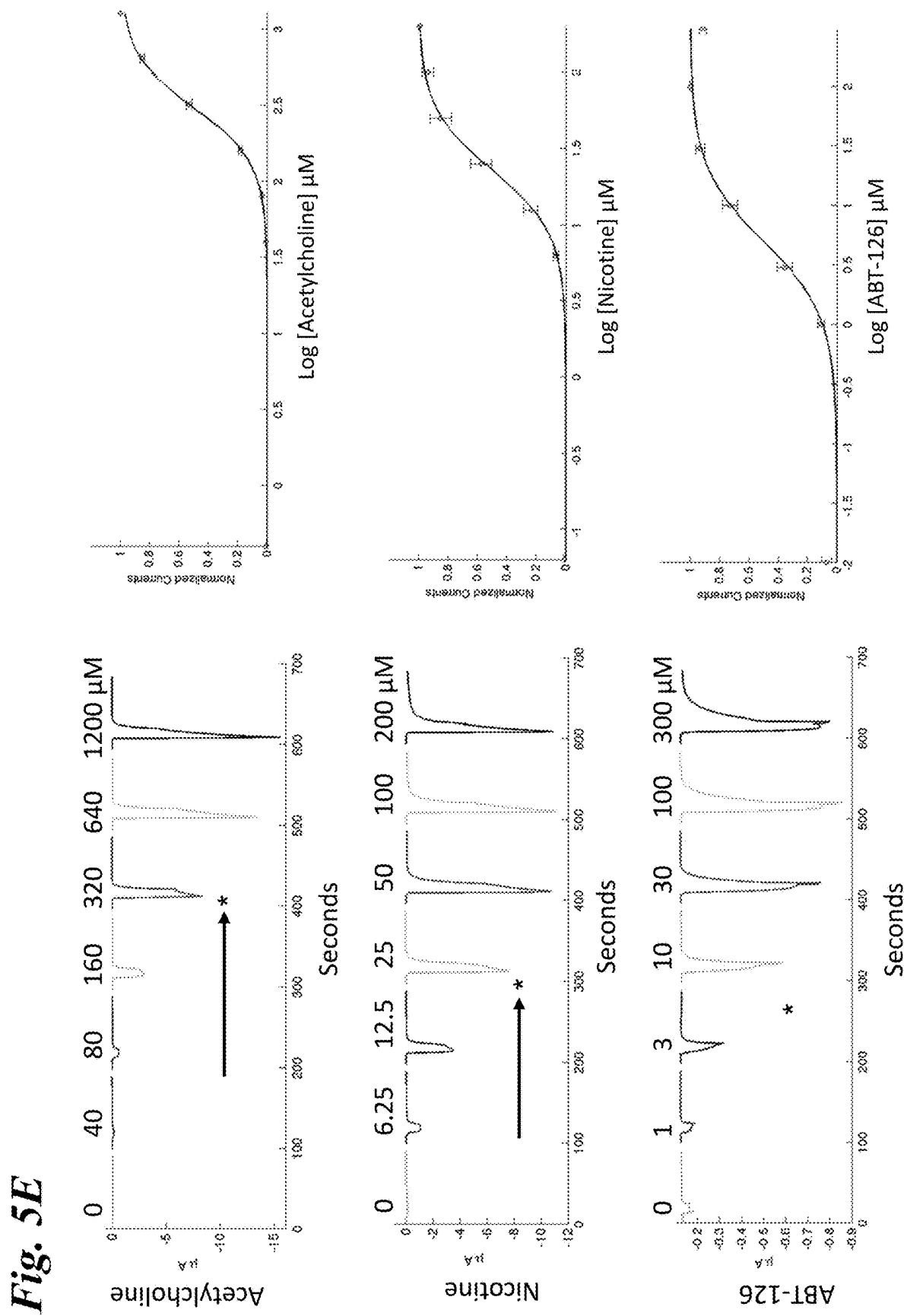
Figure 5F:
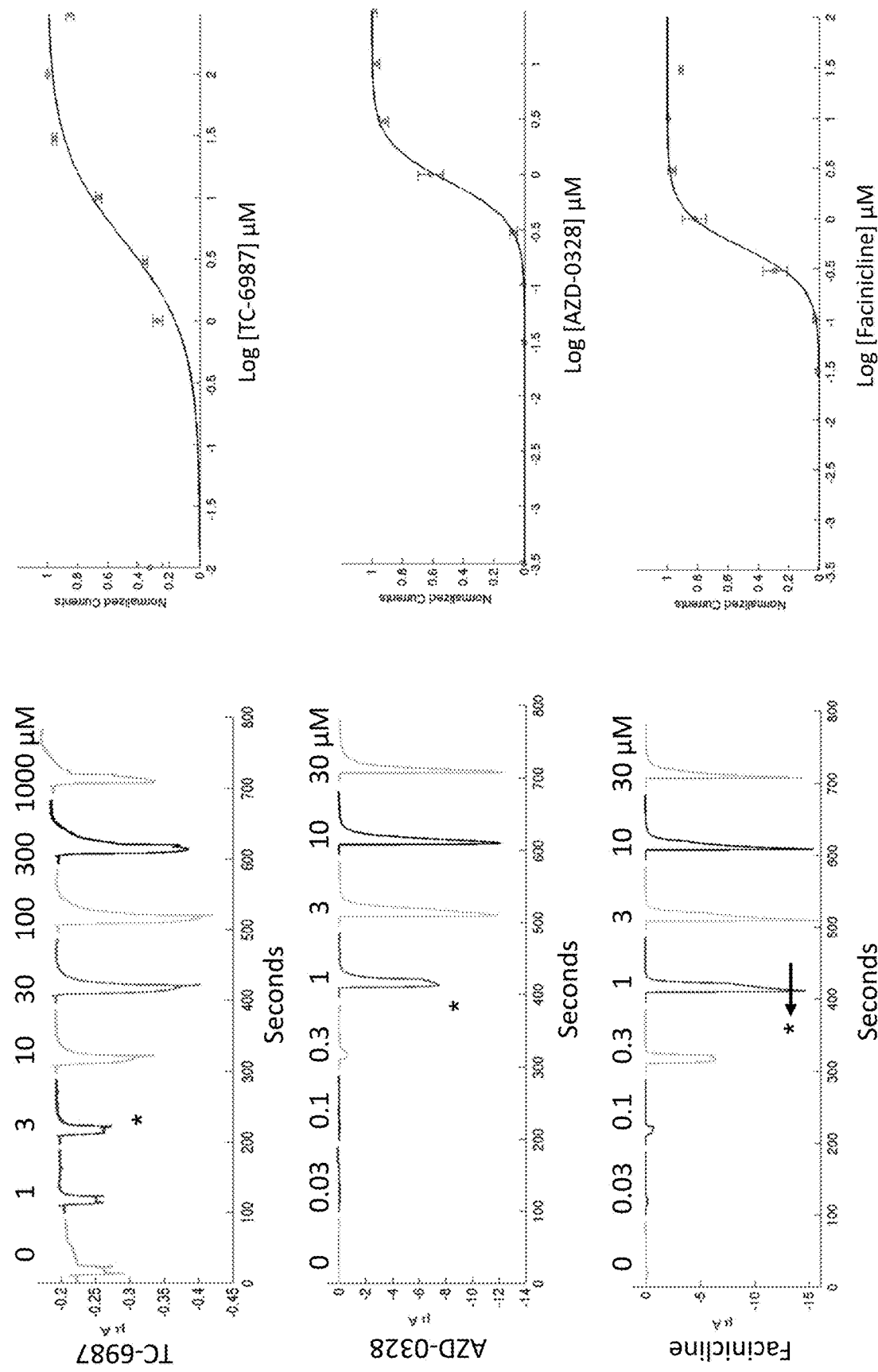

In some embodiments, the chimeric LGIC receptor is a CHRNA7/GLRA1 chimera (R229 junction), comprising the human α7-nAChR signal peptide (italics) and ligand binding domain (bold), fused to the human GlyRα1 ion pore domain (underlined) (e.g. SEQ ID NO:16 of FIG. 3):

```
                    (SEQ ID NO: 16, encoded by SEQ ID NO: 15)
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRRMGYYLIQMYIPSLLIVILSWI

SFWINMDAAPARVGLGITTVLTMTTQSSGSRASLPKVSYVKAIDIWMAVC

LLFVFSALLEYAAVNFVSRQHKELLRFRRKRRHHKSPMLNLFQEDEAGEG

RFNFSAYGMGPACLQAKDGISVKGANNSNTTNPPPAPSKSPEEMRKLFIQ

RAKKIDKISRIGFPMAFLIFNMFYWIIYKIVRREDVHNQ.
```

In some embodiments, the chimeric LGIC receptor is a CHRNA7/GLRA1 (R228 junction) chimera, comprising the human α7-nAChR signal peptide (italics) and ligand binding domain (bold), fused to the human GlyRα1 ion pore domain (underlined):

```
                                        (SEQ ID NO: 17)
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFVECCKEPYPDVTFTVTMRRQMGYYLIQMYIPSLLIVILSWI

SFWINMDAAPARVGLGITTVLTMTTQSSGSRASLPKVSYVKAIDIWMAVC

LLFVFSALLEYAAVNFVSRQHKELLRFRRKRRHHKSPMLNLFQEDEAGEG

RFNFSAYGMGPACLQAKDGISVKGANNSNTTNPPPAPSKSPEEMRKLFIQ

RAKKIDKISRIGFPMAFLIFNMFYWIIYKIVRREDVHNQ.
```

In some embodiments, the chimeric LGIC receptor is a CHRNA7/GLRA1 (V224 junction) chimera, comprising the human α7-nAChR signal peptide (italics) and ligand binding domain (bold), fused to the human GlyRα1 ion pore domain (underlined):

```
                                        (SEQ ID NO: 18)
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFVECCKEPYPDVTFTVHLERQMGVVLIQMYIPSLLIVILSWI

SFWINMDAAPARVGLGITTVLTMTTQSSGSRASLPKVSYVKAIDIWMAVC

LLFVFSALLEYAAVNFVSRQHKELLRFRRKRRHHKSPMLNLFQEDEAGEG

RFNFSAYGMGPACLQAKDGISVKGANNSNTTNPPPAPSKSPEEMRKLFIQ

RAKKIDKISRIGFPMAFLIFNMFYWIIYKIVRREDVHNQ.
```

In some embodiments, the chimeric LGIC receptor is a CHRNA7/GLRA1 (Y233 junction) chimera, comprising the human α7-nAChR signal peptide (italics) and ligand binding domain (bold), fused to the human GlyRα1 ion pore domain (underlined):

```
                                        (SEQ ID NO: 19)
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFVECCKEPYPDVTFTVTMRRRTLYYLIQMVIPSLLIVILSWI

SFWINMDAAPARVGLGITTVLTMTTQSSGSRASLPKVSYVKAIDIWMAVC

LLFVFSALLEYAAVNFVSRQHKELLRFRRKRRHHKSPMLNLFQEDEAGEG

RFNFSAYGMGPACLQAKDGISVKGANNSNTTNPPPAPSKSPEEMRKLFIQ

RAKKIDKISRIGFPMAFLIFNMFYWIIYKIVRREDVHNQ.
```

In some embodiments, the chimeric LGIC receptor is a CHRNA7/GLRA1 chimera (R229 junction), comprising the human α7-nAChR signal peptide (italics) and ligand binding domain (bold), fused to the human GlyRα1 ion pore domain (underlined) comprising an α7-nAChR M2-M3 linker (lowercase):

```
(a)
                    (SEQ ID NO: 21, encoded by SEQ ID NO: 20)
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRRMGYYLIQMYIPSLLIVILSWI

SFWINMDAAPARVGLGITTVLTMTTQSSGSeimpatsdsvSYVKAIDIWM

AVCLLFVFSALLEYAAVNFVSRQHKELLRFRRKRRHHKSPMLNLFQEDEA

GEGRFNFSAYGMGPACLQAKDGISVKGANNSNTTNPPPAPSKSPEEMIRK

LFIQRAKKIDKISRIGFPMAFLIFNMFYWIIYKIVRREDVHNQ;

(b)
                    (SEQ ID NO: 23, encoded by SEQ ID NO: 22)
MRCSPGGVWLALAASLLHVSLQGEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG
```

-continued

IPGKRSERFYECCKEPYPDVTFTVTMRRR<u>MGYYLIQMYIPSLLIVILSWI

SFWINMDAAPARVGLGITTVLTMTTQSSGSeimpatsdsvpliaqAIDIW

MAVCLLFVFSALLEYAAVNFVSRQHKELLRFRRKRRHHKSPMLNLFQEDE

AGEGRFNFSAYGMGPACLQAKDGISVKGANNSNTTNPPPAPSKSPEEMRK

LFIQRAKKIDKISRIGFPMAFLIFNMFYWIIYKIVRREDVHNQ</u>;

(c)

(SEQ ID NO: 25, encoded by SEQ ID NO: 24)
*MRCSPGGVWLALAASLLHVSLQ*GEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRR<u>MGYYLIQMYIPSLLIVILSWI

SFWINMDAAPARVGLGITTVLTMTTQSSGSRASLPKV</u>sdsvpl<u>IDIWMAV

CLLFVFSALLEYAAVNFVSRQHKELLRFRRKRRHHKSPMLNLFQEDEAGE

GRFNFSAYGMGPACLQAKDGISVKGANNSNTTNPPPAPSKSPEEMRKLFI

QRAKKIDKISRIGFPMAFLIFNMFYWIIYKIVRREDVHNQ</u>;

(d)

(SEQ ID NO: 27, encoded by SEQ ID NO: 26)
*MRCSPGGVWLALAASLLHVSLQ*GEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTM<u>ERQMGYYLIQMYIPSLLIVILSWI

SFWINMDAAPARVGLGITTVLTMTTQSSGSeimpatsdsvpliaqAIDIW

MAVCLLFVFSALLEYAAVNFVSRQHKELLRFRRKRRHHKSPMLNLFQEDE

AGEGRFNFSAYGMGPACLQAKDGISVKGANNSNTTNPPPAPSKSPEEMRK

LFIQRAKKIDKISRIGFPMAFLIFNMFYWIIYKIVRREDVHNQ</u>;

(e)

(SEQ ID NO: 29, encoded by SEQ ID NO: 28);
*MRCSPGGVWLALAASLLHVSLQ*GEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRRT<u>GYYLIQMYIPSLLIVILSWI

SFWINMDAAPARVGLGITTVLTMTTQSSGSeimpatsdsvpliaqAIDIW

MAVCLLFVFSALLEYAAVNFVSRQHKELLRFRRKRRHHKSPMLNLFQEDE

AGEGRFNFSAYGMGPACLQAKDGISVKGANNSNTTNPPPAPSKSPEEMRK

LFIQRAKKIDKISRIGFPMAFLIFNMFYWIIYKIVRREDVHNQ</u>
or (f)

(SEQ ID NO: 31, encoded by SEQ ID NO: 30)
*MRCSPGGVWLALAASLLHVSLQ*GEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

IPGKRSERFYECCKEPYPDVTFTVTMRRRT<u>YYLIQMYIPSLLIVILSWI

SFWINMDAAPARVGLGITTVLTMTTQSSGSeimpatsdsvpliaqAIDIW

MAVCLLFVFSALLEYAAVNFVSRQHKELLRFRRKRRHHKSPMLNLFQEDE

AGEGRFNFSAYGMGPACLQAKDGISVKGANNSNTTNPPPAPSKSPEEMRK

LFIQRAKKIDKISRIGFPMAFLIFNMFYWIIYKIVRREDVHNQ</u>.

In some embodiments, the chimeric LGIC receptor is a CHRNA7/GLRA1 chimera comprising the human α7-nAChR signal peptide (italics) and ligand binding domain (bold) comprising an GlyRα1 Cys-loop sequence (lowercase); fused to the human GlyRα1 ion pore domain (underlined) (see, e.g. SEQ ID NO:34 of FIG. 3):

(SEQ ID NO: 33, encoded by SEQ ID NO: 32)
*MRCSPGGVWLALAASLLHVSLQ*GEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSc pmdlknfpmdvqtcKLKFGSWSYGGWSLDLQMQEADISGYIPNGEWDLVG

IPGKRSERFYECCKEPYPDVTFTVTMRRR<u>MGYYLIQMYIPSLLIVILSWI

SFWINMDAAPARVGLGITTVLTMTTQSSGSRASLPKVSYVKAIDIWMAVC

LLFVFSALLEYAAVNFVSRQHKELLRFRRKRRHHKSPMLNLFQEDEAGEG

RFNFSAYGMGPACLQAKDGISVKGANNSNTTNPPPAPSKSPEEMRKLFIQ

RAKKIDKISRIGFPMAFLIFNMFYWITYKIVRREDVHNQ</u>.

(a)

(SEQ ID NO: 35, encoded by SEQ ID NO: 34)
*MRCSPGGVWLALAASLLHVSLQ*GEFQRKLYKELVKNYNPLERPVANDSQP

LTVYFSLSLLQIMDVDEKNQVLTTNIWLQMSWTDHYLQWNVSEYPGVKTV

RFPDGQIWKPDILLYNSADERFDATFHTNVLVNSSGHCQYLPPGIFKSSc pmdlknFPFDVQHCKLKFGSWSYGGWSLDLQMQEADISGYIPNGEWDLVG

IPGKRSERFYECCKEPYPDVTFTVTMRRR<u>MGYYLIQMYIPSLLIVILSWI

SFWINMDAAPARVGLGITTVLTMTTQSSGSRASLPKVSYVKAIDIWMAVC

LLFVFSALLEYAAVNFVSRQHKELLRFRRKRRHHKSPMLNLFQEDEAGEG

RFNFSAYGMGPACLQAKDGISVKGANNSNTTNPPPAPSKSPEEMRKLFIQ

RAKKIDKISRIGFPMAFLIFNMFYWIIYKIVRREDVHNQ</u>.

In some embodiments, the chimeric LGIC receptor is a CHRNA7/GLRA1 chimera comprising the human α7-nAChR signal peptide (italics) and ligand binding domain (bold) comprising an GlyRα1 β1-2 loop sequence (lowercase); fused to the human GlyRα1 ion pore domain (underlined):

(a)

(SEQ ID NO: 37, encoded by SEQ ID NO: 36)
*MRCSPGGVWLALAASLLHVSLQ*GEFQRKLYKELVKNYNPLERPVANDSQP

LTVYFSLSLLQIMDVDettmVLTTNIWLQMSWTDHYLQWNVSEYPGVKTV

RFPDGQIWKPDILLYNSADERFDATFHTNVLVNSSGHCQYLPPGIFKSSC

YIDVRWFPFDVQHCKLKFGSWSYGGWSLDLQMQEADISGYIPNGEWDLVG

-continued
IPGKRSERFYECCKEPYPDVTFTVTMRRR<u>MGYYLIQMYIPSLLIVILSWI</u>
<u>SFWINMDAAPARVGLGITTVLTMTTQSSGSRASLPKVSYVKAIDIWMAVC</u>
<u>LLFVFSALLEYAAVNFVSRQHKELLRFRRKRRHHKSPMLNLFQEDEAGEG</u>
<u>RFNFSAYGMGPACLQAKDGISVKGANNSNTTNPPPAPSKSPEEMRKLFIQ</u>
<u>RAKKIDKISRIGFPMAFLIFNMFYWIIYKIVRREDVHNQ</u>.

In some embodiments, the chimeric LGIC receptor is a CHRNA7/GLRA1 chimera comprising the human α7-nAChR signal peptide (italics) and ligand binding domain (bold) comprising an GlyRα1 β1-2 loop sequence (lowercase) and Cys-loop sequence (lowercase); fused to the human GlyRα1 ion pore domain (underlined) (e.g. SEQ ID NO:41 of FIG. 3):

(a)
(SEQ ID NO: 39, encoded by SEQ ID NO: 38)
*MRCSPGGVWLALAASLLHVSLQ*GEFQRKLYKELVKNYNPLERPVANDSQP
LTVYFSLSLLQIMDiaettmdLTTNIWLQMSWTDHYLQWNVSEYPGVKTV
RFPDGQIWKPDILLYNSADERFDATFHTNVLVNSSGHCQYLPPGIFKSSc
pmdlknfpmdvqtcKLKFGSWSYGGWSLDLQMQEADISGYIPNGEWDLVG
IPGKRSERFYECCKEPYPDVTFTVTMRRR<u>MGYYLIQMYIPSLLIVILSWI</u>
<u>SFWINMDAAPARVGLGITTVLTMTTQSSGSRASLPKVSYVKAIDIWMAVC</u>
<u>LLFVFSALLEYAAVNFVSRQHKELLRFRRKRRHHKSPMLNLFQEDEAGEG</u>
<u>RFNFSAYGMGPACLQAKDGISVKGANNSNTTNPPPAPSKSPEEMRKLFIQ</u>
<u>RAKKIDKISRIGFPMAFLIFNMFYWIIYKIVRREDVHNQ</u>.

(b)
(SEQ ID NO: 41, encoded by SEQ ID NO: 40)
*MRCSPGGVWLALAASLLHVSLQ*GEFQRKLYKELVKNYNPLERPVANDSQP
LTVYFSLSLLQIMDVDettmVLTTNIWLQMSWTDHYLQWNVSEYPGVKTV
RFPDGQIWKPDILLYNSADERFDATFHTNVLVNSSGHCQYLPPGIFKSSc
pmdlknfpmdvqtcKLKFGSWSYGGWSLDLQMQEADISGYIPNGEWDLVG
IPGKRSERFYECCKEPYPDVTFTVTMRRR<u>MGYYLIQMYIPSLLIVILSWI</u>
<u>SFWINMDAAPARVGLGITTVLTMTTQSSGSRASLPKVSYVKAIDIWMAVC</u>
<u>LLFVFSALLEYAAVNFVSRQHKELLRFRRKRRHHKSPMLNLFQEDEAGEG</u>
<u>RFNFSAYGMGPACLQAKDGISVKGANNSNTTNPPPAPSKSPEEMRKLFIQ</u>
<u>RAKKIDKISRIGFPMAFLIFNMFYWIIYKIVRREDVHNQ</u>.

(c)
(SEQ ID NO: 43, encoded by SEQ ID NO: 42)
*MRCSPGGVWLALAASLLHVSLQ*GEFQRKLYKELVKNYNPLERPVANDSQP
LTVYFSLSLLQIMDVDettmVLTTNIWLQMSWTDHYLQWNVSEYPGVKTV
RFPDGQIWKPDILLYNSADERFDATFHTNVLVNSSGHCQYLPPGIFKSSc
pmdlknfpmdvqtcKLKFGSWSYGGWSLDLQMQEADISGYIPNGEWDLVG
IPGKRSERFYECCKEPYPDVTFTVTM<u>ERQ</u>MGYYLIQMYIPSLLIVILSWI
SFWINMDAAPARVGLGITTVLTMTTQSSGSRASLPKVSYVKAIDIWMAVC
LLFVFSALLEYAAVNFVSRQHKELLRFRRKRRHHKSPMLNLFQEDEAGEG
RFNFSAYGMGPACLQAKDGISVKGANNSNTTNPPPAPSKSPEEMRKLFIQ
RAKKIDKISRIGFPMAFLIFNMFYWIIYKIVRREDVHNQ.

(d)
(SEQ ID NO: 45, encoded by SEQ ID NO: 44)
*MRCSPGGVWLALAASLLHVSLQ*GEFQRKLYKELVKNYNPLERPVANDSQP
LTVYFSLSLLQIMDiaettmdLTTNIWLQMSWTDHYLQWNVSEYPGVKTV
RFPDGQIWKPDILLYNSADERFDATFHTNVLVNSSGHCQYLPPGIFKSSc
pmdlknfpmdvqtcKLKFGSWSYGGWSLDLQMQEADISGYIPNGEWDLVG
IPGKRSERFYECCKEPYPDVTFTVTMERQ<u>MGYYLIQMYIPSLLIVILSWI</u>
<u>SFWINMDAAPARVGLGITTVLTMTTQSSGSRASLPKVSYVKAIDIWMAVC</u>
<u>LLFVFSALLEYAAVNFVSRQHKELLRFRRKRRHHKSPMLNLFQEDEAGEG</u>
<u>RFNFSAYGMGPACLQAKDGISVKGANNSNTTNPPPAPSKSPEEMRKLFIQ</u>
<u>RAKKIDKISRIGFPMAFLIFNMFYWIIYKIVRREDVHNQ</u>.

In some embodiments, the chimeric LGIC receptor is a CHRNA7/GLRA1 chimera comprising the human α7-nAChR signal peptide (italics) and ligand binding domain (bold) comprising an GlyRα1 β1-2 loop sequence (lowercase); fused to the human GlyRα1 ion pore domain (underlined) comprising human α7-nAChR M2-M3 linker (lowercase):

(a)
(SEQ ID NO: 47, encoded by SEQ ID NO: 46)
*MRCSPGGVWLALAASLLHVSLQ*GEFQRKLYKELVKNYNPLERPVANDSQP
LTVYFSLSLLQIMDVDettmVLTTNIWLQMSWTDHYLQWNVSEYPGVKTV
RFPDGQIWKPDILLYNSADERFDATFHTNVLVNSSGHCQYLPPGIFKSSC
YIDVRWFPFDVQHCKLKFGSWSYGGWSLDLQMQEADISGYIPNGEWDLVG
IPGKRSERFYECCKEPYPDVTFTVTMRRR<u>MGYYLIQMYIPSLLIVILSWI</u>
<u>SFWINMDAAPARVGLGITTVLTMTTQSSGS</u>eimpatsdsvpliaq<u>AIDIW</u>
<u>MAVCLLFVFSALLEYAAVNFVSRQHKELLRFRRKRRHHKSPMLNLFQEDE</u>
<u>AGEGRFNFSAYGMGPACLQAKDGISVKGANNSNTTNPPPAPSKSPEEMRK</u>
<u>LFIQRAKKIDKISRIGFPMAFLIFNMFYWIIYKIVRREDVHNQ</u>.

In some embodiments, the chimeric LGIC receptor is a CHRNA7/GLRA1 chimera comprising the human α7-nAChR signal peptide (italics) and ligand binding domain (bold) comprising a GlyRα1 Cys-loop sequence (lowercase); fused to the human GlyRα1 ion pore domain (underlined) comprising a human α7-nAChR M2-M3 linker (lowercase):

(a)
(SEQ ID NO: 49, encoded by SEQ ID NO: 48)
*MRCSPGGVWLALAASLLHVSLQ*GEFQRKLYKELVKNYNPLERPVANDSQP
LTVYFSLSLLQIMDVDEKNQVLTTNIWLQMSWTDHYLQWNVSEYPGVKTV
RFPDGQIWKPDILLYNSADERFDATFHTNVLVNSSGHCQYLPPGIFKSSc
pmdlknfpmdvqtcKLKFGSWSYGGWSLDLQMQEADISGYIPNGEWDLVG
IPGKRSERFYECCKEPYPDVTFTVTMRRR<u>MGYYLIQMYIPSLLIVILSWI</u>
<u>SFWINMDAAPARVGLGITTVLTMTTQSSGS</u>eimpatsdsvpliaq<u>AIDIW</u>
<u>MAVCLLFVFSALLEYAAVNFVSRQHKELLRFRRKRRHHKSPMLNLFQEDE</u>
<u>AGEGRFNFSAYGMGPACLQAKDGISVKGANNSNTTNPPPAPSKSPEEMRK</u>
<u>LFIQRAKKIDKISRIGFPMAFLIFNMFYWIIYKIVRREDVHNQ</u>.

In some embodiments, the chimeric LGIC receptor is a HTR3A/GLRA1 chimera (R241 junction), comprising the human 5HT3A serotonin receptor signal peptide (italics) and ligand binding domain (bold), fused to the human GlyRα1 ion pore domain (underlined):

(a)
(SEQ ID NO: 50)
*MLLWVQQALLALLLPTLLAQGEA*RRSRNTTRPALLRLSDYLLTNYRKGVR

PVRDWRKPTTVSIDVIVYAILNVDEKNQVLTTYIWYRQYWTDEFLQWNPE

DFDNITKLSIPTDSIWVPDILINEFVDVGKSPNIPYVYIRHQGEVQNYKP

LQVVTACSLDIYNFPFDVQNCSLTFTSWLHTIQDINISLWRLPEKVKSDR

SVFMNQGEWELLGVLPYFREFSMESSNYYAEMKFYVVIRRR<u>MGYYLIQMY</u>

<u>IPSLLIVILSWISFWINMDAAPARVGLGITTVLTMTTQSSGSRASLPKVS</u>

<u>YVKAIDIWMAVCLLFVFSALLEYAAVNFVSRQHKELLRFRRKRRHHKSPM</u>

<u>LNLFQEDEAGEGRFNFSAYGMGPACLQAKDGISVKGANNSNTTNPPPAPS</u>

<u>KSPEEMRKLFIQRAKKIDKISRIGFPMAFLIFNMFYWIIYKIVRREDVHN</u>

<u>Q</u>.

In some embodiments, the chimeric LGIC receptor is a HTR3A/GLRA1 chimera (V236 junction) comprising the human 5HT3A serotonin receptor signal peptide (italics) and ligand binding domain (bold), fused to the human GlyRα1 ion pore domain (underlined):

(a)
(SEQ ID NO: 51)
*MLLWVQQALLALLLPTLLAQGEA*RRSRNTTRPALLRLSDYLLTNYRKGVR

PVRDWRKPTTVSIDVIVYAILNVDEKNQVLTTYIWYRQYWTDEFLQWNPE

DFDNITKLSIPTDSIWVPDILINEFVDVGKSPNIPYVYIRHQGEVQNYKP

LQVVTACSLDIYNFPFDVQNCSLTFTSWLHTIQDINISLWRLPEKVKSDR

SVFMNQGEWELLGVLPYFREFSMESSNYYAEMKFYV<u>HLERQMGYYLIQMY</u>

<u>IPSLLIVILSWISFWINMDAAPARVGLGITTVLTMTTQSSGSRASLPKVS</u>

<u>YVKAIDIWMAVCLLFVFSALLEYAAVNFVSRQHKELLRFRRKRRHHKSPM</u>

<u>LNLFQEDEAGEGRFNFSAYGMGPACLQAKDGISVKGANNSNTTNPPPAPS</u>

<u>KSPEEMRKLFIQRAKKIDKISRIGFPMAFLIFNMFYWIIYKIVRREDVHN</u>

<u>Q</u>.

In some embodiments, the chimeric LGIC receptor is a GABRB3/GLRA1 chimera (Y245 junction), comprising the human GABA-A β3 signal peptide (italics) and ligand binding domain (bold), fused to the human GlyRα1 ion pore domain (underlined):

(a)
(SEQ ID NO: 52)
*MWGLAGGRLFGIFSAPVLVAVVCCA*QSVNDPGNMSFVKETVDKLLKGYDI

RLRPDFGGPPVCVGMNIDIASIDMVSEVNMDYTLTMYFQQYWRDKRLAYS

GIPLNLTLDNRVADQLWVPDTYFLNDKKSFVHGVTVKNRMIRLHPDGTVL

YGLRITTTAACMMDLRRYPLDEQNCTLEIESYGYTTDDIEFYWRGGDKAV

TGVERIELPQFSIVEHRLVSRNVVFATGAYPRLSLSFRLKRNIGY<u>MGYYL</u>

-continued
<u>IQMVIPSLLIVILSWISFWINMDAAPARVGLGITTVLTMTTQSSGSRASL</u>

<u>PKVSYVKAIDIWMAVCLLFVFSALLEYAAVNFVSRQHKELLRFRRKRRHH</u>

<u>KSPMLNLFQEDEAGEGRFNFSAYGMGPACLQAKDGISVKGANNSNTTNPP</u>

<u>PAPSKSPEEMRKLFIQRAKKIDKISRIGFPMAFLIFNMFYWIIYKIVRRE</u>

<u>DVHNQ</u>.

As discussed above, in some aspects, the subject engineered receptor comprises at least one amino acid mutation that alters the potency of a ligand on the engineered receptor relative to its potency on the unmutated parental receptor. Put another way, the one or more amino acid mutations, e.g. a loss-of-function mutations or a gain-of-function mutations, shift the responsiveness of the engineered receptor to the ligand relative to the responsiveness of the unmutated parental receptor. In some such embodiments the one or more mutations is in the ligand binding domain of the engineered receptor. In some embodiments, as when the ligand binding domain of the engineered receptor is a Cys-loop receptor protein, the one or more amino acid mutations is a substitution at a residue corresponding to a residue of α7-nAChR (SEQ ID NO:4) selected from the group consisting of W77, Y94, R101, W108, Y115, T128, N129, V130, L131, Q139, L141, Y151, S170, W171, S172, S188, Y190, Y210, C212, C213 and Y217. In some embodiments, one residue is substituted. In some embodiments, 2, 3, 4, or 5 or more residues are substituted, e.g. 6, 7, 8, 9 or 10 residues are substituted. In certain embodiments, the residue corresponds to a residue of α7-nAChR (SEQ ID NO:4) that is selected from the group consisting of W77, R101, Y115, N129, L131, S170, S172, and S188. In certain embodiments, the one or more substitutions is selected from a substitution listed in FIG. 8A-I. In certain embodiments, the one or more substitutions is within an α7-nAChR sequence.

In some embodiments, the one or more substitutions decreases, e.g. 2-fold or more, 3-fold or more, 4-fold or more, 5-fold or more, 10-fold or more, 20-fold or more, 30-fold or more, 50-fold or more, or 100-fold, the responsiveness of an engineered receptor to acetylcholine and a non-native ligand. In some such embodiments, the one or more substitutions corresponds to an amino acid substitution in an α7-nAChR sequence described in FIGS. 8A-F and 8H. In certain embodiments, the one or more substitutions is a substitution corresponding to R101I, R101S, R101D, Y115L, Y115M, Y115D, Y115T, T128M, T128R, T128I, N129I, N129V, N129P, N129W, N129T, N129D, N129E, L131P, L131T, L131D, L131S, L141S, L141R, W171F, W171H, S172F, S172Y, S172R, S172D, C212A, C212L, or C213P of α7-nAChR. In other instances, the one or more substitutions decreases the potency of acetylcholine on the engineered receptor selectively. In other words, the one or more substitutions decreases the responsiveness of the engineered receptor to acetylcholine while essentially maintaining responsiveness to non-native ligand or otherwise decreasing the responsiveness of the engineered receptor to acetylcholine 2-fold or more, e.g. 3-fold, 4-fold, 5-fold or more, in some instances 10-fold, 20-fold, 50-fold, or 100-fold or more, than it decreases the responsiveness of the engineered receptor to non-native ligand. Exemplary substitutions include those provided in FIG. 8H, namely, a substitution corresponding to L131S, L131T, L131D, or S172D of α7-nAChR. In yet other embodiments, the one or more substitutions decreases the potency of a non-native ligand on the engineered receptor selectively. In other words, the one or more substitutions decreases the responsiveness of the engineered receptor to non-native ligand while essentially maintaining responsiveness to acetylcholine or otherwise decreasing the responsiveness of the engineered receptor to non-native ligand 2-fold or more, e.g. 3-fold, 5-fold or more, in some instances 10-fold, 20-fold or 50-fold or more, than it decreases the responsiveness of the engineered receptor to acetylcholine. Exemplary substitutions include those in FIG. 8G, namely, a substitution corresponding to W77M, Y115W, S172T, or S172C of α7-nAChR. In certain embodiments, the one or more substitutions is within an α7-nAChR sequence. In certain embodiments, the non-native ligand is selected from AZD-0328, TC6987, ABT-126 and Facinicline/RG3487.

In other embodiments, the one or more substitutions increases, e.g. 2-fold or more, 3-fold or more, 4-fold or more. 5-fold or more, 10-fold or more, 20-fold or more, 30-fold or more, 50-fold or more, or 100-fold, the responsiveness of the engineered receptor to acetylcholine and/or non-native ligand. Exemplary substitutions include those described in FIG. 8G or 8I, i.e. a substitution corresponding to L131N, L141W, S170G, S170A, S170L, S170I, S170V, S170P, S170F, S170M, S170T, S170C, S172T, S172C, S188I, S188V, S188F, S188M, S188Q, S188T, S188P or S188W. In some instance, the one or more substitutions increases potency of both acetylcholine and non-native ligand, e.g. substitutions corresponding to L131N, S170G, S170A, S170L, S170I, S170V, S170P, S170F, S170M, S170T, S170C, S172T, S188I, S188V, S188F, S188M, S188Q and S188T of α7-nAChR. In other instances, the one or more substitutions increases the potency of acetylcholine on the engineered receptor selectively. In other words, the one or more substitutions increases the responsiveness of the engineered receptor to acetylcholine 2-fold or more, e.g. 3-fold, 4-fold, or 5-fold or more, in some instances 10-fold, 20-fold, 50-fold, or 100-fold, than it increases the responsiveness of the engineered receptor to non-native ligand, e.g. substitutions corresponding to L141W, S172T, S172C, S188P or S188W, of α7-nAChR. In certain embodiments, the one or more substitutions is within an α7-nAChR sequence. In certain embodiments, the non-native ligand is selected from AZD-0328, TC6987, ABT-126 and Facinicline/RG3487. In yet other instances, the one or more substitutions increases the potency of the non-native ligand on the engineered receptor selectively. In other words, the one or more substitutions increases the responsiveness of the engineered receptor to non-native ligand 2-fold or more, e.g. 3-fold, 5-fold or more, in some instances 10-fold, 20-fold or 50-fold or more, than it increases the responsiveness of the engineered receptor to acetylcholine.

Typically, the amino acid residue that is mutated in the subject engineered receptor is not an amino acid corresponding to R27, E41, Q79, Q139, 141, G175, Y210, P216, Y217, or D219 of wild type α7 nAChR (SEQ ID NO:4). More typically still, the substitution is not a substitution corresponding to W77F, W77Y, W77M, Q79A, Q79Q, Q79S, Q79G, Y115F, L131A, L131G, L131M, L131N, L131Q, L131V, L131F, Q139G, Q139L, G175K, G175A, G175F, G175H, G175M, G175R, G175S, G175V, Y210F, P216I, Y217F, or D219A in wild type α7 nAChR. Alternatively, if such a substitution does exist within the engineered receptor, it exists in combination with one or more of the amino acid mutations described herein.

For example, it has been discovered that residues Y94, Y115, Y151, and Y190 of α7-nAChR (SEQ ID NO:4) mediate binding of the native ligand acetylcholine. Mutations at these residues will reduce binding of acetylcholine and hence are loss of function mutations. In contrast, residues W77, Y115, N129, V130, L131, Q139, L141, S170, Y210, C212, C213 and Y217 of the α7-nAChR mediate the binding of non-native ligand AZD0328 to this receptor, and mutation of these residues may increase the affinity of AZD0328 and/or other ligands for this receptor and hence be gain-of-function mutations. In some embodiments, the subject engineered receptor comprises a mutation in one or more amino acid residues of the ligand binding domain region of α7-nAChR (SEQ ID NO:4) or the ligand binding domain of a chimeric receptor that comprises the ligand binding domain region of α7-nAChR, where the one or more amino acid residues is selected from the group consisting of W77, Y94, Y115, N129, V130, L131, Q139, L141, Y151, S170, Y190, Y210, C212, C213 and Y217. In certain embodiments, the mutation in the one or more amino acid residues of the ligand binding domain region of α7-nAChR (SEQ ID NO:4) or the ligand binding domain of a chimeric receptor that comprises the ligand binding domain region of α7-nAChR is a substitution at one or more amino acid residues selected from the group consisting of W77, Y94, Y115, N129, V130, L131, Q139, L141, Y151, S170, Y190, Y210, C212, C213 and Y217.

As another example, it has been discovered that residues Y115, L131, L141, S170, W171, S172, C212, and Y217 of α7-nAChR (SEQ ID NO:4) mediate binding of acetylcholine and/or nicotine, and mutations at one or more of these residues will reduce binding of acetylcholine and/or nicotine. R101, Y115, L131, L141, W171, S172, S188, Y210, and Y217 of α7-nAChR mediate binding of the non-native ligand ABT126, and mutation of one or more of these residues is expected to increase the affinity of ABT126 and/or other ligands for α7-nAChR. R101, Y115, T128, N129, L131, L141, W171, S172, Y210, C212, C213 and Y217 of α7-nAChR mediate binding of the non-native ligand TC6987, and mutation of one or more of these residues is expected to increase the affinity of TC6987 and/or other ligands for α7-nAChR. R101, N120, L131, L141, S170, W171, S172, Y210, and Y217 of α7-nAChR mediate binding of the non-native ligand Facinicline/RG3487, and mutation of one or more of these residues is expected to increase the affinity of Facinicline/RG3487 and/or other ligands for α7-nAChR. In some embodiments, the subject engineered receptor comprises a mutation in one or more amino acid residues of the ligand binding domain region of α7-nAChR or the ligand binding domain of a chimeric receptor that comprises the ligand binding domain region of α7-nAChR, where the one or more amino acid residues is selected from the group consisting of R101, Y115, T128, N120, N129, L131, L141, S170, W171, S172, S188, Y210, C212, C213 and Y217. In some embodiments, the one or more amino acid residues alters the binding of acetylcholine and/or nicotine to α7-nAChR, wherein the amino acid is selected from the group consisting of Y115, L131, L141, S170, W171, S172, C212 and Y217 of α7-nAChR. In certain such embodiments, the amino acid is selected from C212 and S170. In some embodiments, the mutation in the one or more amino acid residues alters the binding of ABT126 to α7-nAChR, wherein one or more amino acid residues is selected from the group consisting of R101, Y115, L131, L141, W171, S172, S188, Y210, and Y217 of α7-nAChR. In certain such embodiments, the amino acid is selected from R101, S188, and Y210. In some embodiments, the mutation in the one or more amino acid residues alters the binding of TC6987 to α7-nAChR, wherein one or more amino acid residues is selected from the group consisting of R101, Y115, T128, N129, L131, L141, W171, S172, Y210, C212, C213 and Y217 of α7-nAChR. In certain such embodiments, the amino acid is selected from R101, T128, N129, Y210 and C213. In some embodiments, the mutation in the one or more amino acid residues alters the binding of Facinicline/RG3487 to α7-nAChR, wherein one or more amino acid residues is selected from the group consisting R101, N120, L131, L141, S170, W171, S172, Y210, and Y217 of α7-nAChR. In certain such embodiments, the amino acid is selected from Y210, R101, and N129.

As another example, it has been discovered that residues W85, R87, Y136, Y138, G146, N147, Y148, K149, S177, S178, L179, Y228, and Y229 of 5HT3 (SEQ ID NO:6) mediate binding of serotonin, and mutations at one or more of these residues will reduce binding of serotonin to 5HT3. D64, I66, W85, R87, Y89, N123, G146, Y148, T176, S177, S178, W190, R191, F221, E224, Y228, Y229 and E231 of 5HT3 mediate binding of the non-native ligand Cilansetron, and mutation of one or more of these residues is expected to increase the affinity of Cilansetron and/or other ligands for 5HT3. In some embodiments, the subject engineered receptor comprises a mutation in one or more amino acid residues of the ligand binding domain region 5HT3A or the ligand binding domain of a chimeric receptor that comprises the ligand binding domain region of 5HT3, where the one or more amino acid residues is selected from the group consisting of D64, I66, W85, R87, Y89, N123, Y136, Y138, G146, N147, Y148, K149, T176, S177, S178, L179, W190, R191, F221, E224, Y228, Y229, and E231. In some embodiments, the mutation in the one or more amino acid residues alters the binding of serotonin to 5HT3, wherein the amino acid is selected from the group consisting of W85, R87, Y136, Y138, G146, N147, Y148, K149, S177, S178, L179, Y228, and Y229 of 5HT3A. In certain such embodiments, the amino acid is selected from Y136, Y138, N147, K149, and L179. In some embodiments, the mutation in the one or more amino acid residues alters the binding of Cilansetron to 5HT3 wherein one or more amino acid residues is selected from the group consisting of D64, I66, W85, R87, Y89, N123, G146, Y148, T176, S177, S178, W190, R191, F221, E224, Y228, Y229 and E231 of 5HT3A. In certain such embodiments, the amino acid is selected from D64, I66, Y89, N123, T176, W190, R191, F221, E224, and E231.

In some embodiment, the one or more mutations that affects the ability of a ligand to modulate the activity of the LGIC is located in the ion pore domain of the LGIC. For example, residue T279 of the serotonin receptor 5HT3A mediates the way in which the ligand modulates the activity of the channel, such that mutation of this residue to, e.g. serine (T279S), converts the effect from being antagonistic (i.e., reducing the activity of the LGIC) to agonistic (i.e. promoting the activity of the channel). In some embodiments, the subject ligand gated ion channel comprises a mutation in one or more amino acid residues of the ion pore domain of the human 5HT3A (SEQ ID NO:6) or the ion pore domain of a chimeric LGIC receptor that comprises the ion pore domain of 5HT3A, where the substitution is in an amino acid corresponding to 279 of SEQ ID NO:6. In certain embodiments, the substitution is a T279S substitution relative to SEQ ID NO:6.

In some aspects, the subject ligand-gated ion channel comprises one or more non-desensitizing mutations. When used in the context of a ligand-gated ion channel, "desensitization" refers to the progressive reduction in ionic flux in the prolonged presence of agonist. This results in a progressive loss of responsiveness of the neuron to the ligand. By a non-desensitizing mutation, it is meant an amino acid mutation that prevents the LGIC from becoming desensitized to ligand, thereby preventing the neuron from becoming less responsive or nonresponsive to ligand. Non-desensitizing mutations can be readily identified by introducing the LGIC carrying the mutation into a neuron and analyzing the current flux over time during prolonged exposure to ligand. If the LGIC does not comprise a non-desensitizing mutation, the current will restore from peak to steady state during prolonged exposure, whereas if the LGIC comprises a non-desensitizing mutation, the current will remain at peak flux for the duration of exposure to ligand. Exemplary amino acid mutations that result in desensitization include a V322L mutation in the human GlyRα1 (V294L post-processing of the pro-protein to remove the signal peptide) and a L321V mutation in human GABA-A receptor GABRB3 (L296V post-processing of the pro-protein to remove the signal peptide). In some embodiments, the desensitizing mutation is the replacement of amino acid residues at or near the C-terminus of the LGIC with a desensitizing sequence, for example, a sequence having 90% identity or more to IDRLSRIAFPLLFGIFNLVYWATYLNREPQL (SEQ ID NO:53) derived from the C terminus of the protein encoded by GABAR1, e.g. the replacement of residues 455-479 in GABRR1 with IDRLSRIAFPLLFGIFNLVYWATYLNREPQL (SEQ ID NO:53). LGIC desensitization, methods for measuring desensitization of LGICs, and mutations that are non-desensitizing are well known in the art; see, e.g. Gielen et al. Nat Commun 2015 Apr. 20, 6:6829, and Keramidas et al. Cell Mol Life Sci. 2013 April; 70(7):1241-53, the full disclosures of which are incorporated herein by reference.

In some aspects, the subject ligand-gated ion channel comprises one or more conversion mutations. By a conversion mutation, it is meant a mutation that changes the permeability of the ion pore domain of the LGIC such that it becomes permissive to the conductance of a non-native ion, i.e. an ion that does not naturally allow to pass through. In some cases, the mutation converts the permeability from cation to anion, for example the replacement of amino acid residues 260-281 in human α7-nAChR (CHRNA7) (EKISLGITVLLSLTVFMLLVAE, SEQ ID NO:54) or the corresponding amino acids in another cation-permeable LGIC with the peptide sequence PAKIGLGITVLLSLTTFMSGVAN (SEQ ID NO:55). In some cases, the mutation converts the permeability from anion to cation, for example, the substitution of amino acid residue 279 of GLRA1 or the corresponding amino acid in another anion-permeable LGIC to glutamic acid (E), (which, as an A293E substitution in GLRA1 converts the LGIC from being anion-permissive to calcium-permissive), or the deletion of amino acid residue 278 of GLRA1 or the corresponding amino acid in another anion-permeable LGIC, the substitution of amino acid residue 279 of GLRA1 or the corresponding amino acid in another anion-permeable LGIC to glutamic acid (E), and the substitution of amino acid residue 293 of GLRA1 or the corresponding amino acid in another anion-permeable LGIC to valine (V) (which, as a P278Δ, A279E, T293V in GLRA1 converts the LGIC from being anion-permissive to cation-permissive).

Additional engineered receptors beyond those described herein can be readily identified by in vitro screening and validation methods, for example as described in FIG. 2 and the working examples herein. In some embodiments, a library of parental receptor mutants is generated from a limited number of parental receptors, such as those shown in FIG. 1 and described elsewhere herein. The parental receptors can be mutated using methods known in the art, including error prone PCR. In some embodiments, the library of parental receptor mutants is then transfected into yeast or mammalian cells and screened in high throughput to identify functional receptors (e.g., to identify parental receptor mutants that are capable of signaling in response to a binding agent or ligand). In some embodiments, the functional parental receptor mutants identified in this primary screen is then expressed in mammalian cells and screened for responsiveness to binding agents or ligands, e.g. by the plate reader and/or electrophysiology assays described herein. The parental receptor mutants that demonstrate either increased binding affinity for agonist binding agents, or that enable the use of antagonist or modulator binding agents as agonists in the secondary screen can then be selected and carried though further in vitro and/or in vivo validation and characterization assays. Such screening assays are known in the art, for example Armbruster, B. N. et al. (2007) PNAS, 104, 5163-5168; Nichols, C. D. and Roth, B. L. (2009) Front. Mol. Neurosci. 2, 16; Dong, S. et al. (2010) Nat. Protoc. 5, 561-573; Alexander, G. M. et al. (2009) Neuron 63, 27-39; Guettier, J. M. et al. (2009) PNAS 106, 19197-19202; Ellefson J. W. et al. (2014) Nat Biotechnol. 32(1):97-101; Maranhao A C and Ellington A D. (2017) ACS Synth Biol. 20; 6(1):108-119; Talwar S et al. (2013) PLoS One; 8(3):e58479; Gilbert D. F. et al. (2009) Front Mol Neurosci. 30; 2:17; Lynagh and Lynch, (2010), Biol Chem. 14:285(20), 14890-14897; Islam R. et al. (2016) ACS Chem Neurosci. 21; 7(12):1647-1657; and Myers et al. (2008) Neuron. 8:58(3): 362-373.

D. Binding Agents

The terms "binding agent" or "agent" are used interchangeably herein and refer to exogenous drugs or compounds with a known mechanism of action on a mammalian cell (e.g., are known to act as an agonist, antagonist, or modulator of a receptor). Binding agents can include proteins, lipids, nucleic acids, and/or small molecules. In some embodiments, binding agents include drugs or compounds that have been approved by the US Food and Drug Administration (FDA) for clinical use in the treatment of a particular disease (e.g., a neurological disease). In some embodiments, binding agents include drugs or compounds that have not been approved by the FDA for clinical use, but have been tested in one or more clinical trials, are currently being tested in one or more clinical trials, and/or are anticipated to be tested in one or more clinical trials. In some embodiments, binding agents include drugs or compounds that have not been approved by the FDA for clinical use, but are routinely used in laboratory research. In some embodiments, the binding agent is an analog of one of the aforementioned agents. In particular embodiments, a binding agent is selected from any one of the agents in Tables 2-9. In some such embodiments, the binding agent is selected from the group consisting of AZD0328, ABT-126, AQW-051, Cannabidiol, Cilansetron, PH-399733, FACINICLINE/RG3487/MEM-3454, and TC-5619/AT-101. In particular embodiments, the binding agent is an analog of Cilansetron, e.g. as described by one of the compound formulas 2-7 below in either its R or S enantiomer:

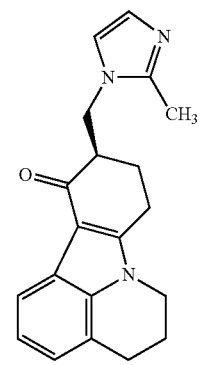

Compound 1 = cilansetron
(——CH3)

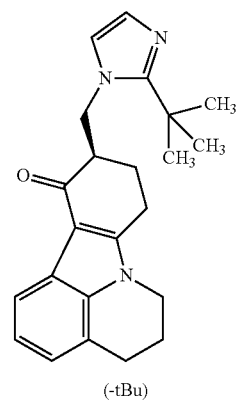

Compound 2

(-tBu)

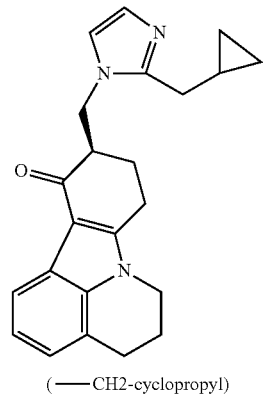

Compound 3

(——CH2-cyclopropyl)

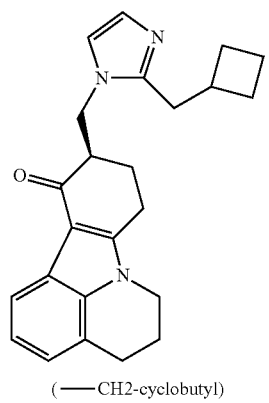

Compound 4

(——CH2-cyclobutyl)

Compound 5

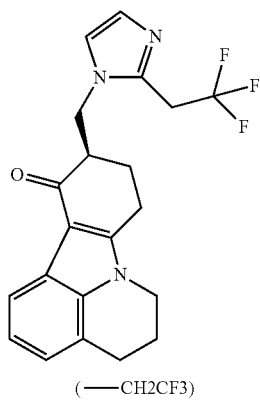

(—CH2CF3)

Compound 6

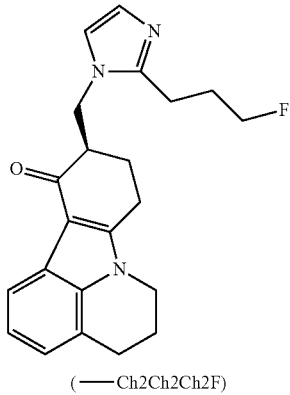

(—Ch2Ch2Ch2F)

Compound 7

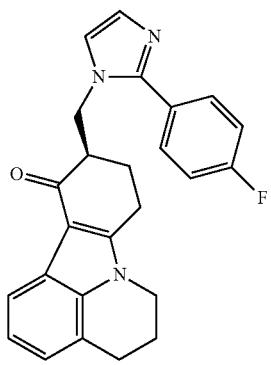

(-p-F-Phenyl)

In some embodiments, the binding agent acts as an agonist. The term "agonist" as used herein refers to a ligand or binding agent that induces a signaling response. In some embodiments, the binding agent acts as an antagonist. The term antagonist is used herein to refer to an agent that inhibits a signaling response.

In some embodiments, the binding agent is an anxiolytic, anticonvulsant, antidepressant, antipsychotic, antiemetic, nootropic, antibiotic, antifungal, antiviral, or an antiparasitic.

TABLE 2

Binding agents for Glycine Receptor (GlyR)

| Agonists | | Modulators/Binders | Antagonists | |
|---|---|---|---|---|
| Bilobalide | L-Serine | Gavestinel | 468816 | Lindane |
| Cannabidiol | MDL-27531 | Halothane | ACEA-2085 | MDL-100748 |
| D-Alanine | Methoxyflurane | | Bicuculline | MDL-102288 |
| D-Serine | Milacemide | | Brucine | MDL-105519 |
| Desflurane | Moxidectin | | Caffeine | PD-165650 |
| Doramectin | NRX-1050 | | Gavestinel | Picrotoxin |
| Emamectin | NRX-1060 | | Ginkgo biloba | Strychnine |
| Eprinomectin | P-9939 | | GV-196771 | Thiocolchicoside |
| Ethanol | Quisqualamine | | GW 468816 | Tutin |
| Glycine | Rapastinel | | HMR-2371 | UK-315716 |
| Hypotaurine | S-18841 | | L-695902 | ZD-9379 |
| Isoflurane | Sarcosine | | L-701324 | |
| Ivermectin | Sevoflurane | | | |
| L-Alanine | Taurine | | | |
| L-Proline | β-Alanine | | | |

TABLE 3

Binding Agents for λ-Aminobutyric Acid A Receptor (GABA-A)

| Agonists | Modulators/Binders | | Antagonists |
|---|---|---|---|
| 3-acyl-4-quinolone | (−)Epigallo-catechin-3-Gallate | Etifoxine | Pentobarbital | (±)-cis-(3-Aminocyclopentyl)butylphosphinic acid |
| Acamprosate | 10-Methoxy-yangonin | Etizolam | Petrichloral | (S)-(4-Aminocyclopent-1-enyl)butylphosphinic acid |
| Alfadolone | 11-Hydroxy-yangonin | Etomidate | PF-4480682 | Amoxapine |

TABLE 3-continued

Binding Agents for λ-Aminobutyric Acid A Receptor (GABA-A)

| Agonists | | Modulators/Binders | | Antagonists |
|---|---|---|---|---|
| Bamaluzole | 11-Methoxy-12-Hydroxy-dehydrokavain | Evt-201 | Phenazepam | Bicuculline |
| Basmisanil | 11-Methoxy-yangonin | Fasiplon | Phenobarbital | CGP-36742 (3-aminopropyl-n-butyl-phosphinic acid) |
| Bretazenil | 123i-Iomazenil | Fg-8205 | Pinazepam | Flumazenil |
| CACA | 2-Oxoquazepam | Fletazepam | Pipequaline | Gabazine |
| CAMP | 3-Hydroxy-phenazepam | Flubromazepam | Pivoxazepam | Ginkgo biloba |
| CP-409092 | 5-Hydroxykavain | Flubromazolam | Potassium Bromide | Lindane |
| Doramectin | 5,6-Dehydro-methysticin | Fludiazepam | Prazepam | Methohexital |
| Emamectin | 5,6-Dihydro-yangonin | Flumazenil | Premazepam | Picrotoxin |
| Eprinomectin | 5,6,7,8-Tetrahydro-yangonin | Flunitrazepam | Primidone | SKF-97541 (3-Aminopropyl (methyl)phosphinic acid) |
| Eszopiclone | 7,8-Dihydrokavain | Flurazepam | Proflazepam | TPMPA |
| Ethanol | 7,8-Dihydro-methysticin | Flutazolam | Propanidid | ZAPA ((Z)-3-[(Aminoiminomethyl)thio]prop-2-enoic acid) |
| Etomidate | 7,8-Dihydro-yangonin | Flutemazepam | Propofol | |
| Flunitrazepam | Abecarnil | Flutoprazepam | PWZ-007A | |
| GABA | Adinazolam | Fosazepam | PWZ-009A1 | |
| Gabamide | Allobarbital | Fospropofol | Pwz-029 | |
| GABOB | Allo-pregnanolone | Ganaxolone | Pyrazolam | |
| Gaboxadol | Alphaxolone | Gbld-345 | PZ-II-028 | |
| Gamma Hydroxybutyric Acid | Alphenal | Gedocarnil | PZ-II-029 | |
| Glutethimide | Alpidem | Gidazepam | Qh-Ii-66 | |
| Ibotenic acid | Alprazolam | Girisopam | Quazepam | |
| Imidazenil | Amentoflavone | Glutethimide | Quinidine Barbiturate | |
| Isoflurane | Amobarbital | Gyki-52466 | Reclazepam | |
| Isoguvacine | Apigenin | Gyki-52895 | Remimazolam | |
| Isonipecotic acid | Aprobarbital | Halazepam | Rilmazafone | |
| Ivermectin | Arfendazam | Haloxazolam | Ripazepam | |
| F-830982 | Avizafone | Heptabarbital | Ro15-4513 | |
| Meprobamate | AZD7325 | Hexobarbital | Ro48-6791 | |
| Methoxyflurane | Baicalein | Iclazepam | Ro48-8684 | |
| MK-0777/L83098 | Baicalin | Imidazenil | Ro4938581 | |
| Methyprylon | Barbital | Indiplon | Rwj-51204 | |
| Moxidectin | Barbituric Acid Derivative | Irazepine | Saripidem | |
| Muscimol | Bentazepam | Kavain | Sarmazenil | |
| N4-Chloroacetyl-cytosine arabinoside | Brallobarbital | Kenazepine | Sb-205,384 | |
| Pagoclone | Bretazenil | Ketazolam | Scutellarein | |
| Phenibut | Bromazepam | L-655708 | Secobarbital | |
| Picamilon | Brotizolam | L-838,417 | Sevoflurane | |
| Piperazine | Butalbital | Lanthanum | Sh-053-R-Ch3-2'F | |
| Piperidine-4-sulfonic acid | Butethal | LAU 156 | Skull-capflavone II | |
| Progabide | Butobarbital | LAU 157 | Sl-651,498 | |
| QH-ii-066 | Camazepam | LAU 159 | Sodium Amytal | |
| Quisqualamine | Carburazepam | LAU 161 | Sodium Pentothal | |
| Sevoflurane | Carisoprodol | LAU 162 | Stiripentol | |
| SL 75102 | CGS 20625 | LAU 163 | Sulazepam | |
| SL-651,498 | CGS 20625 | LAU 176 | Sulfonmethane | |
| Thiamylal | CGS 8216 | LAU 177 | Suproclone | |
| Thiomuscimol | CGS 9895 | LAU 206 | Suriclone | |
| Tolgabide | CGS 9896 | Lofendazam | Sx-3228 | |
| Topiramate | Chloral Hydrate | Lopirazepam | Talampanel | |
| Zolpidem | Chloralose | Loprazolam | Talbutal | |

TABLE 3-continued

Binding Agents for λ-Aminobutyric Acid A Receptor (GABA-A)

| Agonists | Modulators/Binders | | Antagonists |
|---|---|---|---|
| α5IA | Chlordiazepoxide | Lorazepam | Taniplon |
| | Chlormezanone | Lorbamate | Temazepam |
| | Chloroform | Loreclezole | Tetrazepam |
| | Ciclotizolam | Lorediplon | Tetronal |
| | Cinazepam | Lormetazepam | Thdoc |
| | Cinolazepam | Meclonazepam | Theanine |
| | Cl-218,872 | Medazepam | Thiamylal |
| | Clazolam | Menitrazepam | Thieno-diazepine |
| | Climazolam | Mephobarbital | Thiopental |
| | Clobazam | Meprobamate | Tofisopam |
| | Clomethiazole | Metaclazepam | Tolufazepam |
| | Clonazepam | Methaqualone | Tp-003 |
| | Clonazolam | Metharbital | Tp-13 |
| | Clorazepate | Methohexital | Tpa-023 |
| | Clotiazepam | Methyl-phenobarbital | Triazolam |
| | Cloxazolam | Methyprylon | Triflubazam |
| | Cp-1414s | Methysticin | Triflunor-dazepam |
| | CTP-354 | Metizolam | Trional |
| | Cyclobarbital | Mexazolam | Tuclazepam |
| | Cyprazepam | Midazolam | Uldazepam |
| | Delorazepam | Motrazepam | Valerenic Acid |
| | Demoxepam | N-Desalkyl-flurazepam | Valeric Acid |
| | Deschloro-etizolam | Necopidem | Wogonin |
| | Desmethoxy-yangonin | Nerisopam | XHe-II-006 |
| | Desmethyl-flunitrazepam | Niacin | XHe-II-019 |
| | Diazepam | Niacinamide | XHe-II-087c |
| | Diclazepam | Nifoxipam | XHe-II-094 |
| | Diethyl Ether | Nimetazepam | XHe-II-098b |
| | Dihydro-ergotoxine | Nitrazepam | XHe-II-17 |
| | Dihydroquinidine Barbiturate | Nitrazepate | XHe-III-006c |
| | Diproqualone | Nitrazolam | XHe-III-063 |
| | Divaplon | Nordazepam | XHe-III-24 |
| | Doxefazepam | Nortetrazepam | XHe/ON-I |
| | Elb-139 | Ns-2664 | Y-23684 |
| | Elfazepam | Ns-2710 | Yangonin |
| | Estazolam | Ocinaplon | Zaleplon |
| | Eszopiclone | Oroxylin A | Zapizolam |
| | Etaqualone | Oxazepam | Zinc |
| | Etazepine | Oxazolam | Zk-93423 |
| | Etazolate | Pagoclone | Zolazepam |
| | Ethyl Carfluzepate | Panadiplon | Zolpidem |
| | Ethyl Dirazepate | Pazinaclone | Zomebazam |
| | Ethyl Loflazepate | PB-XHe | Zopiclone |

TABLE 4

Binding Agents for 5-Hydroxytryptamine Receptor (5-HT3)

| Agonists | Modulators/Binders | Antagonists | |
|---|---|---|---|
| 2-methyl-5-HT | 5-chloroindole | 3-Tropanyl indole-3-carboxylate | Mianserin |
| Alpha-Methyltryptamine | Trimipramine | Adr-851 | Mirisetron Maleate |
| Bufotenin | | Adr-882 | Mirtazapine |
| Chlorophenyl-biguanide | | Alosetron | Ml-1035 |
| Cisapride | | Amoxapine | Mm-218 |
| DDP733 | | Anpirtoline | N-3256 |
| Ethanol | | Aripiprazole | Netupitant |
| Ethanol | | AS-8112 | Olanzapine |
| Ibogaine | | Azasetron | Ondansetron |
| Metoclopramide | | Batanopride | Org-4419 |
| Phenylbiguanide | | Bimu-1 | Org-4419-2 |
| Quipazine | | Chloroprocaine | Palonosetron |

TABLE 4-continued

Binding Agents for 5-Hydroxytryptamine Receptor (5-HT3)

| Agonists | Modulators/Binders | Antagonists |
|---|---|---|
| RS-56812 | Cilansetron | Pancopride |
| SR-57227 | Clozapine | Procaine |
| Tapentadol | Cp-81386 | Quetiapine |
| Varenicline | Cp-93318 | R-093777 |
| YM-31636 | Cr-3124 | R-Zacopride |
| | DA-9701 | Ramosetron |
| | Daizac | Renzapride |
| | Dat-582 | Rg-12915 |
| | Dau-6285 | Ricasetron |
| | Ddp-225 | Rocuronium |
| | Dolasetron | Rs-16566 |
| | E-3620 | Rs-33800 |
| | Fabesetron | Rs-56532 |
| | Facinicline/RG3487 Hydrochloride | Rs-56812 |
| | Galdansetron | S-21007 |
| | Gastroprokinetics | Sc-50410 |
| | Gk-128 | Sc-52150 |
| | Gr-65630 | Sc-52246 |
| | Granisetron | Sc-52491 |
| | Gyki-46903 | Sc-54750 |
| | Itasetron | Sdz-Icm-567 |
| | Kb-6806 | Sep-226332 |
| | Kf-18259 | Srss-021 |
| | Kf-20170 | Tedatioxetine |
| | Kga-0941 | Thujone |
| | L-683877 | Topiramate |
| | Lamotrigine | Tropisetron |
| | Lerisetron | Tubocurarine |
| | Lintopride | Tzb-30878 |
| | Litoxetine | Va-21B7 |
| | Loxapine | Vi-0134 |
| | Lurosetron | Vortioxetine |
| | Fy-278584 | Vortioxetine Hydrobromide |
| | M1, the major active metabolite of mosapride | Way-100289 |
| | Mci-225 | Ym-114 |
| | Mci-225 | Ym-26103-2 |
| | Memantine | Ym-26308-2 |
| | Menthol | Zacopride |
| | Methadone | Zatosetron |
| | Metoclopramide | Ziprasidone |

TABLE 5

Binding Agents for Nicotinic Acetylcholine Receptor (nAchR)

| Agonists | Modulators/Binders | Antagonists |
|---|---|---|
| (+)-N-(1-azabicyclo[2.2.2]oct-3-yl)benzo[b]furan-2-carboxamide | A-867744 | (−)-7-methyl-2-exo-[3'-(6-[18F]fluoropyridin-2-yl)-5'-pyridinyl]-7-azabicyclo[2.2.1]heptane |
| 3-Bromocytisine | AQW-051 | 2-fluoro-3-(4-nitro-phenyl)deschloroepibatidine |
| A-366,833 | AVL-3288 | Acv-1 |
| A-582941 | Desformylflustrabromine | ACVx |
| A-82695 | Ethanol | Amobarbital |
| A-84,543 | Galantamine | Anandamide |
| ABT-089 | Ivermectin | Anq-9040 |
| ABT-126 | Nefiracetam | Aprobarbital |
| Abt-202 | NS-1738 | ATG-001 |
| ABT-418 | NS-9283 | ATG003 |
| Abt-418 | PNU-120,596 | Atracurium besylate |
| Abt-560 | Tetraethylammonium | Barbital |
| ABT-894 | | Barbituric acid derivative |
| Acetylcholine | | Biperiden |
| Altinicline | | Bupropion |
| Altinicline | | Butabarbital |
| Aminoethoxypyridine | | Butalbital |
| Anabasine | | Butethal |
| AR-R17779 | | Chloroprocaine |
| Asm-024 | | Cisatracurium Besilate |

TABLE 5-continued

| Binding Agents for Nicotinic Acetylcholine Receptor (nAchR) | | |
|---|---|---|
| Agonists | Modulators/Binders | Antagonists |
| AZD-0328 | | Cisatracurium besylate |
| Bupropion Hydrochloride | | Coclaurine |
| Carbachol | | Dehydronorketamine |
| Choline | | Deuterated Bupropion |
| Cm-2433 | | Dextromethorphan |
| CP-601927 | | Doxacurium chloride |
| CP-601932 | | Ethanol |
| Cp-810123 | | Gallamine Triethiodide |
| Cytisine | | Heptabarbital |
| DBO-83 | | Hexobarbital |
| Decamethonium | | Hydroxybupropion |
| Dianicline | | Hydroxynorketamine |
| Dianicline | | Inaperisone |
| Encenicline | | Iptakalim |
| Epibatidine | | Isoflurane |
| EVP-6124 | | Ketamine |
| Evp-6124 | | Kynurenic acid |
| Galantamine | | Levomethadyl Acetate |
| GTS-21 | | Lobeline |
| Gts-21 | | Mecamylamine |
| ICH-3 | | Mecamylamine |
| Ispronicline | | Memantine |
| Levamisole | | Methadone |
| Lobeline | | Metharbital |
| Lobeline Sulphate | | Methyllycaconitine |
| Mem-3454 | | Methylphenobarbital |
| MEM-63908 | | Metocurine |
| Mem-63908 | | Metocurine Iodide |
| N-(3-pyridinyl)-bridged bicyclic diamine | | Mivacurium |
| Nicotine | | Neramexane |
| PH-399733 | | Nic-002 |
| Ph-399733 | | Nitrous oxide |
| PHA-543,613 | | Norketamine |
| Pha-543613 | | Org-9991 |
| PHA-709829 | | Pancuronium |
| PNU-282,987 | | Pentobarbital |
| Pnu-282987 | | Pentolinium |
| Pozanicline | | Phenobarbital |
| Pozanicline | | Pipecuronium |
| Rivanicline | | Pipecuronium |
| Rivanicline | | PNU-120,596 |
| Rjr-1401 | | Primidone |
| Sar-130479 | | Procaine |
| Sazetidine A | | Quinolizidine (−)-1-epi-207I |
| Sib-1663 | | RJR-2531 |
| Sib-1765f | | Rocuronium |
| Sib-3182 | | RPI-78M |
| Sofinicline | | Secobarbital |
| SSR-180,711 | | Talbutal |
| Succinylcholine | | Thiopental |
| Suvn-F90101 | | Trimethaphan |
| Suvn-F91201 | | Tubocurarine |
| Tacrine-huperzine A | | U-2902 |
| TC-1698 | | Vecuronium |
| TC-1827 | | α-Bungarotoxin |
| Tc-2216 | | α-Conotoxin |
| Tc-2403 | | |
| Tc-2429 | | |
| Tc-2559 | | |
| Tc-2696 | | |
| TC-5619 | | |
| Tebanicline | | |
| Tropisetron | | |
| Ub-165 | | |
| Varenicline | | |
| WAY-317,538 | | |

TABLE 6

Binding Agents for ATP-Gated P2X Receptor Cation Channel (P2X)

| Agonists | Modulators/Binders | Antagonists | |
|---|---|---|---|
| ATP | Ivermectin | 4-benzoyl-1-substituted-piperazin-2-ones | MK-801 |
| BzATP | | 5-methyl-6,7-dihydro-5Hcyclopentapyrazine | MRS2159 |
| α,β-meATP | | 5-oxo-3-pyrrolidinecarboxamides | NF023 |
| | | 5,6,7,8-tetrahydropyrido[4,3,d]-pyrimidines | NF279 |
| | | A-317491 | NF449 |
| | | Amitriptyline | Nortriptyline |
| | | Azaindole-3-carboxamides | Oxoisoquinoline carboxamides |
| | | AZD-9056 | Paroxetine |
| | | Benzamide 6 | Piperazines |
| | | Benzofuro-1,4-diazepin-2-ones | Polycyclic guanines |
| | | Benzoimidazoles | PPADS |
| | | Biaryl benzamides | PPNDS |
| | | Carboxamides | Pyrazolo-[1,5,a]-pyridine carboxamides |
| | | CE-224535 | Pyridazinones |
| | | Desipramine | Pyridoxal-5-phosphate |
| | | Diaminopyridines | Pyrrolinones |
| | | Doxepin | Pyrrolo-[2,3,b]-pyridine carboxamides |
| | | Eslicarbazepine acetate | Pyrrolopyrimidin-7-ones |
| | | EVT-401 | Quinoline carboxamides |
| | | Fluoxetine | RO-3 |
| | | Hyaluronic acid derivatives | RO-4 |
| | | Imipramine | RO-51 |
| | | Indole carboxamides | Spinorphins |
| | | Indole-3-carboxamides | Suramin |
| | | Ip5I | Tetrahydro-2H-1,2-thiazine 1,1-dioxides |
| | | Isoquinoline carboxamides | TNP-ATP |
| | | Isothiazolidine 1,1-dioxides | |

TABLE 7

Binding Agents for Inwardly Rectifying Potassium Channel (Kir)

| Agonists | Modulators/Binders | Antagonists |
|---|---|---|
| Diazoxide | | Acetohexamide |
| Iptakalim | | Carbutamide |
| Minoxidil | | Chlorpropamide |
| Nicorandil | | Glibenclamide |
| Phosphatidylinositol 4,5-Bisphosphate | | Glibenclamide |
| Pinacidil | | Glibomuride |
| | | Gliclazide |
| | | Glimepiride |
| | | Glipizide |
| | | Gliquidone |
| | | Glisoxepide |
| | | Glyburide |
| | | Glyclopyramide |
| | | Glycyclamide |
| | | Metahexamide |
| | | Tolazamide |
| | | Tolbutamide |
| | | Tolhexamide |

TABLE 8

Binding Agents for Voltage Dependent Potassium Channel (KCNQ/Kv7)

| Agonists | Modulators/Binders | Antagonists |
|---|---|---|
| Diazoxide | | Azimilide |
| Flupirtine | | Amiodarone |
| Minoxidil | | Bretylium |
| Nicorandil | | Clofilium |
| Pinacidil | | Dalfampridine |
| Retigabine | | Dofetilide |
| | | E-4031 |
| | | Ibutilide |
| | | Nifekalant |
| | | Sematilide |
| | | Sotalol |
| | | Sulfonylureas |
| | | Tedisamil |

TABLE 9

Binding Agents for Cystic Fibrosis Transmembrane Conductance Regulator (CFTR)

| Agonists | Modulators/Binders | Antagonists |
|---|---|---|
| | 8-cyclopentyl-1,3-dipropylxanthine | Bumetanide |
| | 8-methoxypsoralen | Crofelemer |
| | Apigenin | Glyburide |
| | CTP-656 | Ibuprofen |
| | Genistein | |
| | IBMX | |
| | Ivacaftor | |
| | Lumacaftor | |

E. Polynucleotides

In various illustrative embodiments, the present disclosure contemplates, in part, polynucleotides, polynucleotides encoding engineered receptor polypeptides including LGICs, and subunits and muteins thereof, and fusion polypeptides, viral vector polynucleotides, and compositions comprising the same.

As used herein, the terms "polynucleotide," "nucleotide," "nucleotide sequence" or "nucleic acid" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. Polynucleotides may be deoxyribonucleic acid (DNA), ribonucleic acid (RNA) or DNA/RNA hybrids. Polynucleotides may be single-stranded or double-stranded. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, synthetic RNA, genomic RNA (gRNA), plus strand RNA (RNA(+)), minus strand RNA (RNA(−)), synthetic RNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxynucleotides or a modified form of either type of nucleotide, as well as all intermediate lengths. It will be readily understood that "intermediate lengths" in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence described herein or known in the art, typically where the variant maintains at least one biological activity of the reference sequence unless otherwise stated.

As used herein, the term "gene" may refer to a polynucleotide sequence comprising enhancers, promoters, introns, exons, and the like. In particular embodiments, the term "gene" refers to a polynucleotide sequence encoding a polypeptide, regardless of whether the polynucleotide sequence is identical to the genomic sequence encoding the polypeptide.

As used herein, a "cis-acting sequence, "cis-acting regulatory sequence", or "cis-acting nucleotide sequence" or equivalents refers to a polynucleotide sequence that is associated with the expression, e.g. transcription and/or translation, of a gene. In one embodiment, the cis-acting sequence regulates transcription because it is a binding site for a polypeptide that represses or decreases transcription or a polynucleotide sequence associated with a transcription factor binding site that contributes to transcriptional repression. Examples of cis-acting sequences that regulate the expression of polynucleotide sequences and that may be operably linked to the polynucleotides of the present disclosure to regulate the expression of the subject engineered receptors are well known in the art and include such elements as promoter sequences (e.g CAG, CMV, SYN, CamKII, TRPV1), Kozak sequences, enhancers, posttranscriptional regulatory elements, miRNA binding elements, and polyadenylation sequences.

As one non-limiting example, a promoter sequence is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters may be used to drive the various vectors of the present invention. For example, the promoter may be a constitutively active promoter, i.e. a promoter that is active in the absence externally applied agents, e.g. the CMV IE1 promoter, the SV40 promoter, GAPDH promoter, Actin promoter. The promoter may be an inducible promoter, i.e. a promoter whose activity is regulated upon the application of an agent to the cell, e.g. doxycycline, the tet-on or tet-off promoter, the estrogen receptor promoter, etc. The promoter may be a tissue-specific promoter, i.e. a promoter that is active on certain types of cells.

In some embodiments, the promoter is active in an excitable cell. By an "excitable cell", it is meant a cell that is activated by a change in membrane potential, e.g. a neuron or myocyte, e.g. a dorsal root ganglion neuron, a motor neuron, an excitatory neuron, an inhibitory neuron, or a sensory neuron. Promoters that are active in an excitable cell that would find use in the present polynucleotide compositions would include neuronal promoters, for example, the synapsin (SYN), TRPV1, $Na_v1.7$, $Na_v1.8$, $Na_v1.9$, CamKII, NSE, and Advillin promoters; myocyte promoters, e.g. the desmin (Des), alpha-myosin heavy chain (α-MHC), myosin light chain 2 (MLC-2) and cardiac troponin C (cTnC) promoters; and ubiquitous acting promoters, e.g. CAG, CBA, E1Fa, Ubc, CMV, and SV40 promoters.

As used herein, a "regulatory element for inducible expression" refers to a polynucleotide sequence that is a promoter, enhancer, or functional fragment thereof that is operably linked to a polynucleotide to be expressed and that responds to the presence or absence of a molecule that binds the element to increase (turn-on) or decrease (turn-off) the expression of the polynucleotide operably linked thereto. Illustrative regulatory elements for inducible expression include, but are not limited to, a tetracycline responsive promoter, an ecdysone responsive promoter, a cumate responsive promoter, a glucocorticoid responsive promoter, an estrogen responsive promoter, an RU-486 responsive promoter, a PPAR-γ promoter, and a peroxide inducible promoter.

A "regulatory element for transient expression" refers to a polynucleotide sequence that can be used to briefly or temporarily express a polynucleotide nucleotide sequence. In particular embodiments, one or more regulatory elements for transient expression can be used to limit the duration of a polynucleotide. In certain embodiments, the preferred duration of polynucleotide expression is on the order of minutes, hours, or days. Illustrative regulatory elements for transient expression include, but are not limited to, nuclease target sites, recombinase recognition sites, and inhibitory RNA target sites. In addition, to some extent, in particular embodiments, a regulatory element for inducible expression may also contribute to controlling the duration of polynucleotide expression.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence described herein or known in the art, typically where the variant maintains at least one biological activity of the reference sequence unless otherwise stated.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc, 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant DNA, or other polynucleotide that does not exist in nature and that has been made by the hand of man.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The term "flanked" refers to a polynucleotide sequence that is in between an upstream polynucleotide sequence and/or a downstream polynucleotide sequence, i.e., 5' and/or 3', relative to the sequence. For example, a sequence that is "flanked" by two other elements (e.g., ITRs), indicates that one element is located 5' to the sequence and the other is located 3' to the sequence; however, there may be intervening sequences therebetween.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The terms "nucleic acid cassette" or "expression cassette" as used herein refers to polynucleotide sequences within a larger polynucleotide, such as a vector, which are sufficient to express one or more RNAs from a polynucleotide. The expressed RNAs may be translated into proteins, may function as guide RNAs or inhibitory RNAs to target other polynucleotide sequences for cleavage and/or degradation. In one embodiment, the nucleic acid cassette contains one or more polynucleotide(s)-of-interest. In another embodiment, the nucleic acid cassette contains one or more expression control sequences operably linked to one or more polynucleotide(s)-of-interest. Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, e.g., LGICs, and subunits and muteins thereof, as contemplated herein. In a particular embodiment, a polynucleotide-of-interest encodes a polypeptide or fusion polypeptide having one or more enzymatic activities, such as a nuclease activity and/or chromatin remodeling or epigenetic modification activities.

Vectors may comprise 1, 2, 3, 4, 5, 6, 7, 8, 9 or 10 or more nucleic acid cassettes. In a preferred embodiment of the disclosure, a nucleic acid cassette comprises one or more expression control sequences (e.g., a promoter or enhancer operable in a neuronal cell) operably linked to a polynucleotide encoding a engineered receptor, e.g., an LGIC, or subunit or muteins thereof. The cassette can be removed from or inserted into other polynucleotide sequences, e.g., a plasmid or viral vector, as a single unit.

In one embodiment, a polynucleotide contemplated herein comprises 1, 2, 3, 4, 5, 6, 7, 8, 9, or more nucleic acid cassettes any number or combination of which may be in the same or opposite orientations.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated by the present disclosure, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

F. Vectors

In some aspects of the disclosure, a nucleic acid molecule, i.e., a polynucleotide encoding an engineered receptor is delivered to a subject. In some cases, the nucleic acid molecule encoding the engineered receptor is delivered to a subject by a vector. In various embodiments, a vector comprises a one or more polynucleotide sequences contemplated herein. The term "vector" is used herein to refer to a nucleic acid molecule capable of transferring or transporting another nucleic acid molecule. The transferred polynucleotide is generally linked to, e.g., inserted into, the vector nucleic acid molecule. A vector may include sequences that direct autonomous replication in a cell, or may include sequences sufficient to allow integration into host cell DNA. A vector can deliver a target polynucleotide to an organism, a cell or a cellular component. In some cases, the vector is an expression vector. An "expression vector" as used herein refers to a vector, for example, a plasmid, that is capable of promoting expression, as well as replication of a polynucleotide incorporated therein. Typically, the nucleic acid sequence to be expressed is operably linked to cis-acting regulatory sequence, e.g. a promoter and/or enhancer sequence, and is subject to transcription regulatory control by the promoter and/or enhancer. In particular cases, a vector is used to deliver a nucleic acid molecule encoding an engineered receptor of the disclosure to a subject.

In particular embodiments, any vector suitable for introducing an expression cassette or polynucleotide encoding an engineered receptor into a neuronal cell can be employed. Illustrative examples of suitable vectors include plasmids (e.g., DNA plasmids or RNA plasmids), transposons, cosmids, bacterial artificial chromosomes, and viral vectors. In some cases, the vector is a circular nucleic acid, for e.g., a plasmid, a BAC, a PAC, a YAC, a cosmid, a fosmid, and the like. In some cases, circular nucleic acid molecules can be utilized to deliver a nucleic acid molecule encoding an engineered receptor to a subject. For example, a plasmid DNA molecule encoding an engineered receptor can be introduced into a cell of a subject whereby the DNA sequence encoding the engineered receptor is transcribed into mRNA and the mRNA "message" is translated into a protein product. The circular nucleic acid vector will generally include regulatory elements that regulate the expression of the target protein. For example, the circular nucleic acid vector may include any number of promoters, enhancers, terminators, splice signals, origins of replication, initiation signals, and the like.

In some cases, the vector can include a replicon. A replicon may be any nucleic acid molecule capable of self-replication. In some cases, the replicon is an RNA replicon derived from a virus. A variety of suitable viruses (e.g. RNA viruses) are available, including, but not limited to, alphavirus, picornavirus, flavivirus, coronavirus, pestivirus, rubivirus, calcivirus, and hepacivirus.

In some embodiments, the vector is a non-viral vector. By a "non-viral vector", it is meant any delivery vehicle that does not comprise a viral capsid or envelope, e.g. lipid nanoparticles (anionic (negatively charged), neutral, or cat-ionic (positively charged)), heavy metal nanoparticles, polymer-based particles, plasmid DNA, minicircle DNA, minivector DNA, ccDNA, synthetic RNA, exosomes, and the like. Non-viral vectors may be delivered by any suitable method as would be well understood in the art, including, e.g., nanoparticle delivery, particle bombardment, electroporation, sonication, or microinjection. See, e.g. Chen et al. Mol. Therapy, Methods and Clinical Development. 2016 January; Vol 3, issue 1; and Hardy, C E et al. Genes (Basel). 2017 February; 8(2): 65

In other embodiments, the vector is a viral vector. By a "viral vector" it is meant a delivery vehicle that comprises a viral capsid or envelop surrounding a polynucleotide encoding an RNA or polypeptide of interest. In some cases, the viral vector is derived from a replication-deficient virus. Non-limiting examples of viral vectors suitable for delivering a nucleic acid molecule of the disclosure to a subject include those derived from adenovirus, retrovirus (e.g., lentivirus), adeno-associated virus (AAV), and herpes simplex-1 (HSV-1). Illustrative examples of suitable viral vectors include, but are not limited to, retroviral vectors (e.g., lentiviral vectors), herpes virus based vectors and parvovirus based vectors (e.g., adeno-associated virus (AAV) based vectors, AAV-adenoviral chimeric vectors, and adenovirus-based vectors).

The term "parvovirus" as used herein encompasses all parvoviruses, including autonomously-replicating parvoviruses and dependoviruses. The autonomous parvoviruses include members of the genera *Parvovirus, Erythrovirus, Densovirus, Iteravirus*, and *Contravirus*. Exemplary autonomous parvoviruses include, but are not limited to, mouse minute virus, bovine parvovirus, canine parvovirus, chicken parvovirus, feline panleukopenia virus, feline parvovirus, goose parvovirus, and B19 virus. Other autonomous parvoviruses are known to those skilled in the art. See, e.g., Fields et al., 1996 *Virology*, volume 2, chapter 69 (3d ed., Lippincott-Raven Publishers).

The genus *Dependovirus* contains the adeno-associated viruses (AAV), including but not limited to, AAV type 1, AAV type 2, AAV type 3, AAV type 4, AAV type 5, AAV type 6, AAV type 7, AAV type 8, AAV type 9, AAV type rh10, avian AAV, bovine AAV, canine AAV, equine AAV, and ovine AAV.

In a preferred embodiment, the vector is an AAV vector. In particular cases, the viral vector is an AAV-6 or AAV-9 vector.

The genomic organization of all known AAV serotypes is similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid and contribute to the tropism of the virus. The terminal 145 nt ITRs are self-complementary and are organized so that an energetically stable intramolecular duplex forming a T-shaped hairpin may be formed. These hairpin structures function as an origin for viral DNA replication, serving as primers for the cellular DNA polymerase complex. Following wild-type (wt) AAV infection in mammalian cells the Rep genes are expressed and function in the replication of the viral genome.

In some cases, the outer protein "capsid" of the viral vector occurs in nature, e.g. AAV1, AAV2, AAV3, AAV4, AAV5, AAV6, AAV7, AAV8, AAV9, or AAV10. In particular cases, the capsid is synthetically engineered (e.g. through directed evolution or rational design) to possess certain unique characteristics not present in nature such as altered tropism, increased transduction efficiency, or immune evasion. An example of a rationally designed capsid is the mutation of one or more surface-exposed tyrosine (Y), serine (S), threonine (T), and lysine (K) residues on the VP3 viral capsid protein. Non-limiting examples of viral vectors whose VP3 capsid proteins have been synthetically engineered and are amenable for use with the compositions and methods provided herein include: AAV1(Y705+731F+T492V), AAV2(Y444+500+730F+T491V), AAV3(Y705+731F), AAV5(Y436+693+719F), AAV6(Y705+731F+T492V), AAV8(Y733F), AAV9(Y731F), and AAV10 (Y733F). Non-limiting examples of viral vectors that have been engineered through directed evolution and are amenable for use with the compositions and methods provided herein include AAV-7m8 and AAV-ShH10.

A "recombinant parvoviral or AAV vector" (or "rAAV vector") herein refers to a vector comprising one or more polynucleotides contemplated herein that are flanked by one or more AAV ITRs. Such polynucleotides are said to be "heterologous" to the ITRs, as such combinations do not ordinarily occur in nature. Such rAAV vectors can be replicated and packaged into infectious viral particles when present in an insect host cell that is expressing AAV rep and cap gene products (i.e., AAV Rep and Cap proteins). When an rAAV vector is incorporated into a larger nucleic acid construct (e.g., in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

In particular embodiments, any AAV ITR may be used in the AAV vectors, including ITRs from AAV1, AAV2, AAV3, AAV4, AAV5, AAV6, AAV7, AAV8, AAV9, AAV10, AAV11, AAV12, AAV13, AAV14, AAV15, and AAV16. In one preferred embodiment, an AAV vector contemplated herein comprises one or more AAV2 ITRs.

rAAV vectors comprising two ITRs have a payload capacity of about 4.4 kB. Self-complementary rAAV vectors contain a third ITR and package two strands of the recombinant portion of the vector leaving only about 2.1 kB for the polynucleotides contemplated herein. In one embodiment, the AAV vector is an scAAV vector.

Extended packaging capacities that are roughly double the packaging capacity of an rAAV (about 9 kB) have been achieved using dual rAAV vector strategies. Dual vector strategies useful in producing rAAV contemplated herein include, but are not limited to splicing (trans-splicing), homologous recombination (overlapping), or a combination of the two (hybrid). In the dual AAV trans-splicing strategy, a splice donor (SD) signal is placed at the 3' end of the 5'-half vector and a splice acceptor (SA) signal is placed at the 5' end of the 3'-half vector. Upon co-infection of the same cell by the dual AAV vectors and inverted terminal repeat (ITR)-mediated head-to-tail concatemerization of the two halves, trans-splicing results in the production of a mature mRNA and full-size protein (Yan et al., 2000). Trans-splicing has been successfully used to express large genes in muscle and retina (Reich et al., 2003; Lai et al., 2005). Alternatively, the two halves of a large transgene expression cassette contained in dual AAV vectors may contain homologous overlapping sequences (at the 3' end of the 5'-half vector and at the 5' end of the 3'-half vector, dual AAV overlapping), which will mediate reconstitution of a single large genome by homologous recombination (Duan et al., 2001). This strategy depends on the recombinogenic properties of the transgene overlapping sequences (Ghosh et al., 2006). A third dual AAV strategy (hybrid) is based on adding a highly recombinogenic region from an exogenous gene (i.e., alkaline phosphatase; Ghosh et al., 2008, Ghosh et al., 2011)) to the trans-splicing vectors. The added region is placed downstream of the SD signal in the 5'-half vector and upstream of the SA signal in the 3'-half vector in order to increase recombination between the dual AAVs.

A "hybrid AAV" or "hybrid rAAV" refers to an rAAV genome packaged with a capsid of a different AAV serotype (and preferably, of a different serotype from the one or more AAV ITRs), and may otherwise be referred to as a pseudotyped rAAV. For example, an rAAV type 1, 2, 3, 4, 5, 6, 7, 8, 9, 10, 11, 12, 13, 14, 15, or 16 genome may be encapsidated within an AAV type 1, 2, 3, 4, 5, 6, 7, 8, 9, 10, 11, 12, 13, 14, 15, or 16 capsid or variants thereof, provided that the AAV capsid and genome (and preferably, the one or more AAV ITRs) are of different serotypes. In certain embodiments, a pseudotyped rAAV particle may be referred to as being of the type "x/y", where "x" indicates the source of ITRs and "y" indicates the serotype of capsid, for example a ⅖ rAAV particle has ITRs from AAV2 and a capsid from AAV6.

A "host cell" includes cells transfected, infected, or transduced in vivo, ex vivo, or in vitro with a recombinant vector or a polynucleotide of the disclosure. Host cells may include virus producing cells and cells infected with viral vectors. In particular embodiments, host cells in vivo are infected with viral vector contemplated herein. In certain embodiments, the term "target cell" is used interchangeably with host cell and refers to infected cells of a desired cell type.

High titer AAV preparations can be produced using techniques known in the art, e.g., as described in U.S. Pat. Nos. 5,658,776; 6,566,118; 6,989,264; and 6,995,006; U.S. 2006/0188484; WO98/22607; WO2005/072364; and WO/1999/011764; and Viral Vectors for Gene Therapy: Methods and Protocols, ed. Machida, Humana Press, 2003; Samulski et al., (1989) J. Virology 63, 3822; Xiao et al., (1998) J. Virology 72, 2224; Inoue et al., (1998) J. Virol. 72, 7024. Methods of producing pseudotyped AAV vectors have also been reported (e.g., WO 00/28004), as well as various modifications or formulations of AAV vectors, to reduce their immunogenicity upon in vivo administration (see e.g., WO 01/23001; WO 00/73316; WO 04/1 12727; WO 05/005610; WO 99/06562).

G. Pharmaceutical Compositions

Also provided are pharmaceutical preparations, including pharmaceutical preparations of vector and pharmaceutical preparations of binding agent. Pharmaceutical preparations include the subject polynucleotide (RNA or DNA) encoding an engineered receptor, vector carrying a polynucleotide (RNA or DNA) encoding a subject engineered receptor, or binding agent present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a mammal, the compounds and compositions of the disclosure and pharmaceutically acceptable vehicles, excipients, or diluents may be sterile. In some instances, an aqueous medium is employed as a vehicle when the compound of the disclosure is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference.

The choice of excipient will be determined in part by the particular vector, as well as by the particular method used to administer the composition. Accordingly, there is a wide variety of suitable formulations of the pharmaceutical composition of the present disclosure.

For example, the vector may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

As another example, the vector may be formulated into a preparation suitable for oral administration, including (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

As another example, the subject formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (i.e., sunblocking agents), etc.

A compound of the disclosure may be formulated for topical administration. The vehicle for topical application may be in one of various forms, e.g. a lotion, cream, gel, ointment, stick, spray, or paste. They may contain various types of carriers, including, but not limited to, solutions, aerosols, emulsions, gels, and liposomes. The carrier may be formulated, for example, as an emulsion, having an oil-in-water or water-in-oil base. Suitable hydrophobic (oily) components employed in emulsions include, for example, vegetable oils, animal fats and oils, synthetic hydrocarbons, and esters and alcohols thereof, including polyesters, as well as organopolysiloxane oils. Such emulsions also include an emulsifier and/or surfactant, e.g. a nonionic surfactant to disperse and suspend the discontinuous phase within the continuous phase.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

Dose levels can vary as a function of the specific compound, the nature of the delivery vehicle, and the like. Desired dosages for a given compound are readily determinable by a variety of means.

The dose administered to an animal, particularly a human, in the context of the present disclosure should be sufficient to effect a prophylactic or therapeutic response in the animal over a reasonable time frame, e.g., as described in greater detail below. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

In pharmaceutical dosage forms, the ASC inducer compounds may be administered in the form of a free base, their pharmaceutically acceptable salts, or they may also be used alone or in appropriate association, as well as in combination, with other pharmaceutically active compounds.

G. Clinical Applications and Methods of Treatment

The compositions and methods disclosed herein can be utilized to treat a neurological disease or disorder. In some aspects of the disclosure, a method of treating a neurological disease or disorder in a subject is provided, the method comprising the introducing an engineered receptor into a neuronal cell and providing a ligand that activates the engineered receptor in an effective amount to control the activity of the cell, thereby relieving pain in the subject. In some aspects, vectors or compositions disclosed herein are used in the manufacture of a medicament for treating a neurological disease or disorder.

In some cases, the methods and compositions of the disclosure are utilized to treat epilepsy. Compositions described herein may be used to prevent or control epileptic seizures. Epileptic seizures may be classified as tonic-clonic, tonic, clonic, myoclonic, absence or atonic seizures. In some cases, the compositions and methods herein may prevent or reduce the number of epileptic seizures experienced by a subject by about 5%, about 10%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or 100%.

In some cases, the methods and compositions of the disclosure are utilized to treat an eating disorder. An eating disorder may be a mental disorder defined by abnormal eating behaviors that negatively affect a subject's physical or mental health. In some cases, the eating disorder is anorexia nervosa. In other cases, the eating disorder is bulimia nervosa. In some cases, the eating disorder is pica, rumination disorder, avoidant/restrictive food intake disorder, binge eating disorder (BED), other specified feeding and eating disorder (OSFED), compulsive overeating, diabulimia, orthorexia nervosa, selective eating disorder, drunkorexia, pregorexia, or Gourmand syndrome. In some cases, the composition includes a G-protein coupled receptor that increases or decreases the production of one or more molecules associated with an eating disorder. In other cases, the composition includes a ligand-gated ion channel that alters the production of one or more molecules associated with an eating disorder. The one or more molecules associated with an eating disorder may include, without limitation, a molecule of the hypothalamus-pituitary-adrenal (HPA) axis, including vasopressin, corticotropin-releasing hormone (CRH), adrenocorticotropic hormone (ACTH), cortisol, epinephrine, or norepinephrine; as well as serotonin, dopamine, neuropeptide Y, leptin, or ghrelin.

In some cases, the compositions and methods are utilized to treat post-traumatic stress disorder (PTSD), gastroesophageal reflux disease (GERD), addiction (e.g., alcohol, drugs), anxiety, depression, memory loss, dementia, sleep apnea, stroke, urinary incontinence, narcolepsy, essential tremor, movement disorder, atrial fibrillation, cancer (e.g., brain tumors), Parkinson's disease, or Alzheimer's disease. Other non-limiting examples of neurological diseases or disorders that can be treated by the compositions and methods herein include: Abulia, Agraphia, Alcoholism, Alexia, Aneurysm, Amaurosis fugax, Amnesia, Amyotrophic lateral sclerosis (ALS), Angelman syndrome, Aphasia, Apraxia, Arachnoiditis, Arnold-Chiari malformation, Asperger syndrome, Ataxia, Ataxia-telangiectasia, Attention deficit hyperactivity disorder, Auditory processing disorder, Autism spectrum, Bipolar disorder, Bell's palsy, Brachial plexus injury, Brain damage, Brain injury, Brain tumor, Canavan disease, Capgras delusion, Carpal tunnel syndrome, Causalgia, Central pain syndrome, Central pontine myelinolysis, Centronuclear myopathy, Cephalic disorder, Cerebral aneurysm, Cerebral arteriosclerosis, Cerebral atrophy, Cerebral autosomal dominant arteriopathy with subcortical infarcts and leukoencephalopathy (CADASIL), Cerebral gigantism, Cerebral palsy, Cerebral vasculitis, Cervical spinal stenosis, Charcot-Marie-Tooth disease, Chiari malformation, Chorea, Chronic fatigue syndrome, Chronic inflammatory demyelinating polyneuropathy (CIDP), Chronic pain, Coffin-Lowry syndrome, Coma, Complex regional pain syndrome, Compression neuropathy, Congenital facial diplegia, Corticobasal degeneration, Cranial arteritis, Craniosynostosis, Creutzfeldt-Jakob disease, Cumulative trauma disorders, Cushing's syndrome, Cyclothymic disorder, Cytomegalic inclusion body disease (CIBD), Cytomegalovirus Infection, Dandy-Walker syndrome, Dawson disease, De Morsier's syndrome, Dejerine-Klumpke palsy, Dejerine-Sottas disease, Delayed sleep phase syndrome, Dementia, Dermatomyositis, Developmental coordination disorder, Diabetic neuropathy, Diffuse sclerosis, Diplopia, Down syndrome, Dravet syndrome, Duchenne muscular dystrophy, Dysarthria, Dysautonomia, Dyscalculia, Dysgraphia, Dyskinesia, Dyslexia, Dystonia, Empty sella syndrome, Encephalitis, Encephalocele, Encephalotrigeminal angiomatosis, Encopresis, Enuresis, Epilepsy, Epilepsy-intellectual disability in females, Erb's palsy, Erythromelalgia, Exploding head syndrome, Fabry's disease, Fahr's syndrome, Fainting, Familial spastic paralysis, Febrile seizures, Fisher syndrome, Friedreich's ataxia, Fibromyalgia, Foville's syndrome, Fetal alcohol syndrome, Fragile X syndrome, Fragile X-associated tremor/ataxia syndrome (FXTAS), Gaucher's disease, Generalized epilepsy with febrile seizures plus, Gerstmann's syndrome, Giant cell arteritis, Giant cell inclusion disease, Globoid Cell Leukodystrophy, Gray matter heterotopia, Guillain-Barré syndrome, Generalized anxiety disorder, HTLV-1 associated myelopathy, Hallervorden-Spatz disease, Head injury, Headache, Hemifacial Spasm, Hereditary Spastic Paraplegia, Heredopathia atactica polyneuritiformis, Herpes zoster oticus, Herpes zoster, Hirayama syndrome, Hirschsprung's disease, Holmes-Adie syndrome, Holoprosencephaly, Huntington's disease, Hydranencephaly, Hydrocephalus, Hypercortisolism, Hypoxia, Immune-Mediated encephalomyelitis, Inclusion body myositis, Incontinentia pigmenti, Infantile Refsum disease, Infantile spasms, Inflammatory myopathy, Intracranial cyst, Intracranial hypertension, Isodicentric 15, Joubert syndrome, Karak syndrome, Kearns-Sayre syndrome, Kinsbourne syndrome, Kleine-Levin Syndrome, Klippel Feil syndrome, Krabbe disease, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Leukoencephalopathy with vanishing white matter, Lewy body dementia, Lissencephaly, Locked-In syndrome, Lumbar disc disease, Lumbar spinal stenosis, Lyme disease—Neurological Sequelae, Machado-Joseph disease (Spinocerebellar ataxia type 3), Macrencephaly, Macropsia, Mal de debarquement, Megalencephalic leukoencephalopathy with subcortical cysts, Megalencephaly, Melkersson-Rosenthal syndrome, Menieres disease, Meningitis, Menkes disease, Metachromatic leukodystrophy, Microcephaly, Micropsia, Migraine, Miller Fisher syndrome, Mini-stroke (transient ischemic attack), Misophonia, Mitochondrial myopathy, Mobius syndrome, Monomelic amyotrophy, Motor skills disorder, Moyamoya disease, Mucopolysaccharidoses, Multi-infarct dementia, Multifocal motor neuropathy, Multiple sclerosis, Multiple system atrophy, Muscular dystrophy, Myalgic encephalomyelitis, Myasthenia gravis, Myelinoclastic diffuse sclerosis, Myoclonic Encephalopathy of infants, Myoclonus, Myopathy, Myotubular myopathy, Myotonia congenita, Narcolepsy, Neuro-Behçet's disease, Neurofibromatosis, Neuroleptic malignant syndrome, Neurological manifestations of AIDS, Neurological sequelae of lupus, Neuromyotonia, Neuronal ceroid lipofuscinosis, Neuronal migration disorders, Neuropathy, Neurosis, Niemann-Pick disease, Non-24-hour sleep-wake disorder, Nonverbal learning disorder, O'Sullivan-McLeod syndrome, Occipital Neuralgia, Occult Spinal Dysraphism Sequence, Ohtahara syndrome, Olivopontocerebellar atrophy, Opsoclonus myoclonus syndrome, Optic neuritis, Orthostatic Hypotension, Otosclerosis, Overuse syndrome, Palinopsia, Paresthesia, Parkinson's disease, Paramyotonia Congenita, Paraneoplastic diseases, Paroxysmal attacks, Parry-Romberg syndrome, PANDAS, Pelizaeus-Merzbacher disease, Periodic Paralyses, Peripheral neuropathy, Pervasive developmental disorders, Photic sneeze reflex, Phytanic acid storage disease, Pick's disease, Pinched nerve, Pituitary tumors, PMG, Polyneuropathy, Polio, Polymicrogyria, Polymyositis, Porencephaly, Post-Polio syndrome, Postherpetic Neuralgia (PHN), Postural Hypotension, Prader-Willi syndrome, Primary Lateral Sclerosis, Prion diseases, Progressive hemifacial atrophy, Progressive multifocal leukoencephalopathy, Progressive Supranuclear Palsy, Prosopagnosia, Pseudotumor cerebri, Quadrantanopia, Quadriplegia, Rabies, Radiculopathy, Ramsay Hunt syndrome type I, Ramsay Hunt syndrome type II, Ramsay Hunt syndrome type III, Rasmussen encephalitis, Reflex neurovascular dystrophy, Refsum disease, REM sleep behavior disorder, Repetitive stress injury, Restless legs syndrome, Retrovirus-associated myelopathy, Rett syndrome, Reye's syndrome, Rhythmic Movement Disorder, Romberg syndrome, Saint Vitus dance, Sandhoff disease, Schilder's disease, Schizencephaly, Sensory processing disorder, Septo-optic dysplasia, Shaken baby syndrome, Shingles, Shy-Drager syndrome, Sjögren's syndrome, Sleep apnea, Sleeping sickness, Snatiation, Sotos syndrome, Spasticity, Spina bifida, Spinal cord injury, Spinal cord tumors, Spinal muscular atrophy, Spinal and bulbar muscular atrophy, Spinocerebellar ataxia, Split-brain, Steele-Richardson-Olszewski syndrome, Stiff-person syndrome, Stroke, Sturge-Weber syndrome, Stuttering, Subacute sclerosing panencephalitis, Subcortical arteriosclerotic encephalopathy, Superficial siderosis, Sydenham's chorea, Syncope, Synesthesia, Syringomyelia, Tarsal tunnel syndrome, Tardive dyskinesia, Tardive dysphrenia, Tarlov cyst, Tay-Sachs disease, Temporal arteritis, Temporal lobe epilepsy, Tetanus, Tethered spinal cord syndrome, Thomsen disease, Thoracic outlet syndrome, Tic Douloureux, Todd's paralysis, Tourette syndrome, Toxic encephalopathy, Transient ischemic attack, Transmissible spongiform encephalopathies, Transverse myelitis, Traumatic brain injury, Tremor, Trichotillomania, Trigeminal neuralgia, Tropical spastic paraparesis, Trypanosomiasis, Tuberous sclerosis, Unverricht-Lundborg disease, Von Hippel-Lindau disease (VHL), Viliuisk Encephalomyelitis (VE), Wallenberg's syndrome, West syndrome, Whiplash, Williams syndrome, Wilson's disease, or Zellweger syndrome.

In some cases, the compositions and methods disclosed herein can be used to treat brain cancer or brain tumors. Non-limiting examples of brain cancers or tumors that may be amenable to treatment with vectors and compositions described herein include: gliomas including anaplastic astrocytoma (grade III glioma), astrocytoma (grade II glioma), brainstem glioma, ependymoma, ganglioglioma, ganglioneuroma, glioblastoma (grade IV glioma), glioma, juvenile pilocytic astrocytoma (JPA), low-grade astrocytoma (LGA), medullablastoma, mixed glioma, oligodendroglioma, optic nerve glioma, pilocytic astrocytoma (grade I glioma), and primitive neuroectodermal (PNET); skull base tumors including acoustic neuroma (vestibular schwannoma), acromegaly, adenoma, chondrosarcoma, chordoma, craniopharyngioma, epidermoid tumor, glomus jugulare tumor, infratentorial meningioma, meningioma, pituitary adenoma, pituitary tumor, Rathke's cleft cyst; metastatic cancer including brain metastasis, metastatic brain tumor; other brain tumors including brain cyst, choroid plexus papilloma, CNS lymphoma, colloid cyst, cystic tumor, dermoid tumor, germinoma, lymphoma, nasal carcinoma, naso-pharyngeal tumor, pineal tumor, pineoblastoma, pineocytoma, supratentorial meningioma, and vascular tumor; spinal cord tumors including astrocytoma, ependymoma, meningioma, and schwannoma.

The present disclosure contemplates, in part, compositions and methods for controlling, managing, preventing, or treating pain in a subject. "Pain" refers to an uncomfortable feeling and/or an unpleasant sensation in the body of a subject. Feelings of pain can range from mild and occasional to severe and constant. Pain can be classified as acute pain or chronic pain. Pain can be nociceptive pain (i.e., pain caused by tissue damage), neuropathic pain or psychogenic pain. In some cases, the pain is caused by or associated with a disease (e.g., cancer, arthritis, diabetes). In other cases, the pain is caused by injury (e.g., sports injury, trauma). Non-limiting examples of pain that are amenable to treatment with the compositions and methods herein include: neuropathic pain including peripheral neuropathy, diabetic neuropathy, post herpetic neuralgia, trigeminal neuralgia, back pain, neuropathy associated with cancer, neuropathy associated with HIV/AIDS, phantom limb pain, carpal tunnel syndrome, central post-stroke pain, pain associated with chronic alcoholism, hypothyroidism, uremia, pain associated with multiple sclerosis, pain associated with spinal cord injury, pain associated with Parkinson's disease, epilepsy, osteoarthritic pain, rheumatoid arthritic pain, visceral pain, and pain associated with vitamin deficiency; and nociceptive pain including pain associated with central nervous system trauma, strains/sprains, and burns; myocardial infarction, acute pancreatitis, post-operative pain, posttraumatic pain, renal colic, pain associated with cancer, pain associated with fibromyalgia, pain associated with carpal tunnel syndrome, and back pain.

The compositions and methods herein may be utilized to ameliorate a level of pain in a subject. In some cases, a level of pain in a subject is ameliorated by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or 100%. A level of pain in a subject can be assessed by a variety of methods. In some cases, a level of pain is assessed by self-reporting (i.e., a human subject expresses a verbal report of the level of pain he/she is experiencing). In some cases, a level of pain is assessed by behavioral indicators of pain, for example, facial expressions, limb movements, vocalization, restlessness and guarding. These types of assessments may be useful for example when a subject is unable to self-report (e.g., an infant, an unconscious subject, a non-human subject). A level of pain may be assessed after treatment with a composition of the disclosure as compared to the level of pain the subject was experiencing prior to treatment with the composition.

In various embodiments, a method for controlling, managing, preventing, or treating pain in a subject comprises administering to the subject an effective amount of an engineered receptor contemplated herein. Without wishing to be bound by any particular theory, the present disclosure contemplates using the vectors disclosed herein to modulate neuronal activity to alleviate pain in the subject.

In various embodiments, a vector encoding an engineered receptor that activates or depolarizes neuronal cells is administered to (or introduced into) one or more neuronal cells that decrease pain sensation, e.g., inhibitory interneurons. In the presence of ligand the neuronal cell expressing the engineered receptor, is activated and decreases the sensitivity to pain potentiating the analgesic effect of stimulating these neuronal cells.

In various embodiments, a vector encoding an engineered receptor that deactivates or hyperpolarizes neuronal cells is administered to (or introduced into) one or more neuronal cells that increase pain sensation or sensitivity to pain, e.g., nociceptor, peripheral sensory neurons, C-fibers, Aδ fibers, Aβ fibers, DRG neurons, TGG neurons, and the like. In the presence of ligand the neuronal cell expressing the engineered receptor, is deactivated and decreases the sensitivity to pain and potentiating an analgesic effect.

Targeting expression of an engineered receptor to a subpopulation of nociceptors can be achieved by one or more of: selection of the vector (e.g., AAV1, AAV1(Y705+731F+T492V), AAV2(Y444+500+730F+T491V), AAV3(Y705+731F), AAV5, AAV5(Y436+693+719F), AAV6, AAV6 (VP3 variant Y705F/Y731F/T492V), AAV-7m8, AAV8, AAV8 (Y733F), AAV9, AAV9 (VP3 variant Y731F), AAV10 (Y733F), and AAV-ShH10); selection of a promoter; and delivery means.

In particular embodiments, the compositions and methods contemplated herein are effective in reducing pain. Illustrative examples of pain that are amenable to treatment with the vectors, compositions, and methods contemplated herein, include but are not limited to acute pain, chronic pain, neuropathic pain, nociceptive pain, allodynia, inflammatory pain, inflammatory hyperalgesia, neuropathies, neuralgia, diabetic neuropathy, human immunodeficiency virus-related neuropathy, nerve injury, rheumatoid arthritic pain, osteoarthritic pain, burns, back pain, eye pain, visceral pain, cancer pain (e.g., bone cancer pain), dental pain, headache, migraine, carpal tunnel syndrome, fibromyalgia, neuritis, sciatica, pelvic hypersensitivity, pelvic pain, post herpetic neuralgia, post-operative pain, post stroke pain, and menstrual pain.

Pain can be classified as acute or chronic. "Acute pain" refers to pain that begins suddenly and is usually sharp in quality. Acute pain might be mild and last just a moment, or it might be severe and last for weeks or months. In most cases, acute pain does not last longer than three months, and it disappears when the underlying cause of pain has been treated or has healed. Unrelieved acute pain, however, may lead to chronic pain. "Chronic pain" refers to ongoing or recurrent pain, lasting beyond the usual course of acute illness or injury or lasting for more than three to six months, and which adversely affects the individual's well-being. In particular embodiments, the term "chronic pain" refers to pain that continues when it should not. Chronic pain can be nociceptive pain or neuropathic pain.

In particular embodiments, the compositions and methods contemplated herein are effective in reducing acute pain. In particular embodiments, the compositions and methods contemplated herein are effective in reducing chronic pain.

Clinical pain is present when discomfort and abnormal sensitivity feature among the patient's symptoms. Individuals can present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia-Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive pain, inflammatory pain, and neuropathic pain.

In particular embodiments, the compositions and methods contemplated herein are effective in reducing nociceptive pain. In particular embodiments, the compositions and methods contemplated herein are effective in reducing inflammatory pain. In particular embodiments, the compositions and methods contemplated herein are effective in reducing neuropathic pain.

Nociceptive pain is induced by tissue injury or by intense stimuli with the potential to cause injury. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumor related pain (e.g., bone pain, headache, facial pain or visceral pain) or pain associated with cancer therapy (e.g., post chemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain can be defined as pain initiated or caused by a primary lesion or dysfunction in the nervous system. Etiologies of neuropathic pain include, e.g., peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy, and vitamin deficiency.

Neuropathic pain can be related to a pain disorder, a term referring to a disease, disorder or condition associated with or caused by pain. Illustrative examples of pain disorders include arthritis, allodynia, a typical trigeminal neuralgia, trigeminal neuralgia, somatoform disorder, hypoesthesis, hypealgesia, neuralgia, neuritis, neurogenic pain, analgesia, anesthesia dolorosa, causlagia, sciatic nerve pain disorder, degenerative joint disorder, fibromyalgia, visceral disease, chronic pain disorders, migraine/headache pain, chronic fatigue syndrome, complex regional pain syndrome, neurodystrophy, plantar fasciitis or pain associated with cancer.

The inflammatory process is a complex series of biochemical and cellular events, activated in response to tissue injury or the presence of foreign substances, which results in swelling and pain. Arthritic pain is a common inflammatory pain.

Other types of pain that are amenable to treatment with the vectors, compositions, and methods contemplated herein, include but are not limited to pain resulting from musculoskeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardial infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome, and temporomandibular myofascial pain.

The effective amount of the compositions and methods contemplated herein to reduce the amount of pain experienced by a human subject can be determined using a variety of pain scales. Patient self-reporting can be used to assess whether pain is reduced; see, e.g., Katz and Melzack (1999) Surg. Clin. North Am. 79:231. Alternatively, an observational pain scale can be used. The LANSS Pain Scale can be used to assess whether pain is reduced; see, e.g., Bennett (2001) Pain 92:147. A visual analog pain scale can be used; see, e.g., Schmader (2002) Clin. J. Pain 18:350. The Likert pain scale can be used; e.g., where 0 is no pain, 5 is moderate pain, and 10 is the worst pain possible. Self-report pain scales for children include, e.g., Faces Pain Scale; Wong-Baker FACES Pain Rating Scale; and Colored Analog Scale. Self-report pain scales for adults include, e.g., Visual Analog Scale; Verbal Numerical Rating Scale; Verbal Descriptor Scale; and Brief Pain Inventory. Pain measurement scales include, e.g., Alder Hey Triage Pain Score (Stewart et al. (2004) Arch. Dis. Child. 89:625); Behavioral Pain Scale (Payen et al. (2001) Critical Care Medicine 29:2258); Brief Pain Inventory (Cleeland and Ryan (1994) Ann. Acad. Med. Singapore 23: 129); Checklist of Nonverbal Pain Indicators (Feldt (2000) Pain Manag. Nurs. 1: 13); Critical-Care Pain Observation Tool (Gelinas et al. (2006) Am. J. Crit. Care 15:420); COMFORT scale (Ambuel et al. (1992) J. Pediatric Psychol. 17:95); Dallas Pain Questionnaire (Ozguler et al.

(2002) Spine 27:1783); Dolorimeter Pain Index (Hardy et al. (1952) Pain Sensations and Reactions Baltimore: The Williams & Wilkins Co.); Faces Pain Scale—Revised (Hicks et al. (2001) Pain 93:173); Face Legs Activity Cry Consolability Scale; McGill Pain Questionnaire (Melzack (1975) Pain 1:277); Descriptor Differential Scale (Gracely and Kwilosz (1988) Pain 35:279); Numerical 1 1 point Box (Jensen et al. (1989) Clin. J. Pain 5: 153); Numeric Rating Scale (Hartrick et al. (2003) Pain Pract. 3:310); Wong-Baker FACES Pain Rating Scale; and Visual Analog Scale (Huskisson (1982) J. Rheumatol. 9:768).

In particular embodiments, a method of relieving pain in a subject is provided, the method comprising introducing an engineered receptor into a neuronal cell and controlling the activity of the cell by providing an effective amount of a ligand that activates the engineered receptor, thereby relieving pain in the subject. The method provides significant analgesia for pain without off-target effects, such as general central nervous system depression. In certain embodiments, the method provides a 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more reduction in the neuropathic pain in a subject compared to an untreated subject. In some embodiments, the method comprises the step of measuring pain in the subject before and after the administration of the binding agent, wherein the pain in the subject is reduced 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more. In such instances, the measuring may occur 4 hours or more after administration of the binding agent, e.g. 8 hours 12 hours, 16 hours, 24 hours, 36 hours, 48 hours, 3 days, or 4 days or more after administration of the binding agent.

In particular embodiments, the vectors contemplated herein are administered or introduced into one or more neuronal cells. The neuronal cells may be the same type of neuronal cells, or a mixed population of different types of neuronal cells. In one embodiment, the neuronal cell is a nociceptor or peripheral sensory neuron. Illustrative examples of sensory neurons include, but are not limited to, dorsal root ganglion (DRG) neurons and trigeminal ganglion (TGG) neurons. In one embodiment, the neuronal cell is an inhibitory interneuron involved in the neuronal pain circuit.

In some cases, a vector encoding an engineered receptor is administered to a subject in need thereof. Non-limiting examples of methods of administration include subcutaneous administration, intravenous administration, intramuscular administration, intradermal administration, intraperitoneal administration, oral administration, infusion, intracranial administration, intrathecal administration, intranasal administration, intraganglionic administration, intraspinal administration, cisterna magna administration and intraneural administration. In some cases, administration can involve injection of a liquid formulation of the vector. In other cases, administration can involve oral delivery of a solid formulation of the vector. In some cases, the oral formulation can be administered with food. In particular embodiments, a vector is parenterally, intravenously, intramuscularly, intraperitoneally, intrathecally, intraneurally, intraganglionicly, intraspinally, or intraventricularly administered to a subject in order to introduce the vector into one or more neuronal cells. In various embodiments, the vector is rAAV.

In one embodiment, AAV is administered to sensory neuron or nociceptor, e.g., DRG neurons, TGG neurons, etc. by intrathecal (IT) or intraganglionic (IG) administration.

The IT route delivers AAV to the cerebrospinal fluid (CSF). This route of administration may be suitable for the treatment of e.g., chronic pain or other peripheral nervous system (PNS) or central nervous system (CNS) indications. In animals, IT administration has been achieved by inserting an IT catheter through the cisterna magna and advancing it caudally to the lumbar level. In humans, IT delivery can be easily performed by lumbar puncture (LP), a routine bedside procedure with excellent safety profile.

In a particular case, a vector may be administered to a subject by intraganglionic administration. Intraganglionic administration may involve an injection directly into one or more ganglia. The IG route may deliver AAV directly into the DRG or TGG parenchyma. In animals, IG administration to the DRG is performed by an open neurosurgical procedure that is not desirable in humans because it would require a complicated and invasive procedure. In humans, a minimally invasive, CT imaging-guided technique to safely target the DRG can be used. A customized needle assembly for convection enhanced delivery (CED) can be used to deliver AAV into the DRG parenchyma. In a non-limiting example, a vector of the disclosure may be delivered to one or more dorsal root ganglia and/or trigeminal ganglia for the treatment of chronic pain. In another non-limiting example, a vector of the disclosure may be delivered to the nodose ganglion (vagus nerve) to treat epilepsy.

In yet another particular case, a vector may be administered to the subject by intracranial administration (i.e., directly into the brain). In non-limiting examples of intracranial administration, a vector of the disclosure may be delivered into the cortex of the brain to treat e.g., an epileptic seizure focus, into the paraventricular hypothalamus to treat e.g., a satiety disorder, or into the amygdala central nucleus to treat e.g., a satiety disorder. In another particular case, a vector may be administered to a subject by intraneural injection (i.e., directly into a nerve). The nerve may be selected based on the indication to be treated, for example, injection into the sciatic nerve to treat chronic pain or injection into the vagal nerve to treat epilepsy or a satiety disorder. In yet another particular case, a vector may be administered to a subject by subcutaneous injection, for example, into the sensory nerve terminals to treat chronic pain.

A vector dose may be expressed as the number of vector genome units delivered to a subject. A "vector genome unit" as used herein refers to the number of individual vector genomes administered in a dose. The size of an individual vector genome will generally depend on the type of viral vector used. Vector genomes of the disclosure may be from about 1.0 kilobase, 1.5 kilobases, 2.0 kilobases, 2.5 kilobases, 3.0 kilobases, 3.5 kilobases, 4.0 kilobases, 4.5 kilobases, 5.0 kilobases, 5.5 kilobases, 6.0 kilobases, 6.5 kilobases, 7.0 kilobases, 7.5 kilobases, 8.0 kilobases, 8.5 kilobases, 9.0 kilobases, 9.5 kilobases, 10.0 kilobases, to more than 10.0 kilobases. Therefore, a single vector genome may include up to or greater than 10,000 base pairs of nucleotides. In some cases, a vector dose may be about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, $1\times10^{16}$, $2\times10^{16}$, $3\times10^{16}$, $4\times10^{16}$, $5\times10^{16}$, $6\times10^{16}$, $7\times10^{16}$, $8\times10^{16}$, $9\times10^{16}$, $1\times10^{17}$, $2\times10^{17}$, $3\times10^{17}$, $4\times10^{17}$, $5\times10^{17}$, $6\times10^{17}$, $7\times10^{17}$, $8\times10^{17}$, $9\times10^{17}$, $1\times10^{18}$, $2\times10^{18}$, $3\times10^{18}$, $4\times10^{18}$, $5\times10^{18}$, $6\times10^{18}$, $7\times10^{18}$, $8\times10^{18}$, $9\times10^{18}$, $1\times10^{19}$, $2\times10^{19}$, $3\times10^{19}$, $4\times10^{19}$, $5\times10^{19}$, $6\times10^{19}$, $7\times10^{19}$, $8\times10^{19}$, $9\times10^{19}$, $1\times10^{20}$, $2\times10^{20}$, $3\times10^{20}$, $4\times10^{20}$, $5\times10^{20}$, $6\times10^{20}$, $7\times10^{20}$, $8\times10^{20}$, $9\times10^{20}$ or more vector genome units.

In particular embodiments, a vector contemplated herein is administered to a subject at a titer of at least about $1\times10^{9}$ genome particles/mL, at least about $1\times10^{10}$ genome particles/mL, at least about $5\times10^{10}$ genome particles/mL, at least about $1\times10^{11}$ genome particles/mL, at least about $5\times10^{11}$ genome particles/mL, at least about $1\times10^{12}$ genome particles/mL, at least about $5\times10^{12}$ genome particles/mL, at least about $6\times10^{12}$ genome particles/mL, at least about $7\times10^{12}$ genome particles/mL, at least about $8\times10^{12}$ genome particles/mL, at least about $9\times10^{12}$ genome particles/mL, at least about $10\times10^{12}$ genome particles/mL, at least about $15\times10^{12}$ genome particles/mL, at least about $20\times10^{12}$ genome particles/mL, at least about $25\times10^{12}$ genome particles/mL, at least about $50\times10^{12}$ genome particles/mL, or at least about $100\times10^{12}$ genome particles/mL. The terms "genome particles (gp)," or "genome equivalents," or "genome copies" (gc) as used in reference to a viral titer, refer to the number of virions containing the recombinant AAV DNA genome, regardless of infectivity or functionality. The number of genome particles in a particular vector preparation can be measured by well understood methods in the art, for example, quantitative PCR of genomic DNA or for example, in Clark et al. (1999) Hum. Gene Ther., 10:1031-1039; Veldwijk et al. (2002) Mol. Ther., 6:272-278.

A vector of the disclosure may be administered in a volume of fluid. In some cases, a vector may be administered in a volume of about 0.1 mL, 0.2 mL, 0.3 mL, 0.4 mL, 0.5 mL, 0.6 mL, 0.7 mL, 0.8 mL, 0.9 mL, 1.0 mL, 2.0 mL, 3.0 mL, 4.0 mL, 5.0 mL, 6.0 mL, 7.0 mL, 8.0 mL, 9.0 mL, 10.0 mL, 11.0 mL, 12.0 mL, 13.0 mL, 14.0 mL, 15.0 mL, 16.0 mL, 17.0 mL, 18.0 mL, 19.0 mL, 20.0 mL or greater than 20.0 mL. In some cases, a vector dose may be expressed as a concentration or titer of vector administered to a subject. In this case, a vector dose may be expressed as the number of vector genome units per volume (i.e., genome units/volume).

In particular embodiments, a vector contemplated herein is administered to a subject at a titer of at least about $5\times10^{9}$ infectious units/mL, at least about $6\times10^{9}$ infectious units/mL, at least about $7\times10^{9}$ infectious units/mL, at least about $8\times10^{9}$ infectious units/mL, at least about $9\times10^{9}$ infectious units/mL, at least about $1\times10^{10}$ infectious units/mL, at least about $1.5\times10^{10}$ infectious units/mL, at least about $2\times10^{10}$ infectious units/mL, at least about $2.5\times10^{10}$ infectious units/mL, at least about $5\times10^{10}$ infectious units/mL, at least about $1\times10^{11}$ infectious units/mL, at least about $2.5\times10^{11}$ infectious units/mL, at least about $5\times10^{11}$ infectious units/mL, at least about $1\times10^{12}$ infectious units/mL, at least about $2.5\times10^{12}$ infectious units/mL, at least about $5\times10^{12}$ infectious units/mL, at least about $1\times10^{13}$ infectious units/mL, at least about $5\times10^{13}$ infectious units/mL, at least about $1\times10^{14}$ infectious units/mL. The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

In particular embodiments, a vector contemplated herein is administered to a subject at a titer of at least about $5\times10^{10}$ transducing units/mL, at least about $1\times10^{11}$ transducing units/mL, at least about $2.5\times10^{11}$ transducing units/mL, at least about $5\times10^{11}$ transducing units/mL, at least about $1\times10^{12}$ transducing units/mL, at least about $2.5\times10^{12}$ transducing units/mL, at least about $5\times10^{12}$ transducing units/mL, at least about $1\times10^{13}$ transducing units/mL, at least about $5\times10^{13}$ transducing units/mL, at least about $1\times10^{14}$ transducing units/mL. The term "transducing unit" (tu)" as used in reference to a viral titer, refers to the number of infectious recombinant AAV vector particles that result in the production of a functional transgene product as measured in functional assays such as described in, for example, in Xiao et al. (1997) Exp. Neurobiol., 144:113-124; or in Fisher et al. (1996) J. Virol., 70:520-532 (LFU assay).

The vector dose will generally be determined by the route of administration. In a particular example, an intraganglionic injection may include from about $1\times10^{9}$ to about $1\times10^{13}$ vector genomes in a volume from about 0.1 mL to about 1.0 mL. In another particular case, an intrathecal injection may include from about $1\times10^{10}$ to about $1\times10^{15}$ vector genomes in a volume from about 1.0 mL to about 12.0 mL. In yet another particular case, an intracranial injection may include from about $1\times10^{9}$ to about $1\times10^{13}$ vector genomes in a volume from about 0.1 mL to about 1.0 mL. In another particular case, an intraneural injection may include from about $1\times10^{9}$ to about $1\times10^{13}$ vector genomes in a volume from about 0.1 mL to about 1.0 mL. In another particular example, an intraspinal injection may include from about $1\times10^{9}$ to about $1\times10^{13}$ vector genomes in a volume from about 0.1 mL to about 1.0 mL. In yet another particular case, a cisterna magna infusion may include from about $5\times10^{9}$ to about $5\times10^{13}$ vector genomes in a volume from about 0.5 mL to about 5.0 mL. In yet another particular case, a subcutaneous injection may include from about $1\times10^{9}$ to about $1\times10^{13}$ vector genomes in a volume from about 0.1 mL to about 1.0 mL.

In some cases, a vector is delivered to a subject by infusion. A vector dose delivered to a subject by infusion can be measured as a vector infusion rate. Non-limiting examples of vector infusion rates include: 1-10 μL/min for intraganglionic, intraspinal, intracranial or intraneural administration; and 10-1000 μL/min for intrathecal or cisterna magna administration. In some cases, the vector is delivered to a subject by MRI-guided Convection Enhanced Delivery (CED). This technique enables increased viral spread and transduction distributed throughout large volumes of the brain, as well as reduces reflux of the vector along the needle path.

In various embodiments, a method is provided comprising administering a vector encoding a engineered receptor, that deactivates or hyperpolarizes neuronal cells, to one or more neuronal cells that increase pain sensation or sensitivity to pain, and administering a ligand that specifically binds the neuronal cell expressing the engineered receptor to the subject, thereby deactivating the cell, decreasing the sensitivity to pain and potentiating an analgesic effect.

In various embodiments, a method is provided comprising administering a vector encoding a engineered receptor, that activates or polarizes neuronal cells, to one or more neuronal cells that decrease pain sensation or sensitivity to pain, and administering a ligand that specifically binds the neuronal cell expressing the engineered receptor to the subject, thereby activating the cell, decreasing the sensitivity to pain and potentiating an analgesic effect.

Formulations of ligands may be administered to a subject by various routes. Non-limiting examples of methods of administration include subcutaneous administration, intravenous administration, intramuscular administration, transdermal administration, intradermal administration, intraperitoneal administration, oral administration, infusion, intracranial administration, intrathecal administration, intranasal administration, intraganglionic administration, and intraneural administration. In some cases, administration can involve injection of a liquid formulation of the ligand. In other cases, administration can involve oral delivery of a solid formulation of the ligand. In a particular case, a ligand is administered by oral administration (e.g., a pill, tablet, capsule and the like). In some cases, the oral composition can be administered with food. In another particular case, a ligand is administered by intrathecal injection (i.e., into the subarachnoid space of the spinal cord) for delivery to the cerebrospinal fluid (CSF) of the subject. In another particular case, a ligand is administered topically (e.g., dermal patch, cream, lotion, ointment and the like).

The dosages of the ligands administered to a subject are not subject to absolute limits, but will depend on the nature of the composition and its active ingredients and its unwanted side effects (e.g., immune response against the antibody), the subject being treated and the type of condition being treated and the manner of administration. Generally, the dose will be a therapeutically effective amount, such as an amount sufficient to achieve a desired biological effect, for example an amount that is effective to decrease or attenuate the level of pain experienced by the subject. In particular embodiments, the dose can also be a prophylactic amount or an effective amount. A therapeutically effective amount of ligand may depend on the route of administration, the indication being treated, and/or the ligand selected for use.

In one embodiment, the ligand is first administered to the subject prior to administration of the vector. A therapeutically effective amount of ligand may be administered to a subject at some time after delivery of a vector. Generally, after delivery of a vector, there will be a period of time required for one or more cells of the subject to generate a protein (i.e., engineered receptor) encoded by the vector. During this period of time, administration of a ligand to the subject may not be beneficial to the subject. In this situation, it may be suitable to administer the ligand after an amount of engineered receptor has been produced by one or more cells of the subject.

In one embodiment, the ligand is first administered to the subject at about the same time that the vector is administered to the subject.

In one embodiment, the ligand is first administered 1, 2, 3, 4, 5, 6, 7, 8, 9, 11, or 12 hours, days, weeks, months, or years after administration of the vector to the subject. In some cases, a therapeutically effective amount of a ligand may be administered to a subject at least one day, two days, three days, four days, five days, six days, seven days, eight days, nine days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or more than 30 days after delivery of the vector. In a particular example, a therapeutically effective amount of a ligand is administered to a subject at least one week after delivery of a vector. In a further example, the therapeutically effective amount of ligand is administered to the subject daily for at least three consecutive days.

A therapeutically effective amount or dose of a ligand of the disclosure can be expressed as mg or µg of the ligand per kg of subject body mass. In some instances, a therapeutically effective amount of a ligand may be about 0.001 µg/kg, about 0.005 µg/kg, about 0.01 µg/kg, about 0.05 µg/kg, about 0.1 µg/kg, about 0.5 µg/kg, about 1 µg/kg, about 2 µg/kg, about 3 µg/kg, about 4 µg/kg, about 5 µg/kg, about 6 µg/kg, about 7 µg/kg, about 8 µg/kg, about 9 µg/kg, about 10 µg/kg, about 20 µg/kg, about 30 µg/kg, about 40 µg/kg, about 50 µg/kg, about 60 µg/kg, about 70 µg/kg, about 80 µg/kg, about 90 µg/kg, about 100 µg/kg, about 120 µg/kg, about 140 µg/kg, about 160 µg/kg, about 180 µg/kg, about 200 µg/kg, about 220 µg/kg, about 240 µg/kg, about 260 µg/kg, about 280 µg/kg, about 300 µg/kg, about 320 µg/kg, about 340 µg/kg, about 360 µg/kg, about 380 µg/kg, about 400 µg/kg, about 420 µg/kg, about 440 µg/kg, about 460 µg/kg, about 480 µg/kg, about 500 µg/kg, about 520 µg/kg, about 540 µg/kg, about 560 µg/kg, about 580 µg/kg, about 600 µg/kg, about 620 µg/kg, about 640 µg/kg, about 660 µg/kg, about 680 µg/kg, about 700 µg/kg, about 720 µg/kg, about 740 µg/kg, about 760 µg/kg, about 780 µg/kg, about 800 µg/kg, about 820 µg/kg, about 840 µg/kg, about 860 µg/kg, about 880 µg/kg, about 900 µg/kg, about 920 µg/kg, about 940 µg/kg, about 960 µg/kg, about 980 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, or greater than 10 mg/kg.

In particular embodiments, the dose of ligand administered to a subject is at least about 0.001 micrograms per kilogram (m/kg), at least about 0.005 µg/kg, at least about 0.01 µg/kg, at least about 0.05 µg/kg, at least about 0.1 µg/kg, at least about 0.5 µg/kg, 0.001 milligrams per kilogram (mg/kg), at least about 0.005 mg/kg, at least about 0.01 mg/kg, at least about 0.05 mg/kg, at least about 0.1 mg/kg, at least about 0.5 mg/kg, at least about 1 mg/kg, at least about 2 mg/kg, at least about 3 mg/kg, at least about 4 mg/kg, at least about 5 mg/kg, at least about 5 mg/kg, at least about 6 mg/kg, at least about 7 mg/kg, at least about 8 mg/kg, at least about 8 mg/kg, at least about 9 mg/kg, or at least about 10 or more mg/kg.

In particular embodiments, the dose of ligand administered to a subject is at least about 0.001 µg/kg to at least about 10 mg/kg, at least about 0.01 µg/kg to at least about 10 mg/kg, at least about 0.1 µg/kg to at least about 10 mg/kg, at least about 1 µg/kg to at least about 10 mg/kg, at least about 0.01 mg/kg to at least about 10 mg/kg, at least about 0.1 mg/kg to at least about 10 mg/kg, or at least about 1 mg/kg to at least about 10 mg/kg, or any intervening range thereof.

In some aspects, a therapeutically effective amount of a ligand can be expressed as a molar concentration (i.e., M or mol/L). In some cases, a therapeutically effective amount of a ligand can be about 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 200 mM, 300 mM, 400 mM, 500 mM, 600 mM, 700 mM, 800 mM, 900 mM, 1000 mM or greater.

A therapeutically effective amount of a ligand can be administered once or more than once each day. In some cases, a therapeutically effective amount of a ligand is administered as needed (e.g., when pain relief is needed). The ligand may be administered serially (e.g., every day without a break for the duration of the treatment regimen). In some cases, the treatment regimen can be less than a week, a week, two weeks, three weeks, a month, or greater than a month. In some cases, a therapeutically effective amount of a ligand is administered for a day, at least two consecutive days, at least three consecutive days, at least four consecutive days, at least five consecutive days, at least six consecutive days, at least seven consecutive days, at least eight consecutive days, at least nine consecutive days, at least ten consecutive days, or at least greater than ten consecutive days. In a particular case, a therapeutically effective amount of a ligand is administered for three consecutive days. In some cases, a therapeutically effective amount of a ligand can be administered one time per week, two times per week, three times per week, four times per week, five times per week, six times per week, seven times per week, eight times per week, nine times per week, 10 times per week, 11 times per week, 12 times per week, 13 times per week, 14 times per week, 15 times per week, 16 times per week, 17 times per week, 18 times per week, 19 times per week, 20 times per week, 25 times per week, 30 times per week, 35 times per week, 40 times per week, or greater than 40 times per week. In some cases, a therapeutically effective amount of a ligand can be administered one time per day, two times per day, three times per day, four times per day, five times per day, six times per day, seven times per day, eight times per day, nine times per day, 10 times per day, or greater than 10 times per day. In some cases, a therapeutically effective amount of a ligand is administered at least every hour, at least every two hours, at least every three hours, at least every four hours, at least every five hours, at least every six hours, at least every seven hours, at least every eight hours, at least every nine hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day. The dose of ligand may be administered to the subject continuously, or 1, 2, 3, 4, or 5 times a day; 1, 2, 3, 4, 5, 6, or 7 times a week, 1, 2, 3, or 4 times a month, once every 2, 3, 4, 5, or 6 months, or once a year, or at even longer intervals. The duration of treatment can last a day, 1, 2, or 3 weeks, 1, 2, 3, 4, 5, 7, 8, 9, 10, or 11 months, 1, 2, 3, 4, 5, or more years, or longer.

A subject treated by methods and compositions disclosed herein can be a human, or can be a non-human animal. The term "treat" and its grammatical equivalents used herein generally refer to the use of a composition or method to reduce, eliminate, or prevent symptoms of a disease and includes achieving a therapeutic benefit and/or a prophylactic benefit. By therapeutic benefit is meant slowing the progression of, halting the progression of, reversing the progression of, or eradication or amelioration of the symptoms of the disorder or condition being treated. A prophylactic benefit of treatment includes reducing the risk of a condition, retarding the progress of a condition, or decreasing the likelihood of occurrence of a condition.

Non-limiting examples of non-human animals include a non-human primate, a livestock animal, a domestic pet, and a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a lama, a sheep, a goat, a buffalo, a reindeer, a yak, a mouse, a rat, a rabbit, or any other non-human animal. The compositions and methods as described herein are amenable to the treatment of a veterinary animal. A veterinary animal can include, without limitation, a dog, a cat, a horse, a cow, a sheep, a mouse, a rat, a guinea pig, a hamster, a rabbit, a snake, a turtle, and a lizard. In some aspects, contacting the tissue or cell population with a composition comprises administering the composition to a cell population or subject. In some embodiments, administration occurs in vitro, for example by adding the composition to a cell culture system. In some aspects, administration occurs in vivo, for example by administration through a particular route. Wherein more than one composition is to be administered, the compositions may be administered via the same route at the same time (e.g., on the same day), or via the same route at different times. Alternatively, the compositions may be administered via different routes at the same time (e.g., on the same day) or via different routes at different times.

The number of times a composition is administered to an subject in need thereof depends on the discretion of a medical professional, the disorder, the severity of the disorder, and the subject's response to the formulation. In some aspects, administration of a composition occurs at least once. In further aspects, administration occurs more than once, for example 2, 3, 4, 5, 6, 7, 8, 9, 10 or more times in a given period. The dosage of each administration and/or frequency of administrations may be adjusted as necessary based on the patient's condition and physiologically responses.

In some embodiments, compositions may be administered a sufficient amount of times to achieve a desired physiologic effect or improvement in a subject's condition. In the case wherein the subject's condition does not improve, upon the doctor's discretion the composition may be administered chronically, that is, for an extended period of time, including throughout the duration of the subject's life in order to ameliorate or otherwise control or limit the symptoms of the subject's disease or condition. In the case wherein the subject's status does improve, upon the doctor's discretion the composition may administered continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Where compositions are administered more than once, each administration may be performed by the same actor and/or in the same geographical location. Alternatively, each administration may be performed by a different actor and/or in a different geographical location.

With regard to human and veterinary treatment, the amount of a particular agent(s) that is administered may be dependent on a variety of factors, including the disorder being treated and the severity of the disorder; activity of the specific agent(s) employed; the age, body weight, general health, sex and diet of the patient; the time of administration, route of administration, and rate of excretion of the specific agent(s) employed; the duration of the treatment; drugs used in combination or coincidental with the specific agent(s) employed; the judgment of the prescribing physician or veterinarian; and like factors known in the medical and veterinary arts. Similarly, the effective concentration of a given composition may be dependent on a variety of factors including the age, sex, weight, genetic status, and overall health of the patient or subject.

EXAMPLES

Example 1. Discovery and Characterization of Engineered Receptors

Chimeric LGIC receptors comprising the ligand binding domain from the α7-nAChR and the chloride-conducting ion pore domain from the human GlyR1α were engineered and assessed for their responsiveness to acetylcholine, nicotine, and several small molecule agonist ligands. Amino acid substitutions were then generated in these "parental" chimeric receptors and the mutants retested for responsiveness to these ligands.

Differences in potency ($EC_{50}$) and current flow (Imax) were observed, both among the engineered chimeric receptors and between the chimeric receptors and the wild type α7-nAChR, suggesting that the domains that contribute to the extracellular domain of the engineered receptor play an influential role in channel properties. Amino acid substitutions in these engineered channels further altered the responsiveness of the channel, in some cases differentially for different ligands. These results indicate that a toolbox of LGIC receptors can be engineered that have unique channel properties, providing an avenue for the development of therapeutics that can be used to control the activity of neurons in disease.

Materials and Methods

Receptor Construction:

Individual parental chimera receptors were cloned into pcDNA3.1(+) (Invitrogen) using BamHI and EcoRI sites by standard molecular biology techniques. Amino acid substitutions were introduced by site-directed mutagenesis.

Plate Reader YFP Quench Assay:

Lenti-X 293T cells (LX293T, Clontech) were maintained in DMEM containing 10% FBS and 1% penicillin/streptomycin (Invitrogen). For plate reader assays, LX293T cells were infected with a lentivirus to create cells that stably express a mutant YFP (H148Q/I152L) reporter, which displays enhanced sensitivity to anions Two days before assay, cells were split at a density of 20,000 cells/well in a 96-well tissue culture plate coated with poly-d lysine (Thermo Scientific). The next day, the cells were transiently transfected with 0.1 μg of DNA per well using standard Fugene protocol (Promega). On the day of assay, cells were washed 2 times in 1× extracellular solution (1×ECS: 140 mM NaCl, 5 mM KCl, 1 mM MgCl2, 2 mM CaCl2, 10 mM HEPES, 10 mM glucose, pH 7.2, mOsms 300). After the last wash, 100 μL of 1×ECS was added to the wells and the plate was incubated at 37° C. for 30 min. While incubating the plate, the drugs were diluted to a 2× concentration in 1×ECS-NaI (same components as 1×ECS except the 140 mM NaCl was replaced by 140 mM NaI). The plates were then read on a Flexstation3 (Molecular Devices). Each well, 8 wells at a time, of the plate is read for 2 min using a Flexstation3 (Molecular Devices) as follows: 1) a baseline YFP fluorescence is read for 17 sec, 2) 100 μL of ligand is added, and 3) the changes in YFP fluorescence are then measured every 1.3 sec for the remaining time.

Electrophysiology:

For HEK293T studies, cDNAs encoding ion channels were cloned into pcDNA3.1 using standard recombination techniques. HEK293T cells from Clontech (Lenti-X™ 293T Cell Line) were cultured in DMEM supplemented with 10% FBS and 1% Pen/Strep to 40-50% confluence using standard cell culture protocols, transfected with ion channel plasmids at a concentration of 18 μg per 15 cm dish using Fugene 6, and grown for an additional 24 hours. Cells were then assayed on a medium throughput electrophysiological system (IonFluxHT and/or Mercury, Fluxion Biosciences) in which dose-response relationships may be assessed through a microfluidics-based platform for establishing whole cell configurations. Ensemble plates were primed with extracellular buffer (140 mM NaCl, 5 mM KCl, 2 mM $CaCl_2$, 1 mM $MgCl_2$, 10 mM HEPES, and 10 mM glucose, pH 7.2 with NaOH, mOsm 310), intracellular buffer (145 mM CsCl, 2 mM CaCl2, 2 mM MgCl2, 10 mM HEPES, and 10 mM EGTA, pH 7.2 with CsOH, mOsm 305), as adapted from Lynagh and Lynch, and test compounds (stocks prepared fresh) diluted in extracellular buffer. Cells were then released from the plate with Accutase, centrifuged, resuspended in extracellular buffer, and loaded into Ensemble plates. Cells were then subjected to a standard protocol for priming, trapping, breaking, and establishing whole cell configuration, with cells held at −60 mV throughout the recording. After recording baseline, progressive doses of test compounds were applied using the IonFlux software to assess dose response relationships. Data were then analyzed off-line using custom Python scripts to convert data to .csv format, re-plot traces, and apply QC measurements to reject unstable recordings (i.e. thresholding based on access resistance and/or standard deviation in baseline, as well as artifact rejection). Peak currents were then calculated and population data were fit using a 4-parameter logistic equation as described by the Hill Equation For *Xenopus* oocyte studies, injections of cDNAs encoding for ion channels at a final concentration of 0.04 μg/μL were performed using a proprietary automated injection device and receptor expression examined at least two days later. Oocytes were poked with two electrodes and their membrane potential maintained at −80 mV throughout the experiment. All recordings were performed at 18° C. and cells were superfused with OR2 medium containing in mM: NaCl 82.5, KCl 2.5, HEPES 5, CaCl2.2H2O 1.8, MgCl2.6H2O 1, pH 7.4. Recordings progressed if oocytes had sufficiently low holding current, in which case they were then subjected to ligand or test compound application (5-10 s wash intervals), with 100 s of wash in between doses. Currents evoked by acetylcholine or other agonists were recorded using an automated process equipped with standard two electrode voltage clamp configuration (TEVC). Data were captured and analyzed using HiQScreen proprietary data acquisition and analysis software running under Matlab (Mathworks Inc.). Acetylcholine was prepared as a concentrated stock solution (10-1 M) in water and then diluted in the recording medium to obtain the desired test concentration. Nicotine was diluted in water as stock solution (10-1 M), kept frozen and diluted immediately prior to the experiment at the desired concentration. Compounds were prepared as stock solution (10-1M) in OR2 and then diluted in the recording medium to obtain the desired test concentration. Stock solution for Compound-1 was made in OR2 at pH 5 adjusted with HCl. To assess that dilution at the final concentration of this stock solution introduced no significant changes, the pH of the final solution was confirmed using a colorimetric assay (Galietta L. J. V., et al. 2001. FEBS Letters 499: 220-224. Kruger W., et al. (2005). Neuroscience Letters 380: 340-345.)

Results

To generate LGICs that conduct anion current following exposure to non-native small molecule agonists of the human "α7-nAChR", fusion proteins were engineered that comprise the chloride-conducting ion pore domain of the human GlyRα1 subunit fused to the ligand binding domain of α7-nAChR. In some fusion proteins, the β1-β2 loop sequence and/or Cys loop sequence of α7-nAChR was replaced with the corresponding sequence from GlyRα1 (see schematics in FIG. 4). In other fusion proteins, the site of the junction between the 3' sequence of the extracellular domain and the 5' sequence of the ion pore domain (the "pre-M1 linker") was shifted. In yet other fusion proteins, the extracellular loop sequence between transmembrane domain 2 and transmembrane domain 3 of the GlyRα1 ion pore domain (the "M1-M2 linker") was replaced with a corresponding M1-M3 linker sequence from the α7-nAChR. The response of these engineered chimeric LGICs to a range of doses of the native ligand, acetylcholine, was assessed by electrophysiology following application of the acetylcholine for 1 second. Different $EC_{50}$s, Imax values, and desensitization kinetics were observed for each channel (FIG. 3), suggesting that including in the ligand binding domain of the channel heterologous sequences that correspond to extracellular regions of the protein that contributes to the ion pore domain of the chimera will alter the properties of the ion channel.

To better understand the impact of the heterologous domains that had been inserted into the channels, the ligand-dependent response profiles of wild type α7-nAChR and various engineered chimeric LGIC receptors to acetylcholine as well as to non-native ligands TC-6987, AZD-0328, and Facinicline/RG3487 were assessed. Receptors were transiently expressed in HEK291T cells and currents were measured on an automated patch clamp system (Fluxion Biosciences) following 1 second addition of drug. Inclusion of a GlyRα1 Cys-loop sequence in the extracellular domain increased the potency of all small molecules on the engineered receptor (leftward shift in $EC_{50}$) (e.g. SEQ ID NO:35, FIG. 4C vs SEQ ID NO:16, FIG. 4B). Increasing the length of the heterologous Cys loop sequence modestly shifted the $EC_{50}$ rightward for all compounds but increased Imax values significantly (SEQ ID NO:33, FIG. 4D vs SEQ ID NO:35, FIG. 4C), indicated a modest decrease in potency but increase in conductance overall. Inclusion of both the Cys-loop and β1-β2 loop sequences of GlyRα1 in the extracellular domain reduced the sensitivity by about 1 log from that observed with the full Cys-loop sequence alone, but further increased conductance approximately 2-fold and slowed the rate of deactivation of the channel (SEQ ID NO:41, FIG. 4E vs. SEQ ID NO:33, FIG. 4D). These results were confirmed in a second model system in which the receptors were expressed in *Xenopus* oocytes and currents were measured on a manual patch clamp system following 10 s applications of increasing doses of compound (FIG. 5).

Overall, SEQ ID NO:33 is approximately as sensitive to acetylcholine, ABT-126 and TC-6987 as wild type α7-nAChR, with TC-6987 showing partial agonist activity on SEQ ID NO:33 similar to wild type. SEQ ID NO:33 is approximate 2-fold less sensitive to nicotine, and approximately 3-fold and 10-fold more sensitive to AZD-0328 and Facinicline/RG3487, respectively, than wild type. SEQ ID NO:41, further comprising the β1-β2 loop domain from GlyRα1, is comparably sensitive to ABT-126, TC-6987, and AZD-0328 as wild type α7-nAChR but less sensitive to acetylcholine and nicotine, with the $EC_{50}$s for acetylcholine and nicotine on SEQ ID NO:41 being approximately 4-fold and 7-fold larger (right shifted) than for wild type. While SEQ ID NO:41 is less sensitive to Facinicline/RG3487 than SEQ ID NO:33, it is still more sensitive to Facinicline/RG3487 than wild type, with the $EC_{50}$ being approximately 2-fold lower (left shifted) (FIG. 5).

Figure 6:
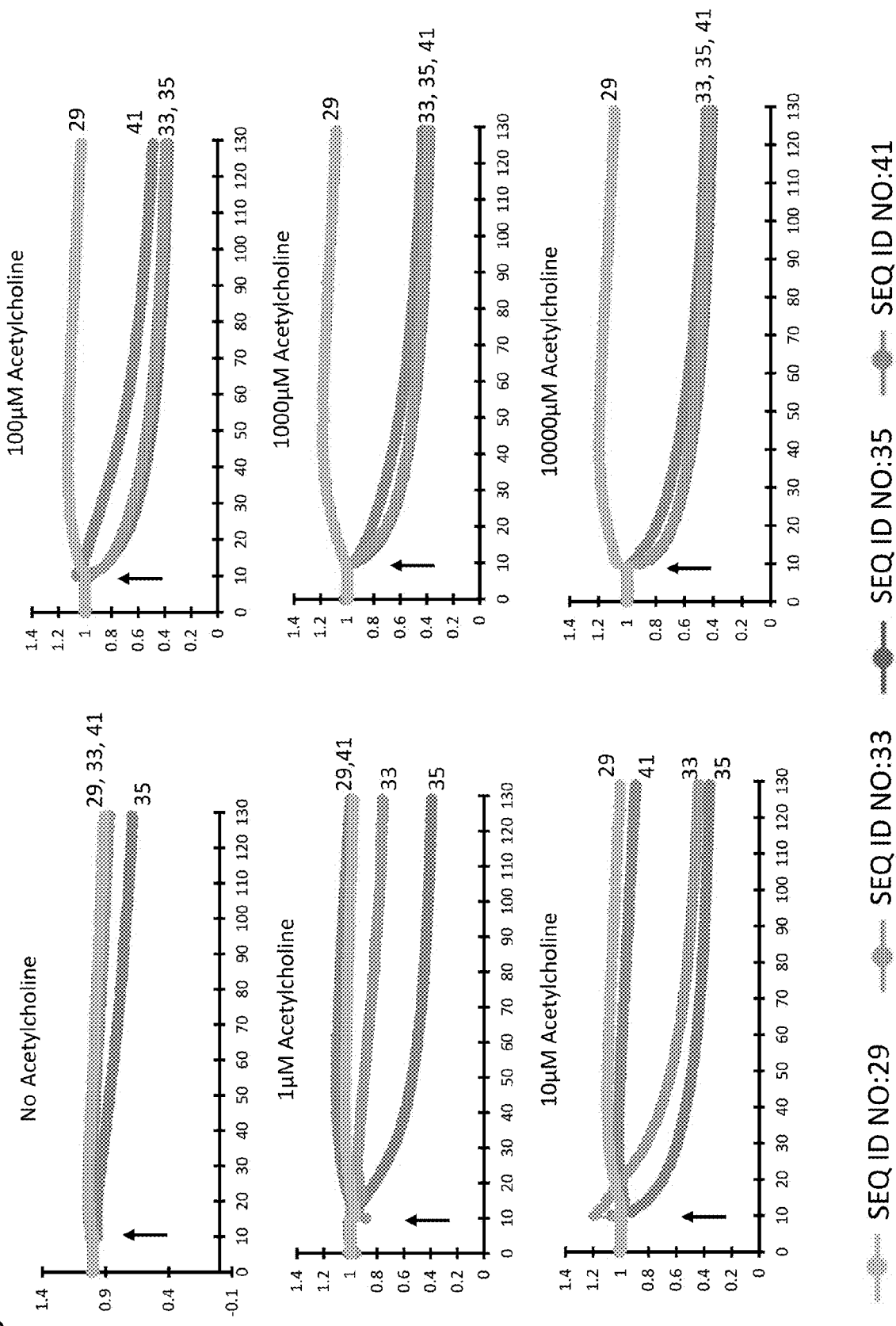
FIG. 6 depicts the responses of four different engineered chimeric LGIC receptors (SEQ ID NO:29, SEQ ID NO:33, SEQ ID NO:35, SEQ ID NO:41) to increasing concentrations of acetylcholine as measure by the quench in YFP fluorescence over time. These quench plots demonstrate by a second approach that different parental chimeras have different $EC_{50}$s and activation kinetics to acetylcholine. The time point of acetylcholine stimulation is indicated by the arrow.
Figure 7A:
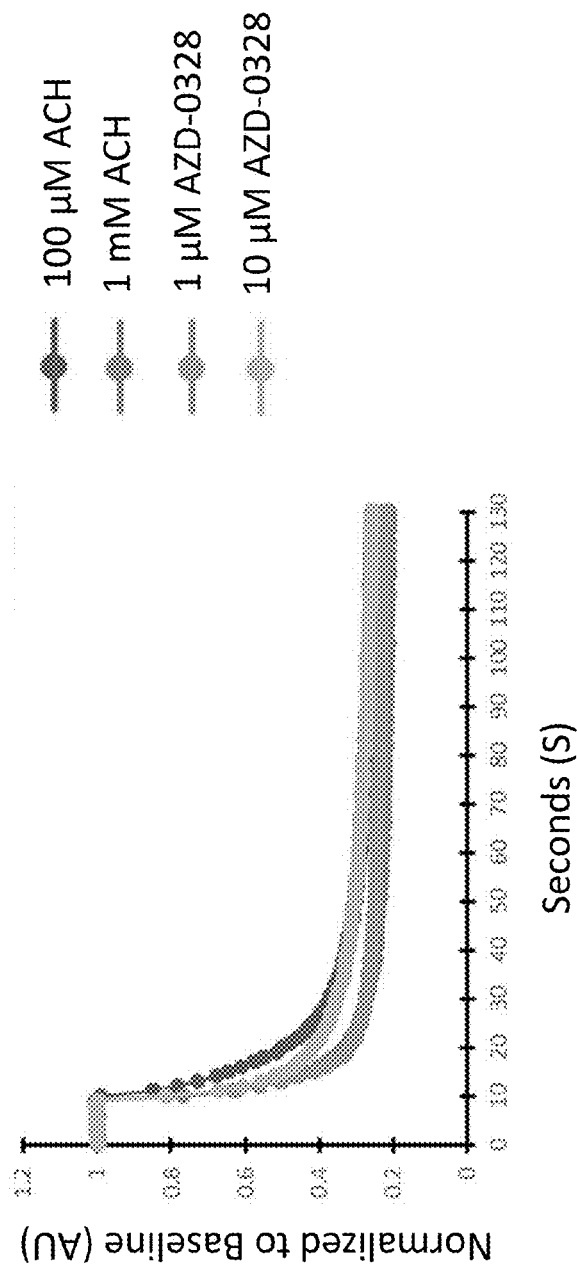
FIG. 7A-FIG. 7B provide quench plots of two engineered chimeric LGIC receptors to either acetylcholine (ACH) or AZD-0328: SEQ ID NO:33 (FIG. 7A) and SEQ ID NO:41 (FIG. 7B. The parental chimeras respond differently to similar concentrations of different ligands. Chimera #41 responds to lower doses of either ACH or AZD-0328 than Chimera #33, indicating that the inclusion of the beta1-2 loop conveys unique binding and activation properties upon the chimeric receptors.
Figure 7B:
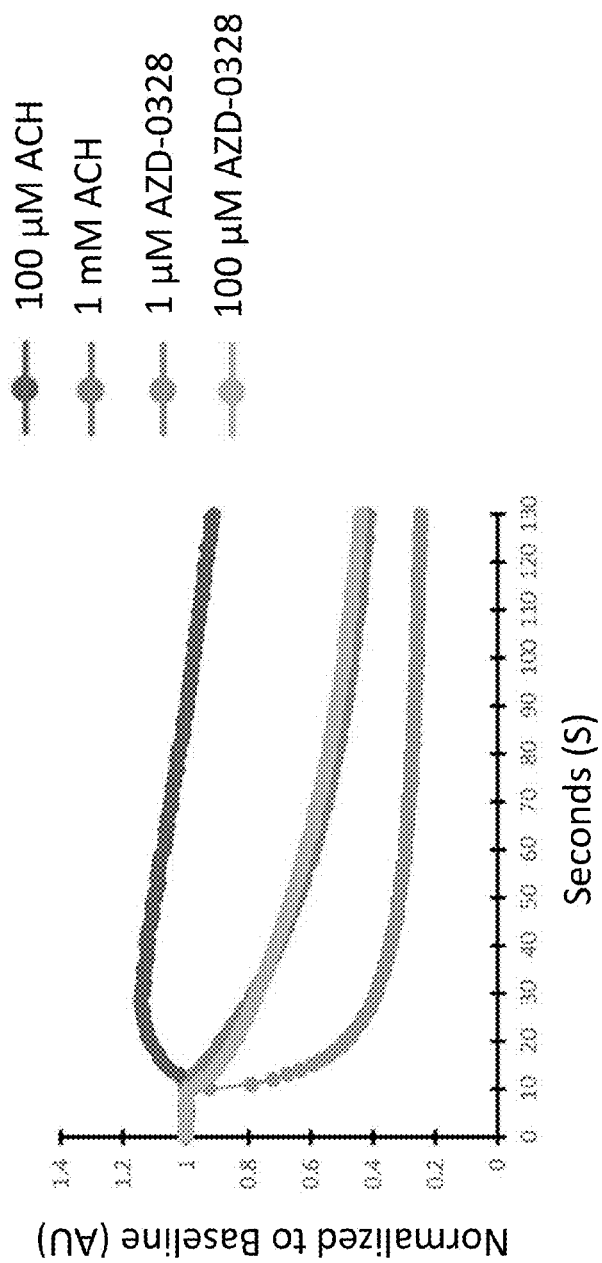

To further tune the responsiveness of the engineered LGIC receptors to native and non-native ligands, the binding pocket of each ligand in the alpha7-nAChR was modeled and the amino acid residues that form the binding pocket were mapped. Libraries of mutant chimeric LGICs were then generated, each mutant chimeric LGIC comprising substitutions in one or more amino acids of the binding pocket. To screen these mutant LGICs for those having novel response profiles to ligands, an anion reporter assay was developed to assess the function of channels in a higher-throughput format. In this assay, cells expressing a YFP reporter whose fluorescence is quenched in the presence of anion are transfected with DNA encoding the channel of interest. Upon exposure to ligand, channels that are activated will flux anion, resulting in a dose-dependent quench of the YFP that can be detected on a plate reader. FIG. 6 depicts the responses of four engineered chimeric LGIC receptors (SEQ ID NO:29, SEQ ID NO:33, SEQ ID NO:35, SEQ ID NO:41) to increasing concentrations of acetylcholine as measured by the quench in fluorescence of YFP over time. These quench plots demonstrate comparability between the electrophysiology and anion reporter approaches. FIG. 7 provides quench plots of the engineered chimeric LGIC receptors SEQ ID NO:33 and SEQ ID NO:41 to either acetylcholine (ACH) or AZD-0328. The parental chimeras respond differently to similar concentrations of different ligands.

Figure 8B:
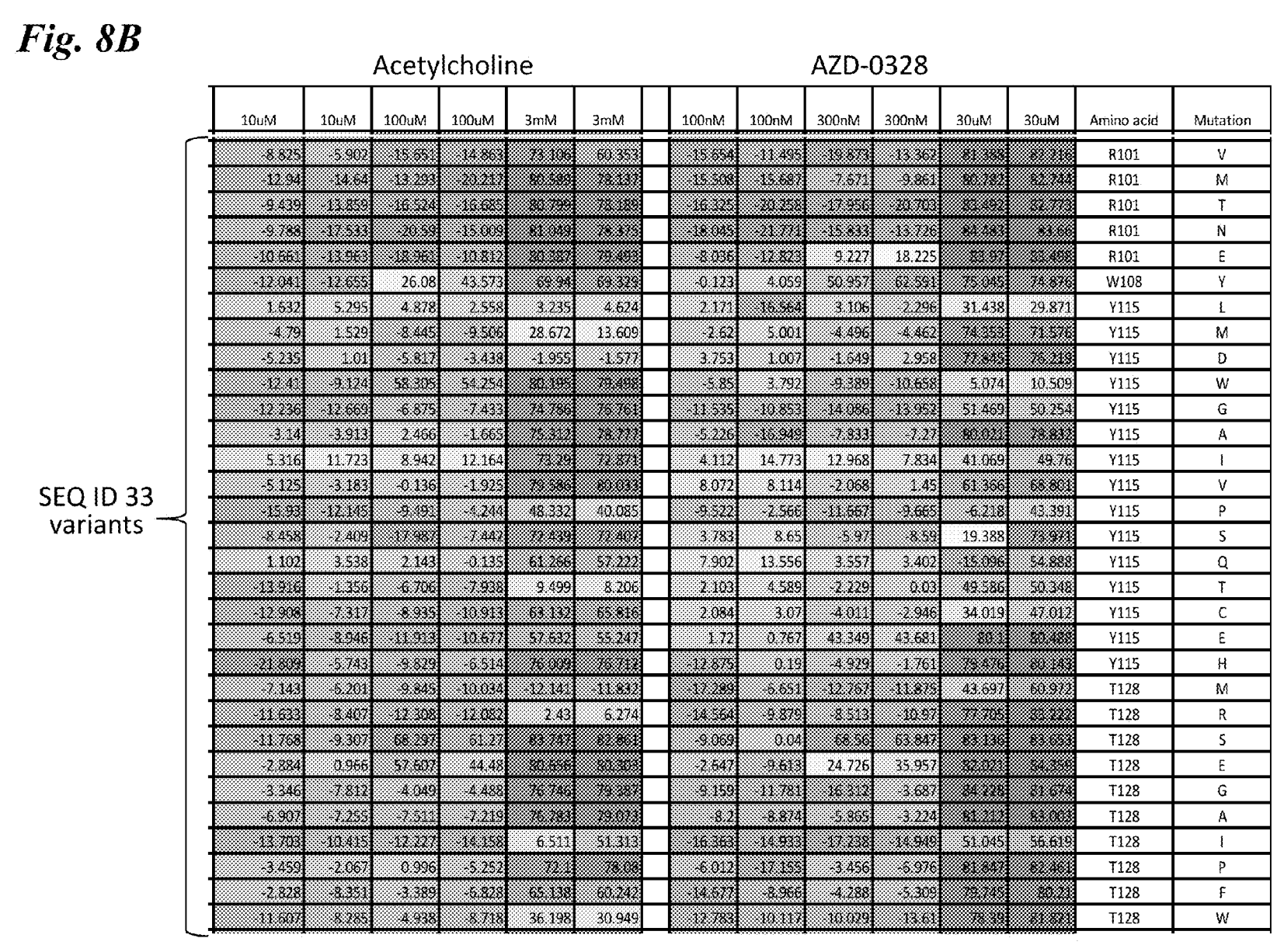
Figure 8I:
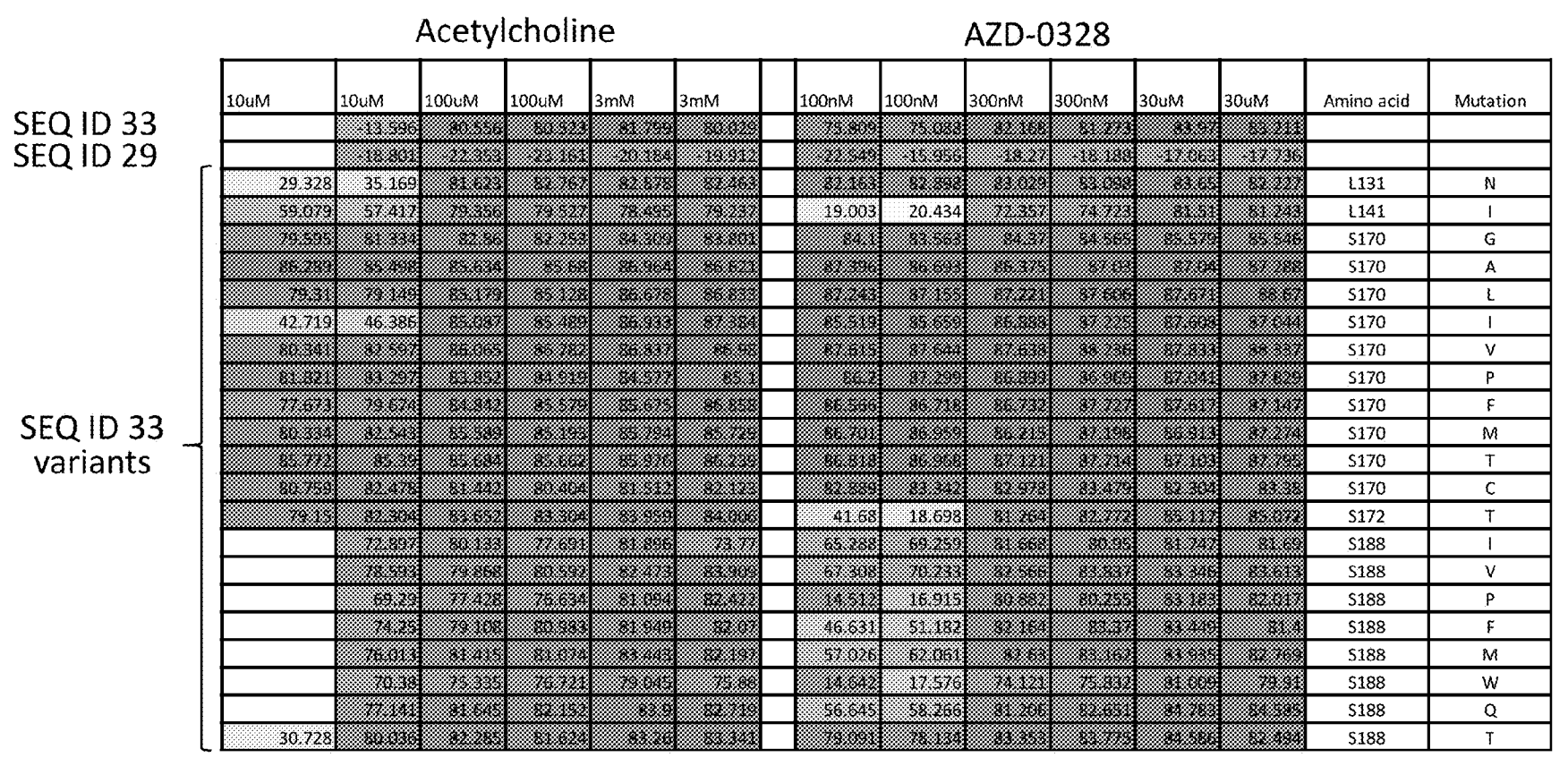

Libraries of mutant chimeric LGIC receptors based on the parental chimera SEQ ID NO:33 were screened for responsiveness to acetylcholine and AZD-0328 using the anion reporter plate reader assay. FIG. 8 provides heat maps of the percent quench of YFP fluorescence following stimulation by various doses of either acetylcholine or AZD-0328. Many amino acid substitutions either reduced responsiveness to both ligands (FIG. 8A-F, rightward shift in $EC_{50}$) or increased responsiveness to ligand (FIG. 8I, leftward shift in $EC_{50}$) suggesting an overlap in the amino acids critical for binding and activation by both compounds. However, mutants were also identified that exhibit a leftward shift in response to acetylcholine but a rightward shift in response to AZD-0328 (FIG. 8G), or that exhibit a far rightward shift to acetylcholine as compared to the parental chimera but no significant change in response to AZD-0328 (FIG. 8H), demonstrating the ability of a single mutation to decouple responses to ligands.

Dose response curves were created for several mutants of interest to better characterize the $EC_{50}$ of different ligands (FIG. 9). Substitutions L131S, L131T, and S172D in SEQ ID NO:33 resulted in a 2 log increase or more in $EC_{50}$ for acetylcholine but only a slight increase (1 log or less, in some cases, less than 0.5 log) in $EC_{50}$ for AZD-0328 as compared to that of unmutated SEQ ID NO:33 (FIG. 9). Substitution of W77M produced no shift in responsiveness to acetylcholine, but produced a significant increase (>2 log) in $EC_{50}$ to AZD-0328. These dose response curves confirmed that substitution of certain amino acid residues can dramatically alter the $EC_{50}$ of select ligands from that observed on the parental chimera.

Figure 10A:
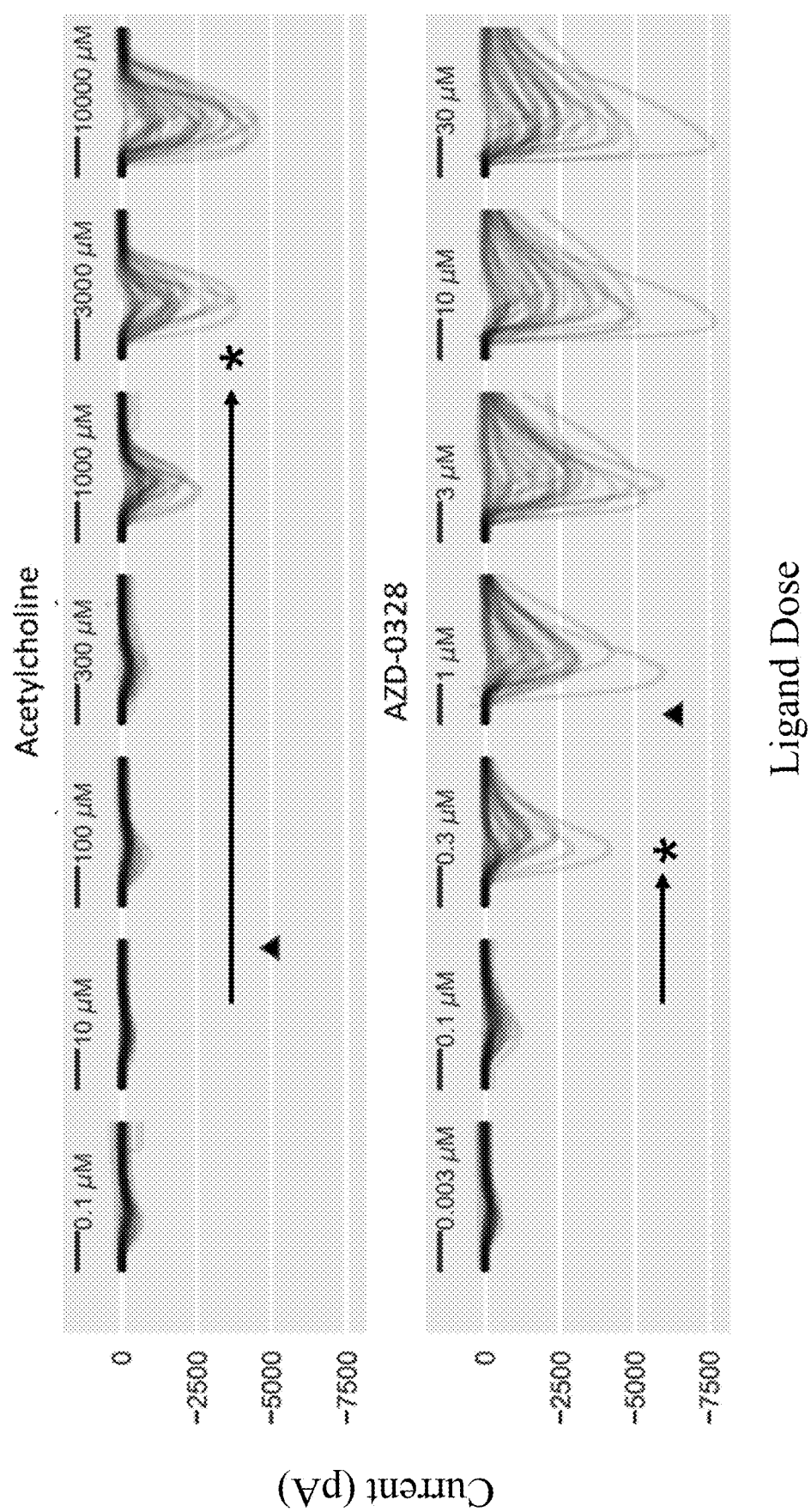
FIG. 10A-FIG. 10D provide electrophysiology data illustrating how single amino acid substitutions in an engineered chimera (SEQ ID NO:33) confer preferential responses to non-native ligands over acetylcholine.
Figure 10B:
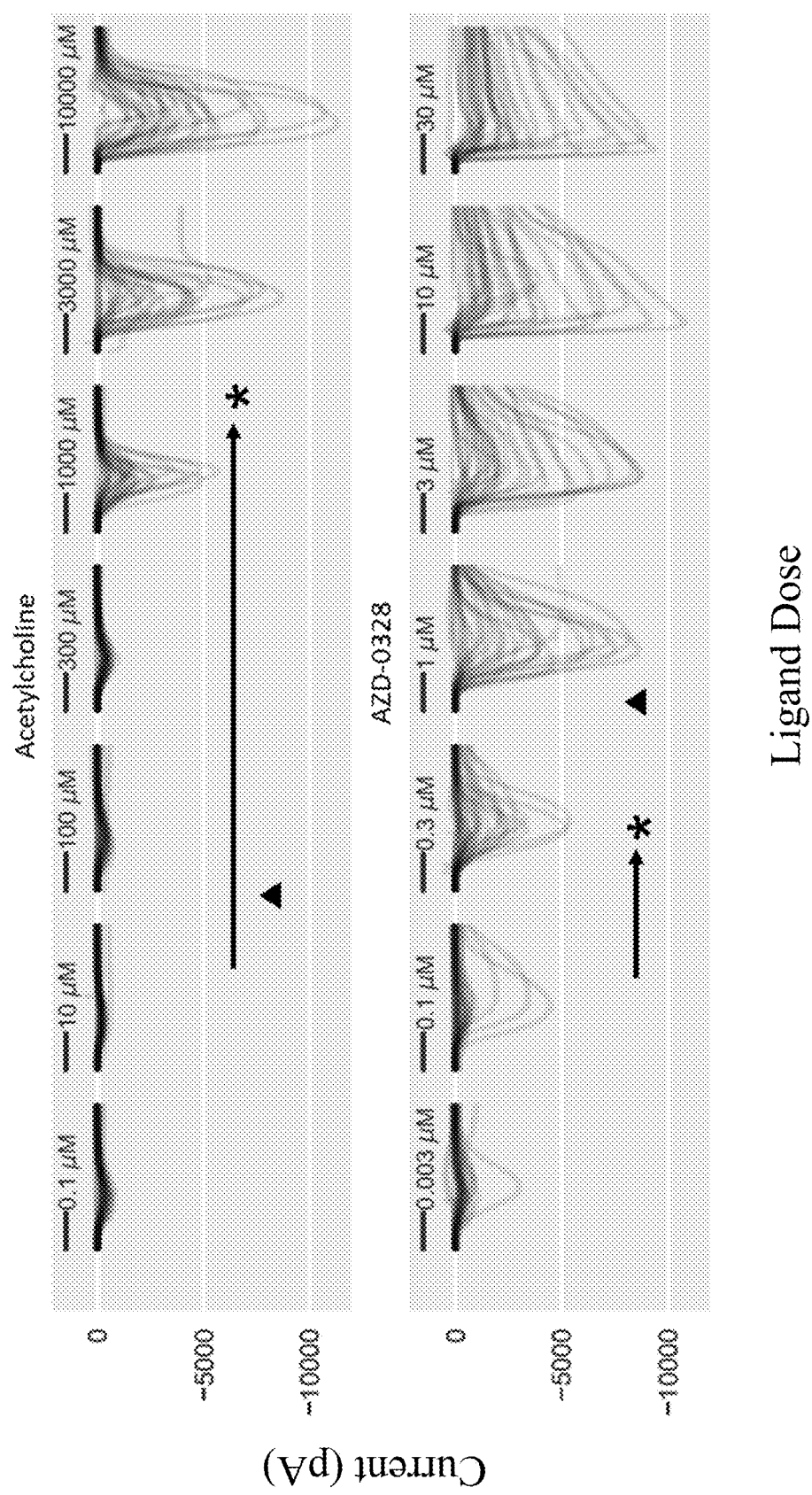
Figure 10C:
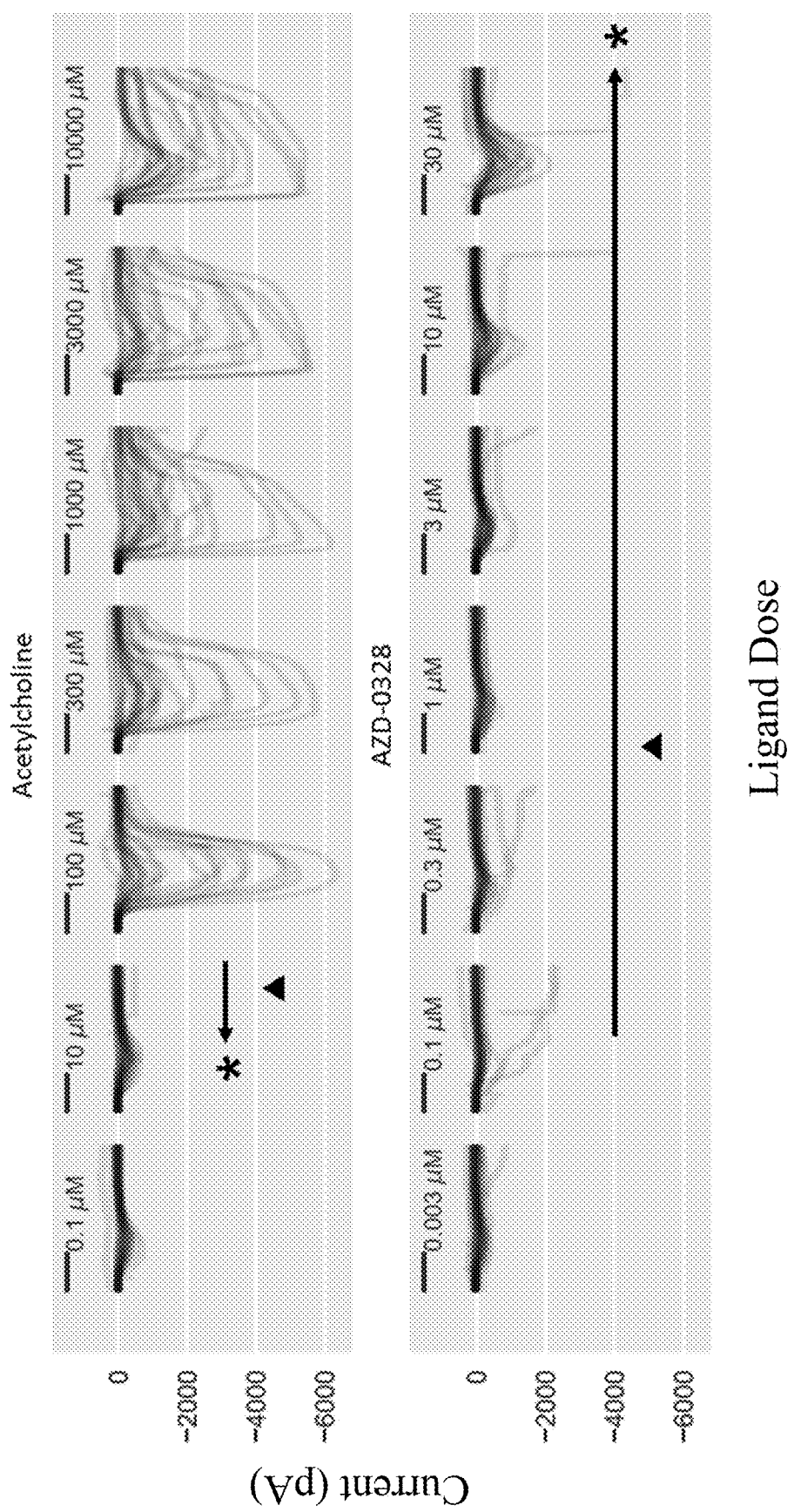
Figure 10D:
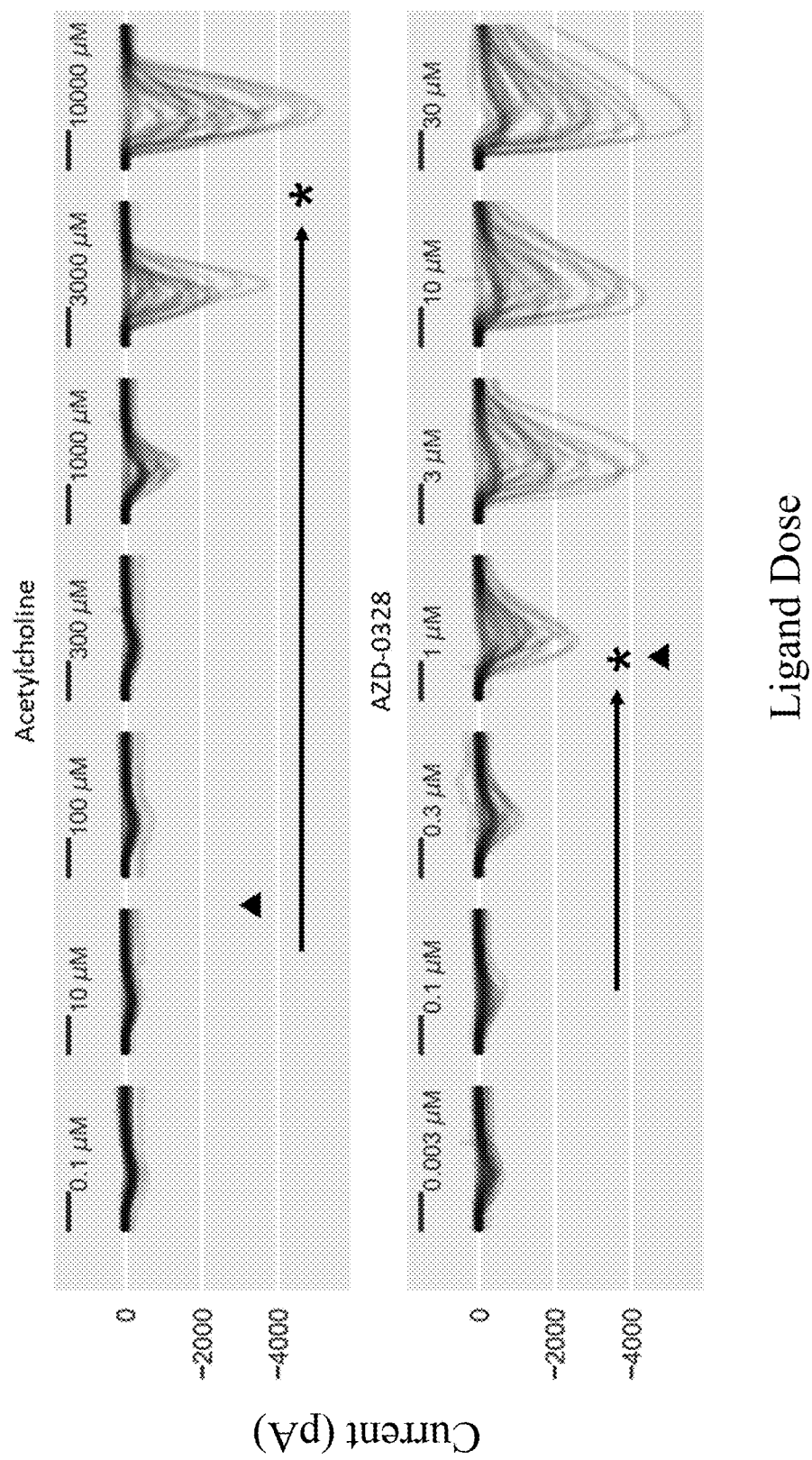

To confirm the $EC_{50}$s determined by plate reader as well as develop a better understanding of maximum current flow, the L131S, L131T, S172D and W77M mutations were assayed using electrophysiology. Substitution of L131S caused a significant right-ward shift (about 2 log, 80-100-fold) in the $EC_{50}$ of acetylcholine relative to parental chimera SEQ ID NO:33, while the $EC_{50}$ for AZD-0328 is only 2-fold right-ward shifted (FIG. 10A). Substitution of residue 131 with a T instead had an even greater impact, resulting in a right-ward shift in $EC_{50}$ of ~2.5 log on acetylcholine and ~1 log on AZD-0328 (FIG. 10D). Substitution of S172D also caused a significant right-ward shift (about 2-log, or 58-fold) in the $EC_{50}$ of acetylcholine relative to the parental chimera, while the $EC_{50}$ for AZD-0328 on S172D is only 2-fold right-ward shifted. Substitution of W77M causes a moderate left-ward shift (2-fold) in the $EC_{50}$ of acetylcholine relative to the parental chimera, while the $EC_{50}$ for AZD-0328 on W77M is significantly right-ward shifted (>2.5 log). These results provide electrophysiological confirmation of the decoupling of acetylcholine and non-native ligand responses with single point mutations observed by plate reader.

Example 2. Assessing the Efficacy of Engineered Receptors to Treat Disease in Animal Models Chimeric LGIC receptors comprising the ligand binding domain from the α7-nAChR and the chloride-conducting ion pore domain from the human GlyRα1 subunit are assessed for their efficacy in providing analgesia in an rat model of neuropathic pain following administration of a small molecule ligand.

Materials and Methods

AAV Vector Production:

Eight expression cassettes are constructed using standard molecular biology techniques. All contain a human synapsin-1 (hSYN) promoter linked to engineered chimeric receptors comprising a ligand binding domain of α7-nAChR and a Cys-loop domain and ion pore domain of GlyRα1. Their design is as follows:

(a) Chimera 1: no additional changes.

(b) Chimera 2: similar to 1, but also comprises an amino acids substitution from FIG. 8H that renders the engineered receptor less responsive to acetylcholine than either the wild type receptor or parental chimeric receptor from which it was derived, but maintains the responsiveness of the receptor to non-native ligand AZD-0328.

(c) Chimera 3: similar to 1, but also comprises an amino acid substitution from FIG. 8A-F that renders the engineered receptor less responsive to both acetylcholine and non-native ligand than either the wild type receptor or parental chimeric receptor from which it was derived.

(d) Chimera 4: similar to, but also comprises an amino acid substitution from FIG. 8I that restores the $EC_{50}$ of non-native ligand AZD-0328 and Facinicline to about wild type receptor levels.

(e) Chimera 5: same as 1, but also comprises a β1-2 loop domain from GlyRα1.

(f) Chimera 6: same as 2, but also comprises a β1-2 loop domain from GlyRα1.

(g) Chimera 7: same as 3, but also comprises a β1-2 loop domain from GlyRα1.

(h) Chimera 8: same as 4, but also comprises a β1-2 loop domain from GlyRα1.

These cassettes are subcloned into AAV bacmids, purified, transfected into Sf9 insect cells to produce recombinant bacuvlovirus, and then amplified. Sf9 cells are double infected using the amplified recombinant baculovirus containing the hSYN-α7-nAChR/GlyRα1 cassettes and another recombinant baculovirus containing the Rep and AAV6 (Y705+731F+T492V) Cap genes to produce recombinant AAV vectors. The viral vectors are purified, viral titer determined using qPCR, and SDS-PAGE used to verify the purity of AAV vectors.

Behavioral Experiments and Pain Models:

To produce mechanical hypersensitivity in a model that mimics a neuropathic pain condition, the spared nerve injury (SNI) model (a validated model of mechanical allodynia) is used (Shields et al., 2003, The Journal of Pain, 4, 465-470). This model is produced by the sectioning of the common peroneal and the sural nerves and isolating the tibial branch. Mechanical withdrawal threshold is assessed by placing rats on an elevated wire-mesh grid and stimulating the plantar surface of the hind paw with von Frey filaments.

AAV Injection into the Spinal Cord of Rats:

A dorsal hemilaminectomy is made at the level of the lumbar enlargement to expose two segments (about 1.5-2 mm) of lumbar spinal cord, after which the dura mater is incised and reflected. The viral solution is loaded into a glass micropipette (prefilled with mineral oil). The micropipette is connected to a manual micro-injector mounted on a stereotactic apparatus. The viral solution is targeted to the dorsal horn (left side). Along the rostro-caudal axis within the exposed region, 6 injections of 240 nl each are performed, in an equidistant linear fashion. After each injection, 1 min of resting time is observed and then the muscle layer is sutured, the skin closed with staples, and the animals were allowed to recover with heated-pad before they were returned to their home cages. Animals are perfused for histological analysis after the last behavior test.

AAV Intraganglionic Injections into the Dorsal Root Ganglion (DRG) of Rats:

The injection is performed with a borosilicate glass capillary (0.78/1 mm internal/external diameters) pulled to a fine point, attached by polyethylene tubing (0.4/0.8 mm internal/external diameters) to a syringe mounted in a microinjection pump. The needle is mounted on an extended arm of a stereotaxic frame swung to the outside (used to hold and manipulate the needle only). Tubing, syringe, and needle are all filled with water. One microliter air is taken up into the needle followed by 3 μL of the viral vector solution. The needle is loaded separately with this volume for each injection. Animals are anesthetized prior to surgery. Following an incision along the dorsal midline, the L4 and L5 DRG are exposed by removal of the lateral processes of the vertebrae. The epineurium lying over the DRG is opened, and the glass needle inserted into the ganglion, to a depth of 400 μm from the surface of the exposed ganglion. After a 3-minute delay to allow sealing of the tissue around the glass capillary tip, 1.1 μL virus solution was injected at a rate of 0.2 μL/minute. After a further delay of 2 minutes, the needle is removed. The L4 ganglion is injected first followed by the L5 ganglion. The muscles overlying the spinal cord are loosely sutured together with a 5-0 suture and the wound closed. Animals are allowed to recover at 37° C. and received postoperative analgesia.

AAV Intrathecal Injections in Rats:

Rats are first anesthetized and then placed vertically with their head fixed in a stereotaxic frame. An incision is made in the base of the neck to expose the groove in the nuchal crest. An incision is made (1-2 mm) in the cisternal membrane to a depth such that cerebrospinal fluid leaks out. A 4 cm 32 G intrathecal catheter is then slowly inserted in the direction of the lumbar spinal cord and skin is closed by suture around the catheter. The rats are then allowed to recover. Rats are then anesthetized and the vector (6 μL) is administered. The catheter is flushed with 6 μL of PBS and then removed and rats allowed to recover.

Results

This SNI model is produced by the sectioning of the common peroneal and the sural nerves and isolating the tibial branch of the rat. The up-down method of Chaplan & Yaksh is used to determine mechanical thresholds before the injection of the AAV.hSYN-α7-nAChR/GlyRα1 into the spinal cord, DRG, or intrathecal space. Three weeks after unilateral vector injection, animals are tested again to verify that their mechanical withdrawal thresholds do not change. Motor coordination is also tested before and after injection, using an accelerating rotarod (Stoelting, USA) at a maximum speed of 33 rpm. The duration that the rat spends on the rotarod is recorded, with a cut-off at 300 sec. Each rat goes through three training trials and is tested two hours later. The animals receiving Chimera 1 and Chimera 5 appear to experience some analgesia even in the absence of synthetic ligand, suggesting that naturally occurring levels of acetylcholine may be activating the chimeric receptor. The remaining animals in the study show no change in mechanical withdrawal or motor coordination resulting from the injection of the AAV.

Subsequently, half of the rats in each chimera cohort are administered a single IP injection of AZD-0328 or Facinicline and mechanical thresholds tested using the up-down method at 1, 2, 5, 7, and 13 days post IP injection. When tested at high dose of ligand, a complete reversal of the mechanical hypersensitivity is observed in all rats. When tested at low dose, rats receiving Chimera 1, 2, 4, 5, 6, and 8 experience a complete reversal of the mechanical hypersensitivity, while rats receiving Chimera 3 and 7 (comprising the substitution that reduces responsiveness to non-native ligand but not the substitution that suppresses that effect) experience only a partial reversal of hypersensitivity. There is no change on the contralateral side, i.e. AZD-0328 has no measurable effect in the absence of vector. The reversal lasted for at least 2 days. On the third day, when the thresholds has returned to post-injury baseline, AZD-0328 is again injected IP and again a recovery to non-injury baseline thresholds is observed. These animals are followed for 48 hours and the thresholds remained at baseline. Animals are then perfused for histology.

Example 3. Treatment of a Patient Suffering from Chronic Pain

In a non-limiting example, a patient suffering from chronic radicular pain is treated using the compositions and methods disclosed herein. The patient is treated on Day One with $10^{13}$ vector genomes of AAV.hSYN-α7-nAChR/GlyRα1 in a volume of 1.0 mL delivered directly into one or more dorsal root ganglia (i.e., intraganglionic convection-enhanced delivery into lumbar, cervical, or thoracic DRGs). In this example, the AAV vector encodes the α7-nAChR/GlyRα1 chimera under the control of the human Synapsin-1 (SYN1) promoter for selective neuronal expression. Two weeks post-injection, the patient returns to the clinic for a prescription for AZD-0328. The patient self-administers 0.1 mg/kg AZD-0328 orally as needed (i.e., during a pain episode).

Example 4. Treatment of a Patient Suffering from Chronic Pain

In a non-limiting example, a patient suffering from chronic craniofacial pain (e.g. trigeminal neuralgia or termporomandibular joint dysfunction) is treated using the compositions and methods disclosed herein. The patient is treated on Day One with $10^{13}$ vector genomes of AAV.hSYN-α7-nAChR/GlyRα1 in a volume of 0.150 mL delivered directly into the trigeminal ganglion (i.e., intraganglionic convection enhanced delivery). In this example, the AAV vector encodes the α7-nAChR/GlyRα1 chimera under the control of the human Synapsin-1 (SYN1) promoter for selective neuronal expression. Two weeks post-injection, the patient returns to the clinic for a prescription for AZD-0328. The patient self-administers 0.1 mg/kg AZD-0328 orally as needed (i.e., during a pain episode).

Example 5. Treatment of a Patient Suffering from Obesity

In a non-limiting example, a patient suffering from obesity is treated using the compositions and methods disclosed herein. The patient is treated on Day One with $10^{13}$ vector genomes of AAV. Ghrelin-α7-nAChR/GlyRα1 in a volume of 1.0 mL delivered directly into the gastric branch of the vagus nerve (i.e., intraneural). In this example, the AAV vector encodes the engineered receptor under the control of the human Ghrelin promoter for selective neuronal expression. Two weeks post-injection, the patient returns to the clinic for a prescription for AZD-0328. The patient self-administers 0.1 mg/kg AZD-0328 orally daily for excess weight loss (i.e. for apetitite suppression).

Example 6. Treatment of a Patient Suffering from Obesity

In a non-limiting example, a patient suffering from obesity is treated using the compositions and methods disclosed herein. The patient is treated on Day One with $10^{13}$ vector genomes of AAV-TRPV1-α7-nAChR/GlyRα1 in a volume of 1.0 mL delivered directly into the dorsal root ganglia innervating the pancreas (i.e., intragangionic). In this example, the AAV vector encodes the engineered receptor under the control of the human TRPV1 promoter for selective neuronal expression in nociceptors. Two weeks post-injection, the patient returns to the clinic for a prescription for AZD-0328. The patient self-administers 0.1 mg/kg AZD-0328 orally daily for excess weight loss.

Example 7. Treatment of a Patient Suffering from Obesity

In a non-limiting example, a patient suffering from obesity is treated using the compositions and methods disclosed herein. The patient is treated on Day One with $10^{13}$ vector genomes of AAV-SIM1-α7-nAChR/GlyRα1 in a volume of 1.0 mL delivered directly into the paraventricular nucleus (PVH) in the hypothalamus (i.e., intracranial, convection enhanced delivery). In this example, the AAV vector encodes the engineered channel under the control of the human Single-Minded Family BHLH Transcription Factor 1 (SIM1) promoter for selective neuronal expression in pro-opiomelanocortin (POMC) neurons and ultimately stimulation of the anorexigenic pathway. Two weeks post-injection, the patient returns to the clinic for a prescription for AZD-0328. The patient self-administers 0.15 mg/kg AZD-0328 orally daily for excess weight loss (i.e. for Apetitite Suppression).

Example 8. Treatment of a Patient Suffering From PTSD

In a non-limiting example, a patient suffering from post-traumatic stress disorder (PTSD) is treated using the compositions and methods disclosed herein. The patient is treated on Day One with $10^{13}$ vector genomes of AAV-hSYN1-α7-nAChR/GlyRα1 in a volume of 1.0 mL delivered directly into the C6 stellate ganglion, (i.e., intraganglionic). In this example, the AAV vector encodes the engineered receptor under the control of the human Synapsin-1 (hSYN1) promoter for selective neuronal expression. Two weeks post-injection, the patient returns to the clinic for a prescription for AZD-0328. The patient self-administers 0.15 mg/kg AZD-0328 orally daily for PTSD symptoms (i.e. for anxiety).

Example 9. Treatment of a Patient Suffering from Depression

In a non-limiting example, a patient suffering from treatment-resistant depression (TRD) is treated using the compositions and methods disclosed herein. The patient is treated on Day One with $10^{13}$ vector genomes of AAV-hSYN1-α7-nAChR/GlyRα1 in a volume of 1.0 mL delivered directly into the vagus nerve, (i.e., intraneural). In this example, the AAV vector encodes the engineered receptor under the control of the human Synapsin-1 (hSYN1) promoter for selective neuronal expression. Two weeks post-injection, the patient returns to the clinic for a prescription for AZD-0328. The patient self-administers 0.1 mg/kg AZD-0328 orally daily for depression symptoms.

Example 10. Treatment of a Patient Suffering from GERD

In a non-limiting example, a patient suffering from gastroesophageal reflux disease (GERD) is treated using the compositions and methods disclosed herein. The patient is treated on Day One with $10^{13}$ vector genomes of AAV-hSYN1-α7-nAChR/GlyRα1 or AAV-CAG-α7-nAChR/GlyRα1 in a volume of 1.0 mL delivered directly into the lower esophageal sphincter (LES) vagus nerve and myenteric plexus (i.e., intraneural) or smooth muscle (intramuscular), respectively. In this example, the AAV vector encodes the engineered receptor under the control of the human Synapsin-1 (hSYN1) promoter for selective neuronal expression or the CAG promoter for expression in LES myocytes. Two weeks post-injection, the patient returns to the clinic for a prescription for AZD-0328. The patient self-administers 0.15 mg/kg AD-0328 orally daily for symptoms of GERD (i.e. acid reflux).

Example 11. Treatment of a Patient Suffering from Epilepsy

In a non-limiting example, a patient suffering from seizures associated with epilepsy is treated using the compositions and methods disclosed herein. The patient is treated on Day One with $10^{13}$ vector genomes of AAV-CamKIIα-α7-nAChR/GlyRα1 in a volume of 1.0 mL delivered directly into a pre-determined seizure focus such as the motor cortex (i.e., intracranial). In this example, the AAV vector encodes the engineered receptor under the control of the human Calcium/calmodulin-dependent protein kinase II α (CamKIIα) promoter for selective neuronal expression in excitatory neurons. Two weeks post-injection, the patient returns to the clinic for a prescription for AZD-0328. The patient self-administers 0.1 mg/kg AZD-0328 orally daily for epileptic symptoms (i.e. seizures).

Example 12. Treatment of a Patient Suffering from a Movement Disorder

In a non-limiting example, a patient suffering from a movement disorder (e.g. Parkinsonian tremor) is treated using the compositions and methods disclosed herein. The patient is treated on Day One with $10^{13}$ vector genomes of AAV-CamKIIα-α7-nAChR/GlyRα1 in a volume of 1.0 mL delivered directly into the subthalamic nucleus (i.e., intracranial STN). In this example, the AAV vector encodes the engineered receptor under the control of the human Calcium/calmodulin-dependent protein kinase II α (CamKIIα) promoter for selective neuronal expression in excitatory neurons. Two weeks post-injection, the patient returns to the clinic for a prescription for AZD-0328. The patient self-administers 0.1 mg/kg AZD-0328 orally daily for movement disorder symptoms (i.e. tremor).

The preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of the present disclosure is embodied by the appended claims.

The invention claimed is:

1. An engineered receptor, wherein the engineered receptor is a chimeric ligand gated ion channel (LGIC) receptor and comprises
   (a) a ligand binding domain derived from the human α7 nicotinic acetylcholine receptor (α7-nAChR) and comprising a Cys-loop domain from the human Glycine receptor α1 subunit; and
   (b) an ion pore domain derived from the human Glycine receptor α1 subunit.

2. The engineered receptor according to claim 1, wherein the Cys-loop domain comprises amino acids 166-172 of SEQ ID NO:2.

3. The engineered receptor according to claim 2, wherein the receptor has a sequence identity of 85% or more to SEQ ID NO:33.

4. The engineered receptor according to claim 3, wherein the ligand binding domain comprises one or more amino acid substitutions at a residue corresponding to a residue of α7-nAChR selected from the group consisting of W77, Y94, R101, W108, Y115, T128, N129, V130, L131, Q139, L141, Y151, S170, W171, S172, S188, Y190, Y210, C212, C213 and Y217.

5. The engineered receptor according to claim 4, wherein the substitution is selected from a substitution corresponding to L131S, L131T, L131D, or S172D of α7-nAChR.

6. The engineered receptor according to claim 1, wherein the ligand binding domain further comprises a β1-2 loop domain from the human Glycine receptor α1 subunit.

7. The engineered receptor according to claim 6, wherein the β1-2 loop domain comprises amino acids 81-84 of SEQ ID NO:2.

8. The engineered receptor according to claim 7, wherein the receptor has a sequence identity of 85% or more to SEQ ID NO:41.

9. The engineered receptor according to claim 8, wherein the ligand binding domain comprises one or more amino acid substitutions at a residue corresponding to a residue of α7-nAChR selected from the group consisting of W77, Y94, R101, W108, Y115, T128, N129, V130, L131, Q139, L141, Y151, S170, W171, S172, S188, Y190, Y210, C212, C213 and Y217.

10. The engineered receptor according to claim 9, wherein the substitution is selected from a substitution corresponding to L131S, L131T, L131D, or S172D of α7-nAChR.

11. A polynucleotide encoding the engineered receptor according to claim 1.

12. A vector comprising the polynucleotide according to claim 11.

13. The vector according to claim 12, wherein the vector is a viral vector selected from the group consisting of an adenoviral vector, a retroviral vector, an adeno-associated viral (AAV) vector, and a herpes simplex-1 viral vector (HSV-1).

14. A pharmaceutical composition comprising the vector according to claim 13 and a pharmaceutically acceptable vehicle.

15. A method of ameliorating a neurological disorder in a subject in need thereof comprising:
    administering to the subject a polynucleotide encoding the engineered ligand-gated ion channel (LGIC) receptor of claim 1, and
    administering to the subject a binding agent, wherein the binding agent acts as an agonist of the engineered LGIC receptor.

16. The method according to claim 15, wherein the polynucleotide is delivered to the subject in a viral vector.

17. The method according to claim 16, wherein the viral vector is an adenoviral vector, a retroviral vector, an adeno-associated viral (AAV) vector, or a herpes simplex-1 viral vector (HSV-1).

18. The method according to claim 17, wherein the AAV vector is AAV5 or a variant thereof, AAV6 or a variant thereof, or AAV9 or a variant thereof.

19. The method according to claim 15, wherein the polynucleotide is administered to the subject by a non-viral method.

20. The method according to claim 19, wherein the non-viral method is lipofection, nanoparticle delivery, particle bombardment, electroporation, sonication, or microinjection.

21. The method according to claim 15, wherein the polynucleotide encoding the engineered receptor is operably linked to a promoter that is active in an excitable cell.

22. The method according to claim 21, wherein the excitable cell is a neuron or a myocyte.

23. The method according to claim 22, wherein the neuron is a dorsal root ganglion, a motor neuron, an excitatory neuron, an inhibitory neuron, or a sensory neuron.

24. The method according to claim 23, wherein the polynucleotide is administered subcutaneously, orally, intrathecally, topically, intravenously, intraganglionically, intraneurally, intracranially, intraspinally, or to the cisterna magna.

25. The method according to claim 15, wherein the binding agent is selected from the group consisting of AZD0328, ABT-126, TC6987, and Facinicline/RG3487.

26. The method according to claim 25, wherein the binding agent is administered orally, subcutaneously, topically, or intravenously.

27. The method according to claim 15, wherein the subject suffers from pain, a seizure disorder, a movement disorder, an eating disorder, a spinal cord injury, neurogenic bladder, a spasticity disorder, or pruritus.

28. The method according to any one of claim 27, wherein the subject is a human.

* * * * *

SEQUENCE LISTING

```
<160> NUMBER OF SEQ ID NOS: 57

<210> SEQ ID NO 1
<211> LENGTH: 1835
<212> TYPE: DNA
<213> ORGANISM: Homo sapiens

<400> SEQUENCE: 1
caacagacac gctggagttt aacaaacagc aatactcttc gcgctcctga aaagcaggtc      60
tggacgctct ccgtggtgct gaaacgcctc gcagccgccg ctgtccgtgg tatctacgac     120
```

```
cccctcgctc caatttcccc tggggctctc cctccgcgcc cctgttcccc gcctcccttt    180
aacatctgga ttattttttg caatagcgct ttctggtttt gtaagtgcca atttgaaaca    240
ttttgcccc cataactcgt ggactacaaa gcacaaggac ctgaaaaatg tacagcttca    300
atactcttcg actctacctt tgggagacca ttgtattctt cagccttgct gcttctaagg    360
aggctgaagc tgctcgctcc gcacccaagc ctatgtcacc ctcggatttc ctggataagc    420
taatggggag aacctccgga tatgatgcca ggatcaggcc caattttaaa ggtcccccag    480
tgaacgtgag ctgcaacatt ttcatcaaca gctttggttc cattgctgag acaaccatgg    540
actatagggt caacatcttc ctgcggcagc aatggaacga ccccgcctg cctataatg      600
aatacctga cgactctctg gacctggacc catccatgct ggactccatc tggaaacctg     660
acctgttctt tgccaacgag aagggggccc acttccatga gatcaccaca gacaacaaat    720
tgctaaggat ctcccggaat gggaatgtcc tctacagcat cagaatcacc ctgacactgg    780
cctgccccat ggacttgaag aatttcccca tggatgtcca gacatgtatc atgcaactgg    840
aaagctttgg atatacgatg aatgacctca tctttgagtg gcaggaacag ggagccgtgc    900
aggtagcaga tggactaact ctgccccagt ttatcttgaa ggaagagaag gacttgagat    960
actgcaccaa gcactacaac acaggtaaat tcacctgcat tgaggccgg ttccacctgg    1020
agcggcagat gggttactac ctgattcaga tgtatattcc cagcctgctc attgtcatcc   1080
tctcatggat ctccttctgg atcaacatgg atgctgcacc tgctcgtgtg gcctaggca    1140
tcaccactgt gctcaccatg accacccaga gctccggctc tcgagcatct ctgcccaagg   1200
tgtcctatgt gaaagccatt gacatttgga tggcagtttg cctgctcttt gtgttctcag   1260
ccctattaga atatgctgcc gttaactttg tgtctcggca acataaggag ctgctccgat   1320
tcaggaggaa gcggagacat cacaagagcc ccatgttgaa tctattccag gaggatgaag   1380
ctggagaagg ccgctttaac ttctctgcct atgggatggg cccagcctgt ctacaggcca   1440
aggatggcat ctcagtcaag ggcgccaaca acagtaacac caccaacccc cctcctgcac   1500
catctaagtc cccagaggag atgcgaaaac tcttcatcca gagggccaag aagatcgaca   1560
aaatatcccg cattggcttc cccatggcct tcctcatttt caacatgttc tactggatca   1620
tctacaagat tgtccgtaga gaggacgtcc acaaccagtg aagggtctga aggttgggg    1680
gaggctggga gaggggaacg tgggaatagc acaggaatct gagagactaa ggaagagaag   1740
gggaacggag ggaggggca cacttacaca actctctctg caatatgtgc aatagcaaaa   1800
tgcagtgatg catgaatttt aaaaaaaaa aaaaa                              1835
```

<210> SEQ ID NO 2
<211> LENGTH: 457
<212> TYPE: PRT
<213> ORGANISM: Homo sapiens

<400> SEQUENCE: 2

```
Met Tyr Ser Phe Asn Thr Leu Arg Leu Tyr Leu Trp Glu Thr Ile Val
1               5                   10                  15

Phe Phe Ser Leu Ala Ala Ser Lys Glu Ala Glu Ala Ala Arg Ser Ala
            20                  25                  30

Pro Lys Pro Met Ser Pro Ser Asp Phe Leu Asp Lys Leu Met Gly Arg
        35                  40                  45

Thr Ser Gly Tyr Asp Ala Arg Ile Arg Pro Asn Phe Lys Gly Pro Pro
    50                  55                  60
```

Val Asn Val Ser Cys Asn Ile Phe Ile Asn Ser Phe Gly Ser Ile Ala
65                  70                  75                  80

Glu Thr Thr Met Asp Tyr Arg Val Asn Ile Phe Leu Arg Gln Gln Trp
            85                  90                  95

Asn Asp Pro Arg Leu Ala Tyr Asn Glu Tyr Pro Asp Asp Ser Leu Asp
            100                 105                 110

Leu Asp Pro Ser Met Leu Asp Ser Ile Trp Lys Pro Asp Leu Phe Phe
            115                 120                 125

Ala Asn Glu Lys Gly Ala His Phe His Glu Ile Thr Thr Asp Asn Lys
            130                 135                 140

Leu Leu Arg Ile Ser Arg Asn Gly Asn Val Leu Tyr Ser Ile Arg Ile
145                 150                 155                 160

Thr Leu Thr Leu Ala Cys Pro Met Asp Leu Lys Asn Phe Pro Met Asp
                165                 170                 175

Val Gln Thr Cys Ile Met Gln Leu Glu Ser Phe Gly Tyr Thr Met Asn
            180                 185                 190

Asp Leu Ile Phe Glu Trp Gln Glu Gln Gly Ala Val Gln Val Ala Asp
            195                 200                 205

Gly Leu Thr Leu Pro Gln Phe Ile Leu Lys Glu Glu Lys Asp Leu Arg
210                 215                 220

Tyr Cys Thr Lys His Tyr Asn Thr Gly Lys Phe Thr Cys Ile Glu Ala
225                 230                 235                 240

Arg Phe His Leu Glu Arg Gln Met Gly Tyr Tyr Leu Ile Gln Met Tyr
            245                 250                 255

Ile Pro Ser Leu Leu Ile Val Ile Leu Ser Trp Ile Ser Phe Trp Ile
            260                 265                 270

Asn Met Asp Ala Ala Pro Ala Arg Val Gly Leu Gly Ile Thr Thr Val
            275                 280                 285

Leu Thr Met Thr Thr Gln Ser Ser Gly Ser Arg Ala Ser Leu Pro Lys
290                 295                 300

Val Ser Tyr Val Lys Ala Ile Asp Ile Trp Met Ala Val Cys Leu Leu
305                 310                 315                 320

Phe Val Phe Ser Ala Leu Leu Glu Tyr Ala Ala Val Asn Phe Val Ser
            325                 330                 335

Arg Gln His Lys Glu Leu Leu Arg Phe Arg Arg Lys Arg Arg His His
            340                 345                 350

Lys Ser Pro Met Leu Asn Leu Phe Gln Glu Asp Glu Ala Gly Glu Gly
            355                 360                 365

Arg Phe Asn Phe Ser Ala Tyr Gly Met Gly Pro Ala Cys Leu Gln Ala
            370                 375                 380

Lys Asp Gly Ile Ser Val Lys Gly Ala Asn Asn Ser Asn Thr Thr Asn
385                 390                 395                 400

Pro Pro Pro Ala Pro Ser Lys Ser Pro Glu Glu Met Arg Lys Leu Phe
            405                 410                 415

Ile Gln Arg Ala Lys Lys Ile Asp Lys Ile Ser Arg Ile Gly Phe Pro
            420                 425                 430

Met Ala Phe Leu Ile Phe Asn Met Phe Tyr Trp Ile Ile Tyr Lys Ile
            435                 440                 445

Val Arg Arg Glu Asp Val His Asn Gln
450                 455

<210> SEQ ID NO 3
<211> LENGTH: 3356
<212> TYPE: DNA

<213> ORGANISM: Homo sapiens

<400> SEQUENCE: 3

| | | | | | |
|---|---|---|---|---|---|
| tccttaaagg | cgcgcgagcc | gagcggcgag | gtgcctctgt | ggccgcaggc | gcaggcccgg | 60 |
| gcgacagccg | agacgtggag | cgcgccggct | cgctgcagct | ccgggactca | acatgcgctg | 120 |
| ctcgccggga | ggcgtctggc | tggcgctggc | cgcgtcgctc | ctgcacgtgt | ccctgcaagg | 180 |
| cgagttccag | aggaagcttt | acaaggagct | ggtcaagaac | tacaatccct | tggagaggcc | 240 |
| cgtggccaat | gactcgcaac | cactcaccgt | ctacttctcc | ctgagcctcc | tgcagatcat | 300 |
| ggacgtggat | gagaagaacc | aagttttaac | caccaacatt | tggctgcaaa | tgtcttggac | 360 |
| agatcactat | ttacagtgga | atgtgtcaga | atatccaggg | gtgaagactg | ttcgtttccc | 420 |
| agatggccag | atttggaaac | cagacattct | tctctataac | agtgctgatg | agcgctttga | 480 |
| cgccacattc | cacactaacg | tgttggtgaa | ttcttctggg | cattgccagt | acctgcctcc | 540 |
| aggcatattc | aagagttcct | gctacatcga | tgtacgctgg | tttcccttttg | atgtgcagca | 600 |
| ctgcaaactg | aagtttgggt | cctggtctta | cggaggctgg | tccttggatc | tgcagatgca | 660 |
| ggaggcagat | atcagtggct | atatccccaa | tggagaatgg | gacctagtgg | aatccccgg | 720 |
| caagaggagt | gaaaggttct | atgagtgctg | caaagagccc | taccccgatg | tcaccttcac | 780 |
| agtgaccatg | cgccgcagga | cgctctacta | tggcctcaac | ctgctgatcc | cctgtgtgct | 840 |
| catctccgcc | ctgcccctgc | tggtgttcct | gcttcctgca | gattccgggg | agaagatttc | 900 |
| cctggggata | acagtcttac | tctctcttac | cgtcttcatg | ctgctcgtgg | ctgagatcat | 960 |
| gcccgcaaca | tccgattcgg | taccattgat | agcccagtac | ttcgccagca | ccatgatcat | 1020 |
| cgtgggcctc | tcggtggtgg | tgacagtgat | cgtgctgcag | taccaccacc | acgaccccga | 1080 |
| cggggggcaag | atgcccaagt | ggaccagagt | catccttctg | aactggtgcg | cgtggttcct | 1140 |
| gcgaatgaag | aggcccgggg | aggacaaggt | gcgcccggcc | tgccagcaca | agcagcggcg | 1200 |
| ctgcagcctg | gccagtgtgg | agatgagcgc | cgtggcgccg | ccgccgcca | gcaacgggaa | 1260 |
| cctgctgtac | atcggcttcc | gcggcctgga | cggcgtgcac | tgtgtcccga | ccccgactc | 1320 |
| tgggggtagtg | tgtggccgca | tggcctgctc | ccccacgcac | gatgagcacc | tcctgcacgg | 1380 |
| cgggcaaccc | cccgaggggg | acccggactt | ggccaagatc | ctggaggagg | tccgctacat | 1440 |
| tgccaaccgc | ttccgctgcc | aggacgaaag | cgaggcggtc | tgcagcgagt | ggaagttcgc | 1500 |
| cgcctgtgtg | gtggaccgcc | tgtgcctcat | ggccttctcg | gtcttcacca | tcatctgcac | 1560 |
| catcggcatc | ctgatgtcgg | ctcccaactt | cgtggaggcc | gtgtccaaag | actttgcgta | 1620 |
| accacgcctg | gttctgtaca | tgtggaaaac | tcacagatgg | gcaaggcctt | tggcttggcg | 1680 |
| agatttgggg | gtgctaatcc | aggacagcat | tacacgccac | aactccagtg | ttcccttctg | 1740 |
| gctgtcagtc | gtgttgctta | cggtttcttt | gttactttag | gtagtagaat | ctcagcactt | 1800 |
| tgtttcatat | tctcagatgg | gctgatagat | atccttggca | catccgtacc | atcggtcagc | 1860 |
| agggccactg | agtagtcatt | tgcccatta | gcccactgcc | tggaaagccc | ttcggagagc | 1920 |
| tccccatggc | tcctcaccac | cgagacagtt | ggttttgcat | gtctgcatga | aggtctacct | 1980 |
| gaaaattcaa | catttgcttt | ttgcttgtgt | acaaacccag | attgaagcta | aaataaacca | 2040 |
| gactcactaa | atcctttcca | ataattgact | ggtggaagga | aaacaaaaaa | caaaaactaa | 2100 |
| aaacctctta | gcttttctgc | aattcaactt | tttatttta | tttttatttc | tatcaaagac | 2160 |
| ggtagagaga | aacagcttga | tgctgttct | acattaaaaa | aaaaaaaaaa | agacagactg | 2220 |
| ttggtcttac | taaggatgtt | tttaccagcc | tgcctgactt | ctgcaaacct | accctgtcaa | 2280 |

```
ggagatcaaa gggacgcagg tttctgttta ttctgaacaa gggccaggcc ccgcggagtg    2340
tctttggtgg atcccagata actcctaggt gctgctctca gacactgagg agttgagcaa    2400
atctgttcta ttctgcagaa cccacaggac aaataagagt tctactagaa ttaacagccc    2460
aaaagaatag ctacagctaa gtgaagccac ttacgtgggc tttaaaaaaa taatgtgtta    2520
gctgattcac atgcactgga gttaattagt cttagaaatg tgtgcatcca tacaaatgca    2580
caacataaag tgaacatatt cctaggccct ttctgcctgt gtcagggcca ggaagtagag    2640
gctgggaact cttctggtcc ccagtatggc aggcgccagg gagggatgg tgtggcccat     2700 cccttctctg gatacctggc cagtggcagg cagcagggag gagctggccg accctcagtg    2760
actgacaagc cagcaattct gagttctggc ctttgggagt ctgcctgctc caagccagtc    2820 cacccccagct gcagcccccaa aagctggctc aaagtccttg ggtggattca ctggagatgg   2880
gcaacttaaa acaagagaaa ctttaatttt taaacctaag tgatgataca gctcttccct    2940
tagattatcg cccaggctgg agtgcagtgg catgatctca gctcactgca agctccacct    3000
cctgggttca tgccattctc ctgcctcagc ctcccccga gtaactggga atacaggcgc     3060
ccgccaccat gcctggctaa ttttttgtat ttttagtaga gatagggttt catcatgtta    3120
gccaggatgg tctcattctt attctttaat gagatcagag ggtaattcac caagaaagac    3180
ctctcctgtt ccattgtgtc atccaacaac tgctcagagc tcaaaattat agaaggcttc    3240
tgagccccta gagatttta atttgcttct aatccctgag gtgggaacat catgagggaa     3300
gatttgattt tcagagttaa ataaattgta tgtgcttttc cagccaaaaa aaaaaa        3356

<210> SEQ ID NO 4
<211> LENGTH: 502
<212> TYPE: PRT
<213> ORGANISM: Homo sapiens

<400> SEQUENCE: 4

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
```

```
            180             185                 190
Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Thr Leu Tyr Tyr Gly Leu Asn Leu Leu Ile Pro
225                 230                 235                 240

Cys Val Leu Ile Ser Ala Leu Ala Leu Leu Val Phe Leu Leu Pro Ala
                    245                 250                 255

Asp Ser Gly Glu Lys Ile Ser Leu Gly Ile Thr Val Leu Leu Ser Leu
                    260                 265                 270

Thr Val Phe Met Leu Leu Val Ala Glu Ile Met Pro Ala Thr Ser Asp
                    275                 280                 285

Ser Val Pro Leu Ile Ala Gln Tyr Phe Ala Ser Thr Met Ile Ile Val
                    290                 295                 300

Gly Leu Ser Val Val Thr Val Ile Val Leu Gln Tyr His His His
305                 310                 315                 320

Asp Pro Asp Gly Gly Lys Met Pro Lys Trp Thr Arg Val Ile Leu Leu
                    325                 330                 335

Asn Trp Cys Ala Trp Phe Leu Arg Met Lys Arg Pro Gly Glu Asp Lys
                    340                 345                 350

Val Arg Pro Ala Cys Gln His Lys Gln Arg Arg Cys Ser Leu Ala Ser
                    355                 360                 365

Val Glu Met Ser Ala Val Ala Pro Pro Ala Ser Asn Gly Asn Leu
            370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                    405                 410                 415

Asp Glu His Leu Leu His Gly Gly Gln Pro Pro Glu Gly Asp Pro Asp
                    420                 425                 430

Leu Ala Lys Ile Leu Glu Glu Val Arg Tyr Ile Ala Asn Arg Phe Arg
            435                 440                 445

Cys Gln Asp Glu Ser Glu Ala Val Cys Ser Glu Trp Lys Phe Ala Ala
            450                 455                 460

Cys Val Val Asp Arg Leu Cys Leu Met Ala Phe Ser Val Phe Thr Ile
465                 470                 475                 480

Ile Cys Thr Ile Gly Ile Leu Met Ser Ala Pro Asn Phe Val Glu Ala
                    485                 490                 495

Val Ser Lys Asp Phe Ala
            500

<210> SEQ ID NO 5
<211> LENGTH: 2343
<212> TYPE: DNA
<213> ORGANISM: Homo sapiens

<400> SEQUENCE: 5
ctctcagctg tcccctcccc tttcctcccg cctgaaacat gatccagctg aaggactgat      60
tgcaggaaaa cttggcagct ccccaacctt ggtggcccag ggagtgtgag gctgcagcct     120
cagaaggtgt gagcagtggc cacgagaggc aggctggctg ggacatgagg ttggcagagg     180
gcaggcaagc tggcccttgg tgggcctcgt cctgagcact cggaggcact cctatgcttg     240
gaaagctcgc tatgctgctg tgggtccagc aggcgctgct cgccttgctc ctccccacac     300
```

```
tcctggcaca gggagaagcc aggaggagcc gaaacaccac caggcccgct ctgctgaggc    360
tgtcggatta cctttgacc aactacagga agggtgtgcg ccccgtgagg gactggagga    420
agccaaccac cgtatccatt gacgtcattg tctatgccat cctcaacgtg gatgagaaga    480
atcaggtgct gaccacctac atctggtacc ggcagtactg gactgatgag tttctccagt    540
ggaaccctga ggactttgac aacatcacca agttgtccat ccccacggac agcatctggg    600
tcccggacat tctcatcaat gagttcgtgg atgtggggaa gtctccaaat atcccgtacg    660
tgtatattcg gcatcaaggc gaagttcaga actacaagcc cttcaggtg gtgactgcct    720 gtagcctcga catctacaac ttccccttcg atgtccagaa ctgctcgctg accttcacca    780
gttggctgca caccatccag gacatcaaca tctctttgtg gcgcttgcca gaaaaggtga    840
aatccgacag gagtgtcttc atgaaccagg gagagtggga gttgctgggg gtgctgccct    900
actttcggga gttcagcatg gaaagcagta actactatgc agaaatgaag ttctatgtgg    960
tcatccgccg gcggcccctc ttctatgtgg tcagcctgct actgcccagc atcttcctca   1020
tggtcatgga catcgtgggc ttctacctgc cccccaacag tggcgagagg gtctctttca   1080
agattacact cctcctgggc tactcggtct tcctgatcat cgtttctgac acgctgccgg   1140
ccactgccat cggcactcct ctcattggta aggcccctcc tggcagcaga gctcagtctg   1200
gtgagaaacc cgccccctcc cacctcctgc atgtgtctct tgcctctgcc ctgggctgca   1260
caggtgtcta ctttgtggtg tgcatggctc tgctggtgat aagtttggcc gagaccatct   1320
tcattgtgcg gctggtgcac aagcaagacc tgcagcagcc cgtgcctgct ggctgcgtc    1380 acctggttct ggagagaatc gcctggctac ttgcctgag ggagcagtca acttcccaga   1440
ggcccccagc cacctcccaa gccaccaaga ctgatgactg ctcagccatg ggaaaccact   1500
gcagccacat gggaggaccc caggacttcg agaagagccc gagggacaga tgtagccctc   1560
ccccaccacc tcgggaggcc tcgctggcgg tgtgtgggct gctgcaggag ctgtcctcca   1620
tccggcaatt cctggaaaag cgggatgaga tccgagaggt ggcccgagac tggctgcgcg   1680
tgggctccgt gctggacaag ctgctattcc acatttacct gctagcggtg ctggcctaca   1740
gcatcaccct ggttatgctc tggtccatct ggcagtacgc ttgagtgggt acagcccagt   1800
ggaggagggg gtacagtcct ggttaggtgg ggacagagga tttctgctta ggcccctcag   1860
gacccaggga atgccaggga catttttcaag acacagacaa agtcccgtgc ctgtttccca   1920
atgccaattc atctcagcaa tcacaagcca aggtctgaac ccttccacca aaaactgggt   1980
gttcaaggcc cttacaccct tgtcccaccc cagcagctc accatggctt taaaacatgc   2040
tgtcttagat caggagaaac tcgggcactc cctaagtcca ctctagttgt ggacttttcc   2100
ccattgaccc tcacctgaat aagggacttt ggaattctgc ttctctttca aactttgct   2160 tttaggttga aggcaaaacc aactctctac tacacaggcc tgataactct gtacgaggct   2220
tctctaaccc ctagtgtctt tttttcttc acctcacttg tggcagcttc cctgaacact   2280
catcccccat cagatgatgg gagtgggaag aataaaatgc agtgaaaccc taaaaaaaaa   2340
aaa                                                                 2343
```

<210> SEQ ID NO 6
<211> LENGTH: 516
<212> TYPE: PRT
<213> ORGANISM: Homo sapiens

<400> SEQUENCE: 6

-continued

```
Met Leu Gly Lys Leu Ala Met Leu Leu Trp Val Gln Gln Ala Leu Leu
1               5                   10                  15

Ala Leu Leu Leu Pro Thr Leu Leu Ala Gln Gly Glu Ala Arg Arg Ser
            20                  25                  30

Arg Asn Thr Thr Arg Pro Ala Leu Leu Arg Leu Ser Asp Tyr Leu Leu
        35                  40                  45

Thr Asn Tyr Arg Lys Gly Val Arg Pro Val Arg Asp Trp Arg Lys Pro
    50                  55                  60

Thr Thr Val Ser Ile Asp Val Ile Val Tyr Ala Ile Leu Asn Val Asp
65                  70                  75                  80

Glu Lys Asn Gln Val Leu Thr Thr Tyr Ile Trp Tyr Arg Gln Tyr Trp
                85                  90                  95

Thr Asp Glu Phe Leu Gln Trp Asn Pro Glu Asp Phe Asp Asn Ile Thr
            100                 105                 110

Lys Leu Ser Ile Pro Thr Asp Ser Ile Trp Val Pro Asp Ile Leu Ile
        115                 120                 125

Asn Glu Phe Val Asp Val Gly Lys Ser Pro Asn Ile Pro Tyr Val Tyr
    130                 135                 140

Ile Arg His Gln Gly Glu Val Gln Asn Tyr Lys Pro Leu Gln Val Val
145                 150                 155                 160

Thr Ala Cys Ser Leu Asp Ile Tyr Asn Phe Pro Phe Asp Val Gln Asn
            165                 170                 175

Cys Ser Leu Thr Phe Thr Ser Trp Leu His Thr Ile Gln Asp Ile Asn
        180                 185                 190

Ile Ser Leu Trp Arg Leu Pro Glu Lys Val Lys Ser Asp Arg Ser Val
    195                 200                 205

Phe Met Asn Gln Gly Glu Trp Glu Leu Leu Gly Val Leu Pro Tyr Phe
210                 215                 220

Arg Glu Phe Ser Met Glu Ser Ser Asn Tyr Tyr Ala Glu Met Lys Phe
225                 230                 235                 240

Tyr Val Val Ile Arg Arg Arg Pro Leu Phe Tyr Val Val Ser Leu Leu
            245                 250                 255

Leu Pro Ser Ile Phe Leu Met Val Met Asp Ile Val Gly Phe Tyr Leu
        260                 265                 270

Pro Pro Asn Ser Gly Glu Arg Val Ser Phe Lys Ile Thr Leu Leu Leu
    275                 280                 285

Gly Tyr Ser Val Phe Leu Ile Ile Val Ser Asp Thr Leu Pro Ala Thr
290                 295                 300

Ala Ile Gly Thr Pro Leu Ile Gly Lys Ala Pro Pro Gly Ser Arg Ala
305                 310                 315                 320

Gln Ser Gly Glu Lys Pro Ala Pro Ser His Leu Leu His Val Ser Leu
            325                 330                 335

Ala Ser Ala Leu Gly Cys Thr Gly Val Tyr Phe Val Val Cys Met Ala
        340                 345                 350

Leu Leu Val Ile Ser Leu Ala Glu Thr Ile Phe Ile Val Arg Leu Val
    355                 360                 365

His Lys Gln Asp Leu Gln Gln Pro Val Pro Ala Trp Leu Arg His Leu
370                 375                 380

Val Leu Glu Arg Ile Ala Trp Leu Leu Cys Leu Arg Glu Gln Ser Thr
385                 390                 395                 400

Ser Gln Arg Pro Pro Ala Thr Ser Gln Ala Thr Lys Thr Asp Asp Cys
            405                 410                 415

Ser Ala Met Gly Asn His Cys Ser His Met Gly Gly Pro Gln Asp Phe
```

|     |     |     |     | 420 |     |     |     | 425 |     |     |     | 430 |     |     |
| --- | --- | --- | --- | --- | --- | --- | --- | --- | --- | --- | --- | --- | --- | --- |
| Glu | Lys | Ser | Pro | Arg | Asp | Arg | Cys | Ser | Pro | Pro | Pro | Arg | Glu |     |
|     |     |     | 435 |     |     |     |     | 440 |     |     |     |     | 445 |     |

| Ala | Ser | Leu | Ala | Val | Cys | Gly | Leu | Leu | Gln | Glu | Leu | Ser | Ser | Ile | Arg |
| --- | --- | --- | --- | --- | --- | --- | --- | --- | --- | --- | --- | --- | --- | --- | --- |
|     |     | 450 |     |     |     |     | 455 |     |     |     |     | 460 |     |     |     |

| Gln | Phe | Leu | Glu | Lys | Arg | Asp | Glu | Ile | Arg | Glu | Val | Ala | Arg | Asp | Trp |
| --- | --- | --- | --- | --- | --- | --- | --- | --- | --- | --- | --- | --- | --- | --- | --- |
| 465 |     |     |     |     | 470 |     |     |     |     | 475 |     |     |     |     | 480 |

| Leu | Arg | Val | Gly | Ser | Val | Leu | Asp | Lys | Leu | Leu | Phe | His | Ile | Tyr | Leu |
| --- | --- | --- | --- | --- | --- | --- | --- | --- | --- | --- | --- | --- | --- | --- | --- |
|     |     |     | 485 |     |     |     |     | 490 |     |     |     |     | 495 |     |     |

| Leu | Ala | Val | Leu | Ala | Tyr | Ser | Ile | Thr | Leu | Val | Met | Leu | Trp | Ser | Ile |
| --- | --- | --- | --- | --- | --- | --- | --- | --- | --- | --- | --- | --- | --- | --- | --- |
|     |     |     | 500 |     |     |     |     | 505 |     |     |     |     | 510 |     |     |

| Trp | Gln | Tyr | Ala |
| --- | --- | --- | --- |
|     |     |     | 515 |

<210> SEQ ID NO 7
<211> LENGTH: 5723
<212> TYPE: DNA
<213> ORGANISM: Homo sapiens

<400> SEQUENCE: 7

| gctccgggcc | agcgcggcgg | cggcggcggc | ggcggcagca | gcaggagcag | ccccggctgc | 60 |
| --- | --- | --- | --- | --- | --- | --- |
| gggtcgcgac | ggcggcgggg | cgccccctcc | cccgtgccgg | ggcgcggcgg | agggatgtgg | 120 |
| ggccttgcgg | gaggaaggct | tttcggcatc | ttctcggccc | cggtgctggt | ggctgtggtg | 180 |
| tgctgcgccc | agagtgtgaa | cgatcccggg | aacatgtcct | tgtgaaggga | cggtggac | 240 |
| aagctgttga | aggctacga | cattcgccta | agacccgact | cggggggtcc | cccggtctgc | 300 |
| gtggggatga | acatcgacat | cgccagcatc | gacatggttt | ccgaagtcaa | catggattat | 360 |
| accttaacca | tgtattttca | acaatattgg | agagataaaa | ggctcgccta | ttctgggatc | 420 |
| cctctcaacc | tcacgcttga | caatcgagtg | gctgaccagc | tatgggtgcc | cgacacatat | 480 |
| ttcttaaatg | acaaaaagtc | atttgtgcat | ggagtgacag | tgaaaaaccg | catgatccgt | 540 |
| cttcaccctg | atgggacagt | gctgtatggg | ctcagaatca | ccacgacagc | agcatgcatg | 600 |
| atggacctca | ggagataccc | cctggacgag | cagaactgca | ctctggaaat | tgaaagctat | 660 |
| ggctacacca | cggatgacat | tgagttttac | tggcgaggcg | gggacaaggc | tgttaccgga | 720 |
| gtggaaagga | ttgagctccc | gcagttctcc | atcgtggagc | accgtctggt | ctcgaggaat | 780 |
| gttgtcttcg | ccacaggtgc | ctatcctcga | ctgtcactga | gctttcggtt | gaagaggaac | 840 |
| attggatact | tcattcttca | gacttatatg | ccctctatac | tgataacgat | tctgtcgtgg | 900 |
| gtgtccttct | ggatcaatta | tgatgcatct | gctgctagag | ttgccctcgg | gatcacaact | 960 |
| gtgctgacaa | tgacaaccat | caacacccac | cttcgggaga | ccttgcccaa | aatcccctat | 1020 |
| gtcaaagcca | ttgacatgta | ccttatgggc | tgcttcgtct | ttgtgttcct | ggcccttctg | 1080 |
| gagtatgcct | tgtcaacta | cattttcttt | ggaagaggcc | ctcaaaggca | gaagaagctt | 1140 |
| gcagaaaaga | cagccaaggc | aaagaatgac | cgttcaaaga | gcgaaagcaa | ccgggtggat | 1200 |
| gctcatggaa | atattctgtt | gacatcgctg | gaagttcaca | atgaaatgaa | tgaggtctca | 1260 |
| ggcggcattg | gcgataccag | gaattcagca | atatccttg | acaactcagg | aatccagtac | 1320 |
| aggaaacaga | gcatgcctcg | agaagggcat | gggcgattcc | tggggacag | aagcctcccg | 1380 |
| cacaagaaga | cccatctacg | gaggaggtct | tcacagctca | aaattaaaat | acctgatcta | 1440 |
| accgatgtga | atgccataga | cagatggtcc | aggatcgtgt | tccattcac | ttttctcttt | 1500 |
| ttcaacttag | tttactggct | gtactatgtt | aactgagtga | ctgtacttga | tttttcaaag | 1560 |

```
acttcatttta acactgagtg aaatattact ctgcctgtca agttttttata cctgtacaca    1620 cacagacaca caagcagaca cacacatata tacatacgca attgtatata tatgtgaact    1680
ttctcagcat atatataaaa tacacgtgta tatgaggatg tatgtgtata tgtttataca    1740
cacaggagtc agtgcccatg tgtatggaag acaaatacac atacatatat acattttgca    1800
gctatggaca atttaccaca ggatgcatat taaagaaagt catagttttt ttcttttta     1860 attgaaaggg acaagtatca tctaaatatt atgccttgag aatgagggcg tgaaacacaa    1920
tatcatcccc aaatgtgtct tgtattatca taagttagat gttttagttt aaaaatcaga    1980
aagacattct tagttaatct ttgaaaactc atacagtggt attgctagtt taaaatgagt    2040
cacttacttc atatcctctc gttcagttta gtaagcaaag gcttcttggc ttctctggtg    2100
atggggtttg ttttcatcgg gcatacgttt tctgcaatgg tttagtggct ggggtgagcc    2160
actggcagtg tgcttacctg ttgtctgaaa catagataga tcccacgttg atgtctgaac    2220
gaccgtcttt tgaaaactca tcgggagtga atggcatctc gttgtaagta ctctaatata    2280
cagtgtgtag tttgtttctg ttgttcactt ggagtggatc cagcttcact gtcatgtgcg    2340
aacacagtga cacgtttggc cagtgacatt tcaatcactg aaaatgtgct ctacatctcg    2400
tatggatttc taggcctgat atccaacaga aagcatagac gtctcaggtt attcgttact    2460
ctaaggtaaa accatctagg atgattttcc cccttgcagt tatgttatca ttcttataac    2520
attgtatgtt aatagaaaat atatttgcat aatatgcata tatatgtata tttaccaaga    2580
ttttgtttct tacgcttgct atcatggcag catgcgatgt catattttcc tttatgtgat    2640
gtaactactt tctgttatct agaaattaag attgaagcta aaacacttct actgttcaat    2700
ttcagaaact aagaatcatc ctcatgcctt tatttctgta tctgacatat ttcataagca    2760
catccaacta ctcctagact gactaggatt ctgcaggaac atgacccgta cacaccacgc    2820
gtcacccaac gacccatgac cgttctctga ggcaaaggag ggcaacctga cagcaaacac    2880
agtcactgtt ggttccttct gatccacagc ctcatcagta tttggacttt ttaaagctcg    2940
tagaaacaag acaaggtgca ccggtttcat agacgcaacc ttaacttact atttagatga    3000
gatctttcta aagaaaaaaa aaagagatga tatatttttt gtaaacaata tttctatcac    3060
aggcatccat aaactgaaat gactacagtt gtgcaaacag gtgtcacagt gaagttgagc    3120
atttggagaa aaaaataaaa agcaaaattt gcaggaagaa ctgctaaatt aatactttat    3180
cccaaaatgc cacgtatgcc tcaccctctc tgttctatcc aaaaccaagg accagagtgc    3240
tccaatggta ggcccccagtt gtctcgatgt aggtagaggc accaccctcc ccgaggatgc    3300
gtgtggtgtg gactatcccc atgagctgac cactacttga ttttttcttg gtggccgtaa    3360 caaccttaa tttgtgggca tctgcaacag ttcaaaaccc accatcagat aaaacataat    3420
ccacaaaatc tcacgctaga ggcaattacc tacttttaga cccttttccc tctttcattc    3480 ctatctttt cctcctaatc gctgctctct ggttttattt tcatctggag actagccagg    3540
gatttctttg gctttggctt ttctctgacc attttttcca tgggtaacaa tggggatcc    3600 taaaagttaa acagattggg aaaaaccttg ttaagtggcc ttatcattat tatcatgtta    3660
aagaaaaaaa atacatttgc aaagacctta tcccttcaa tacttcaggt atctttttct    3720
gtatccagta attaaaggtg tgaggtccac atgcagaaga gggaccccaa aatgtaaatg    3780
gatgtggaca aaaacagtca atggtctatt taagtgtata atttatacta ttcagaactg    3840
tgacattaat tctttctggg agaaaagtga tttaaaactt ttttgatgca tagttgaggt    3900
```

| | |
|---|---:|
| acccaaatat caaaggcaga gaccccatgg ggctccaaag agctgcagtc tccttcccaa | 3960 |
| ggttttctgg atataaattt gcatggtata gtcataatag cttttgagct ttttatatgc | 4020 |
| atttggcacc aagactggga tccacaactt tgtagacact gcgatgaagt taacatatta | 4080 |
| gctatactat aaatagtgtt tgtaactaca cacacacaca cacacacaca cacaaataca | 4140 |
| tacatatatt ctgtaaaaac aaaaaaaaac ttttttaagat ccttgggtat gtgtttgctt | 4200 |
| tactccatttt cagaagaaaa ttacttttct tctaacaaaa ttattttata gcttctccat | 4260 |
| ttttaaaact tgtgagagca ttgagaagag aactctgact gtgttaacag aagagagttg | 4320 |
| aattggagtc tctgttgtgt taaaatgacc tctcgttact ccacagtagt tatttgagcc | 4380 |
| agtgactgag tcgcgttgag gaattctgaa cccggacctc tgacgttgtt gggaggtggc | 4440 |
| tgttacccac acccagacct cttgagtaag gacagaaacg ttatcattgg ggatataatg | 4500 |
| agatttcttt cttaacaatt gaaagtaata aagagttaat tttctcagta gtcctgtctt | 4560 |
| tccaaaatgc gccacagggg ctcaagatct acagaagaat cttgttatga cagtttgtta | 4620 |
| ttacccatat tcagatatcc ttgagataat ggaagagccc tgctacataa ctccctacag | 4680 |
| agaaagactg atagacttga gtagtcctta aaacaagtgt tattcctgtt caccaaccc | 4740 |
| gggactgtgg aggggtttca ctgtctatac catgcgacat ccatttcccc tgaatctcaa | 4800 |
| acgaactaga aagtatgtca tgataatatt tccattagat ttggaagcta cctgtacatc | 4860 |
| tgcaatattg tgttttttaac gccagcaccc agaactttga catgttcagt cactccctga | 4920 |
| aaggcacttc tctcttgtcc aaacacagcg ttgacatttt tactgaggag atcatctcaa | 4980 |
| aggtgatgcc aaacgagtct ggggctggtt taaggggac aggcacattg cagttgtagg | 5040 |
| tgttcatttt cagcatctag tagataatcc attggtgttt gtcccaccat tggtgtattc | 5100 |
| taacaagaat gtgtccaact ttgaatctcc tggcttgaaa gtataaacca tcacttaatt | 5160 |
| cttattttaa ctctccacct gaaaaccagt tcatatttct ggccatttta tgtaagcaaa | 5220 |
| actgaacaat tggtgaaaca ttttgttact cttggaattg actctggctg tcagtgtgag | 5280 |
| ccattagagt aacatcgaat cttggggcaa agaactgccc aggtgaatta aattttttcca | 5340 |
| ggacactagc tagtgtgcct tggattgatt acctcttcta ctgcattgaa aggcgccatg | 5400 |
| ttttcctgaa atactaaatt cccaacacct gggtaaacaa tgaccttcca gagagtggct | 5460 |
| cccgtatgcc tctccctagg accaacccca tgaacatgtt ttgtcacgtt tgtctcatgt | 5520 |
| ttctacttca caagtcagtg agtgtgttta aggtaagtac aggattattc tagtaggaat | 5580 |
| aggcgattgc tgtcataatc aattctcatg ttgatttcat tttattgtaa agataaattt | 5640 |
| aaacccagtt ttgcttaagc acattgatgt aattttttgg tattatttga catgaaaaaa | 5700 |
| cagcaaaatt gagtgataga tac | 5723 |

<210> SEQ ID NO 8
<211> LENGTH: 473
<212> TYPE: PRT
<213> ORGANISM: Homo sapiens

<400> SEQUENCE: 8

Met Trp Gly Leu Ala Gly Gly Arg Leu Phe Gly Ile Phe Ser Ala Pro
1               5                   10                  15

Val Leu Val Ala Val Val Cys Cys Ala Gln Ser Val Asn Asp Pro Gly
            20                  25                  30

Asn Met Ser Phe Val Lys Glu Thr Val Asp Lys Leu Leu Lys Gly Tyr
        35                  40                  45

```
Asp Ile Arg Leu Arg Pro Asp Phe Gly Gly Pro Val Cys Val Gly
    50              55                  60

Met Asn Ile Asp Ile Ala Ser Ile Asp Met Val Ser Glu Val Asn Met
65              70                  75                  80

Asp Tyr Thr Leu Thr Met Tyr Phe Gln Gln Tyr Trp Arg Asp Lys Arg
                85                  90                  95

Leu Ala Tyr Ser Gly Ile Pro Leu Asn Leu Thr Leu Asp Asn Arg Val
            100                 105                 110

Ala Asp Gln Leu Trp Val Pro Asp Thr Tyr Phe Leu Asn Asp Lys Lys
            115                 120                 125

Ser Phe Val His Gly Val Thr Val Lys Asn Arg Met Ile Arg Leu His
130                 135                 140

Pro Asp Gly Thr Val Leu Tyr Gly Leu Arg Ile Thr Thr Thr Ala Ala
145                 150                 155                 160

Cys Met Met Asp Leu Arg Arg Tyr Pro Leu Asp Glu Gln Asn Cys Thr
                165                 170                 175

Leu Glu Ile Glu Ser Tyr Gly Tyr Thr Thr Asp Asp Ile Glu Phe Tyr
            180                 185                 190

Trp Arg Gly Gly Asp Lys Ala Val Thr Gly Val Glu Arg Ile Glu Leu
        195                 200                 205

Pro Gln Phe Ser Ile Val Glu His Arg Leu Val Ser Arg Asn Val Val
        210                 215                 220

Phe Ala Thr Gly Ala Tyr Pro Arg Leu Ser Leu Ser Phe Arg Leu Lys
225                 230                 235                 240

Arg Asn Ile Gly Tyr Phe Ile Leu Gln Thr Tyr Met Pro Ser Ile Leu
                245                 250                 255

Ile Thr Ile Leu Ser Trp Val Ser Phe Trp Ile Asn Tyr Asp Ala Ser
            260                 265                 270

Ala Ala Arg Val Ala Leu Gly Ile Thr Thr Val Leu Thr Met Thr Thr
            275                 280                 285

Ile Asn Thr His Leu Arg Glu Thr Leu Pro Lys Ile Pro Tyr Val Lys
290                 295                 300

Ala Ile Asp Met Tyr Leu Met Gly Cys Phe Val Phe Val Phe Leu Ala
305                 310                 315                 320

Leu Leu Glu Tyr Ala Phe Val Asn Tyr Ile Phe Phe Gly Arg Gly Pro
                325                 330                 335

Gln Arg Gln Lys Lys Leu Ala Glu Lys Thr Ala Lys Ala Lys Asn Asp
            340                 345                 350

Arg Ser Lys Ser Glu Ser Asn Arg Val Asp Ala His Gly Asn Ile Leu
        355                 360                 365

Leu Thr Ser Leu Glu Val His Asn Glu Met Asn Glu Val Ser Gly Gly
370                 375                 380

Ile Gly Asp Thr Arg Asn Ser Ala Ile Ser Phe Asp Asn Ser Gly Ile
385                 390                 395                 400

Gln Tyr Arg Lys Gln Ser Met Pro Arg Glu Gly His Gly Arg Phe Leu
                405                 410                 415

Gly Asp Arg Ser Leu Pro His Lys Lys Thr His Leu Arg Arg Arg Ser
            420                 425                 430

Ser Gln Leu Lys Ile Lys Ile Pro Asp Leu Thr Asp Val Asn Ala Ile
            435                 440                 445

Asp Arg Trp Ser Arg Ile Val Phe Pro Phe Thr Phe Ser Leu Phe Asn
450                 455                 460

Leu Val Tyr Trp Leu Tyr Tyr Val Asn
```

<210> SEQ ID NO 9
<211> LENGTH: 3174
<212> TYPE: DNA
<213> ORGANISM: Homo sapiens

<400> SEQUENCE: 9

```
taataatggc cgtaagctta aaatagatcc agggaggagc tcattaacgt gaacatagaa      60
agcagttccg cacctctggc cttactcctc ttggaaattg ctttggtcca ttttacttc      120
cttttattcg acgcaccaga aaataagact tttaccaaca tttttactgc atttgacgat     180
gaactaattt agaccggcta aaataattgt tccactggga cacaggaatt caacctcagt     240
tcagaaaatc cctgacatct gacgtaggag gatttatagg tttagtggaa attgcttcct    300
cctgctctcc agattgcatc ctgtgggttg attttttttt tgcatgagta acatccttc      360
taataatgaa cagaccaata atgtcttaag agagaaaaag aacaatcttt tccttttgc      420
tgtttctgga gagagctgtt tgaatttgga aacccatgtt ggctgtccca aatatgagat    480
ttggcatctt tcttttgtgg tggggatggg ttttggccac tgaaagcaga atgcactggc    540
ccggaagaga agtccacgag atgtctaaga aaggcaggcc ccaaagacaa agacgagaag    600
tacatgaaga tgcccacaag caagtcagcc caattctgag acgaagtcct gacatcacca    660
aatcgcctct gacaaagtca gaacagcttc tgaggataga tgaccatgat ttcagcatga    720
ggcctggctt tggaggccct gccattcctg ttggtgtgga tgtgcaggtg gagagtttgg    780
atagcatctc agaggttgac atggacttta cgatgaccct ctacctgagg cactactgga    840
aggacgagag gctgtctttt ccaagcacca acaacctcag catgacgttt gacggccggc    900
tggtcaagaa gatctgggtc cctgacatgt ttttcgtgca ctccaaacgc tccttcatcc    960
acgacaccac cacagacaac gtcatgttgc gggtccagcc tgatgggaaa gtgctctata   1020
gtctcagggt tacagtaact gcaatgtgca acatggactt cagccgattt cccttggaca   1080
cacaaacgtg ctctcttgaa attgaaagct atgcctatac agaagatgac ctcatgctgt   1140
actggaaaaa gggcaatgac tccttaaaga cagatgaacg gatctcactc tcccagttcc   1200
tcattcagga attccacacc accaccaaac tggctttcta cagcagcaca ggctggtaca   1260
accgtctcta cattaatttc acgttgcgtc gccacatctt cttcttcttg ctccaaactt   1320
atttccccgc tacccctgatg gtcatgctgt cctgggtgtc cttctggatc gaccgcagag   1380
ccgtgcctgc cagagtcccc ttaggtatca aacggtgct gaccatgtcc accatcatca   1440
cgggcgtgaa tgcctccatg ccgcgcgtct cctacatcaa ggccgtggac atctacctct   1500
gggtcagctt tgtgttcgtg ttcctctcgg tgctggagta tgcggccgtc aactacctga   1560
ccactgtgca ggagaggaag aacagaagc tgcgggagaa gcttccctgc accagcggat   1620
tacctccgcc ccgcactgcg atgctggacg gcaactacag tgatgggagg tgaatgacc    1680
tggacaacta catgccagag aatggagaga agcccgacag gatgatggtg cagctgaccc    1740
tggcctcaga gaggagctcc ccacagagga aaagtcagag aagcagctat gtgagcatga   1800
gaatcgacac ccacgccatt gataaatact ccaggatcat ctttccagca gcatacattt   1860
tattcaattt aatatactgg tctattttct cctagatgct tgtaattcta caaatttcac   1920
atttccatgg catgcactac agaaataact gtataatgaa aaagtattta aggatatggt   1980
taaaaaaaaa tcccaggacc cacccatgtt ttcactatcc cttctgcagc tttccaaagc   2040
tacattgacg agacacttac tggtttaatt tgcacttatt aaccatctat tgaatacaca   2100
```

-continued

```
gcattatatt aggtgctgca ggaaatacga cactgtagcg actgatgtta gttgttaccc    2160 agatccctg gaaaagcaca ctaccagtgt tgtgggcaca tttagttcca cccgttagac     2220
ccttgatgct attcacatga ataatttatt ttcctcaagt gtcattacat tgttcaggct    2280
acgtgaactt ggaagcacct acaggccatt tgcatgaaat tcacatgcac ctaaatcctc    2340
actttgacag aaactcatgc ttcagtttat aacctattac ctattttgta tgcgactcca    2400
cctccgcatg tttattttaa taaaaggcaa tgataacatt cacattattt ttctttatat    2460
gctgtggttc acaggcttta ccccttcaca agaaaagctc tttagattgg cgcaattgct    2520
tctgattttg gtgaaatttt ccctggtagg gaaactttga agataagagt acacacatgc    2580
attttgtctg ttgtgtcata gaggtaacta ggctagaaaa tttgtgttta aatgttccct    2640
attttatata atcaccactt catgtttctt cttcttggag catgtccttg ttcaaagaga    2700
agtgctttct cagtgatgtg atatcttcac tgaggaactt gggtagagaa tgatttcttc    2760
tgcataaaca cttcaaggaa atacataatt tgggactact tgtaactcat tagaatgaga    2820
aatactcaca tggtttctta agagaaaaag aacatcggaa agcaaaataa atgggaagat    2880
atcactggac atctgcattt atactcgaaa taccagcatt ttctatggac cagaaaactg    2940
ccatcaccta gaccacacag cccagatacc aggcagacgg atggcccaat ggcaactgat    3000
gtcagggcat ggggtaaagg agagggttct aatctggtgt atcacttaaa aacagttatt    3060
tatattatat atctgctata tagatcaacc tccaccaaac ttacccaaac agcatttgtt    3120
ttatttgaaa ctcactttaa taaagtgaat tatatacaca aaaaaaaaaa aaaa          3174
```

<210> SEQ ID NO 10
<211> LENGTH: 479
<212> TYPE: PRT
<213> ORGANISM: Homo sapiens

<400> SEQUENCE: 10

```
Met Leu Ala Val Pro Asn Met Arg Phe Gly Ile Phe Leu Leu Trp Trp
1               5                   10                  15

Gly Trp Val Leu Ala Thr Glu Ser Arg Met His Trp Pro Gly Arg Glu
            20                  25                  30

Val His Glu Met Ser Lys Lys Gly Arg Pro Gln Arg Gln Arg Arg Glu
        35                  40                  45

Val His Glu Asp Ala His Lys Gln Val Ser Pro Ile Leu Arg Arg Ser
    50                  55                  60

Pro Asp Ile Thr Lys Ser Pro Leu Thr Lys Ser Glu Gln Leu Leu Arg
65                  70                  75                  80

Ile Asp Asp His Asp Phe Ser Met Arg Pro Gly Phe Gly Gly Pro Ala
                85                  90                  95

Ile Pro Val Gly Val Asp Val Gln Val Glu Ser Leu Asp Ser Ile Ser
            100                 105                 110

Glu Val Asp Met Asp Phe Thr Met Thr Leu Tyr Leu Arg His Tyr Trp
        115                 120                 125

Lys Asp Glu Arg Leu Ser Phe Pro Ser Thr Asn Asn Leu Ser Met Thr
    130                 135                 140

Phe Asp Gly Arg Leu Val Lys Lys Ile Trp Val Pro Asp Met Phe Phe
145                 150                 155                 160

Val His Ser Lys Arg Ser Phe Ile His Asp Thr Thr Thr Asp Asn Val
                165                 170                 175

Met Leu Arg Val Gln Pro Asp Gly Lys Val Leu Tyr Ser Leu Arg Val
```

|  |  |  | 180 |  |  |  | 185 |  |  |  | 190 |  |
| --- | --- | --- | --- | --- | --- | --- | --- | --- | --- | --- | --- | --- |
| Thr | Val | Thr | Ala | Met | Cys | Asn | Met | Asp | Phe | Ser | Arg | Phe | Pro | Leu | Asp |

Thr Gln Thr Cys Ser Leu Glu Ile Glu Ser Tyr Ala Tyr Thr Glu Asp
    195                     200                 205

Asp Leu Met Leu Tyr Trp Lys Lys Gly Asn Asp Ser Leu Lys Thr Asp
210                 215                 220                 225                 230                 235                 240

Glu Arg Ile Ser Leu Ser Gln Phe Leu Ile Gln Glu Phe His Thr Thr
                    245                 250                 255

Thr Lys Leu Ala Phe Tyr Ser Ser Thr Gly Trp Tyr Asn Arg Leu Tyr
            260                 265                 270

Ile Asn Phe Thr Leu Arg Arg His Ile Phe Phe Leu Leu Gln Thr
        275                 280                 285

Tyr Phe Pro Ala Thr Leu Met Val Met Leu Ser Trp Val Ser Phe Trp
        290                 295                 300

Ile Asp Arg Arg Ala Val Pro Ala Arg Val Pro Leu Gly Ile Thr Thr
305                 310                 315                 320

Val Leu Thr Met Ser Thr Ile Ile Thr Gly Val Asn Ala Ser Met Pro
                    325                 330                 335

Arg Val Ser Tyr Ile Lys Ala Val Asp Ile Tyr Leu Trp Val Ser Phe
            340                 345                 350

Val Phe Val Phe Leu Ser Val Leu Glu Tyr Ala Ala Val Asn Tyr Leu
        355                 360                 365

Thr Thr Val Gln Glu Arg Lys Glu Gln Lys Leu Arg Glu Lys Leu Pro
    370                 375                 380

Cys Thr Ser Gly Leu Pro Pro Arg Thr Ala Met Leu Asp Gly Asn
385                 390                 395                 400

Tyr Ser Asp Gly Glu Val Asn Asp Leu Asp Asn Tyr Met Pro Glu Asn
                    405                 410                 415

Gly Glu Lys Pro Asp Arg Met Met Val Gln Leu Thr Leu Ala Ser Glu
            420                 425                 430

Arg Ser Ser Pro Gln Arg Lys Ser Gln Arg Ser Ser Tyr Val Ser Met
        435                 440                 445

Arg Ile Asp Thr His Ala Ile Asp Lys Tyr Ser Arg Ile Ile Phe Pro
    450                 455                 460

Ala Ala Tyr Ile Leu Phe Asn Leu Ile Tyr Trp Ser Ile Phe Ser
465                 470                 475

<210> SEQ ID NO 11
<211> LENGTH: 4620
<212> TYPE: DNA
<213> ORGANISM: Homo sapiens

<400> SEQUENCE: 11

| atgccttatt | ttacaagact | cattttgttc | ttgttttgct | tgatggttct | cgtggagagc | 60 |
| --- | --- | --- | --- | --- | --- | --- |
| agaaaaccca | agaggaagcg | atggacaggg | caggtggaaa | tgcccaagcc | aagtcactta | 120 |
| tataagaaga | accttgatgt | gaccaagatc | cggaagggaa | agcctcagca | gcttctcaga | 180 |
| gtggacgagc | acgacttcag | catgagaccc | gccttcggag | ccctgccat | cccggtgggc | 240 |
| gtggacgtac | aggtggagag | cctggacagc | atctccgagg | tggacatgga | cttcactatg | 300 |
| accctgtacc | tgcggcatta | ctggaaggat | gagaggctag | cttttctccag | cgccagcaac | 360 |
| aagagcatga | ccttcgatgg | ccggctggtg | aagaagatct | gggtccctga | tgtcttcttt | 420 |
| gttcactcca | aaagatcgtt | cactcatgac | accaccactg | acaacatcat | gctgagggtg | 480 |

```
ttcccagatg gacacgtgct gtacagcatg aggattacgg tcactgccat gtgcaacatg      540
gacttcagcc actttcccct ggactcccag acctgttctt tggagctgga gagctatgcc      600
tatacagatg aagatctaat gctgtactgg aagaatgggg atgaatccct aaaaacagat      660
gagaagatct ccttgtctca gtttctgatt cagaaatttc acacaacttc caggctggcc      720
ttctacagca gcactggctg gtacaaccgt ctgtacatta acttcacgtt gcgtcgccac      780
atcttcttct tcttgctcca aacatatttc cctgccactc tgatggtcat gctgtcctgg      840
gtgtccttct ggatcgaccg cagagctgtg cctgccagag tttcactggg tatcacgacg      900
gtgctgacca tgaccaccat catcacgggc gtgaatgcct ccatgccgcg cgtctcctac      960
gtcaaggccg tggacatcta cctctgggtc agctttgtgt tcgtgttcct ctcggtgctg     1020
gagtatgcgg ctgtcaacta cctgaccacc gtgcaggagc gcaaggaacg gaagctgcgg     1080
gagaagttcc cgtgcatgtg tggaatgctt cattcaaaaa ccatgatgct ggatggaagc     1140
tacagtgagt ctgaggccaa cagcctggct gggtacccca aagccatat cctgacagaa     1200 gaagaaaggc aagacaaaat agtggtccac ctgggcctga gtggtgaagc caacgctgcc     1260
agaaagaagg ggcttctgaa gggccagacg ggttttcgta tcttccagaa tacccatgcc     1320
attgacaaat actctaggtt gatattccct gcctcctaca tatttttcaa cttaatttat     1380
tggtcagtgt tttcctaggg gctccaaggc tgttcctaga agagggcata gacatcgagg     1440
gggcctggcc agtcattgac agacggactt gttgaccaca cgcccctcac caaacaatgc     1500
agcagctact ggaccaccct gagcagcact catctctcag agaagcccag gagccttcca     1560
gctgccctga ccccagaccc cgtggggctg ctccatgttc atgctgtctc gcgtcacact     1620
tcacatctct ctgggacctt ctgttcttgt gtgtgaacta attcacaaga actcccctcc     1680
tataaacaag gattcaaatg cctcctagac attcttagac cctcagattg cctaggagtc     1740
agttgtggag ggaaaaggaa aaactgaagt acaagcttag gggcattctg gataggagat     1800
aggaaattaa gaacaaaaaa caccctgtaa acccattgaa cttgattaag tgcctaccta     1860
gaagggaaaa gagctgagat cccagacagg aaatgatttg gcctgtggga gtatggcaac     1920
ccacaggatt ctgcaatatt agaggagatt attcatttat ccatccattc aaccattcat     1980
taaatattga ggtcccactc tgtgccaggt acggtagaaa tgagaaaata gtctctttcc     2040
ttagagatct tctctaagtt gtgctcattc tacatatggc atgatgtact tctgctcttt     2100
cccctccttc aaccccgctt accccacaga cccattctgt ttgctgttgc ttttactctt     2160
aggcatataa ggcagggtcc aggagaggcc aggtccagaa ctttcaacta tcctcctcca     2220
gtgaagttac acagatagca ctaattttgc ccagcaatga catgtagcaa tgtgcatgga     2280
gtattgccag ccagagaaac ttacccaggc tcaccacggt gtacagtttt tttattgggg     2340
tcggtcatgg atttatagct gattgcccac atggctgact ttagtctttt gcccctccag     2400
aggttaagct ggtaccttga ggtccagggc acctatcata aatcacattg ttggcataga     2460
ctatctggtg tggcccaagg ccccagtaga caaagaccct tctatctcac aggacattcc     2520
aagggcatag aggttgcttc ctagtaaagg ttagtccttt actacacagc aactcttgtc     2580
aattccctat tgttaatgtt aattgcggtg ttactattat atattcaggc aataaacatt     2640
ttaaagtatc tctgcactag gtacattggg gtccaaatta agaataagag tagtcgaagc     2700
tctcagagaa ggaactagta aaggaaatac cacacaaata tctataatat aagattaaga     2760
gtgtttagtg cctcagtaat agttcagtgt gagatgggaa ttccaaggga ggaaaaacag     2820
```

```
tcccaccagg gagacagacc tcatggagaa agcagccctg agatgcccct tgaaggtcag     2880
gattttaaga agaagaaatg gagcagaatg catcctagat ctgggctgtc tcatatggta     2940
gccactagcc acatgtctat ttaaatttaa attagtaaaa attaaaaata ttagccaggt     3000
gtggtggtgt gtgcctgggg ttctagctac tcaggaggct gaggcgggag gattgcttga     3060
gcccaggaat ccaggctgc cgtgagctgt gatcaagcca ctgcagtcca gcctgagtga     3120
cagagcgaga ccctatctct aaataataa ttattattat ttaaattagt tgaagttaaa     3180
taaaattgaa aactcagttc cttggttaca ccatccacac tcaagtgggc ttagtaagca     3240
cagttgctag tagctactgc actgggctgg gcagcctaaa gaccaggaag ctctaccagc     3300
caagagacca gcttgagcgg acgcatgggg agaatgggaa ggtttgccat tgcagagaac     3360
agggtttgtg ggcaagtcat tcattttggc aggatcctag gctgtgataa gaggaggtga     3420
gcgactagct ttttccacaa cactagggat caaggcaggt ccccaccatg ccggtgctta     3480
tgaggacagc ttccccacta tggagttgct ggacccaaga ctactagatt tcccagtctc     3540
acagaccaat gaagaacaaa aatgcataaa tatgggtaat tgggtggtac agggcatctg     3600
gacttgttta gaaaccttt tttcttttct gagacagagt ttcactcttg ttgctcaggc     3660
tggagtgcaa tggcttgatc ttggctcacc acaacctctg cctcccgggt tcaagcaatt     3720
ctcctgcctc agcctggag tagctgggat tacaggcatg cgccaccatg cctggctaac     3780 ttttgtatt ttagtagag atggggttc tccatgttag tcagcctggt cttgaactcc     3840
tgacctcagg tgatccgcct gcctcagcct cccaaagtgc tgtgattaca ggcgtgagcc     3900
accacacccg gccagaaacc ttttatctat agagactctc ccaggccaca gtgctgctcg     3960
aagaatgata attctattgt cattaaatat atcatattgc tttgcttgta agtcttattt     4020
aattccaacc cttctctgct tctgactgca ttgttttcat gcattatggc tcatataaca     4080
tagttgcctg ttcacaaatt aaaacaaata tttatttttg ctagcttcta tgttaaactg     4140
gagttaattc tatagcagac atatttgaaa tcataaacag tgttttatca tgcagggcca     4200
tgatacaatg acaccattgt atttagcatt gccttattac agtatactag tctgacacta     4260
cttgagaaaa gtaggaaatt taagaggta aagtggagac aacattggta ggagtagaaa     4320
acaggaacta aggaaatagt gagaacatgg gatgattcac cctggaggca ggaagacaga     4380
gaagcaaaca caattgttat caggaatgca tgaatgatac tttacttcac tgaatctaag     4440
acatggtgaa atgtaagatg caccccatatt ttatgtactg agaaaaaata ctaacaatca     4500
aattctggaa tgccaatgat tataaatatga atcctgattt caccaatatg aaactgtgaa     4560
aaaatgttaa tgttacaata aagaaatgg gtttttataca aaaaaaaaa aaaaaaaaa     4620
```

<210> SEQ ID NO 12
<211> LENGTH: 465
<212> TYPE: PRT
<213> ORGANISM: Homo sapiens

<400> SEQUENCE: 12

```
Met Pro Tyr Phe Thr Arg Leu Ile Leu Phe Leu Phe Cys Leu Met Val
1               5                   10                  15

Leu Val Glu Ser Arg Lys Pro Lys Arg Lys Arg Trp Thr Gly Gln Val
            20                  25                  30

Glu Met Pro Lys Pro Ser His Leu Tyr Lys Lys Asn Leu Asp Val Thr
        35                  40                  45

Lys Ile Arg Lys Gly Lys Pro Gln Gln Leu Leu Arg Val Asp Glu His
    50                  55                  60
```

```
Asp Phe Ser Met Arg Pro Ala Phe Gly Gly Pro Ala Ile Pro Val Gly
 65                  70                  75                  80

Val Asp Val Gln Val Glu Ser Leu Asp Ser Ile Ser Glu Val Asp Met
             85                  90                  95

Asp Phe Thr Met Thr Leu Tyr Leu Arg His Tyr Trp Lys Asp Glu Arg
            100                 105                 110

Leu Ala Phe Ser Ser Ala Ser Asn Lys Ser Met Thr Phe Asp Gly Arg
            115                 120                 125

Leu Val Lys Lys Ile Trp Val Pro Asp Val Phe Phe Val His Ser Lys
            130                 135                 140

Arg Ser Phe Thr His Asp Thr Thr Thr Asp Asn Ile Met Leu Arg Val
145                 150                 155                 160

Phe Pro Asp Gly His Val Leu Tyr Ser Met Arg Ile Thr Val Thr Ala
                165                 170                 175

Met Cys Asn Met Asp Phe Ser His Phe Pro Leu Asp Ser Gln Thr Cys
                180                 185                 190

Ser Leu Glu Leu Glu Ser Tyr Ala Tyr Thr Asp Glu Asp Leu Met Leu
                195                 200                 205

Tyr Trp Lys Asn Gly Asp Glu Ser Leu Lys Thr Asp Glu Lys Ile Ser
            210                 215                 220

Leu Ser Gln Phe Leu Ile Gln Lys Phe His Thr Thr Ser Arg Leu Ala
225                 230                 235                 240

Phe Tyr Ser Ser Thr Gly Trp Tyr Asn Arg Leu Tyr Ile Asn Phe Thr
                245                 250                 255

Leu Arg Arg His Ile Phe Phe Phe Leu Leu Gln Thr Tyr Phe Pro Ala
                260                 265                 270

Thr Leu Met Val Met Leu Ser Trp Val Ser Phe Trp Ile Asp Arg Arg
            275                 280                 285

Ala Val Pro Ala Arg Val Ser Leu Gly Ile Thr Thr Val Leu Thr Met
            290                 295                 300

Thr Thr Ile Ile Thr Gly Val Asn Ala Ser Met Pro Arg Val Ser Tyr
305                 310                 315                 320

Val Lys Ala Val Asp Ile Tyr Leu Trp Val Ser Phe Val Phe Val Phe
                325                 330                 335

Leu Ser Val Leu Glu Tyr Ala Ala Val Asn Tyr Leu Thr Thr Val Gln
                340                 345                 350

Glu Arg Lys Glu Arg Lys Leu Arg Glu Lys Phe Pro Cys Met Cys Gly
            355                 360                 365

Met Leu His Ser Lys Thr Met Met Leu Asp Gly Ser Tyr Ser Glu Ser
            370                 375                 380

Glu Ala Asn Ser Leu Ala Gly Tyr Pro Arg Ser His Ile Leu Thr Glu
385                 390                 395                 400

Glu Glu Arg Gln Asp Lys Ile Val Val His Leu Gly Leu Ser Gly Glu
                405                 410                 415

Ala Asn Ala Ala Arg Lys Lys Gly Leu Leu Lys Gly Gln Thr Gly Phe
                420                 425                 430

Arg Ile Phe Gln Asn Thr His Ala Ile Asp Lys Tyr Ser Arg Leu Ile
            435                 440                 445

Phe Pro Ala Ser Tyr Ile Phe Phe Asn Leu Ile Tyr Trp Ser Val Phe
            450                 455                 460

Ser
465
```

<210> SEQ ID NO 13
<211> LENGTH: 1404
<212> TYPE: DNA
<213> ORGANISM: Homo sapiens

<400> SEQUENCE: 13

| | | | | | |
|---|---|---|---|---|---|
| atggtcctgg | ctttccagtt | agtctccttc | acctacatct | ggatcatatt | gaaaccaaat | 60 |
| gtttgtgctg | cttctaacat | caagatgaca | caccagcggt | gctcctcttc | aatgaaacaa | 120 |
| acctgcaaac | aagaaactag | aatgaagaaa | gatgacagta | ccaaagcgcg | gcctcagaaa | 180 |
| tatgagcaac | ttctccatat | agaggacaac | gatttcgcaa | tgagacctgg | atttggaggg | 240 |
| tctccagtgc | cagtaggtat | agatgtccat | gttgaaagca | ttgacagcat | ttcagagact | 300 |
| aacatggact | ttacaatgac | tttttatctc | aggcattact | ggaaagacga | gaggctctcc | 360 |
| tttcctagca | cagcaaacaa | aagcatgaca | tttgatcata | gattgaccag | aaagatctgg | 420 |
| gtgcctgata | tctttttttgt | ccactctaaa | agatccttca | tccatgatac | aactatggag | 480 |
| aatatcatgc | tgcgcgtaca | ccctgatgga | aacgtcctcc | taagtctcag | gataacggtt | 540 |
| tcggccatgt | gctttatgga | tttcagcagg | tttcctcttg | acactcaaaa | ttgttctctt | 600 |
| gaactggaaa | gctatgccta | caatgaggat | gacctaatgc | tatactggaa | acacggaaac | 660 |
| aagtccttaa | atactgaaga | acatatgtcc | ctttctcagt | tcttcattga | agacttcagt | 720 |
| gcatctagtg | gattagcttt | ctatagcagc | acaggttggt | acaataggct | tttcatcaac | 780 |
| tttgtgctaa | ggaggcatgt | tttcttcttt | gtgctgcaaa | cctatttccc | agccatattg | 840 |
| atggtgatgc | tttcatgggt | ttcattttgg | attgaccgaa | gagctgttcc | tgcaagagtt | 900 |
| tccctgggaa | tcaccacagt | gctgaccatg | tccacaatca | tcactgctgt | gagcgcctcc | 960 |
| atgccccagg | tgtcctacct | caaggctgtg | gatgtgtacc | tgtgggtcag | ctccctcttt | 1020 |
| gtgttcctgt | cagtcattga | gtatgcagct | gtgaactacc | tcaccacagt | ggaagagcgg | 1080 |
| aaacaattca | gaagacagg | aaagatttct | aggatgtaca | atattgatgc | agttcaagct | 1140 |
| atggccttg | atggttgtta | ccatgacagc | gagattgaca | tggaccagac | ttccctctct | 1200 |
| ctaaactcag | aagacttcat | gagaagaaaa | tcgatatgca | gccccagcac | cgattcatct | 1260 |
| cggataaaga | gaagaaaatc | cctaggagga | catgttggta | gaatcattct | ggaaaacaac | 1320 |
| catgtcattg | acacctattc | taggatttta | ttccccattg | tgtatatttt | atttaatttg | 1380 |
| ttttactggg | gtgtatatgt | atga | | | | 1404 |

<210> SEQ ID NO 14
<211> LENGTH: 467
<212> TYPE: PRT
<213> ORGANISM: Homo sapiens

<400> SEQUENCE: 14

Met Val Leu Ala Phe Gln Leu Val Ser Phe Thr Tyr Ile Trp Ile Ile
1               5                   10                  15

Leu Lys Pro Asn Val Cys Ala Ala Ser Asn Ile Lys Met Thr His Gln
            20                  25                  30

Arg Cys Ser Ser Met Lys Gln Thr Cys Lys Gln Glu Thr Arg Met
        35                  40                  45

Lys Lys Asp Asp Ser Thr Lys Ala Arg Pro Gln Lys Tyr Glu Gln Leu
    50                  55                  60

Leu His Ile Glu Asp Asn Asp Phe Ala Met Arg Pro Gly Phe Gly Gly
65                  70                  75                  80

```
Ser Pro Val Pro Val Gly Ile Asp Val His Val Glu Ser Ile Asp Ser
                85                  90                  95

Ile Ser Glu Thr Asn Met Asp Phe Thr Met Thr Phe Tyr Leu Arg His
            100                 105                 110

Tyr Trp Lys Asp Glu Arg Leu Ser Phe Pro Ser Thr Ala Asn Lys Ser
        115                 120                 125

Met Thr Phe Asp His Arg Leu Thr Arg Lys Ile Trp Val Pro Asp Ile
    130                 135                 140

Phe Phe Val His Ser Lys Arg Ser Phe Ile His Asp Thr Thr Met Glu
145                 150                 155                 160

Asn Ile Met Leu Arg Val His Pro Asp Gly Asn Val Leu Leu Ser Leu
                165                 170                 175

Arg Ile Thr Val Ser Ala Met Cys Phe Met Asp Phe Ser Arg Phe Pro
            180                 185                 190

Leu Asp Thr Gln Asn Cys Ser Leu Glu Leu Glu Ser Tyr Ala Tyr Asn
        195                 200                 205

Glu Asp Asp Leu Met Leu Tyr Trp Lys His Gly Asn Lys Ser Leu Asn
    210                 215                 220

Thr Glu Glu His Met Ser Leu Ser Gln Phe Phe Ile Glu Asp Phe Ser
225                 230                 235                 240

Ala Ser Ser Gly Leu Ala Phe Tyr Ser Ser Thr Gly Trp Tyr Asn Arg
                245                 250                 255

Leu Phe Ile Asn Phe Val Leu Arg Arg His Val Phe Phe Phe Val Leu
            260                 265                 270

Gln Thr Tyr Phe Pro Ala Ile Leu Met Val Met Leu Ser Trp Val Ser
        275                 280                 285

Phe Trp Ile Asp Arg Arg Ala Val Pro Ala Arg Val Ser Leu Gly Ile
    290                 295                 300

Thr Thr Val Leu Thr Met Ser Thr Ile Ile Thr Ala Val Ser Ala Ser
305                 310                 315                 320

Met Pro Gln Val Ser Tyr Leu Lys Ala Val Asp Val Tyr Leu Trp Val
                325                 330                 335

Ser Ser Leu Phe Val Phe Leu Ser Val Ile Glu Tyr Ala Ala Val Asn
            340                 345                 350

Tyr Leu Thr Thr Val Glu Glu Arg Lys Gln Phe Lys Lys Thr Gly Lys
        355                 360                 365

Ile Ser Arg Met Tyr Asn Ile Asp Ala Val Gln Ala Met Ala Phe Asp
    370                 375                 380

Gly Cys Tyr His Asp Ser Glu Ile Asp Met Asp Gln Thr Ser Leu Ser
385                 390                 395                 400

Leu Asn Ser Glu Asp Phe Met Arg Arg Lys Ser Ile Cys Ser Pro Ser
                405                 410                 415

Thr Asp Ser Ser Arg Ile Lys Arg Arg Lys Ser Leu Gly Gly His Val
            420                 425                 430

Gly Arg Ile Ile Leu Glu Asn Asn His Val Ile Asp Thr Tyr Ser Arg
        435                 440                 445

Ile Leu Phe Pro Ile Val Tyr Ile Leu Phe Asn Leu Phe Tyr Trp Gly
    450                 455                 460

Val Tyr Val
465

<210> SEQ ID NO 15
<211> LENGTH: 1320
<212> TYPE: DNA
```

<213> ORGANISM: Artificial Sequence
<220> FEATURE:
<223> OTHER INFORMATION: synthetic sequence of chimeric LGIC

<400> SEQUENCE: 15

```
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga agaaccaa gttttaacca ccaacatttg gctgcaaatg       240
tcttggacag atcactattt acagtggaat gtgtcagaat atccaggggt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc tacatcgatg tacgctggtt ccctttgat     480
gtgcagcact gcaaactgaa gtttgggtcc tggtcttacg gaggctggtc cttggatctg     540
cagatgcagg aggcagatat cagtggctat atccccaatg agaatggga cctagtggga     600
atccccggca agaggagtga aaggttctat gagtgctgca agagcccta ccccgatgtc      660
accttcacag tgaccatgcg ccgcaggatg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga ccacccagag ctccggctct     840
cgagcatctc tgcccaaggt gtcctatgtg aaagccattg acatttggat ggcagtttgc     900
ctgctctttg tgttctcagc cctattagaa tatgctgccg ttaactttgt gtctcggcaa     960
cataaggagc tgctccgatt caggaggaag cggagacatc acaagagccc catgttgaat    1020
ctattccagg aggatgaagc tggagaaggc cgctttaact tctctgccta tgggatgggc    1080
ccagcctgtc tacaggccaa ggatggcatc tcagtcaagg gcgccaacaa cagtaacacc    1140
accaaccccc ctcctgcacc atctaagtcc ccagaggaga tgcgaaaact cttcatccag    1200
agggccaaga gatcgacaa atatcccgc attggcttcc ccatggcctt cctcattttc    1260
aacatgttct actggatcat ctacaagatt gtccgtagag aggacgtcca accagtga     1320
```

<210> SEQ ID NO 16
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 16

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
```

```
                100             105             110
Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Ser
                325                 330                 335

Pro Met Leu Asn Leu Phe Gln Glu Asp Glu Ala Gly Glu Gly Arg Phe
            340                 345                 350

Asn Phe Ser Ala Tyr Gly Met Gly Pro Ala Cys Leu Gln Ala Lys Asp
        355                 360                 365

Gly Ile Ser Val Lys Gly Ala Asn Asn Ser Asn Thr Thr Asn Pro Pro
370                 375                 380

Pro Ala Pro Ser Lys Ser Pro Glu Glu Met Arg Lys Leu Phe Ile Gln
385                 390                 395                 400

Arg Ala Lys Lys Ile Asp Lys Ile Ser Arg Ile Gly Phe Pro Met Ala
                405                 410                 415

Phe Leu Ile Phe Asn Met Phe Tyr Trp Ile Ile Tyr Lys Ile Val Arg
            420                 425                 430

Arg Glu Asp Val His Asn Gln
            435

<210> SEQ ID NO 17
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 17

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
```

```
                    20                  25                  30
Leu Val Lys Asn Tyr Asn Pro Leu Glu Arg Pro Val Ala Asn Asp Ser
                35                  40                  45
Gln Pro Leu Thr Val Tyr Phe Ser Leu Ser Leu Gln Ile Met Asp
            50                  55                  60
Val Asp Glu Lys Asn Gln Val Leu Thr Thr Asn Ile Trp Leu Gln Met
65                  70                  75                  80
Ser Trp Thr Asp His Tyr Leu Gln Trp Asn Val Ser Glu Tyr Pro Gly
                85                  90                  95
Val Lys Thr Val Arg Phe Pro Asp Gly Gln Ile Trp Lys Pro Asp Ile
                100                 105                 110
Leu Leu Tyr Asn Ser Ala Asp Glu Arg Phe Asp Ala Thr Phe His Thr
                115                 120                 125
Asn Val Leu Val Asn Ser Ser Gly His Cys Gln Tyr Leu Pro Pro Gly
                130                 135                 140
Ile Phe Lys Ser Ser Cys Tyr Ile Asp Val Arg Trp Phe Pro Phe Asp
145                 150                 155                 160
Val Gln His Cys Lys Leu Lys Phe Gly Ser Trp Ser Tyr Gly Gly Trp
                165                 170                 175
Ser Leu Asp Leu Gln Met Gln Glu Ala Asp Ile Ser Gly Tyr Ile Pro
                180                 185                 190
Asn Gly Glu Trp Asp Leu Val Gly Ile Pro Gly Lys Arg Ser Glu Arg
                195                 200                 205
Phe Tyr Glu Cys Cys Lys Glu Pro Tyr Pro Asp Val Thr Phe Thr Val
                210                 215                 220
Thr Met Arg Arg Gln Met Gly Tyr Tyr Leu Ile Gln Met Tyr Ile Pro
225                 230                 235                 240
Ser Leu Leu Ile Val Ile Leu Ser Trp Ile Ser Phe Trp Ile Asn Met
                245                 250                 255
Asp Ala Ala Pro Ala Arg Val Gly Leu Gly Ile Thr Thr Val Leu Thr
                260                 265                 270
Met Thr Thr Gln Ser Ser Gly Ser Arg Ala Ser Leu Pro Lys Val Ser
                275                 280                 285
Tyr Val Lys Ala Ile Asp Ile Trp Met Ala Val Cys Leu Leu Phe Val
                290                 295                 300
Phe Ser Ala Leu Leu Glu Tyr Ala Ala Val Asn Phe Val Ser Arg Gln
305                 310                 315                 320
His Lys Glu Leu Leu Arg Phe Arg Arg Lys Arg Arg His His Lys Ser
                325                 330                 335
Pro Met Leu Asn Leu Phe Gln Glu Asp Glu Ala Gly Glu Gly Arg Phe
                340                 345                 350
Asn Phe Ser Ala Tyr Gly Met Gly Pro Ala Cys Leu Gln Ala Lys Asp
                355                 360                 365
Gly Ile Ser Val Lys Gly Ala Asn Asn Ser Asn Thr Thr Asn Pro Pro
                370                 375                 380
Pro Ala Pro Ser Lys Ser Pro Glu Glu Met Arg Lys Leu Phe Ile Gln
385                 390                 395                 400
Arg Ala Lys Lys Ile Asp Lys Ile Ser Arg Ile Gly Phe Pro Met Ala
                405                 410                 415
Phe Leu Ile Phe Asn Met Phe Tyr Trp Ile Ile Tyr Lys Ile Val Arg
                420                 425                 430
Arg Glu Asp Val His Asn Gln
                435
```

```
<210> SEQ ID NO 18
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 18

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

His Leu Glu Arg Gln Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
    290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Ser
                325                 330                 335

Pro Met Leu Asn Leu Phe Gln Glu Asp Glu Ala Gly Glu Gly Arg Phe
            340                 345                 350

Asn Phe Ser Ala Tyr Gly Met Gly Pro Ala Cys Leu Gln Ala Lys Asp
        355                 360                 365
```

-continued

```
Gly Ile Ser Val Lys Gly Ala Asn Asn Ser Asn Thr Thr Asn Pro Pro
        370                 375                 380

Pro Ala Pro Ser Lys Ser Pro Glu Glu Met Arg Lys Leu Phe Ile Gln
385                 390                 395                 400

Arg Ala Lys Lys Ile Asp Lys Ile Ser Arg Ile Gly Phe Pro Met Ala
                405                 410                 415

Phe Leu Ile Phe Asn Met Phe Tyr Trp Ile Ile Tyr Lys Ile Val Arg
            420                 425                 430

Arg Glu Asp Val His Asn Gln
            435

<210> SEQ ID NO 19
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 19

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Leu Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285
```

```
Tyr Val Lys Ala Ile Asp Ile Trp Met Ala Val Cys Leu Leu Phe Val
            290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Ser
                325                 330                 335

Pro Met Leu Asn Leu Phe Gln Glu Asp Glu Ala Gly Glu Gly Arg Phe
                340                 345                 350

Asn Phe Ser Ala Tyr Gly Met Gly Pro Ala Cys Leu Gln Ala Lys Asp
            355                 360                 365

Gly Ile Ser Val Lys Gly Ala Asn Asn Ser Asn Thr Thr Asn Pro Pro
        370                 375                 380

Pro Ala Pro Ser Lys Ser Pro Glu Glu Met Arg Lys Leu Phe Ile Gln
385                 390                 395                 400

Arg Ala Lys Lys Ile Asp Lys Ile Ser Arg Ile Gly Phe Pro Met Ala
                405                 410                 415

Phe Leu Ile Phe Asn Met Phe Tyr Trp Ile Ile Tyr Lys Ile Val Arg
                420                 425                 430

Arg Glu Asp Val His Asn Gln
            435

<210> SEQ ID NO 20
<211> LENGTH: 1329
<212> TYPE: DNA
<213> ORGANISM: Artificial Sequence
<220> FEATURE:
<223> OTHER INFORMATION: synthetic sequence of chimeric LGIC

<400> SEQUENCE: 20
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga gaagaaccaa gttttaacca ccaacatttg gctgcaaatg     240
tcttggacag atcactattt acagtggaat gtgtcagaat atccaggggt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc tacatcgatg tacgctggtt tcccttgat      480 gtgcagcact gcaaactgaa gtttgggtcc tggtcttacg aggctggtc cttggatctg     540 cagatgcagg aggcagatat cagtggctat atccccaatg agaatggga cctagtggga     600 atccccggca agaggagtga aaggttctat gagtgctgca agagcccta ccccgatgtc     660 accttcacag tgaccatgcg ccgcaggatg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga cacccagag ctccggctct     840 gagatcatgc cgcaacatc cgattcggta tcctatgtga aagccattga catttggatg     900
gcagtttgcc tgctctttgt gttctcagcc ctattagaat atgctgccgt aactttgtg      960 tctcggcaac ataaggagct gctccgattc aggaggaagc ggagacatca agagcccc     1020 atgttgaatc tattccagga ggatgaagct ggagaaggcc gctttaactt ctctgcctat    1080
gggatgggcc cagcctgtct acaggccaag gatggcatct cagtcaaggg cgccaacaac    1140
```

-continued

```
agtaacacca ccaacccccc tcctgcacca tctaagtccc cagaggagat gcgaaaactc    1200
ttcatccaga gggccaagaa gatcgacaaa atatcccgca ttggcttccc catggccttc    1260
ctcattttca acatgttcta ctggatcatc tacaagattg tccgtagaga ggacgtccac    1320
aaccagtga                                                            1329
```

<210> SEQ ID NO 21
<211> LENGTH: 442
<212> TYPE: PRT
<213> ORGANISM: Artificial Sequence
<220> FEATURE:
<223> OTHER INFORMATION: synthetic sequence of chimeric LGIC

<400> SEQUENCE: 21

| | | | | | | | | | | | | | | | |
|---|---|---|---|---|---|---|---|---|---|---|---|---|---|---|---|
| Met | Arg | Cys | Ser | Pro | Gly | Gly | Val | Trp | Leu | Ala | Leu | Ala | Ala | Ser | Leu |
| 1 | | | | 5 | | | | | 10 | | | | | 15 | |
| Leu | His | Val | Ser | Leu | Gln | Gly | Glu | Phe | Gln | Arg | Lys | Leu | Tyr | Lys | Glu |
| | | | 20 | | | | | 25 | | | | | 30 | | |
| Leu | Val | Lys | Asn | Tyr | Asn | Pro | Leu | Glu | Arg | Pro | Val | Ala | Asn | Asp | Ser |
| | | | 35 | | | | 40 | | | | | 45 | | | |
| Gln | Pro | Leu | Thr | Val | Tyr | Phe | Ser | Leu | Ser | Leu | Leu | Gln | Ile | Met | Asp |
| | 50 | | | | | 55 | | | | | 60 | | | | |
| Val | Asp | Glu | Lys | Asn | Gln | Val | Leu | Thr | Thr | Asn | Ile | Trp | Leu | Gln | Met |
| 65 | | | | | 70 | | | | | 75 | | | | | 80 |
| Ser | Trp | Thr | Asp | His | Tyr | Leu | Gln | Trp | Asn | Val | Ser | Glu | Tyr | Pro | Gly |
| | | | | 85 | | | | | 90 | | | | | 95 | |
| Val | Lys | Thr | Val | Arg | Phe | Pro | Asp | Gly | Gln | Ile | Trp | Lys | Pro | Asp | Ile |
| | | | 100 | | | | | 105 | | | | | 110 | | |
| Leu | Leu | Tyr | Asn | Ser | Ala | Asp | Glu | Arg | Phe | Asp | Ala | Thr | Phe | His | Thr |
| | | | 115 | | | | 120 | | | | | 125 | | | |
| Asn | Val | Leu | Val | Asn | Ser | Ser | Gly | His | Cys | Gln | Tyr | Leu | Pro | Pro | Gly |
| | 130 | | | | | 135 | | | | | 140 | | | | |
| Ile | Phe | Lys | Ser | Ser | Cys | Tyr | Ile | Asp | Val | Arg | Trp | Phe | Pro | Phe | Asp |
| 145 | | | | | 150 | | | | | 155 | | | | | 160 |
| Val | Gln | His | Cys | Lys | Leu | Lys | Phe | Gly | Ser | Trp | Ser | Tyr | Gly | Gly | Trp |
| | | | | 165 | | | | | 170 | | | | | 175 | |
| Ser | Leu | Asp | Leu | Gln | Met | Gln | Glu | Ala | Asp | Ile | Ser | Gly | Tyr | Ile | Pro |
| | | | 180 | | | | | 185 | | | | | 190 | | |
| Asn | Gly | Glu | Trp | Asp | Leu | Val | Gly | Ile | Pro | Gly | Lys | Arg | Ser | Glu | Arg |
| | | | 195 | | | | 200 | | | | | 205 | | | |
| Phe | Tyr | Glu | Cys | Cys | Lys | Glu | Pro | Tyr | Pro | Asp | Val | Thr | Phe | Thr | Val |
| | 210 | | | | | 215 | | | | | 220 | | | | |
| Thr | Met | Arg | Arg | Arg | Met | Gly | Tyr | Tyr | Leu | Ile | Gln | Met | Tyr | Ile | Pro |
| 225 | | | | | 230 | | | | | 235 | | | | | 240 |
| Ser | Leu | Leu | Ile | Val | Ile | Leu | Ser | Trp | Ile | Ser | Phe | Trp | Ile | Asn | Met |
| | | | | 245 | | | | | 250 | | | | | 255 | |
| Asp | Ala | Ala | Pro | Ala | Arg | Val | Gly | Leu | Gly | Ile | Thr | Thr | Val | Leu | Thr |
| | | | 260 | | | | | 265 | | | | | 270 | | |
| Met | Thr | Thr | Gln | Ser | Ser | Gly | Ser | Glu | Ile | Met | Pro | Ala | Thr | Ser | Asp |
| | | | 275 | | | | 280 | | | | | 285 | | | |
| Ser | Val | Ser | Tyr | Val | Lys | Ala | Ile | Asp | Ile | Trp | Met | Ala | Val | Cys | Leu |
| | 290 | | | | | 295 | | | | | 300 | | | | |
| Leu | Phe | Val | Phe | Ser | Ala | Leu | Leu | Glu | Tyr | Ala | Ala | Val | Asn | Phe | Val |
| 305 | | | | | 310 | | | | | 315 | | | | | 320 |
| Ser | Arg | Gln | His | Lys | Glu | Leu | Leu | Arg | Phe | Arg | Arg | Lys | Arg | Arg | His |

|   |   |   | 325 |   |   |   | 330 |   |   |   | 335 |   |   |
|---|---|---|---|---|---|---|---|---|---|---|---|---|---|
| His | Lys | Ser | Pro | Met | Leu | Asn | Leu | Phe | Gln | Glu | Asp | Glu | Ala | Gly | Glu |
|   |   |   | 340 |   |   |   | 345 |   |   |   | 350 |   |   |

Gly Arg Phe Asn Phe Ser Ala Tyr Gly Met Gly Pro Ala Cys Leu Gln
            355                 360                 365

Ala Lys Asp Gly Ile Ser Val Lys Gly Ala Asn Asn Ser Asn Thr Thr
        370                 375                 380

Asn Pro Pro Ala Pro Ser Lys Ser Pro Glu Glu Met Arg Lys Leu
385                 390                 395                 400

Phe Ile Gln Arg Ala Lys Lys Ile Asp Lys Ile Ser Arg Ile Gly Phe
                405                 410                 415

Pro Met Ala Phe Leu Ile Phe Asn Met Phe Tyr Trp Ile Ile Tyr Lys
            420                 425                 430

Ile Val Arg Arg Glu Asp Val His Asn Gln
        435                 440

```
<210> SEQ ID NO 22
<211> LENGTH: 1332
<212> TYPE: DNA
<213> ORGANISM: Artificial Sequence
<220> FEATURE:
<223> OTHER INFORMATION: synthetic sequence of chimeric LGIC

<400> SEQUENCE: 22
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga aagaaccaa gttttaacca ccaacatttg gctgcaaatg     240
tcttggacag atcactattt acagtggaat gtgtcagaat atccaggggt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc tacatcgatg tacgctggtt tcccttgat     480 gtgcagcact gcaaactgaa gtttgggtcc tggtcttacg gaggctggtc cttggatctg     540
cagatgcagg aggcagatat cagtggctat atccccaatg agaatgggga cctagtggga     600
atccccggca agaggagtga aaggttctat gagtgctgca aagagcccta ccccgatgtc     660
accttcacag tgaccatgcg ccgcaggatg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga ccacccagag ctccggctct     840
gagatcatgc ccgcaacatc cgattcggta ccattgatag cccaggccat tgacatttgg     900
atggcagttt gcctgctctt tgtgttctca gccctattag aatatgctgc cgttaacttt     960
gtgtctcggc aacataagga gctgctccga ttcaggagga gcggagaca tcacaagagc    1020 cccatgttga atctattcca ggaggatgaa gctggagaag gccgctttaa cttctctgcc    1080
tatgggatgg gccagcctg tctacaggcc aaggatggca tctcagtcaa gggcgccaac    1140
aacagtaaca ccaccaaccc ccctcctgca ccatctaagt cccagagga gatgcgaaaa    1200 ctcttcatcc agagggccaa gaagatcgac aaaatatccc gcattggctt ccccatggcc    1260
ttcctcattt tcaacatgtt ctactggatc atctacaaga ttgtccgtag agaggacgtc    1320
cacaaccagt ga                                                        1332
```

```
<210> SEQ ID NO 23
<211> LENGTH: 443
<212> TYPE: PRT
<213> ORGANISM: Artificial Sequence
<220> FEATURE:
<223> OTHER INFORMATION: synthetic sequence of chimeric LGIC

<400> SEQUENCE: 23
```

| | | | | | | | | | | | | | | |
|---|---|---|---|---|---|---|---|---|---|---|---|---|---|---|
| Met | Arg | Cys | Ser | Pro | Gly | Gly | Val | Trp | Leu | Ala | Leu | Ala | Ala | Ser | Leu |
| 1 | | | | 5 | | | | | 10 | | | | | 15 | |
| Leu | His | Val | Ser | Leu | Gln | Gly | Glu | Phe | Gln | Arg | Lys | Leu | Tyr | Lys | Glu |
| | | | 20 | | | | | 25 | | | | | 30 | | |
| Leu | Val | Lys | Asn | Tyr | Asn | Pro | Leu | Glu | Arg | Pro | Val | Ala | Asn | Asp | Ser |
| | | 35 | | | | | 40 | | | | | 45 | | | |
| Gln | Pro | Leu | Thr | Val | Tyr | Phe | Ser | Leu | Ser | Leu | Leu | Gln | Ile | Met | Asp |
| 50 | | | | | 55 | | | | | 60 | | | | | |
| Val | Asp | Glu | Lys | Asn | Gln | Val | Leu | Thr | Thr | Asn | Ile | Trp | Leu | Gln | Met |
| 65 | | | | 70 | | | | | 75 | | | | | 80 | |
| Ser | Trp | Thr | Asp | His | Tyr | Leu | Gln | Trp | Asn | Val | Ser | Glu | Tyr | Pro | Gly |
| | | | | 85 | | | | | 90 | | | | | 95 | |
| Val | Lys | Thr | Val | Arg | Phe | Pro | Asp | Gly | Gln | Ile | Trp | Lys | Pro | Asp | Ile |
| | | | 100 | | | | | 105 | | | | | 110 | | |
| Leu | Leu | Tyr | Asn | Ser | Ala | Asp | Glu | Arg | Phe | Asp | Ala | Thr | Phe | His | Thr |
| | | 115 | | | | | 120 | | | | | 125 | | | |
| Asn | Val | Leu | Val | Asn | Ser | Ser | Gly | His | Cys | Gln | Tyr | Leu | Pro | Pro | Gly |
| 130 | | | | | 135 | | | | | 140 | | | | | |
| Ile | Phe | Lys | Ser | Ser | Cys | Tyr | Ile | Asp | Val | Arg | Trp | Phe | Pro | Phe | Asp |
| 145 | | | | | 150 | | | | | 155 | | | | | 160 |
| Val | Gln | His | Cys | Lys | Leu | Lys | Phe | Gly | Ser | Trp | Ser | Tyr | Gly | Gly | Trp |
| | | | | 165 | | | | | 170 | | | | | 175 | |
| Ser | Leu | Asp | Leu | Gln | Met | Gln | Glu | Ala | Asp | Ile | Ser | Gly | Tyr | Ile | Pro |
| | | | 180 | | | | | 185 | | | | | 190 | | |
| Asn | Gly | Glu | Trp | Asp | Leu | Val | Gly | Ile | Pro | Gly | Lys | Arg | Ser | Glu | Arg |
| | | 195 | | | | | 200 | | | | | 205 | | | |
| Phe | Tyr | Glu | Cys | Cys | Lys | Glu | Pro | Tyr | Pro | Asp | Val | Thr | Phe | Thr | Val |
| 210 | | | | | 215 | | | | | 220 | | | | | |
| Thr | Met | Arg | Arg | Arg | Met | Gly | Tyr | Tyr | Leu | Ile | Gln | Met | Tyr | Ile | Pro |
| 225 | | | | | 230 | | | | | 235 | | | | | 240 |
| Ser | Leu | Leu | Ile | Val | Ile | Leu | Ser | Trp | Ile | Ser | Phe | Trp | Ile | Asn | Met |
| | | | | 245 | | | | | 250 | | | | | 255 | |
| Asp | Ala | Ala | Pro | Ala | Arg | Val | Gly | Leu | Gly | Ile | Thr | Thr | Val | Leu | Thr |
| | | | 260 | | | | | 265 | | | | | 270 | | |
| Met | Thr | Thr | Gln | Ser | Ser | Gly | Ser | Glu | Ile | Met | Pro | Ala | Thr | Ser | Asp |
| | | 275 | | | | | 280 | | | | | 285 | | | |
| Ser | Val | Pro | Leu | Ile | Ala | Gln | Ala | Ile | Asp | Ile | Trp | Met | Ala | Val | Cys |
| | 290 | | | | | 295 | | | | | 300 | | | | |
| Leu | Leu | Phe | Val | Phe | Ser | Ala | Leu | Leu | Glu | Tyr | Ala | Ala | Val | Asn | Phe |
| 305 | | | | | 310 | | | | | 315 | | | | | 320 |
| Val | Ser | Arg | Gln | His | Lys | Glu | Leu | Leu | Arg | Phe | Arg | Arg | Lys | Arg | Arg |
| | | | | 325 | | | | | 330 | | | | | 335 | |
| His | His | Lys | Ser | Pro | Met | Leu | Asn | Leu | Phe | Gln | Glu | Asp | Glu | Ala | Gly |
| | | | 340 | | | | | 345 | | | | | 350 | | |
| Glu | Gly | Arg | Phe | Asn | Phe | Ser | Ala | Tyr | Gly | Met | Gly | Pro | Ala | Cys | Leu |
| | | 355 | | | | | 360 | | | | | 365 | | | |

```
Gln Ala Lys Asp Gly Ile Ser Val Lys Gly Ala Asn Asn Ser Asn Thr
    370                 375                 380

Thr Asn Pro Pro Ala Pro Ser Lys Ser Pro Glu Glu Met Arg Lys
385                 390                 395                 400

Leu Phe Ile Gln Arg Ala Lys Lys Ile Asp Lys Ile Ser Arg Ile Gly
                405                 410                 415

Phe Pro Met Ala Phe Leu Ile Phe Asn Met Phe Tyr Trp Ile Ile Tyr
                420                 425                 430

Lys Ile Val Arg Arg Glu Asp Val His Asn Gln
                435                 440

<210> SEQ ID NO 24
<211> LENGTH: 1323
<212> TYPE: DNA
<213> ORGANISM: Artificial Sequence
<220> FEATURE:
<223> OTHER INFORMATION: synthetic sequence of chimeric LGIC

<400> SEQUENCE: 24
```

| | | | | | |
|---|---|---|---|---|---|
| atgcgctgct | cgccgggagg | cgtctggctg | gcgctggccg | cgtcgctcct | gcacgtgtcc | 60
| ctgcaaggcg | agttccagag | gaagctttac | aaggagctgg | tcaagaacta | caatcccttg | 120
| gagaggcccg | tggccaatga | ctcgcaacca | ctcaccgtct | acttctccct | gagcctcctg | 180
| cagatcatgg | acgtggatga | gaagaaccaa | gttttaacca | ccaacatttg | gctgcaaatg | 240
| tcttggacag | atcactattt | acagtggaat | gtgtcagaat | atccaggggt | gaagactgtt | 300
| cgtttcccag | atggccagat | ttggaaacca | gacattcttc | tctataacag | tgctgatgag | 360
| cgctttgacg | ccacattcca | cactaacgtg | ttggtgaact | cttctgggca | ttgccagtac | 420
| ctgcctccag | gcatattcaa | gagttcctgc | tacatcgatg | tacgctggtt | tcccttttgat | 480
| gtgcagcact | gcaaactgaa | gtttgggtcc | tggtcttacg | gaggctggtc | cttggatctg | 540
| cagatgcagg | aggcagatat | cagtggctat | atccccaatg | agaatgggaa | cctagtggga | 600
| atccccggca | agaggagtga | aaggttctat | gagtgctgca | aagagcccta | ccccgatgtc | 660
| accttcacag | tgaccatgcg | ccgcaggatg | ggttactacc | tgattcagat | gtatattccc | 720
| agcctgctca | ttgtcatcct | ctcatggatc | tccttctgga | tcaacatgga | tgctgcacct | 780
| gctcgtgtgg | gcctaggcat | caccactgtg | ctcaccatga | ccacccagag | ctccggctct | 840
| cgagcatctc | tgcccaaggt | gtccgattcg | gtaccattga | ttgacatttg | gatggcagtt | 900
| tgcctgctct | ttgtgttctc | agccctatta | gaatatgctg | ccgttaactt | tgtgtctcgg | 960
| caacataagg | agctgctccg | attcaggagg | aagcggagac | atcacaagag | ccccatgttg | 1020
| aatctattcc | aggaggatga | agctggagaa | ggccgcttta | acttctctgc | ctatggatgg | 1080
| ggcccagcct | gtctacaggc | caaggatggc | atctcagtca | agggcgccaa | caacagtaac | 1140
| accaccaacc | cccctcctgc | accatctaag | tccccagagg | agatgcgaaa | actcttcatc | 1200
| cagagggcca | agaagatcga | caaaatatcc | cgcattggct | tccccatggc | cttcctcatt | 1260
| ttcaacatgt | tctactggat | catctacaag | attgtccgta | gagaggacgt | ccacaaccag | 1320
| tga | | | | | | 1323

```
<210> SEQ ID NO 25
<211> LENGTH: 440
<212> TYPE: PRT
<213> ORGANISM: Artificial Sequence
<220> FEATURE:
<223> OTHER INFORMATION: synthetic sequence of chimeric LGIC
```

<400> SEQUENCE: 25

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Asp Ser Val Pro Leu Ile Asp Ile Trp Met Ala Val Cys Leu Leu Phe
290                 295                 300

Val Phe Ser Ala Leu Leu Glu Tyr Ala Ala Val Asn Phe Val Ser Arg
305                 310                 315                 320

Gln His Lys Glu Leu Arg Phe Arg Lys Arg His His Lys
                325                 330                 335

Ser Pro Met Leu Asn Leu Phe Gln Glu Asp Glu Ala Gly Glu Gly Arg
            340                 345                 350

Phe Asn Phe Ser Ala Tyr Gly Met Gly Pro Ala Cys Leu Gln Ala Lys
        355                 360                 365

Asp Gly Ile Ser Val Lys Gly Ala Asn Asn Ser Asn Thr Thr Asn Pro
370                 375                 380

Pro Pro Ala Pro Ser Lys Ser Pro Glu Glu Met Arg Lys Leu Phe Ile
385                 390                 395                 400

Gln Arg Ala Lys Lys Ile Asp Lys Ile Ser Arg Ile Gly Phe Pro Met
                405                 410                 415
```

Ala Phe Leu Ile Phe Asn Met Phe Tyr Trp Ile Ile Tyr Lys Ile Val
            420                 425                 430

Arg Arg Glu Asp Val His Asn Gln
        435                 440

<210> SEQ ID NO 26
<211> LENGTH: 1332
<212> TYPE: DNA
<213> ORGANISM: Artificial Sequence
<220> FEATURE:
<223> OTHER INFORMATION: synthetic sequence of chimeric LGIC

<400> SEQUENCE: 26

| | |
|---|---|
| atgcgctgct cgccgggagg cgtctggctg gcgctggccg cgtcgctcct gcacgtgtcc | 60 |
| ctgcaaggcg agttccagag gaagctttac aaggagctgg tcaagaacta caatcccttg | 120 |
| gagaggcccg tggccaatga ctcgcaacca ctcaccgtct acttctccct gagcctcctg | 180 |
| cagatcatgg acgtggatga gaagaaccaa gttttaacca ccaacatttg gctgcaaatg | 240 |
| tcttggacag atcactattt acagtggaat gtgtcagaat atccaggggt gaagactgtt | 300 |
| cgttccccag atggccagat ttggaaacca gacattcttc tctataacag tgctgatgag | 360 |
| cgctttgacg ccacattcca cactaacgtg ttggtgaact cttctgggca ttgccagtac | 420 |
| ctgcctccag gcatattcaa gagttcctgc tacatcgatg tacgctggtt tcccttttgat | 480 |
| gtgcagcact gcaaactgaa gtttgggtcc tggtcttacg gaggctggtc cttggatctg | 540 |
| cagatgcagg aggcagatat cagtggctat atccccaatg gagaatggga cctagtggga | 600 |
| atccccggca agaggagtga aggttctat gagtgctgca agagcccta ccccgatgtc | 660 |
| accttcacag tgaccatgga gcggcagatg ggttactacc tgattcagat gtatattccc | 720 |
| agcctgctca ttgtcatcct ctcatggatc tccttctgga tcaacatgga tgctgcacct | 780 |
| gctcgtgtgg gcctaggcat caccactgtg ctcaccatga ccacccagag ctccggctct | 840 |
| gagatcatgc ccgcaacatc cgattcggta ccattgatag cccaggccat tgacatttgg | 900 |
| atggcagttt gcctgctctt tgtgttctca gccctattag aatatgctgc cgttaacttt | 960 |
| gtgtctcggc aacataagga gctgctccga ttcaggagga agcggagaca tcacaagagc | 1020 |
| cccatgttga atctattcca ggaggatgaa gctggagaag ccgctttaa cttctctgcc | 1080 |
| tatgggatgg cccagcctg tctacaggcc aaggatggca tctcagtcaa gggcgccaac | 1140 |
| aacagtaaca ccaccaaccc ccctcctgca ccatctaagt ccccagagga gatgcgaaaa | 1200 |
| ctcttcatcc agagggccaa gaagatcgac aaaatatccc gcattggctt ccccatggcc | 1260 |
| ttcctcattt tcaacatgtt ctactggatc atctacaaga ttgtccgtag agaggacgtc | 1320 |
| cacaaccagt ga | 1332 |

<210> SEQ ID NO 27
<211> LENGTH: 443
<212> TYPE: PRT
<213> ORGANISM: Artificial Sequence
<220> FEATURE:
<223> OTHER INFORMATION: synthetic sequence of chimeric LGIC

<400> SEQUENCE: 27

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

```
Leu Val Lys Asn Tyr Asn Pro Leu Glu Arg Pro Val Ala Asn Asp Ser
         35                  40                  45

Gln Pro Leu Thr Val Tyr Phe Ser Leu Ser Leu Leu Gln Ile Met Asp
 50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Glu Arg Gln Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
            245                 250                 255

Asp Ala Ala Pro Ala Arg Val Gly Leu Gly Ile Thr Thr Val Leu Thr
            260                 265                 270

Met Thr Thr Gln Ser Ser Gly Ser Glu Ile Met Pro Ala Thr Ser Asp
            275                 280                 285

Ser Val Pro Leu Ile Ala Gln Ala Ile Asp Ile Trp Met Ala Val Cys
            290                 295                 300

Leu Leu Phe Val Phe Ser Ala Leu Leu Glu Tyr Ala Ala Val Asn Phe
305                 310                 315                 320

Val Ser Arg Gln His Lys Glu Leu Leu Arg Phe Arg Lys Arg Arg
                325                 330                 335

His His Lys Ser Pro Met Leu Asn Leu Phe Gln Glu Asp Glu Ala Gly
            340                 345                 350

Glu Gly Arg Phe Asn Phe Ser Ala Tyr Gly Met Gly Pro Ala Cys Leu
            355                 360                 365

Gln Ala Lys Asp Gly Ile Ser Val Lys Gly Ala Asn Asn Ser Asn Thr
            370                 375                 380

Thr Asn Pro Pro Pro Ala Pro Ser Lys Ser Pro Glu Glu Met Arg Lys
385                 390                 395                 400

Leu Phe Ile Gln Arg Ala Lys Lys Ile Asp Lys Ile Ser Arg Ile Gly
                405                 410                 415

Phe Pro Met Ala Phe Leu Ile Phe Asn Met Phe Tyr Trp Ile Ile Tyr
            420                 425                 430

Lys Ile Val Arg Arg Glu Asp Val His Asn Gln
            435                 440
```

<210> SEQ ID NO 28
<211> LENGTH: 1332
<212> TYPE: DNA
<213> ORGANISM: Artificial Sequence
<220> FEATURE:
<223> OTHER INFORMATION: synthetic sequence of chimeric LGIC

<400> SEQUENCE: 28

```
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga agaaccaa gttttaacca ccaacatttg gctgcaaatg       240
tcttggacag atcactattt acagtggaat gtgtcagaat atccaggggt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc tacatcgatg tacgctggtt ccctttgat     480
gtgcagcact gcaaactgaa gtttgggtcc tggtcttacg gaggctggtc cttggatctg     540
cagatgcagg aggcagatat cagtggctat atccccaatg agaatggga cctagtggga     600
atccccggca agaggagtga aggttctat gagtgctgca agagcccta ccccgatgtc       660
accttcacag tgaccatgcg ccgcaggacg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga ccacccagag ctccggctct     840
gagatcatgc ccgcaacatc cgattcggta ccattgatag cccaggccat tgacatttgg     900
atggcagttt gcctgctctt tgtgttctca gccctattag aatatgctgc cgttaacttt     960
gtgtctcggc aacataagga gctgctccga ttcaggagga agcggagaca tcacaagagc    1020
cccatgttga atctattcca ggaggatgaa gctggagaag ccgctttaa cttctctgcc    1080
tatgggatgg cccagcctg tctacaggcc aaggatggca tctcagtcaa gggcgccaac    1140
aacagtaaca ccaccaaccc ccctcctgca ccatctaagt ccccagagga gatgcgaaaa    1200
ctcttcatcc agagggccaa gaagatcgac aaaatatccc gcattggctt ccccatggcc    1260
ttcctcattt tcaacatgtt ctactggatc atctacaaga ttgtccgtag agaggacgtc    1320
cacaaccagt ga                                                        1332
```

<210> SEQ ID NO 29
<211> LENGTH: 443
<212> TYPE: PRT
<213> ORGANISM: Artificial Sequence
<220> FEATURE:
<223> OTHER INFORMATION: synthetic sequence of chimeric LGIC

<400> SEQUENCE: 29

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Thr Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Glu Ile Met Pro Ala Thr Ser Asp
        275                 280                 285

Ser Val Pro Leu Ile Ala Gln Ala Ile Asp Ile Trp Met Ala Val Cys
    290                 295                 300

Leu Leu Phe Val Phe Ser Ala Leu Leu Glu Tyr Ala Ala Val Asn Phe
305                 310                 315                 320

Val Ser Arg Gln His Lys Glu Leu Leu Arg Phe Arg Arg Lys Arg Arg
                325                 330                 335

His His Lys Ser Pro Met Leu Asn Leu Phe Gln Glu Asp Glu Ala Gly
            340                 345                 350

Glu Gly Arg Phe Asn Phe Ser Ala Tyr Gly Met Gly Pro Ala Cys Leu
        355                 360                 365

Gln Ala Lys Asp Gly Ile Ser Val Lys Gly Ala Asn Asn Ser Asn Thr
    370                 375                 380

Thr Asn Pro Pro Pro Ala Pro Ser Lys Ser Pro Glu Glu Met Arg Lys
385                 390                 395                 400

Leu Phe Ile Gln Arg Ala Lys Lys Ile Asp Lys Ile Ser Arg Ile Gly
                405                 410                 415

Phe Pro Met Ala Phe Leu Ile Phe Asn Met Phe Tyr Trp Ile Ile Tyr
            420                 425                 430

Lys Ile Val Arg Arg Glu Asp Val His Asn Gln
        435                 440

<210> SEQ ID NO 30
<211> LENGTH: 1332
<212> TYPE: DNA
<213> ORGANISM: Artificial Sequence
<220> FEATURE:
<223> OTHER INFORMATION: synthetic sequence of chimeric LGIC

<400> SEQUENCE: 30

```
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga gaagaaccaa gttttaacca ccaacatttg gctgcaaatg     240
tcttggacag atcactattt acagtggaat gtgtcagaat atccaggggt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc tacatcgatg tacgctggtt tccctttgat     480
gtgcagcact gcaaactgaa gtttgggtcc tggtcttacg gaggctggtc cttggatctg     540
cagatgcagg aggcagatat cagtggctat atccccaatg gagaatggga cctagtggga     600
atccccggca agaggagtga aggttctat gagtgctgca agagcccta ccccgatgtc      660 accttcacag tgaccatgcg ccgcaggacg ctctactacc tgattcagat gtatattccc     720
agcctgctca ttgtcatcct ctcatggatc tccttctgga tcaacatgga tgctgcacct     780
gctcgtgtgg cctaggcat caccactgtg ctcaccatga ccacccagag ctccggctct      840
gagatcatgc ccgcaacatc cgattcggta ccattgatag cccaggccat tgacatttgg     900
atggcagttt gcctgctctt tgtgttctca gccctattag aatatgctgc cgttaacttt     960
gtgtctcggc aacataagga gctgctccga ttcaggagga agcggagaca tcacaagagc    1020
cccatgttga atctattcca ggaggatgaa gctggagaag ccgctttaa cttctctgcc    1080 tatgggatgg gcccagcctg tctacaggcc aaggatggca tctcagtcaa gggcgccaac    1140
aacagtaaca ccaccaaccc ccctcctgca ccatctaagt ccccagagga gatgcgaaaa    1200
ctcttcatcc agagggccaa gaagatcgac aaaatatccc gcattggctt ccccatggcc    1260
ttcctcattt tcaacatgtt ctactggatc atctacaaga ttgtccgtag agaggacgtc    1320
cacaaccagt ga                                                        1332
```

<210> SEQ ID NO 31
<211> LENGTH: 443
<212> TYPE: PRT
<213> ORGANISM: Artificial Sequence
<220> FEATURE:
<223> OTHER INFORMATION: synthetic sequence of chimeric LGIC

<400> SEQUENCE: 31

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
```

```
              115                 120                 125
        Asn Val Leu Val Asn Ser Ser Gly His Cys Gln Tyr Leu Pro Pro Gly
            130                 135                 140
        Ile Phe Lys Ser Ser Cys Tyr Ile Asp Val Arg Trp Phe Pro Phe Asp
        145                 150                 155                 160
        Val Gln His Cys Lys Leu Lys Phe Gly Ser Trp Ser Tyr Gly Gly Trp
                        165                 170                 175
        Ser Leu Asp Leu Gln Met Gln Glu Ala Asp Ile Ser Gly Tyr Ile Pro
                    180                 185                 190
        Asn Gly Glu Trp Asp Leu Val Gly Ile Pro Gly Lys Arg Ser Glu Arg
                195                 200                 205
        Phe Tyr Glu Cys Cys Lys Glu Pro Tyr Pro Asp Val Thr Phe Thr Val
            210                 215                 220
        Thr Met Arg Arg Arg Thr Leu Tyr Tyr Leu Ile Gln Met Tyr Ile Pro
        225                 230                 235                 240
        Ser Leu Leu Ile Val Ile Leu Ser Trp Ile Ser Phe Trp Ile Asn Met
                        245                 250                 255
        Asp Ala Ala Pro Ala Arg Val Gly Leu Gly Ile Thr Thr Val Leu Thr
                    260                 265                 270
        Met Thr Thr Gln Ser Ser Gly Ser Glu Ile Met Pro Ala Thr Ser Asp
                275                 280                 285
        Ser Val Pro Leu Ile Ala Gln Ala Ile Asp Ile Trp Met Ala Val Cys
            290                 295                 300
        Leu Leu Phe Val Phe Ser Ala Leu Leu Glu Tyr Ala Ala Val Asn Phe
        305                 310                 315                 320
        Val Ser Arg Gln His Lys Glu Leu Leu Arg Phe Arg Lys Arg Arg
                        325                 330                 335
        His His Lys Ser Pro Met Leu Asn Leu Phe Gln Glu Asp Glu Ala Gly
                    340                 345                 350
        Glu Gly Arg Phe Asn Phe Ser Ala Tyr Gly Met Gly Pro Ala Cys Leu
                355                 360                 365
        Gln Ala Lys Asp Gly Ile Ser Val Lys Gly Ala Asn Asn Ser Asn Thr
            370                 375                 380
        Thr Asn Pro Pro Pro Ala Pro Ser Lys Ser Pro Glu Glu Met Arg Lys
        385                 390                 395                 400
        Leu Phe Ile Gln Arg Ala Lys Lys Ile Asp Lys Ile Ser Arg Ile Gly
                        405                 410                 415
        Phe Pro Met Ala Phe Leu Ile Phe Asn Met Phe Tyr Trp Ile Ile Tyr
                    420                 425                 430
        Lys Ile Val Arg Arg Glu Asp Val His Asn Gln
                435                 440

<210> SEQ ID NO 32
<211> LENGTH: 1320
<212> TYPE: DNA
<213> ORGANISM: Artificial Sequence
<220> FEATURE:
<223> OTHER INFORMATION: synthetic sequence of chimeric LGIC

<400> SEQUENCE: 32
atgcgctgct cgccgggagg cgtctggctg gcgctggccg cgtcgctcct gcacgtgtcc    60
ctgcaaggcg agttccagag gaagctttac aaggagctgg tcaagaacta caatcccttg   120
gagaggcccg tggccaatga ctcgcaacca ctcaccgtct acttctccct gagcctcctg   180
cagatcatgg acgtggatga gaagaaccaa gttttaacca ccaacatttg gctgcaaatg   240
```

```
tcttggacag atcactattt acagtggaat gtgtcagaat atccagggt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc cccatggact tgaagaattt ccccatggat     480
gtccagacat gcaaactgaa gtttgggtcc tggtcttacg gaggctggtc cttggatctg     540
cagatgcagg aggcagatat cagtggctat atccccaatg gagaatggga cctagtggga     600
atccccggca agaggagtga aaggttctat gagtgctgca agagcccta ccccgatgtc     660
accttcacag tgaccatgcg ccgcaggatg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga ccacccagag ctccggctct     840
cgagcatctc tgcccaaggt gtcctatgtg aaagccattg acatttggat ggcagtttgc     900
ctgctctttg tgttctcagc cctattagaa tatgctgccg ttaactttgt gtctcggcaa     960
cataaggagc tgctccgatt caggaggaag cggagacatc acaagagccc catgttgaat    1020
ctattccagg aggatgaagc tggagaaggc cgctttaact tctctgccta tgggatgggc    1080
ccagcctgtc tacaggccaa ggatggcatc tcagtcaagg gcgccaacaa cagtaacacc    1140
accaaccccc ctcctgcacc atctaagtcc ccagaggaga tgcgaaaact cttcatccag    1200
agggccaaga gatcgacaa aatatcccgc attggcttcc ccatggcctt cctcattttc    1260
aacatgttct actggatcat ctacaagatt gtccgtagag aggacgtcca caaccagtga    1320
```

<210> SEQ ID NO 33
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 33

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Pro Met Asp Leu Lys Asn Phe Pro Met Asp
145                 150                 155                 160

Val Gln Thr Cys Lys Leu Lys Phe Gly Ser Trp Ser Tyr Gly Gly Trp
                165                 170                 175
```

Ser Leu Asp Leu Gln Met Gln Glu Ala Asp Ile Ser Gly Tyr Ile Pro
        180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
        210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
        290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg His His Lys Ser
                325                 330                 335

Pro Met Leu Asn Leu Phe Gln Glu Asp Glu Ala Gly Glu Gly Arg Phe
            340                 345                 350

Asn Phe Ser Ala Tyr Gly Met Gly Pro Ala Cys Leu Gln Ala Lys Asp
        355                 360                 365

Gly Ile Ser Val Lys Gly Ala Asn Asn Ser Asn Thr Thr Asn Pro Pro
        370                 375                 380

Pro Ala Pro Ser Lys Ser Pro Glu Glu Met Arg Lys Leu Phe Ile Gln
385                 390                 395                 400

Arg Ala Lys Lys Ile Asp Lys Ile Ser Arg Ile Gly Phe Pro Met Ala
                405                 410                 415

Phe Leu Ile Phe Asn Met Phe Tyr Trp Ile Ile Tyr Lys Ile Val Arg
            420                 425                 430

Arg Glu Asp Val His Asn Gln
        435

<210> SEQ ID NO 34
<211> LENGTH: 1320
<212> TYPE: DNA
<213> ORGANISM: Artificial Sequence
<220> FEATURE:
<223> OTHER INFORMATION: synthetic sequence of chimeric LGIC

<400> SEQUENCE: 34
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga aagaaccaa gttttaacca ccaacatttg gctgcaaatg     240
tcttggacag atcactattt acagtggaat gtgtcagaat atccagggt gaagactgtt     300 cgtttcccag atggccagat tggaaaacca gacattcttc tctataacag tgctgatgag     360
cgctttgacg ccacattcca cactaacgtg ttggtgaact cttctgggca ttgccagtac     420
ctgcctccag gcatattcaa gagttcctgc cccatggact gaagaatttt tccctttgat     480
gtgcagcact gcaaactgaa gtttgggtcc tggtcttacg gaggctggtc cttggatctg     540

```
cagatgcagg aggcagatat cagtggctat atccccaatg gagaatggga cctagtggga    600
atccccggca agaggagtga aaggttctat gagtgctgca aagagcccta ccccgatgtc    660
accttcacag tgaccatgcg ccgcaggatg ggttactacc tgattcagat gtatattccc    720
agcctgctca ttgtcatcct ctcatggatc tccttctgga tcaacatgga tgctgcacct    780
gctcgtgtgg gcctaggcat caccactgtg ctcaccatga ccacccagag ctccggctct    840
cgagcatctc tgcccaaggt gtcctatgtg aaagccattg acatttggat ggcagtttgc    900
ctgctctttg tgttctcagc cctattagaa tatgctgccg ttaactttgt gtctcggcaa    960
cataaggagc tgctccgatt caggaggaag cggagacatc acaagagccc catgttgaat   1020
ctattccagg aggatgaagc tggagaaggc cgctttaact tctctgccta tgggatgggc   1080
ccagcctgtc tacaggccaa ggatggcatc tcagtcaagg gcgccaacaa cagtaacacc   1140 accaacccccc ctcctgcacc atctaagtcc ccagaggaga tgcgaaaact cttcatccag   1200
agggccaaga gatcgacaa aatatcccgc attggcttcc ccatggcctt cctcattttc   1260
aacatgttct actggatcat ctacaagatt gtccgtagag aggacgtcca caaccagtga   1320
```

<210> SEQ ID NO 35
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 35

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Pro Met Asp Leu Lys Asn Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220
```

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
            245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
    290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Ser
            325                 330                 335

Pro Met Leu Asn Leu Phe Gln Glu Asp Glu Ala Gly Glu Gly Arg Phe
            340                 345                 350

Asn Phe Ser Ala Tyr Gly Met Gly Pro Ala Cys Leu Gln Ala Lys Asp
        355                 360                 365

Gly Ile Ser Val Lys Gly Ala Asn Asn Ser Asn Thr Thr Asn Pro Pro
370                 375                 380

Pro Ala Pro Ser Lys Ser Pro Glu Glu Met Arg Lys Leu Phe Ile Gln
385                 390                 395                 400

Arg Ala Lys Lys Ile Asp Lys Ile Ser Arg Ile Gly Phe Pro Met Ala
            405                 410                 415

Phe Leu Ile Phe Asn Met Phe Tyr Trp Ile Ile Tyr Lys Ile Val Arg
            420                 425                 430

Arg Glu Asp Val His Asn Gln
            435

<210> SEQ ID NO 36
<211> LENGTH: 1320
<212> TYPE: DNA
<213> ORGANISM: Artificial Sequence
<220> FEATURE:
<223> OTHER INFORMATION: synthetic sequence of chimeric LGIC

<400> SEQUENCE: 36
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga caaccatgg ttttaacca ccaacatttg gctgcaaatg      240
tcttggacag atcactattt acagtggaat gtgtcagaat atccagggt gaagactgtt      300 cgtttcccag atggccagat tggaaaacca gacattcttc tctataacag tgctgatgag      360
cgctttgacg ccacattcca cactaacgtg ttggtgaact cttctgggca ttgccagtac      420
ctgcctccag gcatattcaa gagttcctgc tacatcgatg tacgctggtt tccctttgat      480
gtgcagcact gcaaactgaa gtttgggtcc tggtcttacg aggctggtc cttggatctg      540 cagatgcagg aggcagatat cagtggctat atccccaatg agaatggga cctagtggga      600 atccccggca agaggagtga aaggttctat gagtgctgca aagagcccta ccccgatgtc      660
accttcacag tgaccatgcg ccgcaggatg ggttactacc tgattcagat gtatattccc      720
agcctgctca ttgtcatcct ctcatggatc tccttctgga tcaacatgga tgctgcacct      780
gctcgtgtgg gcctaggcat caccactgtg ctcaccatga ccacccagag ctccggctct      840

```
cgagcatctc tgcccaaggt gtcctatgtg aaagccattg acatttggat ggcagtttgc     900
ctgctctttg tgttctcagc cctattagaa tatgctgccg ttaactttgt gtctcggcaa     960
cataaggagc tgctccgatt caggaggaag cggagacatc acaagagccc catgttgaat    1020
ctattccagg aggatgaagc tggagaaggc cgctttaact tctctgccta tgggatgggc    1080
ccagcctgtc tacaggccaa ggatggcatc tcagtcaagg gcgccaacaa cagtaacacc    1140
accaaccccc ctcctgcacc atctaagtcc ccagaggaga tgcgaaaact cttcatccag    1200
agggccaaga gatcgacaa aatatcccgc attggcttcc ccatggcctt cctcattttc    1260
aacatgttct actggatcat ctacaagatt gtccgtagag aggacgtcca caaccagtga    1320
```

<210> SEQ ID NO 37
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 37

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
    50                  55                  60

Val Asp Glu Thr Thr Met Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser

```
              275                 280                 285
Tyr Val Lys Ala Ile Asp Ile Trp Met Ala Val Cys Leu Leu Phe Val
            290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg His His Lys Ser
                325                 330                 335

Pro Met Leu Asn Leu Phe Gln Glu Asp Glu Ala Gly Glu Gly Arg Phe
            340                 345                 350

Asn Phe Ser Ala Tyr Gly Met Gly Pro Ala Cys Leu Gln Ala Lys Asp
                355                 360                 365

Gly Ile Ser Val Lys Gly Ala Asn Asn Ser Asn Thr Thr Asn Pro Pro
            370                 375                 380

Pro Ala Pro Ser Lys Ser Pro Glu Glu Met Arg Lys Leu Phe Ile Gln
385                 390                 395                 400

Arg Ala Lys Lys Ile Asp Lys Ile Ser Arg Ile Gly Phe Pro Met Ala
                405                 410                 415

Phe Leu Ile Phe Asn Met Phe Tyr Trp Ile Ile Tyr Lys Ile Val Arg
            420                 425                 430

Arg Glu Asp Val His Asn Gln
            435
```

<210> SEQ ID NO 38
<211> LENGTH: 1320
<212> TYPE: DNA
<213> ORGANISM: Artificial Sequence
<220> FEATURE:
<223> OTHER INFORMATION: synthetic sequence of chimeric LGIC

<400> SEQUENCE: 38

```
atgcgctgct cgccgggagg cgtctggctg gcgctggccg cgtcgctcct gcacgtgtcc    60
ctgcaaggcg agttccagag gaagctttac aaggagctgg tcaagaacta caatcccttg   120
gagaggcccg tggccaatga ctcgcaacca ctcaccgtct acttctccct gagcctcctg   180
cagatcatgg acattgctga gacaaccatg gacttaacca ccaacatttg gctgcaaatg   240
tcttggacag atcactattt acagtggaat gtgtcagaat atccaggggt gaagactgtt   300
cgtttcccag atggccagat ttggaaacca gacattcttc tctataacag tgctgatgag   360
cgctttgacg ccacattcca cactaacgtg ttggtgaact cttctgggca ttgccagtac   420
ctgcctccag gcatattcaa gagttcctgc cccatggact tgaagaattt ccccatggat   480
gtccagacat gcaaactgaa gtttgggtcc tggtcttacg gaggctggtc cttggatctg   540
cagatgcagg aggcagatat cagtggctat atccccaatg agaatgggaa cctagtggga   600
atccccggca gaggagtgaa aggttctat gagtgctgca agagcccta ccccgatgtc   660
accttcacag tgaccatgcg ccgcaggatg ggttactacc tgattcagat gtatattccc   720
agcctgctca ttgtcatcct ctcatggatc ccttctgga tcaacatgga tgctgcacct   780
gctcgtgtgg gcctaggcat caccactgtg ctcaccatga ccacccagag ctccggctct   840
cgagcatctc tgcccaaggt gtcctatgtg aaagccattg acatttggat ggcagttgc   900
ctgctctttg tgttctcagc cctattagaa tatgctgccg ttaactttgt gtctcggcaa   960
cataaggagc tgctccgatt caggaggaag cggagacatc acaagagccc catgttgaat  1020
ctattccagg aggatgaagc tggagaaggc cgctttaact ctctgcctta tgggatgggc  1080
ccagcctgtc tacaggccaa ggatggcatc tcagtcaagg gcgccaacaa cagtaacacc  1140
```

```
accaaccccc ctcctgcacc atctaagtcc ccagaggaga tgcgaaaact cttcatccag   1200
agggccaaga agatcgacaa aatatcccgc attggcttcc ccatggcctt cctcattttc   1260
aacatgttct actggatcat ctacaagatt gtccgtagag aggacgtcca caaccagtga   1320
```

<210> SEQ ID NO 39
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 39

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Ile Ala Glu Thr Thr Met Asp Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Pro Met Asp Leu Lys Asn Phe Pro Met Asp
145                 150                 155                 160

Val Gln Thr Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
    290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Ser
                325                 330                 335
```

-continued

```
Pro Met Leu Asn Leu Phe Gln Glu Asp Glu Ala Gly Glu Gly Arg Phe
            340                 345                 350
Asn Phe Ser Ala Tyr Gly Met Gly Pro Ala Cys Leu Gln Ala Lys Asp
        355                 360                 365
Gly Ile Ser Val Lys Gly Ala Asn Asn Ser Asn Thr Thr Asn Pro Pro
    370                 375                 380
Pro Ala Pro Ser Lys Ser Pro Glu Glu Met Arg Lys Leu Phe Ile Gln
385                 390                 395                 400
Arg Ala Lys Lys Ile Asp Lys Ile Ser Arg Ile Gly Phe Pro Met Ala
                405                 410                 415
Phe Leu Ile Phe Asn Met Phe Tyr Trp Ile Ile Tyr Lys Ile Val Arg
            420                 425                 430
Arg Glu Asp Val His Asn Gln
        435
```

<210> SEQ ID NO 40
<211> LENGTH: 1320
<212> TYPE: DNA
<213> ORGANISM: Artificial Sequence
<220> FEATURE:
<223> OTHER INFORMATION: synthetic sequence of chimeric LGIC

<400> SEQUENCE: 40

```
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga gacaaccatg gttttaacca ccaacatttg gctgcaaatg     240
tcttggacaa tcactatttt acagtggaat gtgtcagaat atccagggtt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc cccatggact tgaagaattt ccccatggat     480
gtccagacat gcaaactgaa gtttgggtcc tggtcttacg aggctggtc cttggatctg     540
cagatgcagg aggcagatat cagtggctat atccccaatg agaatggga cctagtggga     600
atccccggca agaggagtga aaggttctat gagtgctgca aagagcccta ccccgatgtc     660
accttcacag tgaccatgcg ccgcaggatg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga ccacccagag ctccggctct     840
cgagcatctc tgcccaaggt gtcctatgtg aaagccattg acatttggat ggcagtttgc     900
ctgctctttg tgttctcagc cctattagaa tatgctgccg ttaactttgt gtctcggcaa     960
cataaggagc tgctccgatt caggaggaag cggagacatc acaagagccc catgttgaat    1020
ctattccagg aggatgaagc tggagaaggc cgctttaact ctctgcctta tgggatgggc    1080
ccagcctgtc tacaggccaa ggatggcatc tcagtcaagg gcgccaacaa cagtaacacc    1140
accaaccccc ctcctgcacc atctaagtcc ccagaggaga tgcgaaaact cttcatccag    1200
agggccaaga agatcgacaa aatatcccgc attggcttcc ccatggcctt cctcattttc    1260
aacatgttct actggatcat ctacaagatt gtccgtagag aggacgtcca caaccagtga    1320
```

<210> SEQ ID NO 41
<211> LENGTH: 439

```
<212> TYPE: PRT
<213> ORGANISM: Artificial Sequence
<220> FEATURE:
<223> OTHER INFORMATION: synthetic sequence of chimeric LGIC

<400> SEQUENCE: 41

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Thr Thr Met Val Leu Thr Thr Asn Ile Trp Leu Gln Met
65                  70                  75                  80

Ser Trp Thr Asp His Tyr Leu Gln Trp Asn Val Ser Glu Tyr Pro Gly
            85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Pro Met Asp Leu Lys Asn Phe Pro Met Asp
145                 150                 155                 160

Val Gln Thr Cys Lys Leu Lys Phe Gly Ser Trp Ser Tyr Gly Gly Trp
            165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
            245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
            275                 280                 285

Tyr Val Lys Ala Ile Asp Ile Trp Met Ala Val Cys Leu Leu Phe Val
        290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Ser
            325                 330                 335

Pro Met Leu Asn Leu Phe Gln Glu Asp Glu Ala Gly Glu Gly Arg Phe
            340                 345                 350

Asn Phe Ser Ala Tyr Gly Met Gly Pro Ala Cys Leu Gln Ala Lys Asp
        355                 360                 365

Gly Ile Ser Val Lys Gly Ala Asn Asn Ser Asn Thr Thr Asn Pro Pro
        370                 375                 380
```

```
Pro Ala Pro Ser Lys Ser Pro Glu Glu Met Arg Lys Leu Phe Ile Gln
385                 390                 395                 400

Arg Ala Lys Lys Ile Asp Lys Ile Ser Arg Ile Gly Phe Pro Met Ala
                405                 410                 415

Phe Leu Ile Phe Asn Met Phe Tyr Trp Ile Ile Tyr Lys Ile Val Arg
            420                 425                 430

Arg Glu Asp Val His Asn Gln
        435

<210> SEQ ID NO 42
<211> LENGTH: 1317
<212> TYPE: DNA
<213> ORGANISM: Artificial Sequence
<220> FEATURE:
<223> OTHER INFORMATION: synthetic sequence of chimeric LGIC

<400> SEQUENCE: 42
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga gacaaccatg gttttaacca ccaacatttg gctgcaaatg     240
tcttggacag atcactattt acagtggaat gtgtcagaat atccagggt gaagactgtt     300
cgtttcccag atgccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc cccatggact gaagaatttt ccccatggat     480
gtccagacat gcaaactgaa gtttgggtcc tggtcttacg aggctggtc cttggatctg     540
cagatgcagg aggcagatat cagtggctat atccccaatg gagaatggga cctagtggga     600
atccccggca agaggagtga aaggttctat gagtgctgca aagagcccta ccccgatgtc     660
accttcacag tgaccatgga gcggcagatg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga ccacccagag ctccggctct     840
cgagcatctc tgcccaaggt gtcctatgtg aaagccattg acatttggat ggcagtttgc     900
ctgctctttg tgttctcagc cctattagaa tatgctgccg ttaactttgt gtctcggcaa     960
cataaggagc tgctccgatt caggaggaag cggagacatc acaagagccc catgttgaat    1020
ctattccagg aggatgaagc tggagaaggc cgctttaact tctctgccta tgggatgggc    1080
ccagcctgtc tacaggccaa ggatggcatc tcagtcaagg gcgccaacaa cagtaacacc    1140
accaacccc ctcctgcacc atctaagtcc ccagaggaga tgcgaaaact cttcatccag    1200
agggccaaga gatcgacaa atatcccgc attggcttcc ccatggcctt cctcattttc    1260
aacatgttct actggatcat ctacaagatt gtccgtagag aggacgtcca accag         1317

<210> SEQ ID NO 43
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 43

Met Arg Cys Ser Pro Gly Gly Val Trp Leu Ala Leu Ala Ala Ser Leu
1               5                   10                  15
```

```
Leu His Val Ser Leu Gln Gly Glu Phe Gln Arg Lys Leu Tyr Lys Glu
                20                  25                  30
Leu Val Lys Asn Tyr Asn Pro Leu Glu Arg Pro Val Ala Asn Asp Ser
             35                  40                  45
Gln Pro Leu Thr Val Tyr Phe Ser Leu Ser Leu Leu Gln Ile Met Asp
         50                  55                  60
Val Asp Glu Thr Thr Met Val Leu Thr Thr Asn Ile Trp Leu Gln Met
 65                  70                  75                  80
Ser Trp Thr Asp His Tyr Leu Gln Trp Asn Val Ser Glu Tyr Pro Gly
                 85                  90                  95
Val Lys Thr Val Arg Phe Pro Asp Gly Gln Ile Trp Lys Pro Asp Ile
             100                 105                 110
Leu Leu Tyr Asn Ser Ala Asp Glu Arg Phe Asp Ala Thr Phe His Thr
         115                 120                 125
Asn Val Leu Val Asn Ser Ser Gly His Cys Gln Tyr Leu Pro Pro Gly
         130                 135                 140
Ile Phe Lys Ser Ser Cys Pro Met Asp Leu Lys Asn Phe Pro Met Asp
145                 150                 155                 160
Val Gln Thr Cys Lys Leu Lys Phe Gly Ser Trp Ser Tyr Gly Gly Trp
                 165                 170                 175
Ser Leu Asp Leu Gln Met Gln Glu Ala Asp Ile Ser Gly Tyr Ile Pro
             180                 185                 190
Asn Gly Glu Trp Asp Leu Val Gly Ile Pro Gly Lys Arg Ser Glu Arg
         195                 200                 205
Phe Tyr Glu Cys Cys Lys Glu Pro Tyr Pro Asp Val Thr Phe Thr Val
 210                 215                 220
Thr Met Glu Arg Gln Met Gly Tyr Tyr Leu Ile Gln Met Tyr Ile Pro
225                 230                 235                 240
Ser Leu Leu Ile Val Ile Leu Ser Trp Ile Ser Phe Trp Ile Asn Met
                 245                 250                 255
Asp Ala Ala Pro Ala Arg Val Gly Leu Gly Ile Thr Thr Val Leu Thr
             260                 265                 270
Met Thr Thr Gln Ser Ser Gly Ser Arg Ala Ser Leu Pro Lys Val Ser
         275                 280                 285
Tyr Val Lys Ala Ile Asp Ile Trp Met Ala Val Cys Leu Leu Phe Val
 290                 295                 300
Phe Ser Ala Leu Leu Glu Tyr Ala Ala Val Asn Phe Val Ser Arg Gln
305                 310                 315                 320
His Lys Glu Leu Leu Arg Phe Arg Arg Lys Arg Arg His His Lys Ser
                 325                 330                 335
Pro Met Leu Asn Leu Phe Gln Glu Asp Glu Ala Gly Glu Gly Arg Phe
             340                 345                 350
Asn Phe Ser Ala Tyr Gly Met Gly Pro Ala Cys Leu Gln Ala Lys Asp
         355                 360                 365
Gly Ile Ser Val Lys Gly Ala Asn Asn Ser Asn Thr Thr Asn Pro Pro
         370                 375                 380
Pro Ala Pro Ser Lys Ser Pro Glu Glu Met Arg Lys Leu Phe Ile Gln
385                 390                 395                 400
Arg Ala Lys Lys Ile Asp Lys Ile Ser Arg Ile Gly Phe Pro Met Ala
                 405                 410                 415
Phe Leu Ile Phe Asn Met Phe Tyr Trp Ile Ile Tyr Lys Ile Val Arg
             420                 425                 430
Arg Glu Asp Val His Asn Gln
```

-continued

435

<210> SEQ ID NO 44
<211> LENGTH: 1317
<212> TYPE: DNA
<213> ORGANISM: Artificial Sequence
<220> FEATURE:
<223> OTHER INFORMATION: synthetic sequence of chimeric LGIC

<400> SEQUENCE: 44

```
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acattgctga gacaaccatg gacttaacca ccaacatttg gctgcaaatg     240
tcttggacag atcactattt acagtggaat gtgtcagaat ccaggggt gaagactgtt       300
cgtttcccag atggccagat ttggaaacca gacattcttc tctataacag tgctgatgag    360
cgctttgacg ccacattcca cactaacgtg ttggtgaact cttctgggca ttgccagtac    420
ctgcctccag gcatattcaa gagttcctgc cccatggact tgaagaattt ccccatggat    480
gtccagacat gcaaactgaa gtttgggtcc tggtcttacg gaggctggtc cttggatctg    540
cagatgcagg aggcagatat cagtggctat atccccaatg agaatggga cctagtggga     600
atccccggca agaggagtga aaggttctat gagtgctgca agagcccta ccccgatgtc     660
accttcacag tgaccatgga gcggcagatg ggttactacc tgattcagat gtatattccc    720
agcctgctca ttgtcatcct ctcatggatc tccttctgga tcaacatgga tgctgcacct    780
gctcgtgtgg gcctaggcat caccactgtg ctcaccatga ccacccagag ctccggctct    840
cgagcatctc tgcccaaggt gtcctatgtg aaagccattg acatttggat ggcagtttgc    900
ctgctctttg tgttctcagc cctattagaa tatgctgccg ttaactttgt gtctcggcaa    960
cataaggagc tgctccgatt caggaggaag cggagacatc acaagagccc catgttgaat   1020
ctattccagg aggatgaagc tggagaaggc cgctttaact tctctgccta tgggatgggc   1080
ccagcctgtc tacaggccaa ggatggcatc tcagtcaagg cgccaacaa cagtaacacc    1140
accaaccccc ctcctgcacc atctaagtcc ccagaggaga tgcgaaaact cttcatccag   1200
agggccaaga gatcgacaa atatcccgc attggcttcc ccatggcctt cctcattttc     1260
aacatgttct actggatcat ctacaagatt gtccgtagag aggacgtcca caaccag     1317
```

<210> SEQ ID NO 45
<211> LENGTH: 439
<212> TYPE: PRT
<213> ORGANISM: Artificial Sequence
<220> FEATURE:
<223> OTHER INFORMATION: synthetic sequence of chimeric LGIC

<400> SEQUENCE: 45

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Ile Ala Glu Thr Thr Met Asp Leu Thr Thr Asn Ile Trp Leu Gln Met

```
            65                  70                  75                  80
        Ser Trp Thr Asp His Tyr Leu Gln Trp Asn Val Ser Glu Tyr Pro Gly
                            85                  90                  95

Val Lys Thr Val Arg Phe Pro Asp Gly Gln Ile Trp Lys Pro Asp Ile
                        100                 105                 110

Leu Leu Tyr Asn Ser Ala Asp Glu Arg Phe Asp Ala Thr Phe His Thr
                        115                 120                 125

Asn Val Leu Val Asn Ser Ser Gly His Cys Gln Tyr Leu Pro Pro Gly
                    130                 135                 140

Ile Phe Lys Ser Ser Cys Pro Met Asp Leu Lys Asn Phe Pro Met Asp
        145                 150                 155                 160

Val Gln Thr Cys Lys Leu Lys Phe Gly Ser Trp Ser Tyr Gly Gly Trp
                        165                 170                 175

Ser Leu Asp Leu Gln Met Gln Glu Ala Asp Ile Ser Gly Tyr Ile Pro
                        180                 185                 190

Asn Gly Glu Trp Asp Leu Val Gly Ile Pro Gly Lys Arg Ser Glu Arg
                    195                 200                 205

Phe Tyr Glu Cys Cys Lys Glu Pro Tyr Pro Asp Val Thr Phe Thr Val
                    210                 215                 220

Thr Met Glu Arg Gln Met Gly Tyr Tyr Leu Ile Gln Met Tyr Ile Pro
        225                 230                 235                 240

Ser Leu Leu Ile Val Ile Leu Ser Trp Ile Ser Phe Trp Ile Asn Met
                        245                 250                 255

Asp Ala Ala Pro Ala Arg Val Gly Leu Gly Ile Thr Thr Val Leu Thr
                        260                 265                 270

Met Thr Thr Gln Ser Ser Gly Ser Arg Ala Ser Leu Pro Lys Val Ser
                    275                 280                 285

Tyr Val Lys Ala Ile Asp Ile Trp Met Ala Val Cys Leu Leu Phe Val
                    290                 295                 300

Phe Ser Ala Leu Leu Glu Tyr Ala Ala Val Asn Phe Val Ser Arg Gln
        305                 310                 315                 320

His Lys Glu Leu Leu Arg Phe Arg Arg Lys Arg Arg His His Lys Ser
                        325                 330                 335

Pro Met Leu Asn Leu Phe Gln Glu Asp Glu Ala Gly Glu Gly Arg Phe
                        340                 345                 350

Asn Phe Ser Ala Tyr Gly Met Gly Pro Ala Cys Leu Gln Ala Lys Asp
                    355                 360                 365

Gly Ile Ser Val Lys Gly Ala Asn Asn Ser Asn Thr Thr Asn Pro Pro
                    370                 375                 380

Pro Ala Pro Ser Lys Ser Pro Glu Glu Met Arg Lys Leu Phe Ile Gln
        385                 390                 395                 400

Arg Ala Lys Lys Ile Asp Lys Ile Ser Arg Ile Gly Phe Pro Met Ala
                        405                 410                 415

Phe Leu Ile Phe Asn Met Phe Tyr Trp Ile Ile Tyr Lys Ile Val Arg
                        420                 425                 430

Arg Glu Asp Val His Asn Gln
                435

<210> SEQ ID NO 46
<211> LENGTH: 1329
<212> TYPE: DNA
<213> ORGANISM: Artificial Sequence
<220> FEATURE:
<223> OTHER INFORMATION: synthetic sequence of chimeric LGIC
```

<400> SEQUENCE: 46

```
atgcgctgct cgccgggagg cgtctggctg gcgctggccg cgtcgctcct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga gacaaccatg gttttaacca ccaacatttg gctgcaaatg     240
tcttggacag atcactattt acagtggaat gtgtcagaat atccaggggt gaagactgtt     300
cgtttcccag atggccagat ttggaaacca gacattcttc tctataacag tgctgatgag     360
cgctttgacg ccacattcca cactaacgtg ttggtgaact cttctgggca ttgccagtac     420
ctgcctccag gcatattcaa gagttcctgc tacatcgatg tacgctggtt tccctttgat     480
gtgcagcact gcaaactgaa gtttgggtcc tggtcttacg gaggctggtc cttggatctg     540
cagatgcagg aggcagatat cagtggctat atccccaatg gagaatggga cctagtggga     600
atccccggca gaggagtgaa aggttctat gagtgctgca agagcccta ccccgatgtc       660
accttcacag tgaccatgcg ccgcaggatg ggttactacc tgattcagat gtatattccc     720
agcctgctca ttgtcatcct ctcatggatc tccttctgga tcaacatgga tgctgcacct     780
gctcgtgtgg gcctaggcat caccactgtg ctcaccatga ccacccagag ctccggctct     840
gagatcatgc ccgcaacatc cgattcggta ccattgatag cccaggccat tgacatttgg     900
atggcagttt gcctgctctt tgtgttctca gccctattag aatatgctgc cgttaacttt     960
gtgtctcggc aacataagga gctgctccga ttcaggagga agcggagaca tcacaagagc    1020
cccatgttga atctattcca ggaggatgaa gctggagaag ccgctttaa cttctctgcc     1080
tatgggatgg gccagccctg tctacaggcc aaggatggca tctcagtcaa gggcgccaac    1140
aacagtaaca ccaccaaccc ccctcctgca ccatctaagt ccccagagga gatgcgaaaa    1200
ctcttcatcc agagggccaa gaagatcgac aaaatatccc gcattggctt ccccatggcc    1260
ttcctcattt tcaacatgtt ctactggatc atctacaaga ttgtccgtag agaggacgtc    1320
cacaaccag                                                             1329
```

<210> SEQ ID NO 47
<211> LENGTH: 443
<212> TYPE: PRT
<213> ORGANISM: Artificial Sequence
<220> FEATURE:
<223> OTHER INFORMATION: synthetic sequence of chimeric LGIC

<400> SEQUENCE: 47

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
    50                  55                  60

Val Asp Glu Thr Thr Met Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110
```

```
Leu Leu Tyr Asn Ser Ala Asp Glu Arg Phe Asp Ala Thr Phe His Thr
            115                 120                 125
Asn Val Leu Val Asn Ser Ser Gly His Cys Gln Tyr Leu Pro Pro Gly
    130                 135                 140
Ile Phe Lys Ser Ser Cys Tyr Ile Asp Val Arg Trp Phe Pro Phe Asp
145                 150                 155                 160
Val Gln His Cys Lys Leu Lys Phe Gly Ser Trp Ser Tyr Gly Gly Trp
                165                 170                 175
Ser Leu Asp Leu Gln Met Gln Glu Ala Asp Ile Ser Gly Tyr Ile Pro
            180                 185                 190
Asn Gly Glu Trp Asp Leu Val Gly Ile Pro Gly Lys Arg Ser Glu Arg
    195                 200                 205
Phe Tyr Glu Cys Cys Lys Glu Pro Tyr Pro Asp Val Thr Phe Thr Val
210                 215                 220
Thr Met Arg Arg Arg Met Gly Tyr Tyr Leu Ile Gln Met Tyr Ile Pro
225                 230                 235                 240
Ser Leu Leu Ile Val Ile Leu Ser Trp Ile Ser Phe Trp Ile Asn Met
                245                 250                 255
Asp Ala Ala Pro Ala Arg Val Gly Leu Gly Ile Thr Thr Val Leu Thr
            260                 265                 270
Met Thr Thr Gln Ser Ser Gly Ser Glu Ile Met Pro Ala Thr Ser Asp
    275                 280                 285
Ser Val Pro Leu Ile Ala Gln Ala Ile Asp Ile Trp Met Ala Val Cys
290                 295                 300
Leu Leu Phe Val Phe Ser Ala Leu Leu Glu Tyr Ala Ala Val Asn Phe
305                 310                 315                 320
Val Ser Arg Gln His Lys Glu Leu Leu Arg Phe Arg Arg Lys Arg Arg
                325                 330                 335
His His Lys Ser Pro Met Leu Asn Leu Phe Gln Glu Asp Glu Ala Gly
            340                 345                 350
Glu Gly Arg Phe Asn Phe Ser Ala Tyr Gly Met Gly Pro Ala Cys Leu
    355                 360                 365
Gln Ala Lys Asp Gly Ile Ser Val Lys Gly Ala Asn Asn Ser Asn Thr
370                 375                 380
Thr Asn Pro Pro Pro Ala Pro Ser Lys Ser Pro Glu Glu Met Arg Lys
385                 390                 395                 400
Leu Phe Ile Gln Arg Ala Lys Lys Ile Asp Lys Ile Ser Arg Ile Gly
                405                 410                 415
Phe Pro Met Ala Phe Leu Ile Phe Asn Met Phe Tyr Trp Ile Ile Tyr
            420                 425                 430
Lys Ile Val Arg Arg Glu Asp Val His Asn Gln
        435                 440

<210> SEQ ID NO 48
<211> LENGTH: 1332
<212> TYPE: DNA
<213> ORGANISM: Artificial Sequence
<220> FEATURE:
<223> OTHER INFORMATION: synthetic sequence of chimeric LGIC

<400> SEQUENCE: 48
atgcgctgct cgccgggagg cgtctggctg gcgctggccg cgtcgctcct gcacgtgtcc    60
ctgcaaggcg agttccagag gaagctttac aaggagctgg tcaagaacta caatcccttg   120
gagaggcccg tggccaatga ctcgcaacca ctcaccgtct acttctccct gagcctcctg   180
```

```
cagatcatgg acgtggatga aagaaccaa gttttaacca ccaacatttg gctgcaaatg      240
tcttggacag atcactattt acagtggaat gtgtcagaat atccagggt gaagactgtt     300
cgtttcccag atggccagat ttggaaacca gacattcttc tctataacag tgctgatgag    360
cgctttgacg ccacattcca cactaacgtg ttggtgaact cttctgggca ttgccagtac    420
ctgcctccag gcatattcaa gagttcctgc cccatggact tgaagaattt ccccatggat    480
gtccagacat gcaaactgaa gtttgggtcc tggtcttacg gaggctggtc cttggatctg    540
cagatgcagg aggcagatat cagtggctat atccccaatg gagaatggga cctagtggga    600
atccccggca agaggagtga aaggttctat gagtgctgca agagcccta ccccgatgtc     660
accttcacag tgaccatgcg ccgcaggatg ggttactacc tgattcagat gtatattccc    720
agcctgctca ttgtcatcct ctcatggatc tccttctgga tcaacatgga tgctgcacct    780
gctcgtgtgg gcctaggcat caccactgtg ctcaccatga ccacccagag ctccggctct    840
gagatcatgc ccgcaacatc cgattcggta ccattgatag cccaggccat tgacatttgg    900
atggcagttt gcctgctctt tgtgttctca gccctattag aatatgctgc cgttaacttt    960
gtgtctcggc aacataagga gctgctccga ttcaggagga agcggagaca tcacaagagc   1020
cccatgttga atctattcca ggaggatgaa gctggagaag gccgctttaa cttctctgcc   1080
tatgggatgg gcccagcctg tctacaggcc aaggatggca tctcagtcaa gggcgccaac   1140
aacagtaaca ccaccaaccc ccctcctgca ccatctaagt ccccagagga gatgcgaaaa   1200
ctcttcatcc agagggccaa gaagatcgac aaaatatccc gcattggctt ccccatggcc   1260
ttcctcattt tcaacatgtt ctactggatc atctacaaga ttgtccgtag agaggacgtc   1320
cacaaccagt ga                                                       1332
```

<210> SEQ ID NO 49
<211> LENGTH: 443
<212> TYPE: PRT
<213> ORGANISM: Artificial Sequence
<220> FEATURE:
<223> OTHER INFORMATION: synthetic sequence of chimeric LGIC

<400> SEQUENCE: 49

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Pro Met Asp Leu Lys Asn Phe Pro Met Asp
145                 150                 155                 160
```

```
Val Gln Thr Cys Lys Leu Lys Phe Gly Ser Trp Ser Tyr Gly Gly Trp
            165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
            245                 250                 255

Asp Ala Ala Pro Ala Arg Val Gly Leu Gly Ile Thr Thr Val Leu Thr
            260                 265                 270

Met Thr Thr Gln Ser Ser Gly Ser Glu Ile Met Pro Ala Thr Ser Asp
            275                 280                 285

Ser Val Pro Leu Ile Ala Gln Ala Ile Asp Ile Trp Met Ala Val Cys
            290                 295                 300

Leu Leu Phe Val Phe Ser Ala Leu Leu Glu Tyr Ala Ala Val Asn Phe
305                 310                 315                 320

Val Ser Arg Gln His Lys Glu Leu Leu Arg Phe Arg Lys Arg Arg
            325                 330                 335

His His Lys Ser Pro Met Leu Asn Leu Phe Gln Glu Asp Glu Ala Gly
            340                 345                 350

Glu Gly Arg Phe Asn Phe Ser Ala Tyr Gly Met Gly Pro Ala Cys Leu
            355                 360                 365

Gln Ala Lys Asp Gly Ile Ser Val Lys Gly Ala Asn Asn Ser Asn Thr
            370                 375                 380

Thr Asn Pro Pro Pro Ala Pro Ser Lys Ser Pro Glu Glu Met Arg Lys
385                 390                 395                 400

Leu Phe Ile Gln Arg Ala Lys Lys Ile Asp Lys Ile Ser Arg Ile Gly
            405                 410                 415

Phe Pro Met Ala Phe Leu Ile Phe Asn Met Phe Tyr Trp Ile Ile Tyr
            420                 425                 430

Lys Ile Val Arg Arg Glu Asp Val His Asn Gln
            435                 440

<210> SEQ ID NO 50
<211> LENGTH: 451
<212> TYPE: PRT
<213> ORGANISM: Artificial Sequence
<220> FEATURE:
<223> OTHER INFORMATION: synthetic sequence of chimeric LGIC

<400> SEQUENCE: 50

Met Leu Leu Trp Val Gln Gln Ala Leu Leu Ala Leu Leu Leu Pro Thr
1               5                   10                  15

Leu Leu Ala Gln Gly Glu Ala Arg Arg Ser Arg Asn Thr Thr Arg Pro
            20                  25                  30

Ala Leu Leu Arg Leu Ser Asp Tyr Leu Leu Thr Asn Tyr Arg Lys Gly
            35                  40                  45

Val Arg Pro Val Arg Asp Trp Arg Lys Pro Thr Thr Val Ser Ile Asp
            50                  55                  60

Val Ile Val Tyr Ala Ile Leu Asn Val Asp Glu Lys Asn Gln Val Leu
65                  70                  75                  80
```

Thr Thr Tyr Ile Trp Tyr Arg Gln Tyr Trp Thr Asp Glu Phe Leu Gln
                85                  90                  95

Trp Asn Pro Glu Asp Phe Asp Asn Ile Thr Lys Leu Ser Ile Pro Thr
            100                 105                 110

Asp Ser Ile Trp Val Pro Asp Ile Leu Ile Asn Glu Phe Val Asp Val
        115                 120                 125

Gly Lys Ser Pro Asn Ile Pro Tyr Val Tyr Ile Arg His Gln Gly Glu
    130                 135                 140

Val Gln Asn Tyr Lys Pro Leu Gln Val Val Thr Ala Cys Ser Leu Asp
145                 150                 155                 160

Ile Tyr Asn Phe Pro Phe Asp Val Gln Asn Cys Ser Leu Thr Phe Thr
                165                 170                 175

Ser Trp Leu His Thr Ile Gln Asp Ile Asn Ile Ser Leu Trp Arg Leu
            180                 185                 190

Pro Glu Lys Val Lys Ser Asp Arg Ser Val Phe Met Asn Gln Gly Glu
        195                 200                 205

Trp Glu Leu Leu Gly Val Leu Pro Tyr Phe Arg Glu Phe Ser Met Glu
    210                 215                 220

Ser Ser Asn Tyr Tyr Ala Glu Met Lys Phe Tyr Val Val Ile Arg Arg
225                 230                 235                 240

Arg Met Gly Tyr Tyr Leu Ile Gln Met Tyr Ile Pro Ser Leu Leu Ile
                245                 250                 255

Val Ile Leu Ser Trp Ile Ser Phe Trp Ile Asn Met Asp Ala Ala Pro
            260                 265                 270

Ala Arg Val Gly Leu Gly Ile Thr Thr Val Leu Thr Met Thr Thr Gln
        275                 280                 285

Ser Ser Gly Ser Arg Ala Ser Leu Pro Lys Val Ser Tyr Val Lys Ala
    290                 295                 300

Ile Asp Ile Trp Met Ala Val Cys Leu Leu Phe Val Phe Ser Ala Leu
305                 310                 315                 320

Leu Glu Tyr Ala Ala Val Asn Phe Val Ser Arg Gln His Lys Glu Leu
                325                 330                 335

Leu Arg Phe Arg Arg Lys Arg Arg His His Lys Ser Pro Met Leu Asn
            340                 345                 350

Leu Phe Gln Glu Asp Glu Ala Gly Glu Gly Arg Phe Asn Phe Ser Ala
        355                 360                 365

Tyr Gly Met Gly Pro Ala Cys Leu Gln Ala Lys Asp Gly Ile Ser Val
    370                 375                 380

Lys Gly Ala Asn Asn Ser Asn Thr Thr Asn Pro Pro Ala Pro Ser
385                 390                 395                 400

Lys Ser Pro Glu Glu Met Arg Lys Leu Phe Ile Gln Arg Ala Lys Lys
                405                 410                 415

Ile Asp Lys Ile Ser Arg Ile Gly Phe Pro Met Ala Phe Leu Ile Phe
            420                 425                 430

Asn Met Phe Tyr Trp Ile Ile Tyr Lys Ile Val Arg Arg Glu Asp Val
        435                 440                 445

His Asn Gln
    450

<210> SEQ ID NO 51
<211> LENGTH: 451
<212> TYPE: PRT
<213> ORGANISM: Artificial Sequence
<220> FEATURE:

<223> OTHER INFORMATION: synthetic sequence of chimeric LGIC

<400> SEQUENCE: 51

| | | | | | | | | | | | | | | |
|---|---|---|---|---|---|---|---|---|---|---|---|---|---|---|
| Met | Leu | Leu | Trp | Val | Gln | Gln | Ala | Leu | Leu | Ala | Leu | Leu | Pro | Thr |
| 1 | | | | 5 | | | | | 10 | | | | | 15 |
| Leu | Leu | Ala | Gln | Gly | Glu | Ala | Arg | Arg | Ser | Arg | Asn | Thr | Thr | Arg | Pro |
| | | | 20 | | | | | 25 | | | | | 30 | | |
| Ala | Leu | Leu | Arg | Leu | Ser | Asp | Tyr | Leu | Leu | Thr | Asn | Tyr | Arg | Lys | Gly |
| | | 35 | | | | | 40 | | | | | 45 | | | |
| Val | Arg | Pro | Val | Arg | Asp | Trp | Arg | Lys | Pro | Thr | Thr | Val | Ser | Ile | Asp |
| | 50 | | | | | 55 | | | | | 60 | | | | |
| Val | Ile | Val | Tyr | Ala | Ile | Leu | Asn | Val | Asp | Glu | Lys | Asn | Gln | Val | Leu |
| 65 | | | | | 70 | | | | | 75 | | | | | 80 |
| Thr | Thr | Tyr | Ile | Trp | Tyr | Arg | Gln | Tyr | Trp | Thr | Asp | Glu | Phe | Leu | Gln |
| | | | | 85 | | | | | 90 | | | | | 95 | |
| Trp | Asn | Pro | Glu | Asp | Phe | Asp | Asn | Ile | Thr | Lys | Leu | Ser | Ile | Pro | Thr |
| | | | 100 | | | | | 105 | | | | | 110 | | |
| Asp | Ser | Ile | Trp | Val | Pro | Asp | Ile | Leu | Ile | Asn | Glu | Phe | Val | Asp | Val |
| | | 115 | | | | | 120 | | | | | 125 | | | |
| Gly | Lys | Ser | Pro | Asn | Ile | Pro | Tyr | Val | Tyr | Ile | Arg | His | Gln | Gly | Glu |
| | 130 | | | | | 135 | | | | | 140 | | | | |
| Val | Gln | Asn | Tyr | Lys | Pro | Leu | Gln | Val | Val | Thr | Ala | Cys | Ser | Leu | Asp |
| 145 | | | | | 150 | | | | | 155 | | | | | 160 |
| Ile | Tyr | Asn | Phe | Pro | Phe | Asp | Val | Gln | Asn | Cys | Ser | Leu | Thr | Phe | Thr |
| | | | | 165 | | | | | 170 | | | | | 175 | |
| Ser | Trp | Leu | His | Thr | Ile | Gln | Asp | Ile | Asn | Ile | Ser | Leu | Trp | Arg | Leu |
| | | | 180 | | | | | 185 | | | | | 190 | | |
| Pro | Glu | Lys | Val | Lys | Ser | Asp | Arg | Ser | Val | Phe | Met | Asn | Gln | Gly | Glu |
| | | 195 | | | | | 200 | | | | | 205 | | | |
| Trp | Glu | Leu | Leu | Gly | Val | Leu | Pro | Tyr | Phe | Arg | Glu | Phe | Ser | Met | Glu |
| | 210 | | | | | 215 | | | | | 220 | | | | |
| Ser | Ser | Asn | Tyr | Tyr | Ala | Glu | Met | Lys | Phe | Tyr | Val | His | Leu | Glu | Arg |
| 225 | | | | | 230 | | | | | 235 | | | | | 240 |
| Gln | Met | Gly | Tyr | Tyr | Leu | Ile | Gln | Met | Tyr | Ile | Pro | Ser | Leu | Leu | Ile |
| | | | | 245 | | | | | 250 | | | | | 255 | |
| Val | Ile | Leu | Ser | Trp | Ile | Ser | Phe | Trp | Ile | Asn | Met | Asp | Ala | Ala | Pro |
| | | | 260 | | | | | 265 | | | | | 270 | | |
| Ala | Arg | Val | Gly | Leu | Gly | Ile | Thr | Thr | Val | Leu | Thr | Met | Thr | Thr | Gln |
| | | 275 | | | | | 280 | | | | | 285 | | | |
| Ser | Ser | Gly | Ser | Arg | Ala | Ser | Leu | Pro | Lys | Val | Ser | Tyr | Val | Lys | Ala |
| | 290 | | | | | 295 | | | | | 300 | | | | |
| Ile | Asp | Ile | Trp | Met | Ala | Val | Cys | Leu | Leu | Phe | Val | Phe | Ser | Ala | Leu |
| 305 | | | | | 310 | | | | | 315 | | | | | 320 |
| Leu | Glu | Tyr | Ala | Ala | Val | Asn | Phe | Val | Ser | Arg | Gln | His | Lys | Glu | Leu |
| | | | | 325 | | | | | 330 | | | | | 335 | |
| Leu | Arg | Phe | Arg | Arg | Lys | Arg | Arg | His | His | Lys | Ser | Pro | Met | Leu | Asn |
| | | | 340 | | | | | 345 | | | | | 350 | | |
| Leu | Phe | Gln | Glu | Asp | Glu | Ala | Gly | Glu | Gly | Arg | Phe | Asn | Phe | Ser | Ala |
| | | 355 | | | | | 360 | | | | | 365 | | | |
| Tyr | Gly | Met | Gly | Pro | Ala | Cys | Leu | Gln | Ala | Lys | Asp | Gly | Ile | Ser | Val |
| | 370 | | | | | 375 | | | | | 380 | | | | |
| Lys | Gly | Ala | Asn | Asn | Ser | Asn | Thr | Thr | Asn | Pro | Pro | Ala | Pro | Ser |
| 385 | | | | | 390 | | | | | 395 | | | | | 400 |

```
Lys Ser Pro Glu Glu Met Arg Lys Leu Phe Ile Gln Arg Ala Lys Lys
                405                 410                 415

Ile Asp Lys Ile Ser Arg Ile Gly Phe Pro Met Ala Phe Leu Ile Phe
            420                 425                 430

Asn Met Phe Tyr Trp Ile Ile Tyr Lys Ile Val Arg Arg Glu Asp Val
        435                 440                 445

His Asn Gln
    450

<210> SEQ ID NO 52
<211> LENGTH: 455
<212> TYPE: PRT
<213> ORGANISM: Artificial Sequence
<220> FEATURE:
<223> OTHER INFORMATION: synthetic sequence of chimeric LGIC

<400> SEQUENCE: 52

Met Trp Gly Leu Ala Gly Gly Arg Leu Phe Gly Ile Phe Ser Ala Pro
1               5                   10                  15

Val Leu Val Ala Val Val Cys Cys Ala Gln Ser Val Asn Asp Pro Gly
            20                  25                  30

Asn Met Ser Phe Val Lys Glu Thr Val Asp Lys Leu Leu Lys Gly Tyr
        35                  40                  45

Asp Ile Arg Leu Arg Pro Asp Phe Gly Gly Pro Pro Val Cys Val Gly
    50                  55                  60

Met Asn Ile Asp Ile Ala Ser Ile Asp Met Val Ser Glu Val Asn Met
65                  70                  75                  80

Asp Tyr Thr Leu Thr Met Tyr Phe Gln Gln Tyr Trp Arg Asp Lys Arg
                85                  90                  95

Leu Ala Tyr Ser Gly Ile Pro Leu Asn Leu Thr Leu Asp Asn Arg Val
            100                 105                 110

Ala Asp Gln Leu Trp Val Pro Asp Thr Tyr Phe Leu Asn Asp Lys Lys
        115                 120                 125

Ser Phe Val His Gly Val Thr Val Lys Asn Arg Met Ile Arg Leu His
    130                 135                 140

Pro Asp Gly Thr Val Leu Tyr Gly Leu Arg Ile Thr Thr Thr Ala Ala
145                 150                 155                 160

Cys Met Met Asp Leu Arg Arg Tyr Pro Leu Asp Glu Gln Asn Cys Thr
                165                 170                 175

Leu Glu Ile Glu Ser Tyr Gly Tyr Thr Thr Asp Asp Ile Glu Phe Tyr
            180                 185                 190

Trp Arg Gly Gly Asp Lys Ala Val Thr Gly Val Glu Arg Ile Glu Leu
        195                 200                 205

Pro Gln Phe Ser Ile Val Glu His Arg Leu Val Ser Arg Asn Val Val
    210                 215                 220

Phe Ala Thr Gly Ala Tyr Pro Arg Leu Ser Leu Ser Phe Arg Leu Lys
225                 230                 235                 240

Arg Asn Ile Gly Tyr Met Gly Tyr Tyr Leu Ile Gln Met Tyr Ile Pro
                245                 250                 255

Ser Leu Leu Ile Val Ile Leu Ser Trp Ile Ser Phe Trp Ile Asn Met
            260                 265                 270

Asp Ala Ala Pro Ala Arg Val Gly Leu Gly Ile Thr Thr Val Leu Thr
        275                 280                 285

Met Thr Thr Gln Ser Ser Gly Ser Arg Ala Ser Leu Pro Lys Val Ser
    290                 295                 300
```

```
Tyr Val Lys Ala Ile Asp Ile Trp Met Ala Val Cys Leu Leu Phe Val
305                 310                 315                 320

Phe Ser Ala Leu Leu Glu Tyr Ala Ala Val Asn Phe Val Ser Arg Gln
                325                 330                 335

His Lys Glu Leu Leu Arg Phe Arg Arg Lys Arg Arg His His Lys Ser
            340                 345                 350

Pro Met Leu Asn Leu Phe Gln Glu Asp Glu Ala Gly Glu Gly Arg Phe
            355                 360                 365

Asn Phe Ser Ala Tyr Gly Met Gly Pro Ala Cys Leu Gln Ala Lys Asp
    370                 375                 380

Gly Ile Ser Val Lys Gly Ala Asn Asn Ser Asn Thr Thr Asn Pro Pro
385                 390                 395                 400

Pro Ala Pro Ser Lys Ser Pro Glu Glu Met Arg Lys Leu Phe Ile Gln
                405                 410                 415

Arg Ala Lys Lys Ile Asp Lys Ile Ser Arg Ile Gly Phe Pro Met Ala
                420                 425                 430

Phe Leu Ile Phe Asn Met Phe Tyr Trp Ile Ile Tyr Lys Ile Val Arg
            435                 440                 445

Arg Glu Asp Val His Asn Gln
        450                 455

<210> SEQ ID NO 53
<211> LENGTH: 31
<212> TYPE: PRT
<213> ORGANISM: Artificial Sequence
<220> FEATURE:
<223> OTHER INFORMATION: C-terminal amino acids of GABAR1

<400> SEQUENCE: 53

Ile Asp Arg Leu Ser Arg Ile Ala Phe Pro Leu Leu Phe Gly Ile Phe
1               5                   10                  15

Asn Leu Val Tyr Trp Ala Thr Tyr Leu Asn Arg Glu Pro Gln Leu
            20                  25                  30

<210> SEQ ID NO 54
<211> LENGTH: 22
<212> TYPE: PRT
<213> ORGANISM: Artificial Sequence
<220> FEATURE:
<223> OTHER INFORMATION: Amino acid residues 260-281 of human CHRNA7

<400> SEQUENCE: 54

Glu Lys Ile Ser Leu Gly Ile Thr Val Leu Leu Ser Leu Thr Val Phe
1               5                   10                  15

Met Leu Leu Val Ala Glu
            20

<210> SEQ ID NO 55
<211> LENGTH: 23
<212> TYPE: PRT
<213> ORGANISM: Artificial Sequence
<220> FEATURE:
<223> OTHER INFORMATION: Synthetic polypeptide sequence

<400> SEQUENCE: 55

Pro Ala Lys Ile Gly Leu Gly Ile Thr Val Leu Leu Ser Leu Thr Thr
1               5                   10                  15

Phe Met Ser Gly Val Ala Asn
            20
```

<210> SEQ ID NO 56
<211> LENGTH: 1780
<212> TYPE: DNA
<213> ORGANISM: Homo sapiens

<400> SEQUENCE: 56

| | | | | | | |
|---|---|---|---|---|---|---|
| atgttgtcaa | gtgtaatggc | tccctgtgg | gcctgcatcc | tggtggctgc | aggaattcta | 60 |
| gccacagata | cacatcatcc | ccaggattct | gctctgtatc | atctcagcaa | gcagctatta | 120 |
| cagaaatatc | ataagaagt | gagacctgtt | tacaactgga | ccaaggccac | cacagtctac | 180 |
| ctggacctgt | tcgtccatgc | tatattggat | gtggatgcag | agaatcaaat | attaaagaca | 240 |
| agtgtatggt | accaagaggt | ctggaatgat | gaattttat | cctggaactc | cagcatgttt | 300 |
| gatgagatta | gagagatctc | cctacctcta | agtgccatct | gggcccccga | tatcatcatc | 360 |
| aatgagtttg | tggacattga | agatacccct | gaccttccct | atgtttatgt | gaactcatct | 420 |
| gggaccattg | agaactataa | gcccatccag | gtggtctctg | cgtgcagttt | agagacatat | 480 |
| gcttttccat | tgatgtcca | gaattgcagc | ctgaccttca | agagcattct | gcatacagtg | 540 |
| gaagacgtag | acctggcctt | tctgaggagc | ccagaagaca | ttcagcatga | caaaaaggcg | 600 |
| tttttgaatg | acagtgagtg | ggaacttcta | tctgtgtcct | ccacatacag | catcctgcag | 660 |
| agcagcgctg | gaggatttgc | acagattcag | tttaatgtgg | tgatgcgcag | gcacccctg | 720 |
| gtctatgtcg | tgagtctgct | gattcctagc | atctttctca | tgctggtgga | cctggggagc | 780 |
| ttctacctgc | cacccaactg | ccgagccagg | attgtgttca | agaccagtgt | gctggtgggc | 840 |
| tacaccgtct | tcagggtcaa | catgtccaac | caggtgccac | ggagtgtagg | gagcacccct | 900 |
| ctgattgggc | acttcttcac | catctgcatg | gccttcttgg | ttctcagctt | agctaagtcc | 960 |
| atcgtgttgg | tcaaattcct | ccatgatgag | cagcgtggtg | gacaggagca | gcccttcttg | 1020 |
| tgccttcgag | gggacaccga | tgctgacagg | cctagagtgg | aacccagggc | caacgtgct | 1080 |
| gtggtaacag | agtcctcgct | gtatggagag | cacctggccc | agccaggaac | cctgaaggaa | 1140 |
| gtctggtcgc | agcttcaatc | tatcagcaac | tacctccaaa | ctcaggacca | gacagaccaa | 1200 |
| caggaggcag | agtggctggt | cctcctgtcc | cgctttgacc | gactgctctt | ccaaagctac | 1260 |
| cttttcatgc | tgggatcta | caccatcact | ctgtgctccc | tctgggcact | gtggggcggc | 1320 |
| gtgtgaagac | tgaagtgttc | ttcagtaatt | gtgctggcac | ttaggagaga | gaggagggg | 1380 |
| aataatagtg | ggttaaaaag | ctttctgggt | cgggtgtggt | ggttcttgcc | tatagtccca | 1440 |
| gtgctttggg | aggccatagc | aggaggattg | cttgagccca | ggagttcgag | accagccaga | 1500 |
| gcaacatagt | gagaccacat | ctctaccagt | aaataaataa | ataaataaat | aaataaataa | 1560 |
| ataaataaat | agctgggcat | agtggctcat | gcctgtactc | tcagctactt | gggaggttga | 1620 |
| ggtgggagga | ttgcttgagc | ccaggatttc | aaggctgcag | tgagccatga | ttgcaccact | 1680 |
| gcaccccagc | ctgggtgaca | gagcaagacc | ctgtctcaaa | aaaataaaa | taaaaggctt | 1740 |
| tctgccttca | aaaaaaaaa | aaaaaaaaa | aaaaaaaaa | | | 1780 |

<210> SEQ ID NO 57
<211> LENGTH: 441
<212> TYPE: PRT
<213> ORGANISM: Homo sapiens

```
<400> SEQUENCE: 57

Met Leu Ser Ser Val Met Ala Pro Leu Trp Ala Cys Ile Leu Val Ala
1               5                   10                  15

Ala Gly Ile Leu Ala Thr Asp Thr His His Pro Gln Asp Ser Ala Leu
            20                  25                  30

Tyr His Leu Ser Lys Gln Leu Leu Gln Lys Tyr His Lys Glu Val Arg
        35                  40                  45

Pro Val Tyr Asn Trp Thr Lys Ala Thr Thr Val Tyr Leu Asp Leu Phe
    50                  55                  60

Val His Ala Ile Leu Asp Val Asp Ala Glu Asn Gln Ile Leu Lys Thr
65                  70                  75                  80

Ser Val Trp Tyr Gln Glu Val Trp Asn Asp Glu Phe Leu Ser Trp Asn
                85                  90                  95

Ser Ser Met Phe Asp Glu Ile Arg Glu Ile Ser Leu Pro Leu Ser Ala
            100                 105                 110

Ile Trp Ala Pro Asp Ile Ile Ile Asn Glu Phe Val Asp Ile Glu Arg
        115                 120                 125

Tyr Pro Asp Leu Pro Tyr Val Tyr Val Asn Ser Ser Gly Thr Ile Glu
    130                 135                 140

Asn Tyr Lys Pro Ile Gln Val Val Ser Ala Cys Ser Leu Glu Thr Tyr
145                 150                 155                 160

Ala Phe Pro Phe Asp Val Gln Asn Cys Ser Leu Thr Phe Lys Ser Ile
                165                 170                 175

Leu His Thr Val Glu Asp Val Asp Leu Ala Phe Leu Arg Ser Pro Glu
            180                 185                 190

Asp Ile Gln His Asp Lys Lys Ala Phe Leu Asn Asp Ser Glu Trp Glu
        195                 200                 205

Leu Leu Ser Val Ser Ser Thr Tyr Ser Ile Leu Gln Ser Ser Ala Gly
    210                 215                 220

Gly Phe Ala Gln Ile Gln Phe Asn Val Val Met Arg Arg His Pro Leu
225                 230                 235                 240

Val Tyr Val Val Ser Leu Leu Ile Pro Ser Ile Phe Leu Met Leu Val
                245                 250                 255

Asp Leu Gly Ser Phe Tyr Leu Pro Pro Asn Cys Arg Ala Arg Ile Val
            260                 265                 270

Phe Lys Thr Ser Val Leu Val Gly Tyr Thr Val Phe Arg Val Asn Met
        275                 280                 285

Ser Asn Gln Val Pro Arg Ser Val Gly Ser Thr Pro Leu Ile Gly His
    290                 295                 300

Phe Phe Thr Ile Cys Met Ala Phe Leu Val Leu Ser Leu Ala Lys Ser
305                 310                 315                 320

Ile Val Leu Val Lys Phe Leu His Asp Glu Gln Arg Gly Gly Gln Glu
                325                 330                 335

Gln Pro Phe Leu Cys Leu Arg Gly Asp Thr Asp Ala Asp Arg Pro Arg
            340                 345                 350

Val Glu Pro Arg Ala Gln Arg Ala Val Val Thr Glu Ser Ser Leu Tyr
        355                 360                 365

Gly Glu His Leu Ala Gln Pro Gly Thr Leu Lys Glu Val Trp Ser Gln
    370                 375                 380

Leu Gln Ser Ile Ser Asn Tyr Leu Gln Thr Gln Asp Gln Thr Asp Gln
385                 390                 395                 400

Gln Glu Ala Glu Trp Leu Val Leu Leu Ser Arg Phe Asp Arg Leu Leu
                405                 410                 415
```

-continued

```
Phe Gln Ser Tyr Leu Phe Met Leu Gly Ile Tyr Thr Ile Thr Leu Cys
            420                 425                 430

Ser Leu Trp Ala Leu Trp Gly Gly Val
            435                 440
```